US006916906B1

(12) United States Patent
Arthur et al.

(10) Patent No.: US 6,916,906 B1
(45) Date of Patent: Jul. 12, 2005

(54) POLYPEPTIDES IMPLICATED IN THE EXPRESSION OF RESISTANCE TO GLYCOPEPTIDES, IN PARTICULAR IN GRAM-POSITIVE BACTERIA, NUCLEOTIDE SEQUENCE CODING FOR THESE POLYPEPTIDES AND USE FOR DIAGNOSIS

(75) Inventors: Michel Arthur, Paris (FR); Sylvie Dukta-Malen, Fresnes (FR); Catherine Molinas, Paris (FR); Patrice Courvalin, Paris (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 09/357,375

(22) Filed: Jul. 20, 1999

Related U.S. Application Data

(62) Division of application No. 08/980,357, filed on Nov. 28, 1997, which is a division of application No. 08/286,819, filed on Aug. 5, 1994, now Pat. No. 5,871,910, which is a continuation of application No. 08/174,682, filed on Dec. 28, 1993, now abandoned, which is a continuation of application No. 07/917,146, filed as application No. PCT/FR91/00855 on Oct. 29, 1991, now abandoned.

(30) Foreign Application Priority Data

Oct. 31, 1990 (FR) .......................................... 90 13579

(51) Int. Cl.[7] ......................... C07K 14/00; C07H 21/04

(52) U.S. Cl. ................. 530/350; 435/252.3; 435/320.1; 435/325; 435/183; 435/6; 536/23.7

(58) Field of Search ......................... 435/6, 183, 252.3, 435/320.1, 325; 536/23.7; 530/350

(56) References Cited

U.S. PATENT DOCUMENTS 5,770,361 A 6/1998 Arthur et al.

OTHER PUBLICATIONS

Roper et al., The molecular basis of vancomydcin resistance in clinically relevant Enterococci: Crystal structure of D–alanyl–D–lactate ligase (VanA), Proceedings of the National Academy of Sciences, vol. 97, pp. 8921–8925, Aug. 2000.*

Tremlett et al., Variation in Structure and Location of VanA Glycopeptide Resistance Elements among Enterococci from a Sing Patient, J. Clin. Micro., vol. 37, pp. 818–820, Mar. 1999.*

Kawalec et al., Outbreak of Vancomycin–Resistant Enterococci in a Hospital in Gdansk, Poland, due to Horizontal Transfer of Different Tn1546–Like Transposon Variants and Clonal Spread of Several Strains, J. Clin. Micro., vol. 38, pp 3317–3322, Sep. 2000.*

Darini et al., Disruption of vanS by IS1216V in a Clinical Isolate of Enterococcus faecium with Van A Glycopeptide Resistance Antimicrobial Agents and Chemotherapy, vol. 43, pp 995–996, Apr. 1999.*

* cited by examiner

*Primary Examiner*—Richard Hutson
(74) *Attorney, Agent, or Firm*—Oblon, Spivak, McClelland, Maier & Neustadt, P.C.

(57) ABSTRACT

The invention relates to a composition of polypeptides, characterized in that it contains at least one protein or part of a protein selected from the sequences of amino acids identified in the list of the sequences as SEQ ID NO 1 (VanH), SEQ ID NO 2 (VanA). SEQ ID NO 3 (VanX) or SEQ ID NO 19 (VanC), or any protein or part of a protein recognized by the antibodies directed against VanH, VanA, VanX or VanC, or any protein or part of a protein encoded in a sequence hybridizing with one of the nucleotide sequences identified in the list of the sequences as SEQ ID NO 8, SEQ ID NO 9 or SEQ ID NO 10 or with one of the following sequences V1 or V2 under stringent or only slightly stringent conditions:

Figure 2:
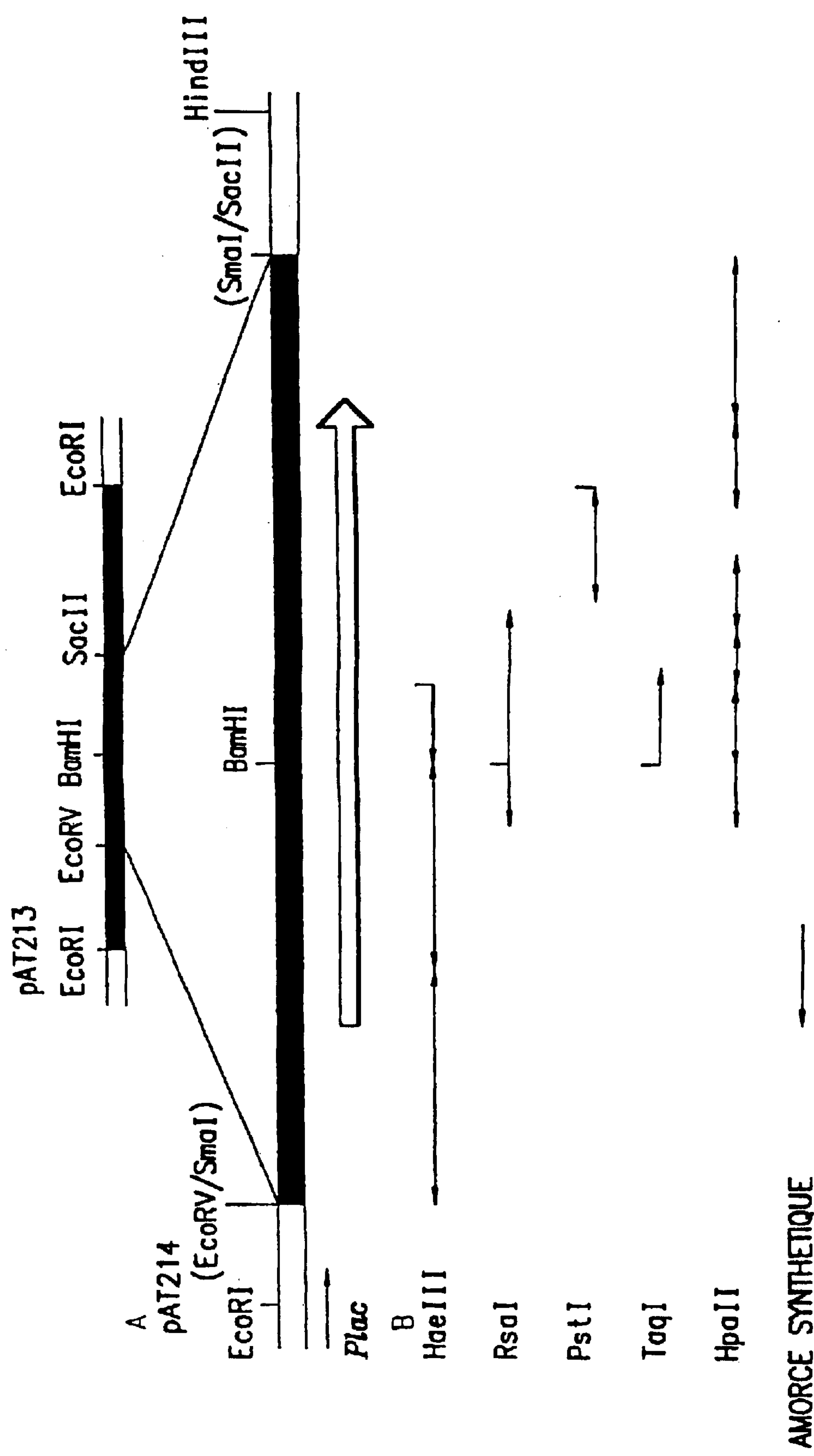

```
V1 : GGX GAA GAT GGX TCX TTX CAA GGX
            G   C       AG  C       G
                            A
V2 : AAT ACX ATX CCX GGX TTT AC
        C       T               C
                C
```

The invention also relates to the nucleotide sequences coding for these polypeptides as well as their utilization for the diagnosis of resistance to the glycopeptides.

6 Claims, 94 Drawing Sheets

```
AAGCTTTTCTTTTTGCTCATTTGTTAGAGATTTACTAACCGTATTAAATAGCTTCTTTTC
AGCCATTGCCCTTGCTTCCCACACCATTCTTTCAAGTGTAGTGATAGCAGGCAGTATAAT
TTTGTTTTTTCTTAGAAAATCTATGCATTCATGCAGTAGATGAATGGCATCACCATTTTC
CAAAGCTAATTGATGAAGGTACTTAAATGTCATTCGATATTCACTCAGGGTAAAAGTTAC
AAAGTCGTATTCACTTCGAATTTCTTTCAAATGATCCCAAAGTGTATTTTCCCTTTGAGG
ATAATGATCAAGCGAGGATGGACTAACACCAATCTGTTTCGATATATATTGTATGACCGA
ATCTGGGATGCTTTTGATATGAGTGTATGGCCAACCGGGATACCGAAGAACAGCTAATTG
AACAGCAAATCCTAAACGGTTTTCTTCCCTCCTTCGCTTATTAACTATTTCTAAATCCCG
TTTGGAAAAAGTGAAGTAGGTCCCCAGTATCCATTCATCTTCAGGGATTTGCATAAAAGC
CTGTCTCTGTTCCGGTGTAAGCAATTCTCTACCTCTCGCAATTTTCATTCAGTATCATTC
CATTTCTGTATTTTCAATTTATTAGTTCAATTATATATCAATAGAGTGTACTCTATTGAT
ACAAATGTAGTAGACTGATAAAATCATAGTTAAGAGCGTCTCATAAGACTTGTCTCAAAA
ATGAGGTGATATTTTGCGGAAAATCGGTTATATTCGTGTCAGTTCGACTAACCAGAATCC
TTCAAGACAATTTCAGCAGTTGAACGAGATCGGAATGGATATTATATAAAGAGAAAGTTT
CAGGAGCAACAAAGGATCGCGAGCAACTTCAAAAAGTGTTAGACGATTTACAGGAAGATG
ACATCATTTATGTTACAGACTTAACTCGAATCACTCGTAGTACACAAGATCTATTTGAAT
TAATCGATAACATACGAGATAAAAAGGCAAGTTTAAAATCACTAAAAGATACATGGCTTG
ATTTATCAGAAGATAATCCATACAGCCAATTCTTAATTACTGTAATGGCTGGTGTTAACC
AATTAGAGCGAGATCTTATTCGGATGAGACAACGTGAAGGGATTGAATTGGCTAAGAAAG
AAGGAAAGTTTAAAGGTCGATTAAAGAAGTATCATAAAAATCACGCAGGAATGAATTATG
CGGXXAAAGCTATATAAAGAAGGAAATATGACTGTAAATCAAATTTGTGAAATTACTAAT
GTATCTAGGGCTTCATTATACAGGAAATTATCAGAAGTGAATAATTAGCCATTCTGTATT
CCGCTAATGGGCAATATTTTTAAAGAAGAAAAGGAAACTATAAAATATTAACAGCCTCCT
AGCGATGCCGAAAAGCCCTTTGATAAAAAAAGAATCATCATCTTAAGAAATTCTTAGTCA
TTTATTATGTAAATGCTTATAAATTCGGCCCTATAATCTGATAAATTATTAAGGGCAAAC
```

*FIG. 4B*

TTATGTGAAAGGGTGATAACTATGAGCGATAAAATACTTATTGTGGATGATGAACATGAA
ATTGCCGATTTGGTTGAATTATACTTAAAAAACGAGAATTATACGGTTTTCAAATACTAT
ACCGCCAAAGAAGCATTGGAATGTATAGACAAGTCTGAGATTGACCTTGCCATATTGGAC
ATCATGCTTCCCGGCACAAGCGGCCTTACTATCTGTCAAAAAATAAGGGACAAGCACACC
TATCCGATTATCATGCTGACCGGGAAAGATACAGAGGTAGATAAAATTACAGGGTTAACA
ATCGGCGCGGATGATTATATAACGAAGCCCTTTCGCCCACTGGAGTTAATTGCTCGGGTA
AAGGCCCAGTTGCGCCGATACAAAAAATTCAGTGGAGTAAAGGAGCAGAACGAAAATGTT
ATCGTCCACTCCGGCCTTGTCATTAATGTTAACACCCATGAGTGTTATCTGAACGAGAAG
CAGTTATCCCTTACTCCCACCGAGTTTTCAATACTGCGAATCCTCTGTGAAAACAAGGGG
AATGTGGTTAGCTCCGAGCTGCTATTTCATGAGATATGGGGCGACGAATATTTCAGCAAG
AGCAACAACACCATCACCGTGCATATCCGGCATTTGCGCGAAAAAATGAACGACACCATT
GATAATCCGAAATATATAAAAACGGTATGGGGGTTGGTTATAAAATTGAAAAATAAAAA
AAACGACTATTCCAAACTAGAACGAAAACTTTACATGTATATCGTTGCAATTGTTGTGGT
AGCAATTGTATTCGTGTTGTATATTCGTTCAATGATCCGAGGGAAACTTGGGGATTGGAT
CTTAAGTATTTTGGAAAACAAATATGACTTAAATCACCTGGACGCGATGAAATTATATCA
ATATTCCATACGGAACAATATAGATATCTTTATTTATGTGGCGATTGTCATTAGTATTCT
TATTCTATGTCGCGTCATGCTTTCAAAATTCGCAAAATACTTTGACGAGATAAATACCGG
CATTGATGTACTTATTCAGAACGAAGATAAACAAATTGAGCTTTCTGCGGAAATGGATGT
TATGGAACAAAAGCTCAACACATTAAAACGGACTCTGGAAAAGCGAGAGCAGGATGCAAA
GCTGGCCGAACAAAGAAAAAATGACGTTGTTATGTACTTGGCGCACGATATTAAAACGCC
CCTTACATCCATTATCGGTTATTTGAGCCTGCTTGACGAGGCTCCAGACATGCCGGTAGA
TCAAAAGGCAAAGTATGTGCATATCACGTTGGACAAAGCGTATCGACTCGAACAGCTAAT
CGACGAGTTTTTTGAGATTACACGGTATAACCTACAAACGATAACGCTAACAAAAACGCA
CATAGACCTATACTATATGCTGGTGCAGATGACCGATGAATTTTATCCTCAGCTTTCCGC
ACATGGAAAACAGGCGGTTATTCACGCCCCCGAGGATCTGACCGTGTCCGGCGACCCTGA

*FIG. 4C*

```
TAAACTCGCGAGAGTCTTTAACAACATTTTGAAAAACGCCGCTGCATACAGTGAGGATAA
CAGCATCATTGACATTACCGCGGGCCTCTCCGGGGATGTGGTGTCAATCGAATTCAAGAA
CACTGGAAGCATCCCAAAAGATAAGCTAGCTGCCATATTTGAAAAGTTCTATAGGCTGGA
CAATTCTCGTTCTTCCGATACGGGTGGCGCGGGACTTGGATTGGCGATTGCAAAAGAAAT
TATTGTTCAGCATGGAGGGCAGATTTACGCGGAAAGCTATGATAACTATACGACGTTTAG
GGTAGAGCTTCCAGCGATGCCAGACTTGGTTGATAAAAGGAGGTCCTAAGAGATGTATAT
AATTTTTTAGGAAAATCTCAAGGTTATCTTTACTTTTTCTTAGGAAATTAACAATTTAAT
ATTAAGAAACGGCTCGTTCTTACACGGTAGACTTAATACCGTAAGAACGAGCCGTTTTCG
TTCTTCAGAGAAAGATTTGACAAGATTACCATTGGCATCCCCGTTTTATTTGGTGCCTTT
CACAGAAAGGGTTGGTCTTAATTATGAATAACATCGGCATTACTGTTTATGGATGTGAGC
AGGATGAGGCAGATGCATTCCATGCTCTTTCGCCTCGCTTTGGCGTTATGGCAACGATAA
TTAACGCCAACGTGTCGGAATCCAACGCCAAATCCGCGCCTTTCAATCAATGTATCAGTG
TGGGACATAAATCAGAGATTTCCGCCTCTATTCTTCTTGCGCTGAAGAGAGCCGGTGTGA
AATATATTTCTACCCGAAGCATCGGCTGCAATCATATAGATACAACTGCTGCTAAGAGAA
TGGGCATCACTGTCGACAATGTGGCGTACTCGCCGGATAGCGTTGCCGATTATACTATGA
TGCTAATTCTTATGGCAGTACGCAACGTAAAATCGATTGTGCGCTCTGTGGAAAAACATG
ATTTCAGGTTGGACAGCGACCGTGGCAAGGTACTCAGCGACATGACAGTTGGTGTGGTGG
GAACGGGCCAGATAGGCAAAGCGGTTATTGAGCGGCTGCGAGGATTTGGATGTAAAGTGT
TGGCTTATAGTCGCAGCCGAAGTATAGAGGTAAACTATGTACCGTTTGATGAGTTGCTGC
AAAATAGCGATATCGTTACGCTTCATGTGCCGCTCAATACGGATACGCACTATATTATCA
GCCACGAACAAATACAGAGAATGAAGCAAGGAGCATTTCTTATCAATACTGGGCGCGGTC
CACTTGTAGATACCTATGAGTTGGTTAAAGCATTAGAAAACGGGAAACTGGGCGGTGCCG
CATTGGATGTATTGGAAGGAGAGGAAGAGTTTTTCTACTCTGATTGCACCCAAAAACCAA
TTGATAATCAATTTTTACTTAAACTTCAAAGAATGCCTAACGTGATAATCACACCGCATA
CGGCCTATTATACCGAGCAAGCGTTGCGTGATACCGTTGAAAAAACCATTAAAAACTGTT
```

FIG. 4D

TGGATTTTGAAAGGAGACAGGAGCATGAATAGAATAAAAGTTGCAATACTGTTTGGGGGT
TGCTCAGAGGAGCATGACGTATCGGTAAAATCTGCAATAGAGATAGCCGCTAACATTAAT
AAAGAAAAAATACGAGCCGTTATACATTGGAATTACGAAATCTGGTGTATGGAAAATGTGC
GAAAAACCTTGCGCGGAATGGGAAAACGACAATTGCTATTCAGCTGTACTCTCGCCGGAT
AAAAAAATGCACGGATTACTTGTTAAAAAGAACCATGAATATGAAATCAACCATGTTGAT
GTAGCATTTTCAGCTTTGCATGGCAAGTCAGGTGAAGATGGATCCATACAAGGTCTGTTT
GAATTGTCCGGTATCCCTTTTGTAGGCTGCGATATTCAAAGCTCAGCAATTTGTATGGAC
AAATCGTTGACATACATCGTTGCGAAAAATGCTGGGATAGCTACTCCCGCCTTTTGGGTT
ATTAATAAAGATGATAGGCCGGTGGCAGCTACGTTTACCTATCCTGTTTTTGTTAAGCCG
GCGCGTTCAGGCTCATCCTTCGGTGTGAAAAAAGTCAATAGCGCGGACGAATTGGACTAC
GCAATTGAATCGGCAAGACAATATGACAGCAAAATCTTAATTGAGCAGGCTGTTTCGGGC
TGTGAGGTCGGTTGTGCGGTATTGGGAAACAGTGCCGCGTTAGTTGTTGGCGAGGTGGAC
CAAATCAGGCTGCAGTACGGAATCTTTCGTATTCATCAGGAAGTCGAGCCGGAAAAAGGC
TCTGAAAACGCAGTTATAACCGTTCCCGCAGACCTTTCAGCAGAGGAGCGAGGACGGATA
CAGGAAACGGCAAAAAAAATATATAAAGCGCTCGGCTGTAGAGGTCTAGCCCGTGTGGAT
ATGTTTTTACAAGATAACGGCCGCATTGTACTGAACGAAGTCAATACTCTGCCCGGTTTC
ACGTCATACAGTCGTTATCCCCGTATGATGGCCGCTGCAGGTATTGCACTTCCCGAACTG
ATTGACCGCTTGATCGTATTAGCGTTAAAGGGGTGATAAGCATGGAAATAGGATTTACTT
TTTTAGATGAAATAGTACACGGTGTTCGTTGGGACGCTAAATATGCCACTTGGGATAATT
TCACCGGAAAACCGGTTGACGGTTATGAAGTAAATCGCATTGTAGGGACATACGAGTTGG
CTGAATCGCTTTTGAAGGCAAAAGAACTGGCTGCTACCCAAGGGTACGGATTGCTTCTAT
GGGACGGTTACCGTCCTAAGCGTGCTGTAAACTGTTTTATGCAATGGGCTGCACAGCCGG
AAAATAACCTGACAAAGGAAAGTTATTATCCCAATATTGACCGAACTGAGATGATTTCAA
AAGGATACGTGGCTTCAAAATCAAGCCATAGCCGCGGCAGTGCCATTGATCTTACGCTTT
ATCGATTAGACACGGGTGAGCTTGTACCAATGGGGAGCCGATTTGATTTTATGGATGAAC

FIG. 4E

GCTCTCATCATGCGGCAAATGGAATATCATGCAATGAAGCGCAAAATCGCAGACGTTTGC
GCTCCATCATGGAAAACAGTGGGTTTGAAGCATATAGCCTCGAATGGTGGCACTATGTAT
TAAGAGACGAACCATACCCCAATAGCTATTTTGATTTCCCCGTTAAATAAACTTTTAACC
GTTGCACGGACAAACTATATAAGCTAACTCTTTCGGCAGGAAACCCGACGTATGTAACTG
GTTCTTAGGGAATTTATATATAGTAGATAGTATTGAAGATGTAAGGCAGAGCGATATTGC
GGTCATTATCTGCGTGCGCTGCGGCAAGATAGCCTGATAATAAGACTGATCGCATAGAGG
GGTGGTATTTCACACCGCCCATTGTCAACAGGCAGTTCAGCCTCGTTAAATTCAGCATGG
GTATCACTTATGAAAATTCATCTACATTGGTGATAATAGTAAATCCAGTAGGGCGAAATA
ATTGACTGTAATTTACGGGGCAAAACGGCACAATCTCAAACGAGATTGTGCCGTTTAAGG
GGAAGATTCTAGAAATATTTCATACTTCCAACTATATAGTTAAGGAGGAGACTGAAAATG
AAGAAGTTGTTTTTTTTATTGTTATTGTTATTCTTAATATACTTAGGTTATGACTACGTT
AATGAAGCACTGTTTTCTCAGGAAAAAGTCGAATTTCAAAATTATGATCAAAATCCCAAA
GAACATTTAGAAAATAGTGGGACTTCTGAAAATACCCAAGAGAAAACAATTACAGAAGAA
CAGGTTTATCAAGGAAATCTGCTATTAATCAATAGTAAATATCCTGTTCGCCAAGAAGTG
TGAAGTCAGATATCGTGAATTTATCTAAACATGACGAATTAATAAATGGATACGGGTTGC
TTGATAGTAATATTTATATGTCAAAAGAAATAGCACAAAAATTTTCAGAGATGGTCAATG
ATGCTGTAAAGGGTGGCGTTAGTCATTTTATTATTAATAGTGGCTATCGAGACTTTGATG
AGCAAAGTGTGCTTTACCAAGAAATGGGGGCTGAGTATGCCTTACCAGCAGGTTATAGTG
AGCATAATTCAGGTTTATCACTAGATGTAGGATCAAGCTTGACGAAAATGGAACGAGCCC
CTGAAGGAAAGTGGATAGAAGAAAATGCTTGGAAATACGGGTTCATTTTACGTTATCCAG
AGGACAAAACAGAGTTAACAGGAATTC

*FIG. 5A*

```
LysLeuPhePheLeuLeuIleCys***ArgPheThrAsnArgIleLys***LeuLeuPhe
 SerPheSerPheCysSerPheValArgAspLeuLeuThrValLeuAsnSerPhePheSer
  AlaPheLeuPheAlaHisLeuLeuGluIleTyr***ProTyr***IleAlaSerPheGlr
AAGCTTTTCTTTTTGCTCATTTGTTAGAGATTTACTAACCGTATTAAATAGCTTCTTTTC
          .         .         .         .         .         .
SerHisCysProCysPheProHisHisSerPheLysCysSerAspSerArgGlnTyrAsn
 AlaIleAlaLeuAlaSerHisThrIleLeuSerSerValValIleAlaGlySerIleIle
  ProLeuProLeuLeuProThrProPhePheGlnVal*********GlnAlaVal***Phe
AGCCATTGCCCTTGCTTCCCACACCATTCTTTCAAGTGTAGTGATAGCAGGCAGTATAAT
          .         .         .        100        .         .
PheValPheSer***LysIleTyrAlaPheMetGln***MetAsnGlyIleThrIlePhe
 LeuPhePheLeuArgLysSerMetHisSerCysSerArg***MetAlaSerProPheSer
  CysPhePheLeuGluAsnLeuCysIleHisAlaValAspGluTrpHisHisHisPhePro
TTTGTTTTTCTTAGAAAATCTATGCATTCATGCAGTAGATGAATGGCATCACCATTTC
          .         .         .         .         .         .
```

```
GlnSer***LeuMetLysValLeuLysCysHisSerIlePheThrGlnGlyLysSerTyr
 LysAlaAsn******ArgTyrLeuAsnValIleArgTyrSerLeuArgValLysValThr
  LysLeuIleAspGluGlyThr***MetSerPheAspIleHisSerGly***LysLeuGln
CAAAGCTAATTGATGAAGGTACTTAAATGTCATTCGATATTCACTCAGGGTAAAAGTTAC
        .      200       .         .         .         .
LysValValPheThrSerAsnPhePheGlnMetIleProLysCysIlePheProLeuArg
 LysSerTyrSerLeuArgIleSerPheLys***SerGlnSerValPheSerLeu***Gly
  SerArgIleHisPheGluPheLeuSerAsnAspProLysValTyrPheProPheGluAsp
AAAGTCGTATTCACTTCGAATTTCTTTCAAATGATCCCAAAGTGTATTTTCCCTTTGAGG
        .         .         .         .         .       300
```

*FIG. 5B*

*FIG. 5C*

```
IleMetIleLysArgGlyTrpThrAsnThrAsnLeuPheArgTyrIleLeuTyrAspArg
 ******SerSerGluAspGlyLeuThrProIleCysPheAspIleTyrCysMetThrGlu
  AsnAspGlnAlaArgMetAsp***HisGlnSerValSerIleTyrIleVal***ProAsn
ATAATGATCAAGCGAGGATGGACTAACACCAATCTGTTTCGATATATATTGTATGACCGA
         .         .         .         .         .         .

IleTrpAspAlaPheAspMetSerValTrpProThrGlyIleProLysAsnSer***Leu
 SerGlyMetLeuLeuIle***ValTyrGlyGlnProGlyTyrArgArgThrAlaAsn***
  LeuGlyCysPhe***TyrGluCysMetAlaAsnArgAspThrGluGluGlnLeuIleGlu
ATCTGGGATGCTTTTGATATGAGTGTATGGCCAACCGGGATACCGAAGAACAGCTAATTG
         .         .         .        400        .         .

AsnSerLysSer***ThrValPhePheProProSerLeuIleAsnTyrPhe***IlePro
 ThrAlaAsnProLysArgPheSerSerLeuLeuArgLeuLeuThrIleSerLysSerArg
  GlnGlnIleLeuAsnGlyPheLeuProSerPheAlaTyr***LeuPheLeuAsnProVal
AACAGCAAATCCTAAACGGTTTTCTTCCCTCCTTCGCTTATTAACTATTTCTAAATCCCG
         .         .         .         .         .         .
```

```
PheGlyLysSerGluValGlyProGlnTyrProPheIlePheArgAspLeuHisLysSer
 LeuGluLysValLys***ValProSerIleHisSerSerSerGlyIleCysIleLysAla
  TrpLysLys***SerArgSerProValSerIleHisLeuGlnGlyPheAla***LysPro
TTTGGAAAAAGTGAAGTAGGTCCCCAGTATCCATTCATCTTCAGGGATTTGCATAAAAGC
      .       500        .        .        .        .
LeuSerLeuPheArgCysLysGlnPheSerThrSerArgAsnPheHisSerValSerPhe
 CysLeuCysSerGlyValSerAsnSerLeuProLeuAlaIlePheIleGlnTyrHisSer
  ValSerValProVal***AlaIleLeuTyrLeuSerGlnPheSerPheSerIleIlePro
CTGTCTCTGTTCCGGTGTAAGCAATTCTCTACCTCTCGCAATTTTCATTCAGTATCATTC
      .        .        .        .        .       600
```

FIG. 5D

FIG. 5E

```
HisPheCysIlePheAsnLeuLeuValGlnLeuTyrIleAsnArgValTyrSerIleAsp
 IleSerValPheSerIleTyr***PheAsnTyrIleSerIleGluCysThrLeuLeuIle
  PheLeuTyrPheGlnPheIleSerSerIleIleTyrGln***SerValLeuTyr***Tyr
CATTTCTGTATTTTCAATTTATTAGTTCAATTATATATCAATAGAGTGTACTCTATTGAT
          .         .         .         .         .         .

ThrAsnValValAsp******AsnHisSer***GluArgLeuIleArgLeuValSerLys
 GlnMet******ThrAspLysIleIleValLysSerValSer***AspLeuSerGlnLys
  LysCysSerArgLeuIleLysSer***LeuArgAlaSerHisLysThrCysLeuLysAsn
ACAAATGTAGTAGACTGATAAAATCATAGTTAAGAGCGTCTCATAAGACTTGTCTCAAAA
          .         .         .       700         .         .

MetArg***TyrPheAlaGluAsnArgLeuTyrSerCysGlnPheAsp***ProGluSer
 ***GlyAspIleLeuArgLysIleGlyTyrIleArgValSerSerThrAsnGlnAsnPro
  GluValIlePheCysGlyLysSerValIlePheValSerValArgLeuThrArgIleLeu
ATGAGGTGATATTTTGCGGAAAATCGGTTATATTCGTGTCAGTTCGACTAACCAGAATCC
          .         .         .         .         .         .
```

```
PheLysThrIleSerAlaValGluArgAspArgAsnGlyTyrTyrIleLysArgLysPhe
 SerArgGlnPheGlnGlnLeuAsnGluIleGlyMetAspIleIle***ArgGluSerPhe
  GlnAspAsnPheSerSer***ThrArgSerGluTrpIleLeuTyrLysGluLysValSer
TTCAAGACAATTTCAGCAGTTGAACGAGATCGGAATGGATATTATATAAAGAGAAAGTTT
         .         800         .         .         .         .
GlnGluGlnGlnArgIleAlaSerAsnPheLysLysCys***ThrIleTyrArgLysMet
 ArgSerAsnLysGlySerArgAlaThrSerLysSerValArgArgPheThrGlyArg***
  GlyAlaThrLysAspArgGluGlnLeuGlnLysValLeuAspAspLeuGlnGluAspAsp
CAGGAGCAACAAAGGATCGCGAGCAACTTCAAAAAGTGTTAGACGATTTACAGGAAGATG
         .         .         .         .         .         900
```

*FIG. 5F*

FIG. 5G

```
ThrSerPheMetLeuGlnThr***LeuGluSerLeuValValHisLysIleTyrLeuAsn
 HisHisLeuCysTyrArgLeuAsnSerAsnHisSer***TyrThrArgSerIle***Ile
  IleIleTyrValThrAspLeuThrArgIleThrArgSerThrGlnAspLeuPheGluLeu
ACATCATTTATGTTACAGACTTAACTCGAATCACTCGTAGTACACAAGATCTATTTGAAT
         .         .         .         .         .         .
***SerIleThrTyrGluIleLysArgGlnVal***AsnHis***LysIleHisGlyLeu
 AsnArg***HisThrArg***LysGlyLysPheLysIleThrLysArgTyrMetAla***
  IleAspAsnIleArgAspLysLysAlaSerLeuLysSerLeuLysAspThrTrpLeuAsp
TAATCGATAACATACGAGATAAAAAGGCAAGTTTAAAATCACTAAAAGATACATGGCTTG
         .         .         .       1000        .         .
IleTyrGlnLysIleIleHisThrAlaAsnSer***LeuLeu***TrpLeuValLeuThr
 PheIleArgArg***SerIleGlnProIleLeuAsnTyrCysAsnGlyTrpCys***Pro
  LeuSerGluAspAsnProTyrSerGlnPheLeuIleThrValMetAlaGlyValAsnGln
ATTTATCAGAAGATAATCCATACAGCCAATTCTTAATTACTGTAATGGCTGGTGTTAACC
         .         .         .         .         .         .
```

```
Asn***SerGluIleLeuPheGly***AspAsnValLysGlyLeuAsnTrpLeuArgLys
 IleArgAlaArgSerTyrSerAspGluThrThr***ArgAsp***IleGly***GluArg
  LeuGluArgAspLeuIleArgMetArgGlnArgGluGlyIleGluLeuAlaLysLysGlu
AATTAGAGCGAGATCTTATTCGGATGAGACAACGTGAAGGGATTGAATTGGCTAAGAAAG
      .       1100        .         .         .         .
LysGluSerLeuLysValAsp***ArgSerIleIleLysIleThrGlnGlu***IleMet
 ArgLysVal***ArgSerIleLysGluValSer***LysSerArgArgAsnGluLeuCys
  GlyLysPheLysGlyArgLeuLysLysTyrHisLysAsnHisAlaGlyMetAsnTyrAla
AAGGAAAGTTTAAAGGTCGATTAAAGAAGTATCATAAAAATCACGCAGGAATGAATTATG
                                                        1200
```

*FIG. 5H*

FIG. 5I

```
ArgArgLysLeuTyrLysGluGlyAsnMetThrValAsnGlnIleCysGluIleThrAsn
 GlyGluSerTyrIleLysLysGluIle***Leu***IleLysPheValLysLeuLeuMet
  AlaLysAlaIle***ArgArgLysTyrAspCysLysSerAsnLeu***AsnTyr***Cys
CGGXXAAAGCTATATAAAGAAGGAAATATGACTGTAAATCAAATTTGTGAAATTACTAAT
         .         .         .         .         .         .
ValSerArgAlaSerLeuTyrArgLysLeuSerGluValAsnAsn***ProPheCysIle
 TyrLeuGlyLeuHisTyrThrGlyAsnTyrGlnLys***IleIleSerHisSerValPhe
  Ile***GlyPheIleIleGlnGluIleIleArgSerGlu***LeuAlaIleLeuTyrSer
GTATCTAGGGCTTCATTATACAGGAAATTATCAGAAGTGAATAATTAGCCATTCTGTATT
         .         .         .       1300        .         .
ProLeuMetGlyAsnIlePheLysGluGluLysGluThrIleLysTyr***GlnProPro
 Arg***TrpAlaIlePheLeuLysLysLysArgLysLeu***AsnIleAsnSerLeuLeu
  AlaAsnGlyGlnTyrPhe***ArgArgLysGlyAsnTyrLysIleLeuThrAlaSer***
CCGCTAATGGGCAATATTTTTAAAGAAGAAAAGGAAACTATAAAATATTAACAGCCTCCT
         .         .         .         .         .         .
```

```
SerAspAlaGluLysProPheAspLysLysArgIleIleIleLeuArgAsnSer***Ser
 AlaMetProLysSerProLeuIleLysLysGluSerSerSer***GluIleLeuSerHis
  ArgCysArgLysAlaLeu******LysLysAsnHisHisLeuLysLysPheLeuValIle
AGCGATGCCGAAAAGCCCTTTGATAAAAAAAGAATCATCATCTTAAGAAATTCTTAGTCA
         .        1400        .         .         .         .
PheIleMet***MetLeuIleAsnSerAlaLeu***SerAspLysLeuLeuArgAlaAsn
 LeuLeuCysLysCysLeu***IleArgProTyrAsnLeuIleAsnTyr***GlyGlnThr
  TyrTyrValAsnAlaTyrLysPheGlyProIleIle******IleIleLysGlyLysLeu
TTTATTATGTAAATGCTTATAAATTCGGCCCTATAATCTGATAAATTATTAAGGGCAAAC
         .         .         .         .         .        1500
```

FIG. 5J

```
LeuCysGluArgValIleThrMetSerAspLysIleLeuIleValAspAspGluHisGlu
 TyrValLysGly******Leu***AlaIleLysTyrLeuLeuTrpMetMetAsnMetLys
  Met***LysGlyAspAsnTyrGluArg***AsnThrTyrCysGly******Thr***Asn
TTATGTGAAAGGGTGATAACTATGAGCGATAAAATACTTATTGTGGATGATGAACATGAA
         .         .         .         .         .         .
IleAlaAspLeuValGluLeuTyrLeuLysAsnGluAsnTyrThrValPheLysTyrTyr
 LeuProIleTrpLeuAsnTyrThr***LysThrArgIleIleArgPheSerAsnThrIle
  CysArgPheGly***IleIleLeuLysLysArgGluLeuTyrGlyPheGlnIleLeuTyr
ATTGCCGATTTGGTTGAATTATACTTAAAAAACGAGAATTATACGGTTTTCAAATACTAT
         .         .         .       1600        .         .
ThrAlaLysGluAlaLeuGluCysIleAspLysSerGluIleAspLeuAlaIleLeuAsp
 ProProLysLysHisTrpAsnVal***ThrSerLeuArgLeuThrLeuProTyrTrpThr
  ArgGlnArgSerIleGlyMetTyrArgGlnVal***Asp***ProCysHisIleGlyHis
ACCGCCAAAGAAGCATTGGAATGTATAGACAAGTCTGAGATTGACCTTGCCATATTGGAC
         .         .         .         .         .         .
```

*FIG. 5K*

```
IleMetLeuProGlyThrSerGlyLeuThrIleCysGlnLysIleArgAspLysHisThr
 SerCysPheProAlaGlnAlaAlaLeuLeuSerValLysLys***GlyThrSerThrPro
  HisAlaSerArgHisLysArgProTyrTyrLeuSerLysAsnLysGlyGlnAlaHisLeu
ATCATGCTTCCCGGCACAAGCGGCCTTACTATCTGTCAAAAAATAAGGGACAAGCACACC
      .        1700      .         .         .         .
TyrProIleIleMetLeuThrGlyLysAspThrGluValAspLysIleThrGlyLeuThr
 IleArgLeuSerCys***ProGlyLysIleGlnArg***IleLysLeuGlnGly***Gln
  SerAspTyrHisAlaAspArgGluArgTyrArgGlyArg***AsnTyrArgValAsnAsn
TATCCGATTATCATGCTGACCGGGAAAGATACAGAGGTAGATAAAATTACAGGGTTAACA
      .         .         .         .         .        1800
```

FIG. 5L

```
IleGlyAlaAspAspTyrIleThrLysProPheArgProLeuGluLeuIleAlaArgVal
 SerAlaArgMetIleIle***ArgSerProPheAlaHisTrpSer***LeuLeuGly***
  ArgArgGly***LeuTyrAsnGluAlaLeuSerProThrGlyValAsnCysSerGlyLys
ATCGGCGCGGATGATTATATAACGAAGCCCTTTCGCCCACTGGAGTTAATTGCTCGGGTA
         .         .         .         .         .         .
LysAlaGlnLeuArgArgTyrLysLysPheSerGlyValLysGluGlnAsnGluAsnVal
 ArgProSerCysAlaAspThrLysAsnSerValGlu***ArgSerArgThrLysMetLeu
  GlyProValAlaProIleGlnLysIleGlnTrpSerLysGlyAlaGluArgLysCysTyr
AAGGCCCAGTTGCGCCGATACAAAAAATTCAGTGGAGTAAAGGAGCAGAACGAAAATGTT
         .         .         .      1900         .         .
IleValHisSerGlyLeuValIleAsnValAsnThrHisGluCysTyrLeuAsnGluLys
 SerSerThrProAlaLeuSerLeuMetLeuThrProMetSerValIle***ThrArgSer
  ArgProLeuArgProCysHis***Cys***HisPro***ValLeuSerGluArgGluAla
ATCGTCCACTCCGGCCTTGTCATTAATGTTAACACCCATGAGTGTTATCTGAACGAGAAG
         .         .         .         .         .         .
```

FIG. 5M

```
GlnLeuSerLeuThrProThrGluPheSerIleLeuArgIleLeuCysGluAsnLysGly
 SerTyrProLeuLeuProProSerPheGlnTyrCysGluSerSerValLysThrArgGly
  ValIleProTyrSerHisArgValPheAsnThrAlaAsnProLeu***LysGlnGlyGlu
CAGTTATCCCTTACTCCCACCGAGTTTTCAATACTGCGAATCCTCTGTGAAAACAAGGGG
        .      2000       .         .        .          .
AsnValValSerSerGluLeuLeuPheHisGluIleTrpGlyAspGluTyrPheSerLys
 MetTrpLeuAlaProSerCysTyrPheMetArgTyrGlyAlaThrAsnIleSerAlaArg
  CysGly***LeuArgAlaAlaIleSer***AspMetGlyArgArgIlePheGlnGlnGlu
AATGTGGTTAGCTCCGAGCTGCTATTTCATGAGATATGGGGCGACGAATATTTCAGCAAG
        .         .         .         .         .       2100
```

FIG. 5N

```
SerAsnAsnThrIleThrValHisIleArgHisLeuArgGluLysMetAsnAspThrIle
 AlaThrThrProSerProCysIleSerGlyIleCysAlaLysLys***ThrThrProLeu
  GlnGlnHisHisHisArgAlaTyrProAlaPheAlaArgLysAsnGluArgHisHis***
AGCAACAACACCATCACCGTGCATATCCGGCATTTGCGCGAAAAAATGAACGACACCATT
         .         .         .         .         .         .
AspAsnProLysTyrIleLysThrValTrpGlyValGlyTyrLysIleGluLys***Lys
 IleIleArgAsnIle***LysArgTyrGlyGlyLeuValIleLysLeuLysAsnLysLys
  ***SerGluIleTyrLysAsnGlyMetGlyGlyTrpLeu***Asn***LysIleLysLys
GATAATCCGAAATATATAAAAACGGTATGGGGGTTGGTTATAAAATTGAAAAATAAAAA
         .         .         .      2200         .         .
LysArgLeuPheGlnThrArgThrLysThrLeuHisValTyrArgCysAsnCysCysGly
 AsnAspTyrSerLysLeuGluArgLysLeuTyrMetTyrIleValAlaIleValValVal
  ThrThrIleProAsn***AsnGluAsnPheThrCysIleSerLeuGlnLeuLeuTrp***
AAACGACTATTCCAAACTAGAACGAAAACTTTACATGTATATCGTTGCAATTGTTGTGGT
         .         .         .         .         .         .
```

*FIG. 50*

```
SerAsnCysIleArgValValTyrSerPheAsnAspProArgGluThrTrpGlyLeuAsp
 AlaIleValPheValLeuTyrIleArgSerMetIleArgGlyLysLeuGlyAspTrpIle
  GlnLeuTyrSerCysCysIlePheValGln***SerGluGlyAsnLeuGlyIleGlySer
AGCAATTGTATTCGTGTTGTATATTCGTTCAATGATCCGAGGGAAACTTGGGGATTGGAT
        .        2300        .         .         .         .

LeuLysTyrPheGlyLysGlnIle***LeuLysSerProGlyArgAspGluIleIleSer
 LeuSerIleLeuGluAsnLysTyrAspLeuAsnHisLeuAspAlaMetLysLeuTyrGln
  ***ValPheTrpLysThrAsnMetThr***IleThrTrpThrArg***AsnTyrIleAsn
CTTAAGTATTTTGGAAAACAAATATGACTTAAATCACCTGGACGCGATGAAATTATATCA
        .         .         .         .         .        2400
```

FIG. 5P

*FIG. 5Q*

```
IlePheHisThrGluGlnTyrArgTyrLeuTyrLeuCysGlyAspCysHis***TyrSer
 TyrSerIleArgAsnAsnIleAspIlePheIleTyrValAlaIleValIleSerIleLeu
  IleProTyrGlyThrIle***IleSerLeuPheMetTrpArgLeuSerLeuValPheLeu
ATATTCCATACGGAACAATATAGATATCTTTATTTATGTGGCGATTGTCATTAGTATTCT

TyrSerMetSerArgHisAlaPheLysIleArgLysIleLeu***ArgAspLysTyrArg
 IleLeuCysArgValMetLeuSerLysPheAlaLysTyrPheAspGluIleAsnThrGly
  PheTyrValAlaSerCysPheGlnAsnSerGlnAsnThrLeuThrArg***IleProAla
TATTCTATGTCGCGTCATGCTTTCAAAATTCGCAAAATACTTTGACGAGATAAATACCGG
                                   2500
His***CysThrTyrSerGluArgArg***ThrAsn***AlaPheCysGlyAsnGlyCys
 IleAspValLeuIleGlnAsnGluAspLysGlnIleGluLeuSerAlaGluMetAspVal
  LeuMetTyrLeuPheArgThrLysIleAsnLysLeuSerPheLeuArgLysTrpMetLeu
CATTGATGTACTTATTCAGAACGAAGATAAACAAATTGAGCTTTCTGCGGAAATGGATGT
```

```
TyrGlyThrLysAlaGlnHisIleLysThrAspSerGlyLysAlaArgAlaGlyCysLys
 MetGluGlnLysLeuAsnThrLeuLysArgThrLeuGluLysArgGluGlnAspAlaLys
  TrpAsnLysSerSerThrHis***AsnGlyLeuTrpLysSerGluSerArgMetGlnSer
TATGGAACAAAAGCTCAACACATTAAAACGGACTCTGGAAAAGCGAGAGCAGGATGCAAA
        .         2600         .         .         .         .
AlaGlyArgThrLysLysLys***ArgCysTyrValLeuGlyAlaArgTyr***AsnAla
 LeuAlaGluGlnArgLysAsnAspValValMetTyrLeuAlaHisAspIleLysThrPro
  TrpProAsnLysGluLysMetThrLeuLeuCysThrTrpArgThrIleLeuLysArgPro
GCTGGCCGAACAAAGAAAAAATGACGTTGTTATGTACTTGGCGCACGATATTAAAACGCC
        .         .         .         .         .         2700
```

FIG. 5R

FIG. 5S

```
ProTyrIleHisTyrArgLeuPheGluProAla***ArgGlySerArgHisAlaGlyArg
 LeuThrSerIleIleGlyTyrLeuSerLeuLeuAspGluAlaProAspMetProValAsp
  LeuHisProLeuSerValIle***AlaCysLeuThrArgLeuGlnThrCysArg***Ile
CCTTACATCCATTATCGGTTATTTGAGCCTGCTTGACGAGGCTCCAGACATGCCGGTAGA
        .         .         .         .         .         .
SerLysGlyLysValCysAlaTyrHisValGlyGlnSerValSerThrArgThrAlaAsn
 GlnLysAlaLysTyrValHisIleThrLeuAspLysAlaTyrArgLeuGluGlnLeuIle
  LysArgGlnSerMetCysIleSerArgTrpThrLysArgIleAspSerAsnSer***Ser
TCAAAAGGCAAAGTATGTGCATATCACGTTGGACAAAGCGTATCGACTCGAACAGCTAAT
        .         .         .       2800        .         .
ArgArgValPhe***AspTyrThrVal***ProThrAsnAspAsnAlaAsnLysAsnAla
 AspGluPhePheGluIleThrArgTyrAsnLeuGlnThrIleThrLeuThrLysThrHis
  ThrSerPheLeuArgLeuHisGlyIleThrTyrLysArg***Arg***GlnLysArgThr
CGACGAGTTTTTTGAGATTACACGGTATAACCTACAAACGATAACGCTAACAAAAACGCA
        .         .         .         .         .         .
```

```
HisArgProIleLeuTyrAlaGlyAlaAspAspArg***IleLeuSerSerAlaPheArg
 IleAspLeuTyrTyrMetLeuValGlnMetThrAspGluPheTyrProGlnLeuSerAla
  ***ThrTyrThrIleCysTrpCysArg***ProMetAsnPheIleLeuSerPheProHis
CATAGACCTATACTATATGCTGGTGCAGATGACCGATGAATTTATCCTCAGCTTTCCGC
         .      2900         .         .         .         .

ThrTrpLysThrGlyGlyTyrSerArgProArgGlySerAspArgValArgArgPro***
 HisGlyLysGlnAlaValIleHisAlaProGluAspLeuThrValSerGlyAspProAsp
  MetGluAsnArgArgLeuPheThrProProArgIle***ProCysProAlaThrLeuIle
ACATGGAAAACAGGCGGTTATTCACGCCCCCGAGGATCTGACCGTGTCCGGCGACCCTGA
         .         .         .         .         .      3000
```

*FIG. 5T*

FIG. 5U

```
***ThrArgGluSerLeu***GlnHisPheGluLysArgArgCysIleGln***Gly***
 LysLeuAlaArgValPheAsnAsnIleLeuLysAsnAlaAlaAlaTyrSerGluAspAsn
  AsnSerArgGluSerLeuThrThrPhe***LysThrProLeuHisThrValArgIleThr
TAAACTCGCGAGAGTCTTTAACAACATTTTGAAAAACGCCGCTGCATACAGTGAGGATAA
         .         .         .         .         .         .

GlnHisHis***HisTyrArgGlyProLeuArgGlyCysGlyValAsnArgIleGlnGlu
 SerIleIleAspIleThrAlaGlyLeuSerGlyAspValValSerIleGluPheLysAsn
  AlaSerLeuThrLeuProArgAlaSerProGlyMetTrpCysGlnSerAsnSerArgThr
CAGCATCATTGACATTACCGCGGGCCTCTCCGGGGATGTGGTGTCAATCGAATTCAAGAA
         .         .         .      3100         .         .

HisTrpLysHisProLysArg***AlaSerCysHisIle***LysValLeu***AlaGly
 ThrGlySerIleProLysAspLysLeuAlaAlaIlePheGluLysPheTyrArgLeuAsp
  LeuGluAlaSerGlnLysIleSer***LeuProTyrLeuLysSerSerIleGlyTrpThr
CACTGGAAGCATCCCAAAAGATAAGCTAGCTGCCATATTTGAAAAGTTCTATAGGCTGGA
         .         .         .         .         .         .
```

```
GlnPheSerPhePheArgTyrGlyTrpArgGlyThrTrpIleGlyAspCysLysArgAsn
 AsnSerArgSerSerAspThrGlyGlyAlaGlyLeuGlyLeuAlaIleAlaLysGluIle
  IleLeuValLeuProIleArgValAlaArgAspLeuAspTrpArgLeuGlnLysLysLeu
CAATTCTCGTTCTTCCGATACGGGTGGCGCGGGACTTGGATTGGCGATTGCAAAAGAAAT
         .        3200         .           .         .         .
TyrCysSerAlaTrpArgAlaAspLeuArgGlyLysLeu******LeuTyrAspVal***
 IleValGlnHisGlyGlyGlnIleTyrAlaGluSerTyrAspAsnTyrThrThrPheArg
  LeuPheSerMetGluGlyArgPheThrArgLysAlaMetIleThrIleArgArgLeuGly
TATTGTTCAGCATGGAGGGCAGATTTACGCGGAAAGCTATGATAACTATACGACGTTTAG
         .         .         .         .         .      3300
```

*FIG. 5V*

FIG. 5W

```
GlyArgAlaSerSerAspAlaArgLeuGly******LysGluValLeuArgAspValTyr
 ValGluLeuProAlaMetProAspLeuValAspLysArgArgSer***GluMetTyrIle
  ***SerPheGlnArgCysGlnThrTrpLeuIleLysGlyGlyProLysArgCysIle***
GGTAGAGCTTCCAGCGATGCCAGACTTGGTTGATAAAAGGAGGTCCTAAGAGATGTATAT
         .         .         .         .         .         .

AsnPheLeuGlyLysSerGlnGlyTyrLeuTyrPhePheLeuGlyAsn***GlnPheAsn
 IlePhe***GluAsnLeuLysValIlePheThrPheSer***GluIleAsnAsnLeuIle
  PhePheArgLysIleSerArgLeuSerLeuLeuPheLeuArgLysLeuThrIle***Tyr
AATTTTTTAGGAAAATCTCAAGGTTATCTTTACTTTTTCTTAGGAAATTAACAATTTAAT
         .         .         .       3400        .         .

IleLysLysArgLeuValLeuThrArg***Thr***TyrArgLysAsnGluProPheSer
 LeuArgAsnGlySerPheLeuHisGlyArgLeuAsnThrValArgThrSerArgPheArg
  ***GluThrAlaArgSerTyrThrValAspLeuIlePro***GluArgAlaValPheVal
ATTAAGAAACGGCTCGTTCTTACACGGTAGACTTAATACCGTAAGAACGAGCCGTTTTCG
         .         .         .         .         .         .
```

```
PhePheArgGluArgPheAspLysIleThrIleGlyIleProValLeuPheGlyAlaPhe
 SerSerGluLysAspLeuThrArgLeuProLeuAlaSerProPheTyrLeuValProPhe
  LeuGlnArgLysIle***GlnAspTyrHisTrpHisProArgPheIleTrpCysLeuSer
TTCTTCAGAGAAAGATTTGACAAGATTACCATTGGCATCCCCGTTTTATTTGGTGCCTTT
         .      3500          .         .         .         .
HisArgLysGlyTrpSer***Leu***IleThrSerAlaLeuLeuPheMetAspValSer
 ThrGluArgValGlyLeuAsnTyrGlu***HisArgHisTyrCysLeuTrpMet***Ala
  GlnLysGlyLeuValLeuIleMetAsnAsnIleGlyIleThrValTyrGlyCysGluGln
CACAGAAAGGGTTGGTCTTAATTATGAATAACATCGGCATTACTGTTTATGGATGTGAGC
         .         .         .         .         .      3600
```

*FIG. 5X*

```
ArgMetArgGlnMetHisSerMetLeuPheArgLeuAlaLeuAlaLeuTrpGlnArg***
 Gly***GlyArgCysIleProCysSerPheAlaSerLeuTrpArgTyrGlyAsnAspAsn
  AspGluAlaAspAlaPheHisAlaLeuSerProArgPheGlyValMetAlaThrIleIle
AGGATGAGGCAGATGCATTCCATGCTCTTTCGCCTCGCTTTGGCGTTATGGCAACGATAA
         .         .         .         .         .         .
LeuThrProThrCysArgAsnProThrProAsnProArgLeuSerIleAsnValSerVal
 ***ArgGlnArgValGlyIleGlnArgGlnIleArgAlaPheGlnSerMetTyrGlnCys
  AsnAlaAsnValSerGluSerAsnAlaLysSerAlaProPheAsnGlnCysIleSerVal
TTAACGCCAACGTGTCGGAATCCAACGCCAAATCCGCGCCTTTCAATCAATGTATCAGTG
         .         .         .      3700         .         .
TrpAspIleAsnGlnArgPheProProLeuPhePheLeuArg***ArgGluProVal***
 GlyThr***IleArgAspPheArgLeuTyrSerSerCysAlaGluGluSerArgCysGlu
  GlyHisLysSerGluIleSerAlaSerIleLeuLeuAlaLeuLysArgAlaGlyValLys
TGGGACATAAATCAGAGATTTCCGCCTCTATTCTTCTTGCGCTGAAGAGAGCCGGTGTGA
         .         .         .         .         .         .
```

FIG. 5Y

AsnIlePheLeuProGluAlaSerAlaAlaIleIle***IleGlnLeuLeuLeuArgGlu

IleTyrPheTyrProLysHisArgLeuGlnSerTyrArgTyrAsnCysCys***GluAsn

TyrIleSerThrArgSerIleGlyCysAsnHisIleAspThrThrAlaAlaLysArgMet

AATATATTTCTACCCGAAGCATCGGCTGCAATCATATAGATACAACTGCTGCTAAGAGAA

. 3800 . . . .

TrpAlaSerLeuSerThrMetTrpArgThrArgArgIleAlaLeuProIleIleLeu***

GlyHisHisCysArgGlnCysGlyValLeuAlaGly***ArgCysArgLeuTyrTyrAsp

GlyIleThrValAspAsnValAlaTyrSerProAspSerValAlaAspTyrThrMetMet

TGGGCATCACTGTCGACAATGTGGCGTACTCGCCGGATAGCGTTGCCGATTATACTATGA

```
Cys***PheLeuTrpGlnTyrAlaThr***AsnArgLeuCysAlaLeuTrpLysAsnMet
 AlaAsnSerTyrGlySerThrGlnArgLysIleAspCysAlaLeuCysGlyLysThr***
  LeuIleLeuMetAlaValArgAsnValLysSerIleValArgSerValGluLysHisAsp
TGCTAATTCTTATGGCAGTACGCAACGTAAAATCGATTGTGCGCTCTGTGGAAAAACATG
        .         .         .         .         .         .
IleSerGlyTrpThrAlaThrValAlaArgTyrSerAlaThr***GlnLeuValTrpTrp
 PheGlnValGlyGlnArgProTrpGlnGlyThrGlnArgHisAspSerTrpCysGlyGly
  PheArgLeuAspSerAspArgGlyLysValLeuSerAspMetThrValGlyValValGly
ATTTCAGGTTGGACAGCGACCGTGGCAAGGTACTCAGCGACATGACAGTTGGTGTGGTGG
        .         .         .      4000         .         .
GluArgAlaArg***AlaLysArgLeuLeuSerGlyCysGluAspLeuAspValLysCys
 AsnGlyProAspArgGlnSerGlyTyr***AlaAlaAlaArgIleTrpMet***SerVal
  ThrGlyGlnIleGlyLysAlaValIleGluArgLeuArgGlyPheGlyCysLysValLeu
GAACGGGCCAGATAGGCAAAGCGGTTATTGAGCGGCTGCGAGGATTTGGATGTAAAGTGT
        .         .         .         .         .         .
```

```
TrpLeuIleValAlaAlaGluVal***Arg***ThrMetTyrArgLeuMetSerCysCys
 GlyLeu***SerGlnProLysTyrArgGlyLysLeuCysThrVal******ValAlaAla
  AlaTyrSerArgSerArgSerIleGluValAsnTyrValProPheAspGluLeuLeuGln
TGGCTTATAGTCGCAGCCGAAGTATAGAGGTAAACTATGTACCGTTTGATGAGTTGCTGC
          .     4100          .          .          .          .
LysIleAlaIleSerLeuArgPheMetCysArgSerIleArgIleArgThrIleLeuSer
 Lys***ArgTyrArgTyrAlaSerCysAlaAlaGlnTyrGlyTyrAlaLeuTyrTyrGln
  AsnSerAspIleValThrLeuHisValProLeuAsnThrAspThrHisTyrIleIleSer
AAAATAGCGATATCGTTACGCTTCATGTGCCGCTCAATACGGATACGCACTATATTATCA
          .          .          .          .          .     4200
```

*FIG. 5BB*

*FIG. 5CC*

```
AlaThrAsnLysTyrArgGlu***SerLysGluHisPheLeuSerIleLeuGlyAlaVal
 ProArgThrAsnThrGluAsnGluAlaArgSerIleSerTyrGlnTyrTrpAlaArgSer
  HisGluGlnIleGlnArgMetLysGlnGlyAlaPheLeuIleAsnThrGlyArgGlyPro
GCCACGAACAAATACAGAGAATGAAGCAAGGAGCATTTCTTATCAATACTGGGCGCGGTC
         .         .         .         .         .         .
HisLeu***IleProMetSerTrpLeuLysHis***LysThrGlyAsnTrpAlaValPro
 ThrCysArgTyrLeu***ValGly***SerIleArgLysArgGluThrGlyArgCysArg
  LeuValAspThrTyrGluLeuValLysAlaLeuGluAsnGlyLysLeuGlyGlyAlaAla
CACTTGTAGATACCTATGAGTTGGTTAAAGCATTAGAAAACGGGAAACTGGGCGGTGCCG
         .         .         .       4300        .         .
HisTrpMetTyrTrpLysGluArgLysSerPheSerThrLeuIleAlaProLysAsnGln
 IleGlyCysIleGlyArgArgGlyArgValPheLeuLeu***LeuHisProLysThrAsn
  LeuAspValLeuGluGlyGluGluPhePheTyrSerAspCysThrGlnLysProIle
CATTGGATGTATTGGAAGGAGAGGAAGAGTTTTTCTACTCTGATTGCACCCAAAAACCAA
         .         .         .         .         .         .
```

```
LeuIleIleAsnPheTyrLeuAsnPheLysGluCysLeuThr******SerHisArgIle
 ******SerIlePheThr***ThrSerLysAsnAla***ArgAspAsnHisThrAlaTyr
  AspAsnGlnPheLeuLeuLysLeuGlnArgMetProAsnValIleIleThrProHisThr
TTGATAATCAATTTTTACTTAAACTTCAAAGAATGCCTAACGTGATAATCACACCGCATA
          .       4400          .          .         .          .
ArgProIleIleProSerLysArgCysValIleProLeuLysLysProLeuLysThrVal
 GlyLeuLeuTyrArgAlaSerValAla***TyrArg***LysAsnHis***LysLeuPhe
  AlaTyrTyrThrGluGlnAlaLeuArgAspThrValGluLysThrIleLysAsnCysLeu
CGGCCTATTATACCGAGCAAGCGTTGCGTGATACCGTTGAAAAACCATTAAAAACTGTT
          .          .          .          .          .      4500
```

*FIG. 5DD*

FIG. 5EE

```
TrpIleLeuLysGlyAspArgSerMetAsnArgIleLysValAlaIleLeuPheGlyGly
 GlyPhe***LysGluThrGlyAla***IleGlu***LysLeuGlnTyrCysLeuGlyVal
  AspPheGluArgArgGlnGluHisGlu***AsnLysSerCysAsnThrValTrpGlyLeu
TGGATTTTGAAAGGAGACAGGAGCATGAATAGAATAAAAGTTGCAATACTGTTTGGGGGT
        .         .         .         .         .         .
CysSerGluGluHisAspValSerValLysSerAlaIleGluIleAlaAlaAsnIleAsn
 AlaGlnArgSerMetThrTyrArg***AsnLeuGln***Arg***ProLeuThrLeuIle
  LeuArgGlyAla***ArgIleGlyLysIleCysAsnArgAspSerArg***His******
TGCTCAGAGGAGCATGACGTATCGGTAAAATCTGCAATAGAGATAGCCGCTAACATTAAT
        .         .         .      4600         .         .
LysGluLysTyrGluProLeuTyrIleGlyIleThrLysSerGlyValTrpLysMetCys
 LysLysAsnThrSerArgTyrThrLeuGluLeuArgAsnLeuValTyrGlyLysCysAla
  ArgLysIleArgAlaValIleHisTrpAsnTyrGluIleTrpCysMetGluAsnValArg
AAAGAAAAATACGAGCCGTTATACATTGGAATTACGAAATCTGGTGTATGGAAAATGTGC
        .         .         .         .         .         .
```

```
GluLysProCysAlaGluTrpGluAsnAspAsnCysTyrSerAlaValLeuSerProAsp
 LysAsnLeuAlaArgAsnGlyLysThrThrIleAlaIleGlnLeuTyrSerArgArgIle
  LysThrLeuArgGlyMetGlyLysArgGlnLeuLeuPheSerCysThrLeuAlaGly***
GAAAAACCTTGCGCGGAATGGGAAAACGACAATTGCTATTCAGCTGTACTCTCGCCGGAT
         .      4700          .          .          .          .
LysLysMetHisGlyLeuLeuValLysLysAsnHisGluTyrGluIleAsnHisValAsp
 LysLysCysThrAspTyrLeuLeuLysArgThrMetAsnMetLysSerThrMetLeuMet
  LysAsnAlaArgIleThrCys***LysGluPro***Ile***AsnGlnProCys***Cys
AAAAAAATGCACGGATTACTTGTTAAAAAGAACCATGAATATGAAATCAACCATGTTGAT
         .          .          .          .          .      4800
```

FIG. 5FF

FIG. 5GG

```
ValAlaPheSerAlaLeuHisGlyLysSerGlyGluAspGlySerIleGlnGlyLeuPhe
 ***HisPheGlnLeuCysMetAlaSerGlnValLysMetAspProTyrLysValCysLeu
  SerIlePheSerPheAlaTrpGlnValArg***ArgTrpIleHisThrArgSerVal***
GTAGCATTTTCAGCTTTGCATGGCAAGTCAGGTGAAGATGGATCCATACAAGGTCTGTTT
        .         .         .         .         .         .
GluLeuSerGlyIleProPheValGlyCysAspIleGlnSerSerAlaIleCysMetAsp
 AsnCysProValSerLeuLeu***AlaAlaIlePheLysAlaGlnGlnPheValTrpThr
  IleValArgTyrProPheCysArgLeuArgTyrSerLysLeuSerAsnLeuTyrGlyGln
GAATTGTCCGGTATCCCTTTTGTAGGCTGCGATATTCAAAGCTCAGCAATTTGTATGGAC
        .         .         .       4900        .         .
LysSerLeuThrTyrIleValAlaLysAsnAlaGlyIleAlaThrProAlaPheTrpVal
 AsnArg***HisThrSerLeuArgLysMetLeuGly***LeuLeuProProPheGlyLeu
  IleValAspIleHisArgCysGluLysCysTrpAspSerTyrSerArgLeuLeuGlyTyr
AAATCGTTGACATACATCGTTGCGAAAAATGCTGGGATAGCTACTCCCGCCTTTTGGGTT
        .         .         .         .         .         .
```

```
IleAsnLysAspAspArgProValAlaAlaThrPheThrTyrProValPheValLysPro
 LeuIleLysMetIleGlyArgTrpGlnLeuArgLeuProIleLeuPheLeuLeuSerArg
  ******Arg******AlaGlyGlySerTyrValTyrLeuSerCysPheCys***AlaGly
ATTAATAAAGATGATAGGCCGGTGGCAGCTACGTTTACCTATCCTGTTTTTGTTAAGCCG
         .      5000         .         .         .         .
AlaArgSerGlySerSerPheGlyValLysLysValAsnSerAlaAspGluLeuAspTyr
 ArgValGlnAlaHisProSerVal***LysLysSerIleAlaArgThrAsnTrpThrThr
  AlaPheArgLeuIleLeuArgCysGluLysSerGln***ArgGlyArgIleGlyLeuArg
GCGCGTTCAGGCTCATCCTTCGGTGTGAAAAAAGTCAATAGCGCGGACGAATTGGACTAC
         .         .         .         .         .      5100
```

*FIG. 5HH*

```
AlaIleGluSerAlaArgGlnTyrAspSerLysIleLeuIleGluGlnAlaValSerGly
 GlnLeuAsnArgGlnAspAsnMetThrAlaLysSer***LeuSerArgLeuPheArgAla
  Asn***IleGlyLysThrIle***GlnGlnAsnLeuAsn***AlaGlyCysPheGlyLeu
GCAATTGAATCGGCAAGACAATATGACAGCAAAATCTTAATTGAGCAGGCTGTTTCGGGC
         .         .         .         .         .         .
CysGluValGlyCysAlaValLeuGlyAsnSerAlaAlaLeuValValGlyGluValAsp
 ValArgSerValValArgTyrTrpGluThrValProArg***LeuLeuAlaArgTrpThr
  ***GlyArgLeuCysGlyIleGlyLysGlnCysArgValSerCysTrpArgGlyGlyPro
TGTGAGGTCGGTTGTGCGGTATTGGGAAACAGTGCCGCGTTAGTTGTTGGCGAGGTGGAC
         .         .         .       5200        .         .
GlnIleArgLeuGlnTyrGlyIlePheArgIleHisGlnGluValGluProGluLysGly
 LysSerGlyCysSerThrGluSerPheValPheIleArgLysSerSerArgLysLysAla
  AsnGlnAlaAlaValArgAsnLeuSerTyrSerSerGlySerArgAlaGlyLysArgLeu
CAAATCAGGCTGCAGTACGGAATCTTTCGTATTCATCAGGAAGTCGAGCCGGAAAAAGGC
         .         .         .         .         .         .
```

FIG. 5II

```
SerGluAsnAlaValIleThrValProAlaAspLeuSerAlaGluGluArgGlyArgIle
 LeuLysThrGlnLeu***ProPheProGlnThrPheGlnGlnArgSerGluAspGlyTyr
  ***LysArgSerTyrAsnArgSerArgArgProPheSerArgGlyAlaArgThrAspThr
TCTGAAAACGCAGTTATAACCGTTCCCGCAGACCTTTCAGCAGAGGAGCGAGGACGGATA
          .         5300         .         .         .         .
GlnGluThrAlaLysLysIleTyrLysAlaLeuGlyCysArgGlyLeuAlaArgValAsp
 ArgLysArgGlnLysLysTyrIleLysArgSerAlaValGluVal***ProValTrpIle
  GlyAsnGlyLysLysAsnIle***SerAlaArgLeu***ArgSerSerProCysGlyTyr
CAGGAAACGGCAAAAAAAATATATAAAGCGCTCGGCTGTAGAGGTCTAGCCCGTGTGGAT
          .         .         .         .         .       5400
```

*FIG. 5JJ*

*FIG. 5KK*

MetPheLeuGlnAspAsnGlyArgIleValLeuAsnGluValAsnThrLeuProGlyPhe

CysPheTyrLysIleThrAlaAlaLeuTyr***ThrLysSerIleLeuCysProValSer

ValPheThrArg***ArgProHisCysThrGluArgSerGlnTyrSerAlaArgPheHis

ATGTTTTTACAAGATAACGGCCGCATTGTACTGAACGAAGTCAATACTCTGCCCGGTTTC

. . . . . .

ThrSerTyrSerArgTyrProArgMetMetAlaAlaAlaGlyIleAlaLeuProGluLeu

ArgHisThrValValIleProVal*TrpProLeuGlnValLeuHisPheProAsn*

ValIleGlnSerLeuSerProTyrAspGlyArgCysArgTyrCysThrSerArgThrAsp

ACGTCATACAGTCGTTATCCCCGTATGATGGCCGCTGCAGGTATTGCACTTCCCGAACTG

. . . 5500 . .

IleAspArgLeuIleValLeuAlaLeuLysGly****AlaTrpLys*AspLeuLeu

LeuThrAla*SerTyr*Arg***ArgGlyAspLysHisGlyAsnArgIleTyrPhe

***ProLeuAspArgIleSerValLysGlyValIleSerMetGluIleGlyPheThrPhe

ATTGACCGCTTGATCGTATTAGCGTTAAAGGGGTGATAAGCATGGAAATAGGATTTACTT

. . . . . .

```
Phe***MetLys***TyrThrValPheValGlyThrLeuAsnMetProLeuGlyIleIle
 PheArg***AsnSerThrArgCysSerLeuGlyArg***IleCysHisLeuGly***Phe
  LeuAspGluIleValHisGlyValArgTrpAspAlaLysTyrAlaThrTrpAspAsnPhe
TTTTAGATGAAATAGTACACGGTGTTCGTTGGGACGCTAAATATGCCACTTGGGATAATT
          .        5600        .         .         .         .
SerProGluAsnArgLeuThrValMetLys***IleAlaLeu***GlyHisThrSerTrp
 HisArgLysThrGly***ArgLeu***SerLysSerHisCysArgAspIleArgValGly
  ThrGlyLysProValAspGlyTyrGluValAsnArgIleValGlyThrTyrGluLeuAla
TCACCGGAAAACCGGTTGACGGTTATGAAGTAAATCGCATTGTAGGGACATACGAGTTGG
          .         .         .         .         .      5700
```

FIG. 5LL

FIG. 5MM

```
LeuAsnArgPhe***ArgGlnLysAsnTrpLeuLeuProLysGlyThrAspCysPheTyr
 ***IleAlaPheGluGlyLysArgThrGlyCysTyrProArgValArgIleAlaSerMet
  GluSerLeuLeuLysAlaLysGluLeuAlaAlaThrGlnGlyTyrGlyLeuLeuLeuTrp
CTGAATCGCTTTTGAAGGCAAAAGAACTGGCTGCTACCCAAGGGTACGGATTGCTTCTAT
         .         .         .         .         .         .

GlyThrValThrValLeuSerValLeu***ThrValLeuCysAsnGlyLeuHisSerArg
 GlyArgLeuProSer***AlaCysCysLysLeuPheTyrAlaMetGlyCysThrAlaGly
  AspGlyTyrArgProLysArgAlaValAsnCysPheMetGlnTrpAlaAlaGlnProGlu
GGGACGGTTACCGTCCTAAGCGTGCTGTAAACTGTTTTATGCAATGGGCTGCACAGCCGG
         .         .         .       5800        .         .

LysIleThr***GlnArgLysValIleIleProIleLeuThrGluLeuArg***PheGln
 Lys***ProAspLysGlyLysLeuLeuSerGlnTyr***ProAsn***AspAspPheLys
  AsnAsnLeuThrLysGluSerTyrTyrProAsnIleAspArgThrGluMetIleSerLys
AAAATAACCTGACAAAGGAAAGTTATTATCCCAATATTGACCGAACTGAGATGATTTCAA
         .         .         .         .         .         .
```

```
LysAspThrTrpLeuGlnAsnGlnAlaIleAlaAlaAlaValProLeuIleLeuArgPhe
 ArgIleArgGlyPheLysIleLysPro***ProArgGlnCysHis***SerTyrAlaLeu
  GlyTyrValAlaSerLysSerSerHisSerArgGlySerAlaIleAspLeuThrLeuTyr
AAGGATACGTGGCTTCAAAATCAAGCCATAGCCGCGGCAGTGCCATTGATCTTACGCTTT
          .         5900        .         .         .         .
IleAsp***ThrArgValSerLeuTyrGlnTrpGlyAlaAspLeuIleLeuTrpMetAsn
 SerIleArgHisGly***AlaCysThrAsnGlyGluProIle***PheTyrGly***Thr
  ArgLeuAspThrGlyGluLeuValProMetGlySerArgPheAspPheMetAspGluArg
ATCGATTAGACACGGGTGAGCTTGTACCAATGGGGAGCCGATTTGATTTTATGGATGAAC
          .         .         .         .         .      6000
```

FIG. 5NN

FIG. 500

```
AlaLeuIleMetArgGlnMetGluTyrHisAlaMetLysArgLysIleAlaAspValCys
 LeuSerSerCysGlyLysTrpAsnIleMetGln***SerAlaLysSerGlnThrPheAla
  SerHisHisAlaAlaAsnGlyIleSerCysAsnGluAlaGlnAsnArgArgArgLeuArg
GCTCTCATCATGCGGCAAATGGAATATCATGCAATGAAGCGCAAAATCGCAGACGTTTGC
         .         .         .         .         .         .

AlaProSerTrpLysThrValGlyLeuLysHisIleAlaSerAsnGlyGlyThrMetTyr
 LeuHisHisGlyLysGlnTrpVal***SerIle***ProArgMetValAlaLeuCysIle
  SerIleMetGluAsnSerGlyPheGluAlaTyrSerLeuGluTrpTrpHisTyrValLeu
GCTCCATCATGGAAAACAGTGGGTTTGAAGCATATAGCCTCGAATGGTGGCACTATGTAT
         .         .         .       6100        .         .

***GluThrAsnHisThrProIleAlaIleLeuIleSerProLeuAsnLysLeuLeuThr
 LysArgArgThrIleProGln***LeuPhe***PheProArg***IleAsnPhe***Pro
  ArgAspGluProTyrProAsnSerTyrPheAspPheProValLys***ThrPheAsnArg
TAAGAGACGAACCATACCCCAATAGCTATTTTGATTTCCCCGTTAAATAAACTTTTAACC
         .         .         .         .         .         .
```

```
ValAlaArgThrAsnTyrIleSer***LeuPheArgGlnGluThrArgArgMet***Leu
 LeuHisGlyGlnThrIle***AlaAsnSerPheGlyArgLysProAspValCysAsnTrp
  CysThrAspLysLeuTyrLysLeuThrLeuSerAlaGlyAsnProThrTyrValThrGly
GTTGCACGGACAAACTATATAAGCTAACTCTTTCGGCAGGAAACCCGACGTATGTAACTG
          .      6200          .          .          .          .
ValLeuArgGluPheIleTyrSerArg***Tyr***ArgCysLysAlaGluArgTyrCys
 PheLeuGlyAsnLeuTyrIleValAspSerIleGluAspValArgGlnSerAspIleAla
  Ser***GlyIleTyrIle******IleValLeuLysMet***GlyArgAlaIleLeuArg
GTTCTTAGGGAATTTATATATAGTAGATAGTATTGAAGATGTAAGGCAGAGCGATATTGC
          .          .          .          .          .     6300
```

FIG. 5PP

*FIG. 5QQ*

```
GlyHisTyrLeuArgAlaLeuArgGlnAspSerLeuIleIleArgLeuIleAla***Arg
 ValIleIleCysValArgCysGlyLysIleAla*********Asp***SerHisArgGly
  SerLeuSerAlaCysAlaAlaAlaArg***ProAspAsnLysThrAspArgIleGluGly
GGTCATTATCTGCGTGCGCTGCGGCAAGATAGCCTGATAATAAGACTGATCGCATAGAGG
         .         .         .         .         .         .
GlyGlyIleSerHisArgProLeuSerThrGlySerSerAlaSerLeuAsnSerAlaTrp
 ValValPheHisThrAlaHisCysGlnGlnAlaValGlnProArg***IleGlnHisGly
  TrpTyrPheThrProProIleValAsnArgGlnPheSerLeuValLysPheSerMetGly
GGTGGTATTTCACACCGCCCATTGTCAACAGGCAGTTCAGCCTCGTTAAATTCAGCATGG
         .         .         .      6400         .         .
ValSerLeuMetLysIleHisLeuHisTrp************IleGln***GlyGluIle
 TyrHisLeu***LysPheIleTyrIleGlyAspAsnSerLysSerSerArgAlaLys***
  IleThrTyrGluAsnSerSerThrLeuValIleIleValAsnProValGlyArgAsnAsn
GTATCACTTATGAAAATTCATCTACATTGGTGATAATAGTAAATCCAGTAGGGCGAAATA
         .         .         .         .         .         .
```

```
IleAspCysAsnLeuArgGlyLysThrAlaGlnSerGlnThrArgLeuCysArgLeuArg
 LeuThrValIleTyrGlyAlaLysArgHisAsnLeuLysArgAspCysAlaVal***Gly
  ***Leu***PheThrGlyGlnAsnGlyThrIleSerAsnGluIleValProPheLysGly
ATTGACTGTAATTTACGGGGCAAAACGGCACAATCTCAAACGAGATTGTGCCGTTTAAGG
        .        6500         .          .          .         .

GlyArgPhe***LysTyrPheIleLeuProThrIle***LeuArgArgArgLeuLysMet
 GluAspSerArgAsnIleSerTyrPheGlnLeuTyrSer***GlyGlyAsp***Lys***
  LysIleLeuGluIlePheHisThrSerAsnTyrIleValLysGluGluThrGluAsnGlu
GGAAGATTCTAGAAATATTTCATACTTCCAACTATATAGTTAAGGAGGAGACTGAAAATG
        .         .         .         .         .        6600
```

FIG. 5RR

*FIG.5SS*

```
LysLysLeuPhePheLeuLeuLeuLeuLeuPheLeuIleTyrLeuGlyTyrAspTyrVal
 ArgSerCysPhePheTyrCysTyrCysTyrSer***TyrThr***ValMetThrThrLeu
  GluValValPhePheIleValIleValIleLeuAsnIleLeuArgLeu***LeuArg***
AAGAAGTTGTTTTTTTATTGTTATTGTTATTCTTAATATACTTAGGTTATGACTACGTT
          .          .          .          .          .          .

AsnGluAlaLeuPheSerGlnGluLysValGluPheGlnAsnTyrAspGlnAsnProLys
 MetLysHisCysPheLeuArgLysLysSerAsnPheLysIleMetIleLysIleProLys
  ***SerThrValPheSerGlyLysSerArgIleSerLysLeu***SerLysSerGlnArg
AATGAAGCACTGTTTTCTCAGGAAAAAGTCGAATTTCAAAATTATGATCAAAATCCCAAA
          .          .          .        6700          .          .

GluHisLeuGluAsnSerGlyThrSerGluAsnThrGlnGluLysThrIleThrGluGlu
 AsnIle***LysIleValGlyLeuLeuLysIleProLysArgLysGlnLeuGlnLysAsn
  ThrPheArgLys***TrpAspPhe***LysTyrProArgGluAsnAsnTyrArgArgThr
GAACATTTAGAAAATAGTGGGACTTCTGAAAATACCCAAGAGAAAACAATTACAGAAGAA
          .          .          .          .          .          .
```

```
GlnValTyrGlnGlyAsnLeuLeuLeuIleAsnSerLysTyrProValArgGlnGluVal
 ArgPheIleLysGluIleCysTyr***SerIleValAsnIleLeuPheAlaLysLysCys
  GlyLeuSerArgLysSerAlaIleAsnGln******IleSerCysSerProArgSerVal
CAGGTTTATCAAGGAAATCTGCTATTAATCAATAGTAAATATCCTGTTCGCCAAGAAGTG
         .         6800         .         .         .         .
***SerGlnIleSer***IleTyrLeuAsnMetThrAsn******MetAspThrGlyCys
 GluValArgTyrArgGluPheIle***Thr***ArgIleAsnLysTrpIleArgValAla
  LysSerAspIleValAsnLeuSerLysHisAspGluLeuIleAsnGlyTyrGlyLeuLeu
TGAAGTCAGATATCGTGAATTTATCTAAACATGACGAATTAATAAATGGATACGGGTTGC
         .         .         .         .         .      6900
```

FIG. 5TT

```
LeuIleValIlePheIleCysGlnLysLys***HisLysAsnPheGlnArgTrpSerMet
 *********TyrLeuTyrValLysArgAsnSerThrLysIlePheArgAspGlyGln***
  AspSerAsnIleTyrMetSerLysGluIleAlaGlnLysFheSerGluMetValAsnAsp
TTGATAGTAATATTTATATGTCAAAAGAAATAGCACAAAAATTTTCAGAGATGGTCAATG
          .         .         .         .         .         .

MetLeu***ArgValAlaLeuValIleLeuLeuLeuIleValAlaIleGluThrLeuMet
 CysCysLysGlyTrpArg***SerPheTyrTyr******TrpLeuSerArgLeu******
  AlaValLysGlyGlyValSerHisPheIleIleAsnSerGlyTyrArgAspPheAspGlu
ATGCTGTAAAGGGTGGCGTTAGTCATTTTATTATTAATAGTGGCTATCGAGACTTTGATG
          .         .         .       7000          .         .

SerLysValCysPheThrLysLysTrpGlyLeuSerMetPrcTyrGlnGlnValIleVal
 AlaLysCysAlaLeuProArgAsnGlyGly***ValCysLeuThrSerArgLeu******
  GlnSerValLeuTyrGlnGluMetGlyAlaGluTyrAlaLeuProAlaGlyTyrSerGlu
AGCAAAGTGTGCTTTACCAAGAAATGGGGGCTGAGTATGCCTTACCAGCAGGTTATAGTG
          .         .         .         .         .         .
```

FIG. 5UU

```
SerIleIleGlnValTyrHis***Met***AspGlnAla***ArgLysTrpAsnGluPro
 Ala***PheArgPheIleThrArgCysArgIleLysLeuAspGluAsnGlyThrSerPro
  HisAsnSerGlyLeuSerLeuAspValGlySerSerLeuThrLysMetGluArgAlaPro
AGCATAATTCAGGTTTATCACTAGATGTAGGATCAAGCTTGACGAAAATGGAACGAGCCC
         .      7100         .         .         .         .
LeuLysGluSerGly***LysLysMetLeuGlyAsnThrGlySerPheTyrValIleGln
 ***ArgLysValAspArgArgLysCysLeuGluIleArgValHisPheThrLeuSerArg
  GluGlyLysTrpIleGluGluAsnAlaTrpLysTyrGlyPheIleLeuArgTyrProGlu
CTGAAGGAAAGTGGATAGAAGAAAATGCTTGGAAATACGGGTTCATTTTACGTTATCCAG
         .         .         .         .         .      7200
```

FIG. 5VV

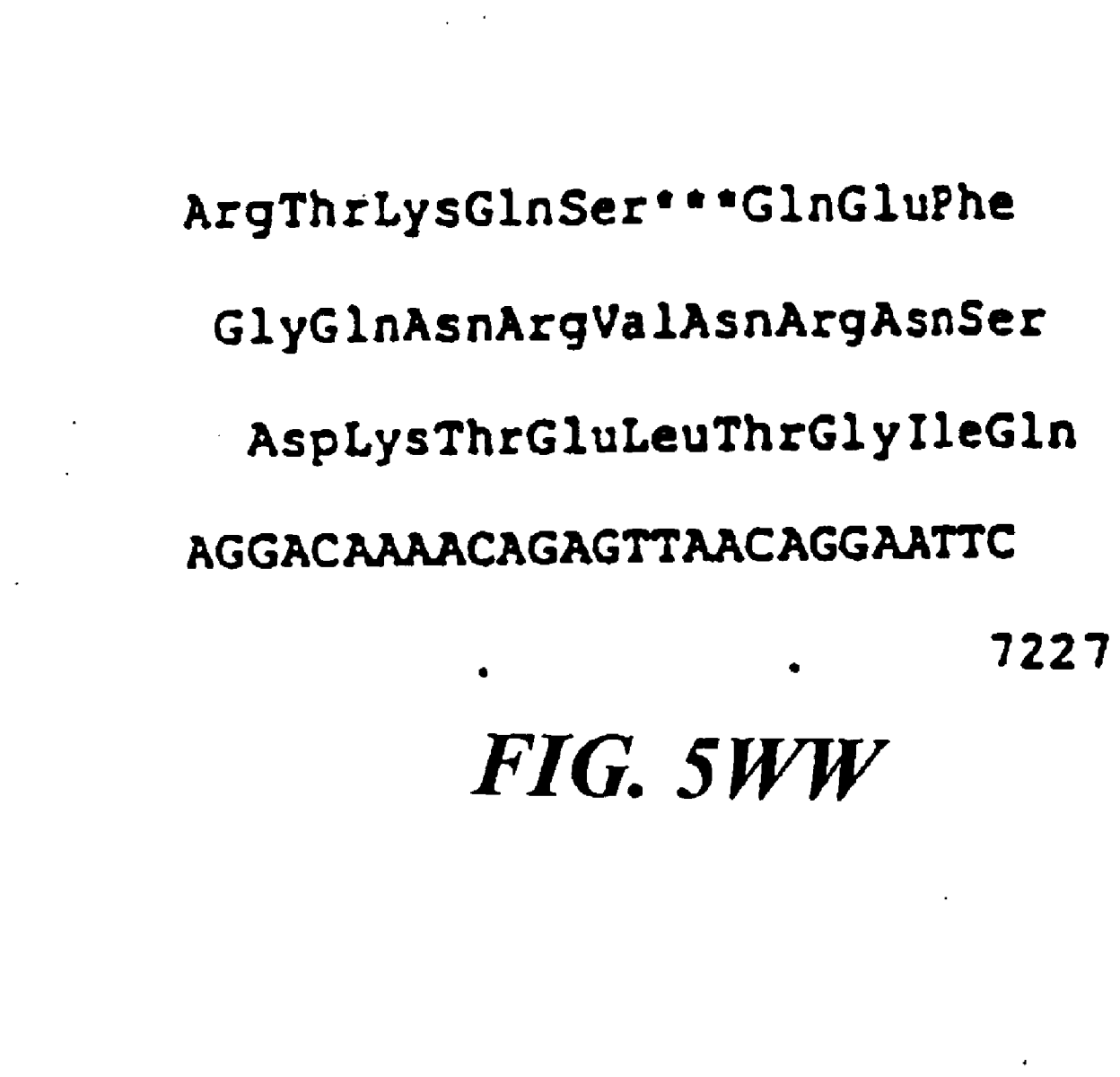

ArgThrLysGlnSer***GlnGluPhe

GlyGlnAsnArgValAsnArgAsnSer

AspLysThrGluLeuThrGlyIleGln

AGGACAAAACAGAGTTAACAGGAATTC

```
                       EcoRV
                       GATATCGTTACGCTTCATGTGCCGCTCAATACGGATACGCACTATATTATCAGCCACGAACAAA  64
TACAGAGAATGAAGCAAGGAGCATTTCTTATCAATACTGGGCGCGGTCCACTTGTAGATACCTATGAGTTGGTTAAAGCATTAGAAAACGG 155
GAAACTGGGCGGTGCCGCATTGGATGTATTGGAAGGAGAGGAAGAGTTTTTCTACTCTGATTGCACCCAAAAACCAATTGATAATCAATTT 246
TTACTTAAACTTCAAAGAATGCCTAACGTGATAATCACACCGCATACGGCCTATTATACCGAGCAAGCGTTGCGTGATACCGTTGAAAAAA 337
                                                HaeIII
                       RBS        ▼MET ASN ARG ILE LYS VAL ALA ILE LEU PHE GLY GLY CYS
CCATTAAAAACTGTTTGGATTTTGAAAGGAGACAGGAGC ATG AAT AGA ATA AAA GTT GCA ATA CTG TTT GGG GGT TGC 415
                                        NlaIII
SER GLU GLU HIS ASP VAL SER VAL LYS SER ALA ILE GLU ILE ALA ALA ASN ILE ASN LYS GLU LYS TYR
TCA GAG GAG AAT GAC GTA TCG GTA AAA TCT GCA ATA GAG ATA GCC GCT AAC ATT AAT AAA GAA AAA TAC 484

GLU PRO LEU TYR ILE GLY ILE THR LYS SER GLY VAL TRP LYS MET CYS GLU LYS PRO CYS ALA GLU TRP
GAG CCG TTA TAC ATT GGA ATT ACG AAA TCT GGT GTA TGG AAA ATG TGC GAA AAA CCT TGC GCG GAA TGG 553

GLU ASN ASP ASN CYS TYR SER ALA VAL LEU SER PRO ASP LYS LYS MET HIS GLY LEU LEU VAL LYS LYS
GAA AAC GAC AAT TGC TAT TCA GCT GTA CTC TCG CCG GAT AAA AAA ATG CAC GGA TTA CTT GTT AAA AAG 622

ASN HIS GLU TYR GLU ILE ASN HIS VAL ASP VAL ALA PHE SER ALA LEU HIS GLY LYS SER GLY GLU ASP
AAC CAT GAA TAT GAA ATC AAC CAT GTT GAT GTA GCA TTT TCA GCT TTG CAT GGC AAG TCA GGT GAA GAT 691

GLY SER ILE GLN GLY LEU PHE GLU LEU SER GLY ILE PRO PHE VAL GLY CYS ASP ILE GLN SER SER ALA
GGA TCC ATA CAA GGT CTG TTT GAA TTG TCC GGT ATC CCT TTT GTA GGC TGC GAT ATT CAA AGC TCA GCA 760

ILE CYS MET ASP LYS SER LEU THR TYR ILE VAL ALA LYS ASN ALA GLY ILE ALA THR PRO ALA PHE TRP
ATT TGT ATG GAC AAA TCG TTG ACA TAC ATC GTT GCG AAA AAT GCT GGG ATA GCT ACT CCC GCC TTT TGG 829

VAL ILE ASN LYS ASP ASP ARG PRO VAL ALA ALA THR PHE THR TYR PRO VAL PHE VAL LYS PRO ALA ARG
GTT ATT AAT AAA GAT GAT AGG CCG GTG GCA GCT ACG TTT ACC TAT CCT GTT TTT GTT AAG CCG GCG CGT 898
```

```
SER GLY SER SER PHE GLY VAL LYS LYS VAL ASN SER ALA ASP CLU LEU ASP TYR ALA ILE GLU SER ALA
TCA GGC TCA TCC TTC GGT GTG AAA AAA GTC AAT AGC GCG GAC GAA TTG GAC TAC GCA ATT GAA TCG GCA  967

ARG GLN TYR ASP SER LYS ILE LEU ILE GLU GLN ALA VAL SER GLY CYS GLU VAL GLY CYS ALA VAL LEU
AGA CAA TAT GAC AGC AAA ATC TTA ATT GAG CAG GCT GTT TCG GGC TGT GAG GTC GGT TGT GCG GTA TTG 1036

GLY ASN SER ALA ALA LEU VAL VAL GLY GLU VAL ASP GLN ILE ARG LEU GLN TYR GLY ILE PHE ARG ILE
GGA AAC AGT GCC GCG TTA GTT GTT GGC GAG GTG GAC CAA ATC AGG CTG CAG TAC GGA ATC TTT CGT ATT 1105

HIS GLN GLU VAL GLU PRO GLU LYS GLY SER GLU ASN ALA VAL ILE THR VAL PRO ALA ASP LEU SER ALA
CAT CAG GAA GTC GAG CCG GAA AAA GGC TCT GAA AAC GCA GTT ATA ACC GTT CCC GCA GAC CTT TCA GCA 1174

GLU GLU ARG GLY ARG ILL GLN GLU THR ALA LYS LYS ILE TYR LYS ALA LEU GLY CYS ARG GLY LEU ALA
GAG GAG CGA GGA CGG ATA CAG GAA ACG GCA AAA AAA ATA TAT AAA GCG CTC GGC TGT AGA GGT CTA GCC 1243

ARG VAL ASP MET PHL LEU GLN ASP ASN GLY ARG ILE VAL LEU ASN GLU VAL ASN THR LEU PRO GLY PHE
CGT GTG GAT ATG TTT TTA CAA GAT AAC GGC CGC ATT GTA CTG AAC GAA GTC AAT ACT CTG CCC GGT TTC 1312

THR SER TYR SER ARG TYR PRO ARG MET MET ALA ALA ALA GLY ILE ALA LEU PRO GLU LEU ILE ASP ARG
ACG TCA TAC AGT CGT TAT CCC CGT ATG ATG GCC GCT GCA GGT ATT GCA CTT CCC GAA CTG ATT GAC CGC 1381

LEU ILE VAL LEU ALA LEU LYS GLY *** ***
TTG ATC GTA TTA GCG TTA AAG GGG TGA TAA GCATGGAAATAGGATTTACTTTTTTAGATGAAATAGTACACGGTGTTCGTT 1462
                                 ▲        NlaIII
GGGACGCTAAATATGCCACTTGGGATAATTTCACCGGAAAACCGGTTGACGGTTATGAAGTAAATCGCATTGTAGGGACATACGAGTTGGC 1553
TGAATCGCTTTTGAAGGCAAAAGAACTGGCTGCTACCCAAGGGTACGGATTGCTTCTATGGGACGGTTACCGTCCTAAGCGTGCTGTAAAC 1644
TGTTTTATGCAATGGGCTGCACAGCCGGAAAATAACCTGACAAAGGAAAGTTATTATCCCAATATTGACCGAACTGAGATGATTTCAAAAG 1735
                              sacII
GGATACGTGGcTTCAAAATCAAGCCATAGCCGCG                                                          1769
```

*FIG. 6B*

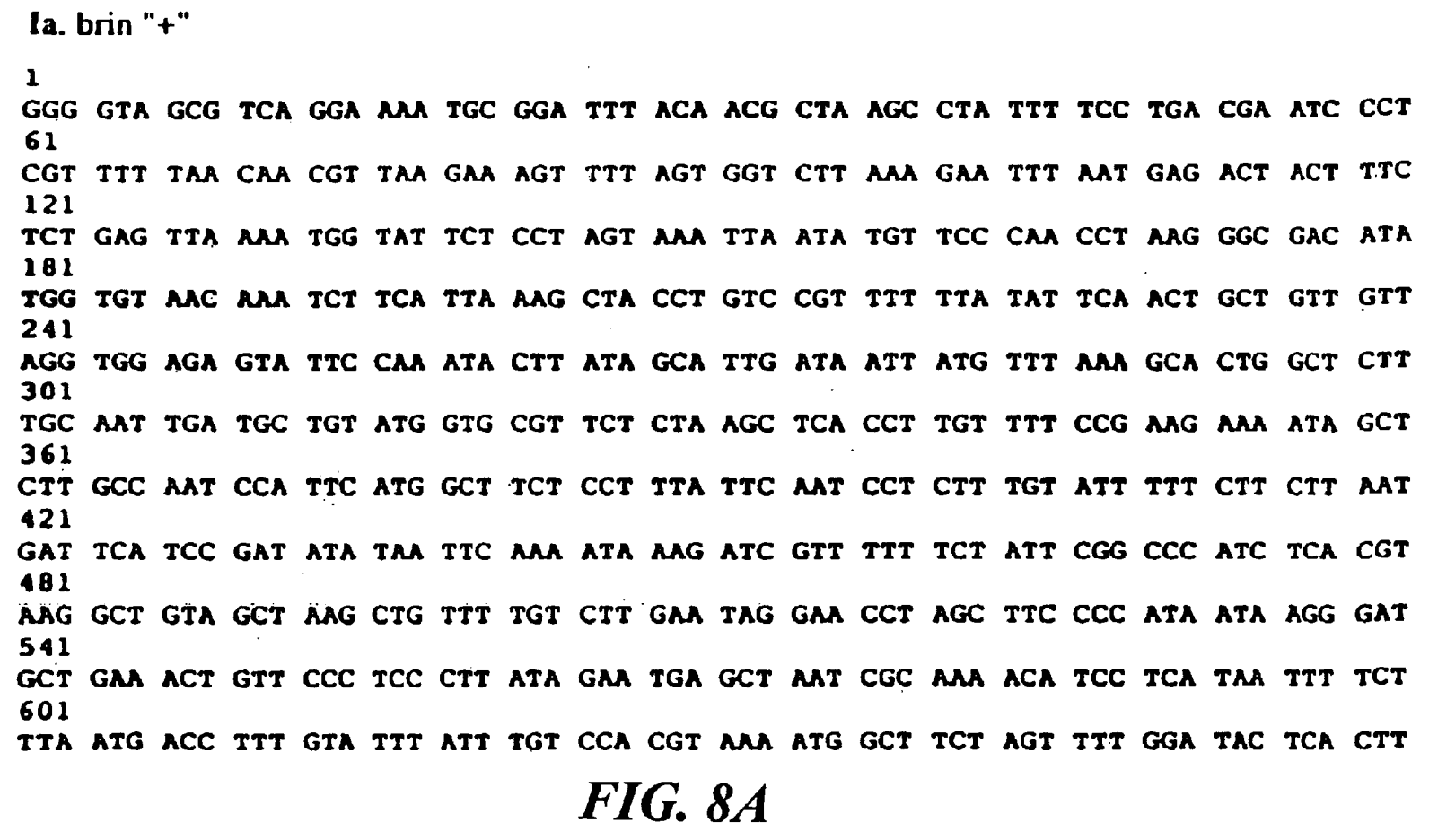

Ia. brin "+"

1
GGG GTA GCG TCA GGA AAA TGC GGA TTT ACA ACG CTA AGC CTA TTT TCC TGA CGA ATC CCT
61
CGT TTT TAA CAA CGT TAA GAA AGT TTT AGT GGT CTT AAA GAA TTT AAT GAG ACT ACT TTC
121
TCT GAG TTA AAA TGG TAT TCT CCT AGT AAA TTA ATA TGT TCC CAA CCT AAG GGC GAC ATA
181
TGG TGT AAC AAA TCT TCA TTA AAG CTA CCT GTC CGT TTT TTA TAT TCA ACT GCT GTT GTT
241
AGG TGG AGA GTA TTC CAA ATA CTT ATA GCA TTG ATA ATT ATG TTT AAA GCA CTG GCT CTT
301
TGC AAT TGA TGC TGT ATG GTG CGT TCT CTA AGC TCA CCT TGT TTT CCG AAG AAA ATA GCT
361
CTT GCC AAT CCA TTC ATG GCT TCT CCT TTA TTC AAT CCT CTT TGT ATT TTT CTT CTT AAT
421
GAT TCA TCC GAT ATA TAA TTC AAA ATA AAG ATC GTT TTT TCT ATT CGG CCC ATC TCA CGT
481
AAG GCT GTA GCT AAG CTG TTT TGT CTT GAA TAG GAA CCT AGC TTC CCC ATA ATA AGG GAT
541
GCT GAA ACT GTT CCC TCC CTT ATA GAA TGA GCT AAT CGC AAA ACA TCC TCA TAA TTT TCT
601
TTA ATG ACC TTT GTA TTT ATT TGT CCA CGT AAA ATG GCT TCT AGT TTT GGA TAC TCA CTT

FIG. 8A

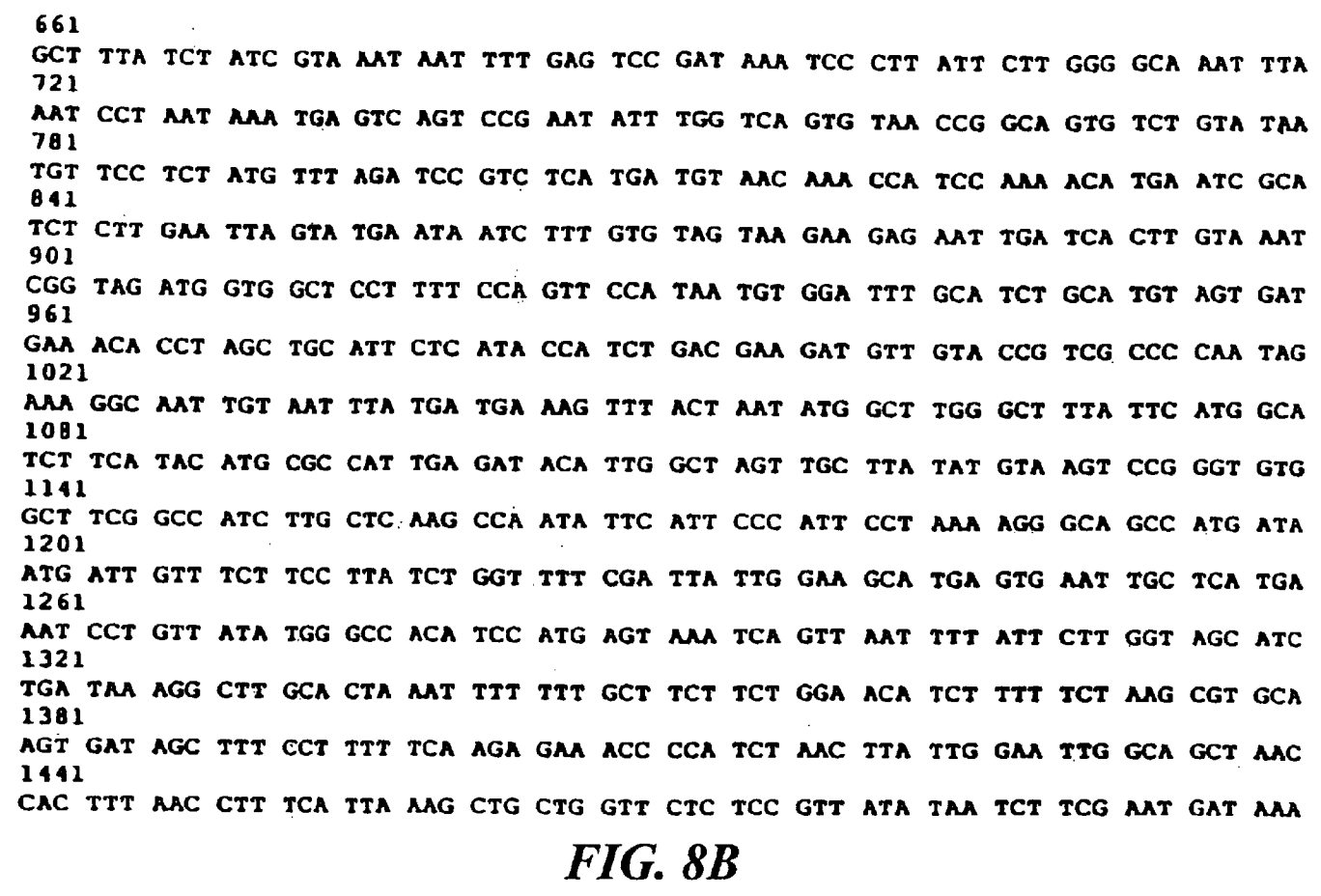

661
GCT TTA TCT ATC GTA AAT AAT TTT GAG TCC GAT AAA TCC CTT ATT CTT GGG GCA AAT TTA
721
AAT CCT AAT AAA TGA GTC AGT CCG AAT ATT TGG TCA GTG TAA CCG GCA GTG TCT GTA TAA
781
TGT TCC TCT ATG TTT AGA TCC GTC TCA TGA TGT AAC AAA CCA TCC AAA ACA TGA ATC GCA
841
TCT CTT GAA TTA GTA TGA ATA ATC TTT GTG TAG TAA GAA GAG AAT TGA TCA CTT GTA AAT
901
CGG TAG ATG GTG GCT CCT TTT CCA GTT CCA TAA TGT GGA TTT GCA TCT GCA TGT AGT GAT
961
GAA ACA CCT AGC TGC ATT CTC ATA CCA TCT GAC GAA GAT GTT GTA CCG TCG CCC CAA TAG
1021
AAA GGC AAT TGT AAT TTA TGA TGA AAG TTT ACT AAT ATG GCT TGG GCT TTA TTC ATG GCA
1081
TCT TCA TAC ATG CGC CAT TGA GAT ACA TTG GCT AGT TGC TTA TAT GTA AGT CCG GGT GTG
1141
GCT TCG GCC ATC TTG CTC AAG CCA ATA TTC ATT CCC ATT CCT AAA AGG GCA GCC ATG ATA
1201
ATG ATT GTT TCT TCC TTA TCT GGT TTT CGA TTA TTG GAA GCA TGA GTG AAT TGC TCA TGA
1261
AAT CCT GTT ATA TGG GCC ACA TCC ATG AGT AAA TCA GTT AAT TTT ATT CTT GGT AGC ATC
1321
TGA TAA AGG CTT GCA CTA AAT TTT TTT GCT TCT TCT GGA ACA TCT TTT TCT AAG CGT GCA
1381
AGT GAT AGC TTT CCT TTT TCA AGA GAA ACC CCA TCT AAC TTA TTG GAA TTG GCA GCT AAC
1441
CAC TTT AAC CTT TCA TTA AAG CTG CTG GTT CTC TCC GTT ATA TAA TCT TCG AAT GAT AAA

FIG. 8B

```
1501
CTA ACT GAT AAT CTC GTA TTC CCC TTC GAT TGA TTC CAT GTA TCT TCC GAA AAC AAA TAT
1561
TCC TCA AAA TCC CTA TAT TGT CTG CTG CCA ACA ATG GAA ACA TCT CCT GCC CGA ACA TGC
1621
TCC CGA AGT TCT GTT AAA ACA GCC ATT TCA TAG TAA TGA CGA TTA ATT GTT GTA CCA TCA
1681
TCC TCG TAT AAA TGT CTT TTC CAT CGT TTT GAA ATA AAA TCC ACA GGT GAG TCA TCA GGC
1741
ACT TTT CGC TTT CCA GAT TCG TTC ATT CCT CGG ATA ATC TCA ACA GCT TGT AAA AGT GGC
1801
TCA TTT GCC TTT GTA GAA TGA AAT TCC AAT ACT CTT AAT AGC GTT GGC GTA TAT TTT CTT
1861
AGT GAA TAA AAC CGT TTT TGC AGT AAG TCT AAA TAA TCA TAG TCG GCA GGA CGT GCA AGT
1921
TCC TGA GCC TCT TCT ACT GAA GAG ACA AAG GTA TTC CAT TCA ATA ACC GAT TCT AAA ACC
1981
TTA AAA ACG TCT AAT TTT TCC TCT CTT GCT TTA ATT AAT GCT TGT CCG ATG TTC GTA AAG
2041
TGT ATA ACT TTC TCA TTT AGC TTT TTA CCG TTT TGT TTC TGG ATT TCC TCT TGA GCC TTA
2101
CGA CCT TTT GAT AAC AAA CTA AGT ATT TGC CTA TCA TGA ATT TCA AAC GCT TTA TCC GTT
2161
AGC TCC TGA GTA AGT TGT AAT AAA TAG ATG GTT AAT ATC GAA TAA CGT TTA TTT TCT TGA
2221
AAG TCA CGG AAT GCA TAC GGC TCG TAT CTT GAG CCT AAG CGA GAC AGC TGC AAC AGG CGG
2281
TTA CGG TGC AAA TGA CTA ATT TGC ACT GTT TCT AAA TCC ATT CCT CGT ATG TAT TCG AGT
2341
```

*FIG. 8C*

*FIG. 8D*

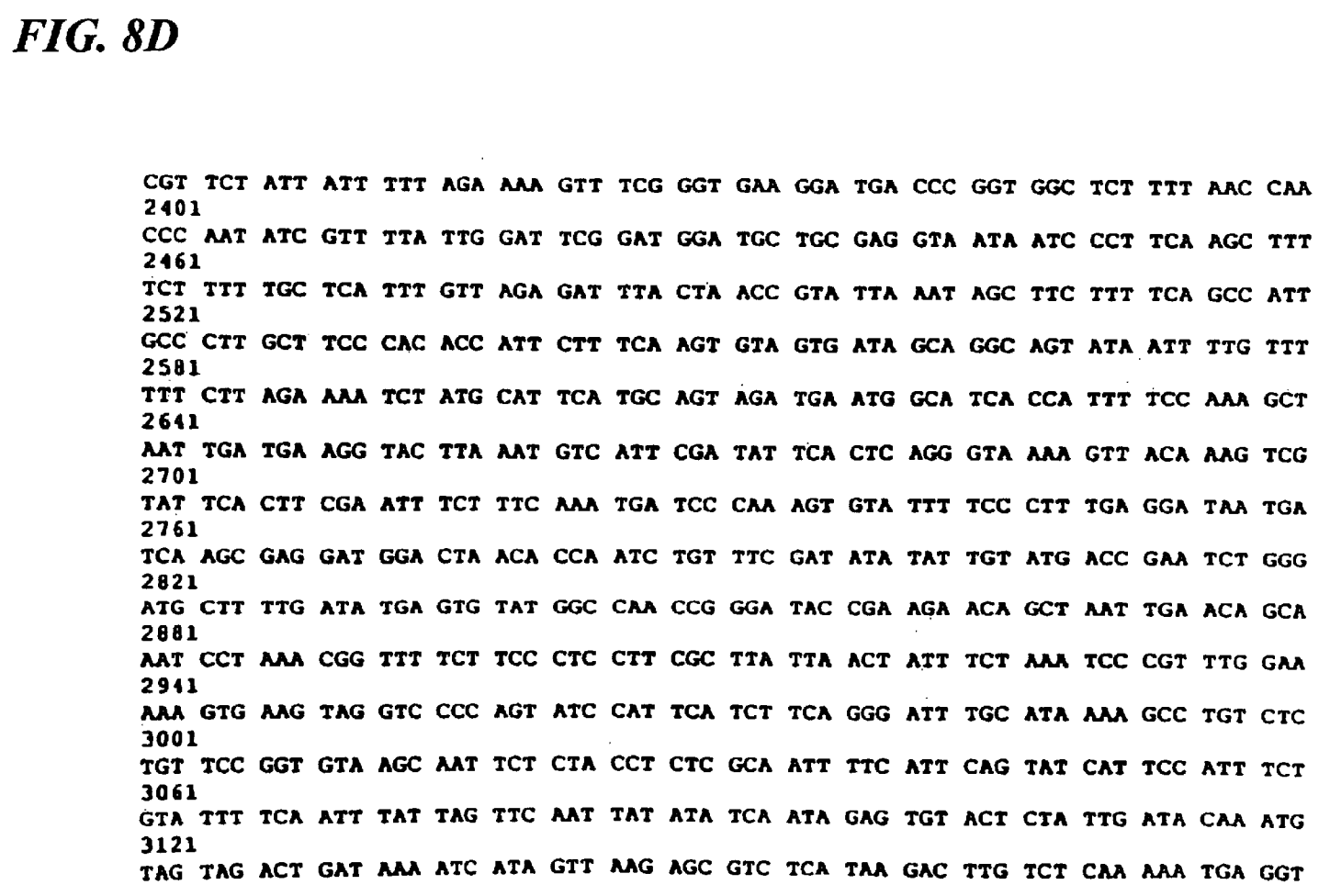

CGT TCT ATT ATT TTT AGA AAA GTT TCG GGT GAA GGA TGA CCC GGT GGC TCT TTT AAC CAA
2401
CCC AAT ATC GTT TTA TTG GAT TCG GAT GGA TGC TGC GAG GTA ATA ATC CCT TCA AGC TTT
2461
TCT TTT TGC TCA TTT GTT AGA GAT TTA CTA ACC GTA TTA AAT AGC TTC TTT TCA GCC ATT
2521
GCC CTT GCT TCC CAC ACC ATT CTT TCA AGT GTA GTG ATA GCA GGC AGT ATA ATT TTG TTT
2581
TTT CTT AGA AAA TCT ATG CAT TCA TGC AGT AGA TGA ATG GCA TCA CCA TTT TCC AAA GCT
2641
AAT TGA TGA AGG TAC TTA AAT GTC ATT CGA TAT TCA CTC AGG GTA AAA GTT ACA AAG TCG
2701
TAT TCA CTT CGA ATT TCT TTC AAA TGA TCC CAA AGT GTA TTT TCC CTT TGA GGA TAA TGA
2761
TCA AGC GAG GAT GGA CTA ACA CCA ATC TGT TTC GAT ATA TAT TGT ATG ACC GAA TCT GGG
2821
ATG CTT TTG ATA TGA GTG TAT GGC CAA CCG GGA TAC CGA AGA ACA GCT AAT TGA ACA GCA
2881
AAT CCT AAA CGG TTT TCT TCC CTC CTT CGC TTA TTA ACT ATT TCT AAA TCC CGT TTG GAA
2941
AAA GTG AAG TAG GTC CCC AGT ATC CAT TCA TCT TCA GGG ATT TGC ATA AAA GCC TGT CTC
3001
TGT TCC GGT GTA AGC AAT TCT CTA CCT CTC GCA ATT TTC ATT CAG TAT CAT TCC ATT TCT
3061
GTA TTT TCA ATT TAT TAG TTC AAT TAT ATA TCA ATA GAG TGT ACT CTA TTG ATA CAA ATG
3121
TAG TAG ACT GAT AAA ATC ATA GTT AAG AGC GTC TCA TAA GAC TTG TCT CAA AAA TGA GGT

```
3181      resolvase
        LEU ARG LYS ILE GLY TYR ILE ARG VAL SER SER THR ASN GLN ASN PRO SER ARG
GAT ATT TTG CGG AAA ATC GGT TAT ATT CGT GTC AGT TCG ACT AAC CAG AAT CCT TCA AGA
3241
GLN PHE GLN GLN LEU ASN GLU ILE GLY MET ASP ILE ILE TYR GLU GLU LYS VAL SER GLY
CAA TTT CAG CAG TTG AAC GAG ATC GGA ATG GAT ATT ATA TAT GAA GAG AAA GTT TCA GGA
3301
ALA THR LYS ASP ARG GLU GLN LEU GLN LYS VAL LEU ASP ASP LEU GLN GLU ASP ASP ILE
GCA ACA AAG GAT CGC GAG CAA CTT CAA AAA GTG TTA GAC GAT TTA CAG GAA GAT GAC ATC
3361
ILE TYR VAL THR ASP LEU THR ARG ILE THR ARG SER THR GLN ASP LEU PHE GLU LEU ILE
ATT TAT GTT ACA GAC TTA ACT CGA ATC ACT CGT AGT ACA CAA GAT CTA TTT GAA TTA ATC
3421
ASP ASN ILE ARG ASP LYS LYS ALA SER LEU LYS SER LEU LYS ASP THR TRP LEU ASP LEU
GAT AAC ATA CGA GAT AAA AAG GCA AGT TTA AAA TCA CTA AAA GAT ACA TGG CTT GAT TTA
3481
SER GLU ASP ASN PRO TYR SER GLN PHE LEU ILE THR VAL MET ALA GLY VAL ASN GLN LEU
TCA GAA GAT AAT CCA TAC AGC CAA TTC TTA ATT ACT GTA ATG GCT GGT GTT AAC CAA TTA
3541
GLU ARG ASP LEU ILE ARG MET ARG GLN ARG GLU GLY ILE GLU LEU ALA LYS LYS GLU GLY
GAG CGA GAT CTT ATT CGG ATG AGA CAA CGT GAA GGG ATT GAA TTG GCT AAG AAA GAA GGA
3601
LYS PHE LYS GLY ARG LEU LYS LYS TYR HIS LYS ASN HIS ALA GLY MET ASN TYR ALA VAL
AAG TTT AAA GGT CGA TTA AAG AAG TAT CAT AAA AAT CAC GCA GGA ATG AAT TAT GCG GTA
3661
LYS LEU TYR LYS GLU GLY ASN MET THR VAL ASN GLN ILE CYS GLU ILE THR ASN VAL SER
AAG CTA TAT AAA GAA GGA AAT ATG ACT GTA AAT CAA ATT TGT GAA ATT ACT AAT GTA TCT
3721
ARG ALA SER LEU TYR ARG LYS LEU SER GLU VAL ASN ASN
AGG GCT TCA TTA TAC AGG AAA TTA TCA GAA GTG AAT AAT TAG CCA TTC TGT ATT CCG CTA
```

*FIG. 8E*

```
3781
ATG GGC AAT ATT TTT AAA GAA GAA AAG GAA ACT ATA AAA TAT TAA CAG CCT CCT AGC GAT
3841
GCC GAA AAG CCC TTT GAT AAA AAA AGA ATC ATC ATC TTA AGA AAT TCT TAG TCA TTT ATT
3901
ATG TAA ATG CTT ATA AAT TCG GCC CTA TAA TCT GAT AAA TTA TTA AGG GCA AAC TTA TGT

3961            VanR  MET SER ASP LYS ILE LEU ILE VAL ASP ASP GLU HIS GLU ILE ALA
GAA AGG GTG ATA ACT ATG AGC GAT AAA ATA CTT ATT GTG GAT GAT GAA CAT GAA ATT GCC
4021
ASP LEU VAL GLU LEU TYR LEU LYS ASN GLU ASN TYR THR VAL PHE LYS TYR TYR THR ALA
GAT TTG GTT GAA TTA TAC TTA AAA AAC GAG AAT TAT ACG GTT TTC AAA TAC TAT ACC GCC
4081
LYS GLU ALA LEU GLU CYS ILE ASP LYS SER GLU ILE ASP LEU ALA ILE LEU ASP ILE MET
AAA GAA GCA TTG GAA TGT ATA GAC AAG TCT GAG ATT GAC CTT GCC ATA TTG GAC ATC ATG
4141
LEU PRO GLY THR SER GLY LEU THR ILE CYS GLN LYS ILE ARG ASP LYS HIS THR TYR PRO
CTT CCC GGC ACA AGC GGC CTT ACT ATC TGT CAA AAA ATA AGG GAC AAG CAC ACC TAT CCG
4201
ILE ILE MET LEU THR GLY LYS ASP THR GLU VAL ASP LYS ILE THR GLY LEU THR ILE GLY
ATT ATC ATG CTG ACC GGG AAA GAT ACA GAG GTA GAT AAA ATT ACA GGG TTA ACA ATC GGC
4261
ALA ASP ASP TYR ILE THR LYS PRO PHE ARG PRO LEU GLU LEU ILE ALA ARG VAL LYS ALA
GCG GAT GAT TAT ATA ACG AAG CCC TTT CGC CCA CTG GAG TTA ATT GCT CGG GTA AAG GCC
4321
GLN LEU ARG ARG TYR LYS LYS PHE SER GLY VAL LYS GLU GLN ASN GLU ASN VAL ILE VAL
CAG TTG CGC CGA TAC AAA AAA TTC AGT GGA GTA AAG GAG CAG AAC GAA AAT GTT ATC GTC
```

FIG. 8F

FIG. 8G

```
4381
HIS SER GLY LEU VAL ILE ASN VAL ASN THR HIS GLU CYS TYR LEU ASN GLU LYS GLN LEU
CAC TCC GGC CTT GTC ATT AAT GTT AAC ACC CAT GAG TGT TAT CTG AAC GAG AAG CAG TTA
4441
SER LEU THR PRO THR GLU PHE SER ILE LEU ARG ILE LEU CYS GLU ASN LYS GLY ASN VAL
TCC CTT ACT CCC ACC GAG TTT TCA ATA CTG CGA ATC CTC TGT GAA AAC AAG GGG AAT GTG
4501
VAL SER SER GLU LEU LEU PHE HIS GLU ILE TRP GLY ASP GLU TYR PHE SER LYS SER ASN
GTT AGC TCC GAG CTG CTA TTT CAT GAG ATA TGG GGC GAC GAA TAT TTC AGC AAG AGC AAC
4561
ASN THR ILE THR VAL HIS ILE ARG HIS LEU ARG GLU LYS MET ASN ASP THR ILE ASP ASN
AAC ACC ATC ACC GTG CAT ATC CGG CAT TTG CGC GAA AAA ATG AAC GAC ACC ATT GAT AAT
4621
PRO LYS TYR ILE LYS THR VAL TRP GLY VALGLYTYRLYSILEGLULYS
CCG AAA TAT ATA AAA ACG GTA TGG GGG GTTGGTTATAAAATTGAAAAAT AAA AAA AAC GAC
                                VanS    LEUVALILELYSLEULYSASN LYS LYS ASN ASP
4682
TYR SER LYS LEU GLU ARG LYS LEU TYR MET TYR ILE VAL ALA ILE VAL VAL VAL ALA ILE
TAT TCC AAA CTA GAA CGA AAA CTT TAC ATG TAT ATC GTT GCA ATT GTT GTG GTA GCA ATT
4742
VAL PHE VAL LEU TYR ILE ARG SER MET ILE ARG GLY LYS LEU GLY ASP TRP ILE LEU SER
GTA TTC GTG TTG TAT ATT CGT TCA ATG ATC CGA GGG AAA CTT GGG GAT TGG ATC TTA AGT
4802
ILE LEU GLU ASN LYS TYR ASP LEU ASN HIS LEU ASP ALA MET LYS LEU TYR GLN TYR SER
ATT TTG GAA AAC AAA TAT GAC TTA AAT CAC CTG GAC GCG ATG AAA TTA TAT CAA TAT TCC
4862
ILE ARG ASN ASN ILE ASP ILE PHE ILE TYR VAL ALA ILE VAL ILE SER ILE LEU ILE LEU
ATA CGG AAC AAT ATA GAT ATC TTT ATT TAT GTG GCG ATT GTC ATT AGT ATT CTT ATT CTA
4922
CYS ARG VAL MET LEU SER LYS PHE ALA LYS TYR PHE ASP GLU ILE ASN THR GLY ILE ASP
TGT CGC GTC ATG CTT TCA AAA TTC GCA AAA TAC TTT GAC GAG ATA AAT ACC GGC ATT GAT
```

```
4982
VAL LEU ILE GLN ASN GLU ASP LYS GLN ILE GLU LEU SER ALA GLU MET ASP VAL MET GLU
GTA CTT ATT CAG AAC GAA GAT AAA CAA ATT GAG CTT TCT GCG GAA ATG GAT GTT ATG GAA
5042
GLN LYS LEU ASN THR LEU LYS ARG THR LEU GLU LYS ARG GLU GLN ASP ALA LYS LEU ALA
CAA AAG CTC AAC ACA TTA AAA CGG ACT CTG GAA AAG CGA GAG CAG GAT GCA AAG CTG GCC
5102
GLU GLN ARG LYS ASN ASP VAL VAL MET TYR LEU ALA HIS ASP ILE LYS THR PRO LEU THR
GAA CAA AGA AAA AAT GAC GTT GTT ATG TAC TTG GCG CAC GAT ATT AAA ACG CCC CTT ACA
5162
SER ILE ILE GLY TYR LEU SER LEU LEU ASP GLU ALA PRO ASP MET PRO VAL ASP GLN LYS
TCC ATT ATC GGT TAT TTG AGC CTG CTT GAC GAG GCT CCA GAC ATG CCG GTA GAT CAA AAG
5222
ALA LYS TYR VAL HIS ILE THR LEU ASP LYS ALA TYR ARG LEU GLU GLN LEU ILE ASP GLU
GCA AAG TAT GTG CAT ATC ACG TTG GAC AAA GCG TAT CGA CTC GAA CAG CTA ATC GAC GAG
5282
PHE PHE GLU ILE THR ARG TYR ASN LEU GLN THR ILE THR LEU THR LYS THR HIS ILE ASP
TTT TTT GAG ATT ACA CGG TAT AAC CTA CAA ACG ATA ACG CTA ACA AAA ACG CAC ATA GAC
5342
LEU TYR TYR MET LEU VAL GLN MET THR ASP GLU PHE TYR PRO GLN LEU SER ALA HIS GLY
CTA TAC TAT ATG CTG GTG CAG ATG ACC GAT GAA TTT TAT CCT CAG CTT TCC GCA CAT GGA
5402
LYS GLN ALA VAL ILE HIS ALA PRO GLU ASP LEU THR VAL SER GLY ASP PRO ASP LYS LEU
AAA CAG GCG GTT ATT CAC GCC CCC GAG GAT CTG ACC GTG TCC GGC GAC CCT GAT AAA CTC
5462
ALA ARG VAL PHE ASN ASN ILE LEU LYS ASN ALA ALA ALA TYR SER GLU ASP ASN SER ILE
GCG AGA GTC TTT AAC AAC ATT TTG AAA AAC GCC GCT GCA TAC AGT GAG GAT AAC AGC ATC
```

FIG. 8H

```
5522
ILE ASP ILE THR ALA GLY LEU SER GLY ASP VAL VAL SER ILE GLU PHE LYS ASN THR GLY
ATT GAC ATT ACC GCG GGC CTC TCC GGG GAT GTG GTG TCA ATC GAA TTC AAG AAC ACT GGA
5582
SER ILE PRO LYS ASP LYS LEU ALA ALA ILE PHE GLU LYS PHE TYR ARG LEU ASP ASN ALA
AGC ATC CCA AAA GAT AAG CTA GCT GCC ATA TTT GAA AAG TTC TAT AGG CTG GAC AAT GCT
5642
ARG SER SER ASP THR GLY GLY ALA GLY LEU GLY LEU ALA ILE ALA LYS GLU ILE ILE VAL
CGT TCT TCC GAT ACG GGT GGC GCG GGA CTT GGA TTG GCG ATT GCA AAA GAA ATT ATT GTT
5702
GLN HIS GLY GLY GLN ILE TYR ALA GLU SER ASN ASP ASN TYR THR THR PHE ARG VAL GLU
CAG CAT GGA GGG CAG ATT TAC GCG GAA AGC AAT GAT AAC TAT ACG ACG TTT AGG GTA GAG
5762
LEU PRO ALA MET PRO ASP LEU VAL ASP LYS ARG ARG SER
CTT CCA GCG ATG CCA GAC TTG GTT GAT AAA AGG AGG TCC TAA GA GAT GTA TAT AAT TTT
5821
TTA GGA AAA TCT CAA GGT TAT CTT TAC TTT TTC TTA GGA AAT TAA CAA TTT AAT ATT AAG
5881
AAA CGG CTC GTT CTT ACA CGG TAG ACT TAA TAC CGT AAG AAC GAG CCG TTT TCG TTC TTC
5941
AGA GAA AGA TTT GAC AAG ATT ACC ATT GGC ATC CCC GTT TTA TTT GGT GCC TTT CAC AGA
6001

          VanH           MET ASN ASN ILE GLY ILE THR VAL TYR GLY CYS GLU GLN ASP GLU
AAGGGTTGG TCT TAA TT ATG AAT AAC ATC GGC ATT ACT GTT TAT GGA TGT GAG CAG GAT GAG
6063
ALA ASP ALA PHE HIS ALA LEU SER PRO ARG PHE GLY VAL MET ALA THR ILE ILE ASN ALA
GCA GAT GCA TTC CAT GCT CTT TCG CCT CGC TTT GGC GTT ATG GCA ACG ATA ATT AAC GCC
6123
```

*FIG. 8I*

ASN VAL SER GLU SER ASN ALA LYS SER ALA PRO PHE ASN GLN CYS ILE SER VAL GLY HIS
AAC GTG TCG GAA TCC AAC GCC AAA TCC GCG CCT TTC AAT CAA TGT ATC AGT GTG GGA CAT
6183
LYS SER GLU ILE SER ALA SER ILE LEU LEU ALA LEU LYS ARG ALA GLY VAL LYS TYR ILE
AAA TCA GAG ATT TCC GCC TCT ATT CTT CTT GCG CTG AAG AGA GCC GGT GTG AAA TAT ATT
6243
SER THR ARG SER ILE GLY CYS ASN HIS ILE ASP THR THR ALA ALA LYS ARG MET GLY ILE
TCT ACC CGA AGC ATC GGC TGC AAT CAT ATA GAT ACA ACT GCT GCT AAG AGA ATG GGC ATC
6303
THR VAL ASP ASN VAL ALA TYR SER PRO ASP SER VAL ALA ASP TYR THR MET MET LEU ILE
ACT GTC GAC AAT GTG GCG TAC TCG CCG GAT AGC GTT GCC GAT TAT ACT ATG ATG CTA ATT
6363
LEU MET ALA VAL ARG ASN VAL LYS SER ILE VAL ARG SER VAL GLU LYS HIS ASP PHE ARG
CTT ATG GCA GTA CGC AAC GTA AAA TCG ATT GTG CGC TCT GTG GAA AAA CAT GAT TTC AGG
6423
LEU ASP SER ASP ARG GLY LYS VAL LEU SER ASP MET THR VAL GLY VAL VAL GLY THR GLY
TTG GAC AGC GAC CGT GGC AAG GTA CTC AGC GAC ATG ACA GTT GGT GTG GTG GGA ACG GGC
6483
GLN ILE GLY LYS ALA VAL ILE GLU ARG LEU ARG GLY PHE GLY CYS LYS VAL LEU ALA TYR
CAG ATA GGC AAA GCG GTT ATT GAG CGG CTG CGA GGA TTT GGA TGT AAA GTG TTG GCT TAT
6543
SER ARG SER ARG SER ILE GLU VAL ASN TYR VAL PRO PHE ASP GLU LEU LEU GLN ASN SER
AGT CGC AGC CGA AGT ATA GAG GTA AAC TAT GTA CCG TTT GAT GAG TTG CTG CAA AAT AGC
6603
ASP ILE VAL THR LEU HIS VAL PRO LEU ASN THR ASP THR HIS TYR ILE ILE SER HIS GLU
GAT ATC GTT ACG CTT CAT GTG CCG CTC AAT ACG GAT ACG CAC TAT ATT ATC AGC CAC GAA
6663
GLN ILE GLN ARG MET LYS GLN GLY ALA PHE LEU ILE ASN THR GLY ARG GLY PRO LEU VAL
CAA ATA CAG AGA ATG AAG CAA GGA GCA TTT CTT ATC AAT ACT GGG CGC GGT CCA CTT GTA

FIG. 8J

```
6723
ASP THR TYR GLU LEU VAL LYS ALA LEU GLU ASN GLY LYS LEU GLY GLY ALA ALA LEU ASP
GAT ACC TAT GAG TTG GTT AAA GCA TTA GAA AAC GGG AAA CTG GGC GGT GCC GCA TTG GAT
6783
VAL LEU GLU GLY GLU GLU GLU PHE PHE TYR SER ASP CYS THR GLN LYS PRO ILE ASP ASN
GTA TTG GAA GGA GAG GAA GAG TTT TTC TAC TCT GAT TGC ACC CAA AAA CCA ATT GAT AAT
6843
GLN PHE LEU LEU LYS LEU GLN ARG MET PRO ASN VAL ILE ILE THR PRO HIS THR ALA TYR
CAA TTT TTA CTT AAA CTT CAA AGA ATG CCT AAC GTG ATA ATC ACA CCG CAT ACG GCC TAT
6903
TYR THR GLU GLN ALA LEU ARG ASP THR VAL GLU LYS THR ILE LYS ASN CYS LEU ASP PHE
TAT ACC GAG CAA GCG TTG CGT GAT ACC GTT GAA AAA ACC ATT AAA AAC TGT TTG GAT TTT
6963
            VanA     METASN ARG ILE LYS VAL ALA ILE LEU PHE GLY GLY CYS SER
GAA AGG AGA CAG GAG CATGAAT AGA ATA AAA GTT GCA ATA CTG TTT GGG GGT TGC TCA
GLU ARG ARG GLN GLU HISGLU
7021
GLU GLU HIS ASP VAL SER VAL LYS SER ALA ILE GLU ILE ALA ALA ASN ILE ASN LYS GLU
GAG GAG CAT GAC GTA TCG GTA AAA TCT GCA ATA GAG ATA GCC GCT AAC ATT AAT AAA GAA
7081
LYS TYR GLU PRO LEU TYR ILE GLY ILE THR LYS SER GLY VAL TRP LYS MET CYS GLU LYS
AAA TAC GAG CCG TTA TAC ATT GGA ATT ACG AAA TCT GGT GTA TGG AAA ATG TGC GAA AAA
7141
PRO CYS ALA GLU TRP GLU ASN ASP ASN CYS TYR SER ALA VAL LEU SER PRO ASP LYS LYS
CCT TGC GCG GAA TGG GAA AAC GAC AAT TGC TAT TCA GCT GTA CTC TCG CCG GAT AAA AAA
7201
MET HIS GLY LEU LEU VAL LYS LYS ASN HIS GLU TYR GLU ILE ASN HIS VAL ASP VAL ALA
ATG CAC GGA TTA CTT GTT AAA AAG AAC CAT GAA TAT GAA ATC AAC CAT GTT GAT GTA GCA
7261
```

*FIG. 8K*

```
PHE SER ALA LEU HIS GLY LYS SER GLY GLU ASP GLY SER ILE GLN GLY LEU PHE GLU LEU
TTT TCA GCT TTG CAT GGC AAG TCA GGT GAA GAT GGA TCC ATA CAA GGT CTG TTT GAA TTG
7321
SER GLY ILE PRO PHE VAL GLY CYS ASP ILE GLN SER SER ALA ILE CYS MET ASP LYS SER
TCC GGT ATC CCT TTT GTA GGC TGC GAT ATT CAA AGC TCA GCA ATT TGT ATG GAC AAA TCG
7381
LEU THR TYR ILE VAL ALA LYS ASN ALA GLY ILE ALA THR PRO ALA PHE TRP VAL ILE ASN
TTG ACA TAC ATC GTT GCG AAA AAT GCT GGG ATA GCT ACT CCC GCC TTT TGG GTT ATT AAT
7441
LYS ASP ASP ARG PRO VAL ALA ALA THR PHE THR TYR PRO VAL PHE VAL LYS PRO ALA ARG
AAA GAT GAT AGG CCG GTG GCA GCT ACG TTT ACC TAT CCT GTT TTT GTT AAG CCG GCG CGT
7501
SER GLY SER SER PHE GLY VAL LYS LYS VAL ASN SER ALA ASP GLU LEU ASP TYR ALA ILE
TCA GGC TCA TCC TTC GGT GTG AAA AAA GTC AAT AGC GCG GAC GAA TTG GAC TAC GCA ATT
7561
GLU SER ALA ARG GLN TYR ASP SER LYS ILE LEU ILE GLU GLN ALA VAL SER GLY CYS GLU
GAA TCG GCA AGA CAA TAT GAC AGC AAA ATC TTA ATT GAG CAG GCT GTT TCG GGC TGT GAG
7621
VAL GLY CYS ALA VAL LEU GLY ASN SER ALA ALA LEU VAL VAL GLY GLU VAL ASP GLN ILE
GTC GGT TGT GCG GTA TTG GGA AAC AGT GCC GCG TTA GTT GTT GGC GAG GTG GAC CAA ATC
7681
ARG LEU GLN TYR GLY ILE PHE ARG ILE HIS GLN GLU VAL GLU PRO GLU LYS GLY SER GLU
AGG CTG CAG TAC GGA ATC TTT CGT ATT CAT CAG GAA GTC GAG CCG GAA AAA GGC TCT GAA
7741
ASN ALA VAL ILE THR VAL PRO ALA ASP LEU SER ALA GLU GLU ARG GLY ARG ILE GLN GLU
AAC GCA GTT ATA ACC GTT CCC GCA GAC CTT TCA GCA GAG GAG CGA GGA CGG ATA CAG GAA
7801
THR ALA LYS LYS ILE TYR LYS ALA LEU GLY CYS ARG GLY LEU ALA ARG VAL ASP MET PHE
ACG GCA AAA AAA ATA TAT AAA GCG CTC GGC TGT AGA GGT CTA GCC CGT GTG GAT ATG TTT
```

*FIG. 8L*

```
7861
LEU GLN ASP ASN GLY ARG ILE VAL LEU ASN GLU VAL ASN THR LEU PRO GLY PHE THR SER
TTA CAA GAT AAC GGC CGC ATT GTA CTG AAC GAA GTC AAT ACT CTG CCC GGT TTC ACG TCA
7921
TYR SER ARG TYR PRO ARG MET MET ALA ALA ALA GLY ILE ALA LEU PRO GLU LEU ILE ASP
TAC AGT CGT TAT CCC CGT ATG ATG GCC GCT GCA GGT ATT GCA CTT CCC GAA CTG ATT GAC
7981
ARG LEU ILE VAL LEU ALA LEU LYS GLY
CGC TTG ATC GTA TTA GCG TTA AAG GGG TGATAAGC ATG GAA ATA GGA TTT ACT TTT TTA GAT
                                    VanX     MET GLU ILE GLY PHE THR PHE LEU ASP
8043
GLU ILE VAL HIS GLY VAL ARG TRP ASP ALA LYS TYR ALA THR TRP ASP ASN PHE THR GLY
GAA ATA GTA CAC GGT GTT CGT TGG GAC GCT AAA TAT GCC ACT TGG GAT AAT TTC ACC GGA
8103
LYS PRO VAL ASP GLY TYR GLU VAL ASN ARG ILE VAL GLY THR TYR GLU LEU ALA GLU SER
AAA CCG GTT GAC GGT TAT GAA GTA AAT CGC ATT GTA GGG ACA TAC GAG TTG GCT GAA TCG
8163
LEU LEU LYS ALA LYS GLU LEU ALA ALA THR GLN GLY TYR GLY LEU LEU LEU TRP ASP GLY
CTT TTG AAG GCA AAA GAA CTG GCT GCT ACC CAA GGG TAC GGA TTG CTT CTA TGG GAC GGT
8223
TYR ARG PRO LYS ARG ALA VAL ASN CYS PHE MET GLN TRP ALA ALA GLN PRO GLU ASN ASN
TAC CGT CCT AAG CGT GCT GTA AAC TGT TTT ATG CAA TGG GCT GCA CAG CCG GAA AAT AAC
8283
LEU THR LYS GLU SER TYR TYR PRO ASN ILE ASP ARG THR GLU MET ILE SER LYS GLY TYR
CTG ACA AAG GAA AGT TAT TAT CCC AAT ATT GAC CGA ACT GAG ATG ATT TCA AAA GGA TAC
8343
VAL ALA SER LYS SER SER HIS SER ARG GLY SER ALA ILE ASP LEU THR LEU TYR ARG LEU
GTG GCT TCA AAA TCA AGC CAT AGC CGC GGC AGT GCC ATT GAT CTT ACG CTT TAT CGA TTA
8403
ASP THR GLY GLU LEU VAL PRO MET GLY SER ARG PHE ASP PHE MET ASP GLU ARG SER HIS
GAC ACG GGT GAG CTT GTA CCA ATG GGG AGC CGA TTT GAT TTT ATG GAT GAA CGC TCT CAT
```

*FIG. 8M*

```
8463
HIS ALA ALA ASN GLY ILE SER CYS ASN GLU ALA GLN ASN ARG ARG ARG LEU ARG SER ILE
CAT GCG GCA AAT GGA ATA TCA TGC AAT GAA GCG CAA AAT CGC AGA CGT TTG CGC TCC ATC
8523
MET GLU ASN SER GLY PHE GLU ALA TYR SER LEU GLU TRP TRP HIS TYR VAL LEU ARG ASP
ATG GAA AAC AGT GGG TTT GAA GCA TAT AGC CTC GAA TGG TGG CAC TAT GTA TTA AGA GAC
8583
GLU PRO TYR PRO ASN SER TYR PHE ASP PHE PRO VAL LYS
GAA CCA TAC CCC AAT AGC TAT TTT GAT TTC CCC GTT AAA TAAA CTT TTA ACC GTT GCA
8641
CGG ACA AAC TAT ATA AGC TAA CTC TTT CGG CAG GAA ACC CGA CGT ATG TAA CTG GTT CTT
8701
AGG GAA TTT ATA TAT AGT AGA TAG TAT TGA AGA TGT AAG GCA GAG CGA TAT TGC GGT CAT
8761
TAT CTG CGT GCG CTG CGG CAA GAT AGC CTG ATA ATA AGA CTG ATC GCA TAG AGG GGT GGT
8821
ATT TCA CAC CGC CCA TTG TCA ACA GGC AGT TCA GCC TCG TTA AAT TCA GCA TGG GTA TCA
8881
CTT ATG AAA ATT CAT CTA CAT TGG TGA TAA TAG TAA ATC CAG TAG GGC GAA ATA ATT GAC
8941
TGT AAT TTA CGG GGC AAA ACG GCA CAA TCT CAA ACG AGA TTG TGC CGT TTA AGG GGA AGA
9001
                                                            VanY    MET LYS LYS
TTC TAG AAA TAT TTC ATA CTT CCA ACT ATA TAG TTA AGG AGG AGA CTG AAA ATG AAG AAG
9061
LEU PHE PHE LEU LEU LEU LEU LEU PHE LEU ILE TYR LEU GLY TYR ASP TYR VAL ASN GLU
TTG TTT TTT TTA TTG TTA TTG TTA TTC TTA ATA TAC TTA GGT TAT GAC TAC GTT AAT GAA
```

*FIG. 8N*

9121
ALA LEU PHE SER GLN GLU LYS VAL GLU PHE GLN ASN TYR ASP GLN ASN PRO LYS GLU HIS
GCA CTG TTT TCT CAG GAA AAA GTC GAA TTT CAA AAT TAT GAT CAA AAT CCC AAA GAA CAT
9181
LEU GLU ASN SER GLY THR SER GLU ASN THR GLN GLU LYS THR ILE THR GLU GLU GLN VAL
TTA GAA AAT AGT GGG ACT TCT GAA AAT ACC CAA GAG AAA ACA ATT ACA GAA GAA CAG GTT
9241
TYR GLN GLY ASN LEU LEU LEU ILE ASN SER LYS TYR PRO VAL ARG GLN GLU SER VAL LYS
TAT CAA GGA AAT CTG CTA TTA ATC AAT AGT AAA TAT CCT GTT CGC CAA GAA AGT GTG AAG
9301
SER ASP ILE VAL ASN LEU SER LYS HIS ASP GLU LEU ILE ASN GLY TYR GLY LEU LEU ASP
TCA GAT ATC GTG AAT TTA TCT AAA CAT GAC GAA TTA ATA AAT GGA TAC GGG TTG CTT GAT
9361
SER ASN ILE TYR MET SER LYS GLU ILE ALA GLN LYS PHE SER GLU MET VAL ASN ASP ALA
AGT AAT ATT TAT ATG TCA AAA GAA ATA GCA CAA AAA TTT TCA GAG ATG GTC AAT GAT GCT
9421
VAL LYS GLY GLY VAL SER HIS PHE ILE ILE ASN SER GLY TYR ARG ASP PHE ASP GLU GLN
GTA AAG GGT GGC GTT AGT CAT TTT ATT ATT AAT AGT GGC TAT CGA GAC TTT GAT GAG CAA
9481
SER VAL LEU TYR GLN GLU MET GLY ALA GLU TYR ALA LEU PRO ALA GLY TYR SER GLU HIS
AGT GTG CTT TAC CAA GAA ATG GGG GCT GAG TAT GCC TTA CCA GCA GGT TAT AGT GAG CAT
9541
ASN SER GLY LEU SER LEU ASP VAL GLY SER SER LEU THR LYS MET GLU ARG ALA PRO GLU
AAT TCA GGT TTA TCA CTA GAT GTA GGA TCA AGC TTG ACG AAA ATG GAA CGA GCC CCT GAA
9601
GLY LYS TRP ILE GLU GLU ASN ALA TRP LYS TYR GLY PHE ILE LEU ARG TYR PRO GLU ASP
GGA AAG TGG ATA GAA GAA AAT GCT TGG AAA TAC GGG TTC ATT TTA CGT TAT CCA GAG GAC
9661
LYS THR GLU LEU THR GLY ILE GLN TYR GLU PRO TRP HIS ILE ARG TYR VAL GLY LEU PRO
AAA ACA GAG TTA ACA GGA ATT CAA TAT GAA CCA TGG CAT ATT CGC TAT GTT GGT TTA CCA
9721

*FIG. 80*

```
HIS SER ALA ILE MET LYS GLU LYS ASN PHE VAL LEU GLU GLU TYR MET ASP TYR LEU LYS
CAT AGT GCG ATT ATG AAA GAA AAG AAT TTC GTT CTC GAG GAA TAT ATG GAT TAC CTA AAA
9781
GLU GLU LYS THR ILE SER VAL SER VAL ASN GLY GLU LYS TYR GLU ILE PHE TYR TYR PRO
GAA GAA AAA ACC ATT TCT GTT AGT GTA AAT GGG GAA AAA TAT GAG ATC TTT TAT TAT CCT
9841
VAL THR LYS ASN THR THR ILE HIS VAL PRO THR ASN LEU ARG TYR GLU ILE SER GLY ASN
GTT ACT AAA AAT ACC ACC ATT CAT GTG CCG ACT AAT CTT CGT TAT GAG ATA TCA GGA AAC
9901
ASN ILE ASP GLY VAL ILE VAL THR VAL PHE PRO GLY SER THR HIS THR ASN SER ARG ARG
AAT ATA GAC GGT GTA ATT GTG ACA GTG TTT CCC GGA TCA ACA CAT ACT AAT TCA AGG AGG
9961
TAA GGA TGG CGG AAT GAA ACC AAC GAA ATT AAT GAA CAG CAT TAT TGT ACT AGC ACT TTT
10021
GGG GTA ACG TTA GCT TTT TAA TTT AAA ACC CAC GTT AAC TAG GAC ATT GCT ATA CTA ATG

10081                                        VanZ      LEU GLY LYS ILE LEU SER ARG GLY LEU
ATA CAA CTT AAA CAA AAG AATTAGAGG AAA TTA TA TTG GGA AAA ATA TTA TCT AGA GGA TTG
10143
LEU ALA LEU TYR LEU VAL THR LEU ILE TRP LEU VAL LEU PHE LYS LEU GLN TYR ASN ILE
CTA GCT TTA TAT TTA GTG ACA CTA ATC TGG TTA GTG TTA TTC AAA TTA CAA TAC AAT ATT
10203
LEU SER VAL PHE ASN TYR HIS GLN ARG SER LEU ASN LEU THR PRO PHE THR ALA THR GLY
TTA TCA GTA TTT AAT TAT CAT CAA AGA AGT CTT AAC TTG ACT CCA TTT ACT GCT ACT GGG
10263
ASN PHE ARG GLU MET ILE ASP ASN VAL ILE ILE PHE ILE PRO PHE GLY LEU LEU LEU ASN
AAT TTC AGA GAG ATG ATA GAT AAT GTT ATA ATC TTT ATT CCA TTT GGC TTG CTT TTG AAT
```

*FIG. 8P*

```
10323
VAL ASN PHE LYS GLU ILE GLY PHE LEU PRO LYS PHE ALA PHE VAL LEU VAL LEU SER LEU
GTC AAT TTT AAA GAA ATC GGA TTT TTA CCT AAG TTT GCT TTT GTA CTG GTT TTA AGT CTT
10383
THR PHE GLU ILE ILE GLN PHE ILE PHE ALA ILE GLY ALA THR ASP ILE THR ASP VAL ILE
ACT TTT GAA ATA ATT CAA TTT ATC TTC GCT ATT GGA GCG ACA GAC ATA ACA GAT GTA ATT
10443
THR ASN THR VAL GLY GLY PHE LEU GLY LEU LYS LEU TYR GLY LEU SER ASN LYS HIS MET
ACA AAT ACT GTT GGA GGC TTT CTT GGA CTG AAA TTA TAT GGT TTA AGC AAT AAG CAT ATG
10503
ASN GLN LYS LYS LEU ASP ARG VAL ILE ILE PHE VAL GLY ILE LEU LEU LEU VAL LEU LEU
AAT CAA AAA AAA TTA GAC AGA GTT ATT ATT TTT GTA GGT ATA CTT TTG CTC GTA TTA TTG
10563
LEU VAL TYR ARG THR HIS LEU ARG ILE ASN TYR VAL
CTC GTT TAC CGT ACC CAT TTA AGA ATA AAT TAC GTG TAAG ATG TCT AAA TCA AGC AAT
10621
CTG ATC TTT CAT ACA CAT AAA GAT ATT GAA TGA ATT GGA TTA GAT GGA AAA CGG GAT GTG
10681
GGG AAA CTC GCC CGT AGG TGT GAA GTG AGG GGA AAA CCG GTG ATA AAG TAA AAA GCT TAC
10741
CTA ACA CTA TAG TAA CAA AGA AAG CCC AAT TAT CAA TTT TAG TGC TGA GGA ATT GGT CTC
10801
TTT AAT AAA TTT CCT TAA CGT TGT AAA TCC GCA TTT TCC TGA CGG TAC CCC
```

FIG. 8Q

Ib brin(-)

```
1
CAA AAT ATC ACC TCA TTT TTG AGA CAA GTC TTA TGA GAC GCT CTT AAC TAT GAT TTT ATC
61
AGT CTA CTA CAT TTG TAT CAA TAG AGT ACA CTC TAT TGA TAT ATA ATT GAA CTA ATA AAT

121                  Transposase       MET LYS ILE ALA ARG GLY ARG GLU LEU LEU THR
TGA AAA TAC AGA AAT GGA ATGATACTG AA ATG AAA ATT GCG AGA GGT AGA GAA TTG CTT ACA
182
PRO GLU GLN ARG GLN ALA PHE MET GLN ILE PRO GLU ASP GLU TRP ILE LEU GLY THR TYR
CCG GAA CAG AGA CAG GCT TTT ATG CAA ATC CCT GAA GAT GAA TGG ATA CTG GGG ACC TAC
242
PHE THR PHE SER LYS ARG ASP LEU GLU ILE VAL ASN LYS ARG ARG ARG GLU GLU ASN ARG
TTC ACT TTT TCC AAA CGG GAT TTA GAA ATA GTT AAT AAG CGA AGG AGG GAA GAA AAC CGT
302
LEU GLY PHE ALA VAL GLN LEU ALA VAL LEU ARG TYR PRO GLY TRP PRO TYR THR HIS ILE
TTA GGA TTT GCT GTT CAA TTA GCT GTT CTT CGG TAT CCC GGT TGG CCA TAC ACT CAT ATC
362
LYS SER ILE PRO ASP SER VAL ILE GLN TYR ILE SER LYS GLN ILE GLY VAL SER PRO SER
AAA AGC ATC CCA GAT TCG GTC ATA CAA TAT ATA TCG AAA CAG ATT GGT GTT AGT CCA TCC
422
SER LEU ASP HIS TYR PRO GLN ARG GLU ASN THR LEU TRP ASP HIS LEU LYS GLU ILE ARG
TCG CTT GAT CAT TAT CCT CAA AGG GAA AAT ACA CTT TGG GAT CAT TTG AAA GAA ATT CGA
```

FIG. 8R

```
482
SER GLU TYR ASP PHE VAL THR PHE THR LEU SER GLU TYR ARG MET THR PHE LYS TYR LEU
AGT GAA TAC GAC TTT GTA ACT TTT ACC CTG AGT GAA TAT CGA ATG ACA TTT AAG TAC CTT
542
HIS GLN LEU ALA LEU GLU ASN GLY ASP ALA ILE HIS LEU LEU HIS GLU CYS ILE ASP PHE
CAT CAA TTA GCT TTG GAA AAT GGT GAT GCC ATT CAT CTA CTG CAT GAA TGC ATA GAT TTT
602
LEU ARG LYS ASN LYS ILE ILE LEU PRO ALA ILE THR THR LEU GLU ARG MET VAL TRP GLU
CTA AGA AAA AAC AAA ATT ATA CTG CCT GCT ATC ACT ACA CTT GAA AGA ATG GTG TGG GAA
662
ALA ARG ALA MET ALA GLU LYS LYS LEU PHE ASN THR VAL SER LYS SER LEU THR ASN GLU
GCA AGG GCA ATG GCT GAA AAG AAG CTA TTT AAT ACG GTT AGT AAA TCT CTA ACA AAT GAG
722
GLN LYS GLU LYS LEU GLU GLY ILE ILE THR SER GLN HIS PRO SER GLU SER ASN LYS THR
CAA AAA GAA AAG CTT GAA GGG ATT ATT ACC TCG CAG CAT CCA TCC GAA TCC AAT AAA ACG
782
ILE LEU GLY TRP LEU LYS GLU PRO PRO GLY HIS PRO SER PRO GLU THR PHE LEU LYS ILE
ATA TTG GGT TGG TTA AAA GAG CCA CCG GGT CAT CCT TCA CCC GAA ACT TTT CTA AAA ATA
842
ILE GLU ARG LEU GLU TYR ILE ARG GLY MET ASP LEU GLU THR VAL GLN ILE SER HIS LEU
ATA GAA CGA CTC GAA TAC ATA CGA GGA ATG GAT TTA GAA ACA GTG CAA ATT AGT CAT TTG
902
HIS ARG ASN ARG LEU LEU GLN LEU SER ARG LEU GLY SER ARG TYR GLU PRO TYR ALA PHE
CAC CGT AAC CGC CTG TTG CAG CTG TCT CGC TTA GGC TCA AGA TAC GAG CCG TAT GCA TTC
962
ARG ASP PHE GLN GLU ASN LYS ARG TYR SER ILE LEU THR ILE TYR LEU LEU GLN LEU THR
CGT GAC TTT CAA GAA AAT AAA CGT TAT TCG ATA TTA ACC ATC TAT TTA TTA CAA CTT ACT
1022
GLN GLU LEU THR ASP LYS ALA PHE GLU ILE HIS ASP ARG GLN ILE LEU SER LEU LEU SER
CAG GAG CTA ACG GAT AAA GCG TTT GAA ATT CAT GAT AGG CAA ATA CTT AGT TTG TTA TCA
```

FIG. 8S

1082
LYS GLY ARG LYS ALA GLN GLU GLU ILE GLN LYS GLN ASN GLY LYS LYS LEU ASN GLU LYS
AAA GGT CGT AAG GCT CAA GAG GAA ATC CAG AAA CAA AAC GGT AAA AAG CTA AAT GAG AAA
1142
VAL ILE HIS PHE THR ASN ILE GLY GLN ALA LEU ILE LYS ALA ARG GLU GLU LYS LEU ASP
GTT ATA CAC TTT ACG AAC ATC GGA CAA GCA TTA ATT AAA GCA AGA GAG GAA AAA TTA GAC
1202
VAL PHE LYS VAL LEU GLU SER VAL ILE GLU TRP ASN THR PHE VAL SER SER VAL GLU GLU
GTT TTT AAG GTT TTA GAA TCG GTT ATT GAA TGG AAT ACC TTT GTC TCT TCA GTA GAA GAG
1262
ALA GLN GLU LEU ALA ARG PRO ALA ASP TYR ASP TYR LEU ASP LEU LEU GLN LYS ARG PHE
GCT CAG GAA CTT GCA CGT CCT GCC GAC TAT GAT TAT TTA GAC TTA CTG CAA AAA CGG TTT
1322
TYR SER LEU ARG LYS TYR THR PRO THR LEU LEU ARG VAL LEU GLU PHE HIS SER THR LYS
TAT TCA CTA AGA AAA TAT ACG CCA ACG CTA TTA AGA GTA TTG GAA TTT CAT TCT ACA AAG
1382
ALA ASN GLU PRO LEU LEU GLN ALA VAL GLU ILE ILE ARG GLY MET ASN GLU SER GLY LYS
GCA AAT GAG CCA CTT TTA CAA GCT GTT GAG ATT ATC CGA GGA ATG AAC GAA TCT GGA AAG
1442
ARG LYS VAL PRO ASP ASP SER PRO VAL ASP PHE ILE SER LYS ARG TRP LYS ARG HIS LEU
CGA AAA GTG CCT GAT GAC TCA CCT GTG GAT TTT ATT TCA AAA CGA TGG AAA AGA CAT TTA
1502
TYR GLU ASP ASP GLY THR THR ILE ASN ARG HIS TYR TYR GLU MET ALA VAL LEU THR GLU
TAC GAG GAT GAT GGT ACA ACA ATT AAT CGT CAT TAC TAT GAA ATG GCT GTT TTA ACA GAA
1562
LEU ARG GLU HIS VAL ARG ALA GLY ASP VAL SER ILE VAL GLY SER ARG GLN TYR ARG ASP
CTT CGG GAG CAT GTT CGG GCA GGA GAT GTT TCC ATT GTT GGC AGC AGA CAA TAT AGG GAT

*FIG. 8T*

```
1622
PHE GLU GLU TYR LEU PHE SER GLU ASP THR TRP ASN GLN SER LYS GLY ASN THR ARG LEU
TTT GAG GAA TAT TTG TTT TCG GAA GAT ACA TGG AAT CAA TCG AAG GGG AAT ACG AGA TTA
1682
SER VAL SER LEU SER PHE GLU ASP TYR ILE THR GLU ARG THR SER SER PHE ASN GLU ARG
TCA GTT AGT TTA TCA TTC GAA GAT TAT ATA ACG GAG AGA ACC AGC AGC TTT AAT GAA AGG
1742
LEU LYS TRP LEU ALA ALA ASN SER ASN LYS LEU ASP GLY VAL SER LEU GLU LYS GLY LYS
TTA AAG TGG TTA GCT GCC AAT TCC AAT AAG TTA GAT GGG GTT TCT CTT GAA AAA GGA AAG
1802
LEU SER LEU ALA ARG LEU GLU LYS ASP VAL PRO GLU GLU ALA LYS LYS PHE SER ALA SER
CTA TCA CTT GCA CGC TTA GAA AAA GAT GTT CCA GAA GAA GCA AAA AAA TTT AGT GCA AGC
1862
LEU TYR GLN MET LEU PRO ARG ILE LYS LEU THR ASP LEU LEU MET ASP VAL ALA HIS ILE
CTT TAT CAG ATG CTA CCA AGA ATA AAA TTA ACT GAT TTA CTC ATG GAT GTG GCC CAT ATA
1922
THR GLY PHE HIS GLU GLN PHE THR HIS ALA SER ASN ASN ARG LYS PRO ASP LYS GLU GLU
ACA GGA TTT CAT GAG CAA TTC ACT CAT GCT TCC AAT AAT CGA AAA CCA GAT AAG GAA GAA
1982
THR ILE ILE ILE MET ALA ALA LEU LEU GLY MET GLY MET ASN ILE GLY LEU SER LYS MET
ACA ATC ATT ATC ATG GCT GCC CTT TTA GGA ATG GGA ATG AAT ATT GGC TTG AGC AAG ATG
2042
ALA GLU ALA THR PRO GLY LEU THR TYR LYS GLN LEU ALA ASN VAL SER GLN TRP ARG MET
GCC GAA GCC ACA CCC GGA CTT ACA TAT AAG CAA CTA GCC AAT GTA TCT CAA TGG CGC ATG
2102
TYR GLU ASP ALA MET ASN LYS ALA GLN ALA ILE LEU VAL ASN PHE HIS HIS LYS LEU GLN
TAT GAA GAT GCC ATG AAT AAA GCC CAA GCC ATA TTA GTA AAC TTT CAT CAT AAA TTA CAA
2162
LEU PRO PHE TYR TRP GLY ASP GLY THR THR SER SER SER ASP GLY MET ARG MET GLN LEU
TTG CCT TTC TAT TGG GGC GAC GGT ACA ACA TCT TCG TCA GAT GGT ATG AGA ATG CAG CTA
```

FIG. 8U

```
2222
GLY VAL SER SER LEU HIS ALA ASP ALA ASN PRO HIS TYR GLY THR GLY LYS GLY ALA THR
GGT GTT TCA TCA CTA CAT GCA GAT GCA AAT CCA CAT TAT GGA ACT GGA AAA GGA GCC ACC
2282
ILE TYR ARG PHE THR SER ASP GLN PHE SER SER TYR TYR THR LYS ILE ILE HIS THR ASN
ATC TAC CGA TTT ACA AGT GAT CAA TTC TCT TCT TAC TAC ACA AAG ATT ATT CAT ACT AAT
2342
SER ARG ASP ALA ILE HIS VAL LEU ASP GLY LEU LEU HIS HIS GLU THR ASP LEU ASN ILE
TCA AGA GAT GCG ATT CAT GTT TTG GAT GGT TTG TTA CAT CAT GAG ACG GAT CTA AAC ATA
2402
GLU GLU HIS TYR THR ASP THR ALA GLY TYR THR ASP GLN ILE PHE GLY LEU THR HIS LEU
GAG GAA CAT TAT ACA GAC ACT GCC GGT TAC ACT GAC CAA ATA TTC GGA CTG ACT CAT TTA
2462
LEU GLY PHE LYS PHE ALA PRO ARG ILE ARG ASP LEU SER ASP SER LYS LEU PHE THR ILE
TTA GGA TTT AAA TTT GCC CCA AGA ATA AGG GAT TTA TCG GAC TCA AAA TTA TTT ACG ATA
2522
ASP LYS ALA SER GLU TYR PRO LYS LEU GLU ALA ILE LEU ARG GLY GLN ILE ASN THR LYS
GAT AAA GCA AGT GAG TAT CCA AAA CTA GAA GCC ATT TTA CGT GGA CAA ATA AAT ACA AAG
2582
VAL ILE LYS GLU ASN TYR GLU ASP VAL LEU ARG LEU ALA HIS SER ILE ARG GLU GLY THR
GTC ATT AAA GAA AAT TAT GAG GAT GTT TTG CGA TTA GCT CAT TCT ATA AGG GAG GGA ACA
2642
AGT TTC AGC ATC CCT TAT TAT GGG GAA GCT AGG TTC CTA TTC AAG ACA AAA CAG CTT AGC
VAL SER ALA SER LEU ILE MET GLY LYS LEU GLY SER TYR SER ARG GLN ASN SER LEU ALA
GTT TCA GCA TCC CTT ATT ATG GGG AAG CTA GGT TCC TAT TCA AGA CAA AAC AGC TTA GCT
2702
THR ALA LEU ARG GLU MET GLY ARG ILE GLU LYS THR ILE PHE ILE LEU ASN TYR ILE SER
ACA GCC TTA CGT GAG ATG GGC CGA ATA GAA AAA ACG ATC TTT ATT TTG AAT TAT ATA TCG
```

*FIG. 8V*

```
2762
ASP GLU SER LEU ARG ARG LYS ILE GLN ARG GLY LEU ASN LYS GLY GLU ALA MET ASN GLY
GAT GAA TCA TTA AGA AGA AAA ATA CAA AGA GGA TTG AAT AAA GGA GAA GCC ATG AAT GGA
2822
LEU ALA ARG ALA ILE PHE PHE GLY LYS GLN GLY GLU LEU ARG GLU ARG THR ILE GLN HIS
TTG GCA AGA GCT ATT TTC TTC GGA AAA CAA GGT GAG CTT AGA GAA CGC ACC ATA CAG CAT
2882
GLN LEU GLN ARG ALA SER ALA LEU ASN ILE ILE ILE ASN ALA ILE SER ILE TRP ASN THR
CAA TTG CAA AGA GCC AGT GCT TTA AAC ATA ATT ATC AAT GCT ATA AGT ATT TGG AAT ACT
2942
TCT CCA CCT AAC AAC AGC AGT TGA ATA TAA AAA ACG GAC AGG TAG CTT TAA TGA AGA TTT
LEU HIS LEU THR THR ALA VAL GLU TYR LYS LYS ARG THR GLY SER PHE ASN GLU ASP LEU
CTC CAC CTA ACA ACA GCA GTT GAA TAT AAA AAA CGG ACA GGT AGC TTT AAT GAA GAT TTG
3002
LEU HIS HIS MET SER PRO LEU GLY TRP GLU HIS ILE ASN LEU LEU GLY GLU TYR HIS PHE
TTA CAC CAT ATG TCG CCC TTA GGT TGG GAA CAT ATT AAT TTA CTA GGA GAA TAC CAT TTT
3062
ASN SER GLU LYS VAL VAL SER LEU ASN SER LEU ARG PRO LEU LYS LEU SER
AAC TCA GAG AAA GTA GTC TCA TTA AAT TCT TTA AGA CCA CTA AAA CTT TCT TAA CGT TG
3121
TTA AAA ACG AGG GAT TCG TCA GGA AAA TAG GCT TAG CGT TGT AAA TCC GCA TTT TCC TGA
3181
CGC TAC CCC
```

FIG.8W

```
                                                SacI
                                                GAGCTCTTCCTTCAACGCACTTCTGTACCAAGAGTTGTTGTC 42

CATTTGATCACTAACAATAGCTTCCCCTGCTTTCTTCAAGCCCTTTGTCATAAAATCGTTAGATTTTCA 111

TCATAAAAATACGAGAAAGACAACAGGAAGACCGCAAATTTTCTTTTCTTTTCCTAGGTACACTGAATG 180

                            RBS                 M  K  K  I  A  V  L  F  G  G
TAACCTTAAAAGAAAAAAGGAAAGGAAGAAAATGATGAAAAAAATTGCCGTTTTATTTGGAGGG 244

N  S  P  E  Y  S  V  S  L  T  S  A  A  S  V  I  Q  A  I  D
AATTCTCCAGAATACTCAGTGTCACTAACCTCAGCAGCAAGTGTGATCCAAGCTATTGAC 304

P  L  K  Y  E  V  M  T  I  G  I  A  P  T  M  D  W  Y  W  Y
CCGCTGAAATATGAAGTAATGACCATTGGCATCGCACCAACAATGGATTGGTATTGGTAT 364

Q  G  N  L  A  N  V  R  N  D  T  W  L  E  D  H  K  N  C  H
CAAGGAAACCTCGCGAATGTTCGCAATGATACTTGGCTAGAAGATCACAAAAACTGTCAC 424

Q  L  T  F  S  S  Q  G  F  I  L  G  E  K  R  I  V  P  D  V
CAGCTGACTTTTTCTAGCCAAGGATTTATATTAGGAGAAAAACGAATCGTCCCTGATGTC 484

L  F  P  V  L  H  G  K  Y  G  E  D  G  C  I  Q  G  L  L  E
CTCTTTCCAGTCTTGCATGGAAGTATGGCGAGGATGGCTGTATCCAAGGACTGCTTGAA 544

L  M  N  L  P  Y  V  G  C  H  V  A  A  S  A  L  C  M  N  K
CTAATGAACCTGCCTTATGTTGGTTGCCATGTCGCTGCCTCCGCATTATGTATGAACAAA 604
```

*FIG. 9A*

```
 W  L  L  H  Q  L  A  D  T  M  G  I  A  S  A  P  T  L  L  L
TGGCTCTTGCATCAACTTGCTGATACCATGGGAATCGCTAGTGCTCCCACTTTGCTTTTA  664

 S  R  Y  E  N  D  P  A  T  I  D  R  F  I  Q  D  H  G  F  P
TCCCGCTATGAAAACGATCCTGCCACAATCGATCGTTTTATTCAAGACCATGGATTCCCG  724

 I  F  I  K  P  N  E  A  G  S  S  K  G  I  T  K  V  T  D  K
ATCTTTATCAAGCCGAATGAAGCCGGTTCTTCAAAAGGGATCACAAAAGTAACTGACAAA  784

 T  A  L  Q  S  A  L  T  T  A  F  A  Y  G  S  T  V  L  I  Q
ACAGCGCTCCAATCTGCATTAACGACTGCTTTTGCTTACGGTTCTACTGTGTTGATCCAA  844

 K  A  I  A  G  I  E  I  G  C  G  I  L  G  N  E  Q  L  T  I
AAGGCGATAGCGGGTATTGAAATTGGCTGCGGCATCTTAGGAAATGAGCAATTGACGATT  904

 G  A  C  D  A  I  S  L  V  D  G  F  F  D  F  E  E  K  Y  Q
GGTGCTTGTGATGCGATTTCTCTTGTCGACGGTTTTTTTGATTTTGAAGAGAAATACCAA  964

 L  I  S  A  T  I  T  V  P  A  P  L  P  L  A  L  E  S  Q  I
TTAATCAGCGCCACGATCACTGTCCCAGCACCATTGCCTCTCGCGCTTGAATCACAGATC  1024

 K  E  Q  A  Q  L  L  Y  R  N  L  G  L  T  G  L  A  R  I  D
AAGGAGCAGGCACAGCTGCTTTATCGAAACTTGGGATTGACGGGTCTGGCTCGAATCGAT  1084

 F  F  V  T  N  Q  G  A  I  Y  L  N  E  I  N  T  M  P  G  F
TTTTTCGTCACCAATCAAGGAGCGATTTATTTAAACGAAATCAACACCATGCCGGGATTT  1144
```

FIG. 9B

```
 T  G  H  S  R  Y  P  A  M  M  A  E  V  G  L  S  Y  E  I  L
ACTGGGCACTCCCGCTACCCAGCTATGATGGCGGAAGTCGGGTTATCCTACGAAATATTA  1204

 V  E  Q  L  E  A  L  A  E  E  D  K  R  *
GTAGAGCAATTGATTGCACTGGCAGAGGAGGACAAACGATGAACACATTACAATTGATCAATA  1267

AAAACCATCCATTGAAAAAAAATCAAGAGCCCCCGCACTTAGTGCTAGCTCCTTTTAGCGATCACGATG  1336

TTTACCTGCAG                                                           1347
      PstI
```

FIG. 9C

```
VanC  --MKKIAVLF GGNSPEYSVS LTSAASVIQA IDPLKYEVMT IGIAPTMDWY WYQGNLANVR NDTWLEDHKN CHQLTFSSQG FILGEKRIVP ---------D
VanA  MNRIKVAILF GGCSEEHDVS VKSAIEIAAN INKEKYEPLY IGITKSGVWK MCEKPCAEWE NDNCYSAVLS PDKKMHGLLV KKNHEYEINH --------VD
DdlA  MEKLRVGIVF GGKSAEHEVS LQSAKNIVDA IDKSRFDVVL LGIDKQGQWH VSDASHYLLN ADDPAHIALR PSATSLAQVP GKHEHQLIDA QNGQPLPTVD
DdlB  -MTDKAIVLL GGTSAEREVS LNSGAAVLAG LREGGIDAYP VDPKEVDVTQ LKSMGFQKV- ---------- ---------- ---------- ----------
        CCCCCC II I I  II C IC  C    C     C   C C
                   domaine 1

              <--1-->
VanC  VLFPVLHGKY GEDGCIQGLL ELMNLPYVGC HVAASALCMN KWLLHQLADT MGIASAPTLL LSRYEND--- PATIDRFIQD HGFPIFIKPN EAGSSKGITK
VanA  VAFSALHGKS GEDGSIQGLF ELSGIPFVGC DIQSSAICMD KSLTYIVAKN AGIATPAFWV INKDDRP--- ------VAAT FTYPVFVKPA RSGSSFGVKK
DdlA  VIFPIVHGTL GEDGSLQGML RVANLPFVGS DVLASAACMD KDVTKRLLRD AGLNIAPFIT LTRANRHNIS FAE---VESK LGLPLFVKPA NQGSSVGVSK
DdlB  --FIALHGRG GEDGTLQGML ELMGLPYTGS GVMASALSMD KLRSKLLWQG AGLPVAPWVA LTRAEFEKGL SDKQLAEISA LGLPVIVKPS REGSSVGMSK
       I  CII   IIIICCIICC      CI  IC  C  II CI  I     C     IC       CCC                      ICCCII    III IC I
                                  domaine 2

VanC  VTDKTALQSA LTTAFAYGST VLIQKAIAGI EIGCGILGNE -QLTIGACDA ISLVDGFFDF EEKYQLIS-- --ATITVPAP LPLALESQIK EQAQLLYRNL
VanA  VNSADELDYA IESARQYDSK ILIEQAVSGC EVGCAVLGNS AALVVGEVDQ IRLQYGIFRI HQEVEPEKGS ENAVITVPAD LSAEERGRIQ ETAKKIYKAL
DdlA  VTSEEQYATA VALAFEFDHK VIVEQGIKGR EIECAVLGND NP----QAST CGEIVLTSDF YAYDTKYIDE DGAKVVVPAA IAPEINDKIR AIAVQAYQTL
DdlB  VVAENALQDA LRLAFQHDEE VLIEKWLSGP EFTVAILGEE IL-------P SIRIQPSGTF YDYEAKYLSD ETQYFC-PAG LEASQEANLQ ALVLKAWTTL
      I        I C  I        CCC  CC I  IC  CCII                                              II  C       C        I
                 domaine 3

                        <--2-->
VanC  GLTGLARIDF FVTNQGAIYL NEINTMPGFT GHSRYPAMMA EVGLSYEILV EQLIALAEED KR
VanA  GCRGLARVDM FLQDNGRIVL NEVNTLPGFT SYSRYPRMMA AAGIALPELI DRLIVLALKG
DdlA  GCAGMARVDV FLTPENEVVI NEINTLPGFT NISMYPKLWQ ASGLGYTDLI TRLIELALER HAANNALKTT M
DdlB  GCKGWGRIDV MLDSDGQFYL LEANTSPGMT SHSLVPMAAR QAGMSFSQLV VRILELAD
      I  I CICIC CC     C C  I II IICI   I  I        IC    IC   CC II
                 domaine 4
```

FIG. 10

```
VanS 126 EMDVMEQKLNTLKRTLEKREQDAKLAEQRKNDVVMYLAHDIKTPLTSIIGYLSLLDEAP 184
PhoR 176 EIRVMPYTHKQLLMVARDVTQMHQLEGARRN-FFANVSHELRTPLTVLQGYLEMMNEQP 233
EnvZ 210 ASEVRSVTRAFNHMAA----GVKQLADDRTL-LMAGVSHDLRTPLTRIRLATEMMSEQD 263
                                             ------I------

VanS     DMPVDQKAKYVHITLDKAYRLEQLIDEFFEITRYNLQTITLTKTHIDLYYMLVQMTDEF 243
PhoR     LEGAV-REKALHTMREQTQRMEGLVKQLLTLSKIEAAPTHLLNEKVDVPMMLRVVEREA 291
EnvZ     GYLAESINK---------DIEECNAIIEQFIDYLRTGQEMPM--EMADLNAVLGEVIAAE 312

VanS     YPQLSAHGKQAVIHAPEDLIVSGDPDKLARVFNNILKNAAAYSEDNSIIDITAGLSG-- 300
PhoR     -QTLSQKKQTFTFEIDNGLKVSGNEDQLRSAISNLVYNAVNHTPEGTHITVRWQRVPHG 349
EnvZ     ---SGYEREIETALYPGSIEVKMHPLSIKRAVANMVVNAARYG--NGWIKVSSGTEPNR 366
                                -------II-------

VanS     DVVSIEFKNTGSIPKDKLAAIFEKFYRLDNARSSDTGGAGLGLAIAKEIIVQHGGQIYA 359
PhoR     AEFSVEDNGPGIAPEHI-PRLTERFYRVDKARSRQTGGSGLGLAIVKHAVNHHESRLNI 407
EnvZ     AWFQVEDDGPGIAPEQR-KHLFQPFVRGDSART--ISGTGLGLAIVQRIVDNHNGMLEL 422
            ---IIIa---                                 ---IIIb---

VanS     ESNDNYIT-FRVELPAMPDLVDKRRS    384
PhoR     ESTVGKGTRFSFVIPERLIAKNSD      432
EnvZ     GTSERGGLSIRAWLPVPVTRAQGTTKEG  450
```

FIG. 14

```
VanR --MSDKIL---IVDDEHEIADLVELYLKNENYTIVFK-YYTAKEALECIDKSEIDLAILDIML  56
OmpR MQENYKIL---VVDDDMRLRALLERYLTEQGFQVRS-VANAEQMDRLLTRESFHLMVLDLML  58
PhoB --MARRIL---VVEDEAPIREMVCFVLEQNGFQPVE-AEDYDSAVNQLNEPWPDLILLDWML  56
CheY --MADKELKFLVVDDFSTMRRIVRNLLKELGFNNVEEAEDGVDALNKLQAGGFGFIISDWNM  60

VanR PGTSGLTICQKIRDKHTY---PIIMLTGKDTEVDKITGLTIGADDYITKPFRPLELIARVKA 115
OmpR PGEDGLSICRRLRSQSNPM--PIIMVTAKGEEVDRIVGLEIGADDYIPKPFNPRELLARIRA 118
PhoB PGGSGIQFIKHLKRESMTRDIPVVMLTARGEEEDRVRGLETGADDYITKPFSPKELVARIKA 118
Chey PNMDGLELLKTIRADSAMSALPVLMVTAEAKKENIIAAAQAGASGYVVKPFTAATLEEKLNK 122

VanR QLRRYKK-FSGVKEQNENVTIVHSGLVINVNTHECYLNEKQLSLTPTEFSILRILCENKGNVV 176
OmpR VLRRQANELPGAPSQEEAVIAFGKFKLNLGTREMFREDEPMPLTSGEFAVLKALVSHPREPL 180
PhoB VMRRISP-------MAVEEVIEMQGLSLDPTSHRVMAGEEPLEMGPTEFKLLHFFMTHPERVY 174
CheY IFEKLGM 129

VanR SSELLFHEIWGDEYFSKSNNTITVHIRHLREKMNDTIDNPKYIKTVWGVGYKIEK        231
OmpR SRDKLMNLARGREYSAMER-SIDVQISRLRRMVEEDPAHPRYIQTVWGLGYVFVPDGSKA   239
PhoB SREQLLNHVWGTNVYVEDR-TVDVHIRRLR-KALEPGGHDRMVQTVRGTGYRFSTRF     229
```

*FIG. 15*

SEQUENCE LISTING (1) GENERAL INFORMATION:

(iii) NUMBER OF SEQUENCES: 54

(2) INFORMATION FOR SEQ ID NO:1:

(i) SEQUENCE CHARACTERISTICS:
(A) LENGTH: 966 base pairs
(B) TYPE: nucleic acid
(C) STRANDEDNESS: unknown
(D) TOPOLOGY: linear (ii) MOLECULE TYPE: DNA (genomic)

(ix) FEATURE:
(A) NAME/KEY: CDS
(B) LOCATION: 1..966

(xi) SEQUENCE DESCRIPTION: SEQ ID NO:1:

```
ATG AAT AAC ATC GGC ATT ACT GTT TAT GGA TGT GAG CAG GAT GAG GCA       48
Met Asn Asn Ile Gly Ile Thr Val Tyr Gly Cys Glu Gln Asp Glu Ala
  1               5                  10                  15
```

-continued

```
GAT GCA TTC CAT GCT CTT TCG CCT CGC TTT GGC GTT ATG GCA ACG ATA        96
Asp Ala Phe His Ala Leu Ser Pro Arg Phe Gly Val Met Ala Thr Ile
             20                  25                  30

ATT AAC GCC AAC GTG TCG GAA TCC AAC GCC AAA TCC GCG CCT TTC AAT       144
Ile Asn Ala Asn Val Ser Glu Ser Asn Ala Lys Ser Ala Pro Phe Asn
         35                  40                  45

CAA TGT ATC AGT GTG GGA CAT AAA TCA GAG ATT TCC GCC TCT ATT CTT       192
Gln Cys Ile Ser Val Gly His Lys Ser Glu Ile Ser Ala Ser Ile Leu
     50                  55                  60

CTT GCG CTG AAG AGA GCC GGT GTG AAA TAT ATT TCT ACC CGA AGC ATC       240
Leu Ala Leu Lys Arg Ala Gly Val Lys Tyr Ile Ser Thr Arg Ser Ile
 65                  70                  75                  80

GGC TGC AAT CAT ATA GAT ACA ACT GCT GCT AAG AGA ATG GGC ATC ACT       288
Gly Cys Asn His Ile Asp Thr Thr Ala Ala Lys Arg Met Gly Ile Thr
                 85                  90                  95

GTC GAC AAT GTG GCG TAC TCG CCG GAT AGC GTT GCC GAT TAT ACT ATG       336
Val Asp Asn Val Ala Tyr Ser Pro Asp Ser Val Ala Asp Tyr Thr Met
            100                 105                 110

ATG CTA ATT CTT ATG GCA GTA CGC AAC GTA AAA TCG ATT GTG CGC TCT       384
Met Leu Ile Leu Met Ala Val Arg Asn Val Lys Ser Ile Val Arg Ser
        115                 120                 125

GTG GAA AAA CAT GAT TTC AGG TTG GAC AGC GAC CGT GGC AAG GTA CTC       432
Val Glu Lys His Asp Phe Arg Leu Asp Ser Asp Arg Gly Lys Val Leu
    130                 135                 140

AGC GAC ATG ACA GTT GGT GTG GTG GGA ACG GGC CAG ATA GGC AAA GCG       480
Ser Asp Met Thr Val Gly Val Val Gly Thr Gly Gln Ile Gly Lys Ala
145                 150                 155                 160

GTT ATT GAG CGG CTG CGA GGA TTT GGA TGT AAA GTG TTG GCT TAT AGT       528
Val Ile Glu Arg Leu Arg Gly Phe Gly Cys Lys Val Leu Ala Tyr Ser
                165                 170                 175

CGC AGC CGA AGT ATA GAG GTA AAC TAT GTA CCG TTT GAT GAG TTG CTG       576
Arg Ser Arg Ser Ile Glu Val Asn Tyr Val Pro Phe Asp Glu Leu Leu
            180                 185                 190

CAA AAT AGC GAT ATC GTT ACG CTT CAT GTG CCG CTC AAT ACG GAT ACG       624
Gln Asn Ser Asp Ile Val Thr Leu His Val Pro Leu Asn Thr Asp Thr
        195                 200                 205

CAC TAT ATT ATC AGC CAC GAA CAA ATA CAG AGA ATG AAG CAA GGA GCA       672
His Tyr Ile Ile Ser His Glu Gln Ile Gln Arg Met Lys Gln Gly Ala
    210                 215                 220

TTT CTT ATC AAT ACT GGG CGC GGT CCA CTT GTA GAT ACC TAT GAG TTG       720
Phe Leu Ile Asn Thr Gly Arg Gly Pro Leu Val Asp Thr Tyr Glu Leu
225                 230                 235                 240

GTT AAA GCA TTA GAA AAC GGG AAA CTG GGC GGT GCC GCA TTG GAT GTA       768
Val Lys Ala Leu Glu Asn Gly Lys Leu Gly Gly Ala Ala Leu Asp Val
                245                 250                 255

TTG GAA GGA GAG GAA GAG TTT TTC TAC TCT GAT TGC ACC CAA AAA CCA       816
Leu Glu Gly Glu Glu Glu Phe Phe Tyr Ser Asp Cys Thr Gln Lys Pro
            260                 265                 270

ATT GAT AAT CAA TTT TTA CTT AAA CTT CAA AGA ATG CCT AAC GTG ATA       864
Ile Asp Asn Gln Phe Leu Leu Lys Leu Gln Arg Met Pro Asn Val Ile
        275                 280                 285

ATC ACA CCG CAT ACG GCC TAT TAT ACC GAG CAA GCG TTG CGT GAT ACC       912
Ile Thr Pro His Thr Ala Tyr Tyr Thr Glu Gln Ala Leu Arg Asp Thr
    290                 295                 300

GTT GAA AAA ACC ATT AAA AAC TGT TTG GAT TTT GAA AGG AGA CAG GAG       960
Val Glu Lys Thr Ile Lys Asn Cys Leu Asp Phe Glu Arg Arg Gln Glu
305                 310                 315                 320

CAT GAA                                                               966
His Glu
```

(2) INFORMATION FOR SEQ ID NO:2:

(i) SEQUENCE CHARACTERISTICS:
(A) LENGTH: 322 amino acids
(B) TYPE: amino acid
(D) TOPOLOGY: linear (ii) MOLECULE TYPE: protein (xi) SEQUENCE DESCRIPTION: SEQ ID NO:2:

```
Met Asn Asn Ile Gly Ile Thr Val Tyr Gly Cys Glu Gln Asp Glu Ala
  1               5                  10                  15

Asp Ala Phe His Ala Leu Ser Pro Arg Phe Gly Val Met Ala Thr Ile
             20                  25                  30

Ile Asn Ala Asn Val Ser Glu Ser Asn Ala Lys Ser Ala Pro Phe Asn
         35                  40                  45

Gln Cys Ile Ser Val Gly His Lys Ser Glu Ile Ser Ala Ser Ile Leu
     50                  55                  60

Leu Ala Leu Lys Arg Ala Gly Val Lys Tyr Ile Ser Thr Arg Ser Ile
 65                  70                  75                  80

Gly Cys Asn His Ile Asp Thr Thr Ala Ala Lys Arg Met Gly Ile Thr
                 85                  90                  95

Val Asp Asn Val Ala Tyr Ser Pro Asp Ser Val Ala Asp Tyr Thr Met
            100                 105                 110

Met Leu Ile Leu Met Ala Val Arg Asn Val Lys Ser Ile Val Arg Ser
        115                 120                 125

Val Glu Lys His Asp Phe Arg Leu Asp Ser Asp Arg Gly Lys Val Leu
    130                 135                 140

Ser Asp Met Thr Val Gly Val Val Gly Thr Gly Gln Ile Gly Lys Ala
145                 150                 155                 160

Val Ile Glu Arg Leu Arg Gly Phe Gly Cys Lys Val Leu Ala Tyr Ser
                165                 170                 175

Arg Ser Arg Ser Ile Glu Val Asn Tyr Val Pro Phe Asp Glu Leu Leu
            180                 185                 190

Gln Asn Ser Asp Ile Val Thr Leu His Val Pro Leu Asn Thr Asp Thr
        195                 200                 205

His Tyr Ile Ile Ser His Glu Gln Ile Gln Arg Met Lys Gln Gly Ala
    210                 215                 220

Phe Leu Ile Asn Thr Gly Arg Gly Pro Leu Val Asp Thr Tyr Glu Leu
225                 230                 235                 240

Val Lys Ala Leu Glu Asn Gly Lys Leu Gly Gly Ala Ala Leu Asp Val
                245                 250                 255

Leu Glu Gly Glu Glu Glu Phe Phe Tyr Ser Asp Cys Thr Gln Lys Pro
            260                 265                 270

Ile Asp Asn Gln Phe Leu Leu Lys Leu Gln Arg Met Pro Asn Val Ile
        275                 280                 285

Ile Thr Pro His Thr Ala Tyr Tyr Thr Glu Gln Ala Leu Arg Asp Thr
    290                 295                 300

Val Glu Lys Thr Ile Lys Asn Cys Leu Asp Phe Glu Arg Arg Gln Glu
305                 310                 315                 320

His Glu
```

(2) INFORMATION FOR SEQ ID NO:3:

(i) SEQUENCE CHARACTERISTICS:
(A) LENGTH: 1029 base pairs

-continued

```
         (B) TYPE: nucleic acid
         (C) STRANDEDNESS: unknown
         (D) TOPOLOGY: linear

    (ii) MOLECULE TYPE: DNA (genomic)

    (ix) FEATURE:
         (A) NAME/KEY: CDS
         (B) LOCATION: 1..1029

    (xi) SEQUENCE DESCRIPTION: SEQ ID NO:3:

ATG AAT AGA ATA AAA GTT GCA ATA CTG TTT GGG GGT TGC TCA GAG GAG       48
Met Asn Arg Ile Lys Val Ala Ile Leu Phe Gly Gly Cys Ser Glu Glu
  1               5                  10                  15

CAT GAC GTA TCG GTA AAA TCT GCA ATA GAG ATA GCC GCT AAC ATT AAT       96
His Asp Val Ser Val Lys Ser Ala Ile Glu Ile Ala Ala Asn Ile Asn
             20                  25                  30

AAA GAA AAA TAC GAG CCG TTA TAC ATT GGA ATT ACG AAA TCT GGT GTA      144
Lys Glu Lys Tyr Glu Pro Leu Tyr Ile Gly Ile Thr Lys Ser Gly Val
         35                  40                  45

TGG AAA ATG TGC GAA AAA CCT TGC GCG GAA TGG GAA AAC GAC AAT TGC      192
Trp Lys Met Cys Glu Lys Pro Cys Ala Glu Trp Glu Asn Asp Asn Cys
     50                  55                  60

TAT TCA GCT GTA CTC TCG CCG GAT AAA AAA ATG CAC GGA TTA CTT GTT      240
Tyr Ser Ala Val Leu Ser Pro Asp Lys Lys Met His Gly Leu Leu Val
 65                  70                  75                  80

AAA AAG AAC CAT GAA TAT GAA ATC AAC CAT GTT GAT GTA GCA TTT TCA      288
Lys Lys Asn His Glu Tyr Glu Ile Asn His Val Asp Val Ala Phe Ser
                 85                  90                  95

GCT TTG CAT GGC AAG TCA GGT GAA GAT GGA TCC ATA CAA GGT CTG TTT      336
Ala Leu His Gly Lys Ser Gly Glu Asp Gly Ser Ile Gln Gly Leu Phe
            100                 105                 110

GAA TTG TCC GGT ATC CCT TTT GTA GGC TGC GAT ATT CAA AGC TCA GCA      384
Glu Leu Ser Gly Ile Pro Phe Val Gly Cys Asp Ile Gln Ser Ser Ala
        115                 120                 125

ATT TGT ATG GAC AAA TCG TTG ACA TAC ATC GTT GCG AAA AAT GCT GGG      432
Ile Cys Met Asp Lys Ser Leu Thr Tyr Ile Val Ala Lys Asn Ala Gly
    130                 135                 140

ATA GCT ACT CCC GCC TTT TGG GTT ATT AAT AAA GAT GAT AGG CCG GTG      480
Ile Ala Thr Pro Ala Phe Trp Val Ile Asn Lys Asp Asp Arg Pro Val
145                 150                 155                 160

GCA GCT ACG TTT ACC TAT CCT GTT TTT GTT AAG CCG GCG CGT TCA GGC      528
Ala Ala Thr Phe Thr Tyr Pro Val Phe Val Lys Pro Ala Arg Ser Gly
                165                 170                 175

TCA TCC TTC GGT GTG AAA AAA GTC AAT AGC GCG GAC GAA TTG GAC TAC      576
Ser Ser Phe Gly Val Lys Lys Val Asn Ser Ala Asp Glu Leu Asp Tyr
            180                 185                 190

GCA ATT GAA TCG GCA AGA CAA TAT GAC AGC AAA ATC TTA ATT GAG CAG      624
Ala Ile Glu Ser Ala Arg Gln Tyr Asp Ser Lys Ile Leu Ile Glu Gln
        195                 200                 205

GCT GTT TCG GGC TGT GAG GTC GGT TGT GCG GTA TTG GGA AAC AGT GCC      672
Ala Val Ser Gly Cys Glu Val Gly Cys Ala Val Leu Gly Asn Ser Ala
    210                 215                 220

GCG TTA GTT GTT GGC GAG GTG GAC CAA ATC AGG CTG CAG TAC GGA ATC      720
Ala Leu Val Val Gly Glu Val Asp Gln Ile Arg Leu Gln Tyr Gly Ile
225                 230                 235                 240

TTT CGT ATT CAT CAG GAA GTC GAG CCG GAA AAA GGC TCT GAA AAC GCA      768
Phe Arg Ile His Gln Glu Val Glu Pro Glu Lys Gly Ser Glu Asn Ala
                245                 250                 255

GTT ATA ACC GTT CCC GCA GAC CTT TCA GCA GAG GAG CGA GGA CGG ATA      816
Val Ile Thr Val Pro Ala Asp Leu Ser Ala Glu Glu Arg Gly Arg Ile
            260                 265                 270
```

-continued

```
CAG GAA ACG GCA AAA AAA ATA TAT AAA GCG CTC GGC TGT AGA GGT CTA      864
Gln Glu Thr Ala Lys Lys Ile Tyr Lys Ala Leu Gly Cys Arg Gly Leu
        275                 280                 285

GCC CGT GTG GAT ATG TTT TTA CAA GAT AAC GGC CGC ATT GTA CTG AAC      912
Ala Arg Val Asp Met Phe Leu Gln Asp Asn Gly Arg Ile Val Leu Asn
    290                 295                 300

GAA GTC AAT ACT CTG CCC GGT TTC ACG TCA TAC AGT CGT TAT CCC CGT      960
Glu Val Asn Thr Leu Pro Gly Phe Thr Ser Tyr Ser Arg Tyr Pro Arg
305                 310                 315                 320

ATG ATG GCC GCT GCA GGT ATT GCA CTT CCC GAA CTG ATT GAC CGC TTG     1008
Met Met Ala Ala Ala Gly Ile Ala Leu Pro Glu Leu Ile Asp Arg Leu
                325                 330                 335

ATC GTA TTA GCG TTA AAG GGG                                         1029
Ile Val Leu Ala Leu Lys Gly
            340
```

(2) INFORMATION FOR SEQ ID NO:4:

(i) SEQUENCE CHARACTERISTICS:
(A) LENGTH: 343 amino acids
(B) TYPE: amino acid
(D) TOPOLOGY: linear (ii) MOLECULE TYPE: protein (xi) SEQUENCE DESCRIPTION: SEQ ID NO:4:

```
Met Asn Arg Ile Lys Val Ala Ile Leu Phe Gly Gly Cys Ser Glu Glu
  1               5                  10                  15

His Asp Val Ser Val Lys Ser Ala Ile Glu Ile Ala Ala Asn Ile Asn
             20                  25                  30

Lys Glu Lys Tyr Glu Pro Leu Tyr Ile Gly Ile Thr Lys Ser Gly Val
        35                  40                  45

Trp Lys Met Cys Glu Lys Pro Cys Ala Glu Trp Glu Asn Asp Asn Cys
    50                  55                  60

Tyr Ser Ala Val Leu Ser Pro Asp Lys Lys Met His Gly Leu Leu Val
 65                  70                  75                  80

Lys Lys Asn His Glu Tyr Glu Ile Asn His Val Asp Val Ala Phe Ser
                 85                  90                  95

Ala Leu His Gly Lys Ser Gly Glu Asp Gly Ser Ile Gln Gly Leu Phe
             100                 105                 110

Glu Leu Ser Gly Ile Pro Phe Val Gly Cys Asp Ile Gln Ser Ser Ala
        115                 120                 125

Ile Cys Met Asp Lys Ser Leu Thr Tyr Ile Val Ala Lys Asn Ala Gly
    130                 135                 140

Ile Ala Thr Pro Ala Phe Trp Val Ile Asn Lys Asp Asp Arg Pro Val
145                 150                 155                 160

Ala Ala Thr Phe Thr Tyr Pro Val Phe Val Lys Pro Ala Arg Ser Gly
                165                 170                 175

Ser Ser Phe Gly Val Lys Lys Val Asn Ser Ala Asp Glu Leu Asp Tyr
            180                 185                 190

Ala Ile Glu Ser Ala Arg Gln Tyr Asp Ser Lys Ile Leu Ile Glu Gln
        195                 200                 205

Ala Val Ser Gly Cys Glu Val Gly Cys Ala Val Leu Gly Asn Ser Ala
    210                 215                 220

Ala Leu Val Val Gly Glu Val Asp Gln Ile Arg Leu Gln Tyr Gly Ile
225                 230                 235                 240

Phe Arg Ile His Gln Glu Val Glu Pro Glu Lys Gly Ser Glu Asn Ala
```

```
              245                 250                 255

Val Ile Thr Val Pro Ala Asp Leu Ser Ala Glu Glu Arg Gly Arg Ile
            260                 265                 270

Gln Glu Thr Ala Lys Lys Ile Tyr Lys Ala Leu Gly Cys Arg Gly Leu
        275                 280                 285

Ala Arg Val Asp Met Phe Leu Gln Asp Asn Gly Arg Ile Val Leu Asn
    290                 295                 300

Glu Val Asn Thr Leu Pro Gly Phe Thr Ser Tyr Ser Arg Tyr Pro Arg
305                 310                 315                 320

Met Met Ala Ala Ala Gly Ile Ala Leu Pro Glu Leu Ile Asp Arg Leu
                325                 330                 335

Ile Val Leu Ala Leu Lys Gly
            340
```

(2) INFORMATION FOR SEQ ID NO:5:

(i) SEQUENCE CHARACTERISTICS:
(A) LENGTH: 606 base pairs
(B) TYPE: nucleic acid
(C) STRANDEDNESS: unknown
(D) TOPOLOGY: linear (ii) MOLECULE TYPE: DNA (genomic)

(ix) FEATURE:
(A) NAME/KEY: CDS
(B) LOCATION: 1..606

(xi) SEQUENCE DESCRIPTION: SEQ ID NO:5:

```
ATG GAA ATA GGA TTT ACT TTT TTA GAT GAA ATA GTA CAC GGT GTT CGT        48
Met Glu Ile Gly Phe Thr Phe Leu Asp Glu Ile Val His Gly Val Arg
  1               5                  10                  15

TGG GAC GCT AAA TAT GCC ACT TGG GAT AAT TTC ACC GGA AAA CCG GTT        96
Trp Asp Ala Lys Tyr Ala Thr Trp Asp Asn Phe Thr Gly Lys Pro Val
             20                  25                  30

GAC GGT TAT GAA GTA AAT CGC ATT GTA GGG ACA TAC GAG TTG GCT GAA       144
Asp Gly Tyr Glu Val Asn Arg Ile Val Gly Thr Tyr Glu Leu Ala Glu
         35                  40                  45

TCG CTT TTG AAG GCA AAA GAA CTG GCT GCT ACC CAA GGG TAC GGA TTG       192
Ser Leu Leu Lys Ala Lys Glu Leu Ala Ala Thr Gln Gly Tyr Gly Leu
     50                  55                  60

CTT CTA TGG GAC GGT TAC CGT CCT AAG CGT GCT GTA AAC TGT TTT ATG       240
Leu Leu Trp Asp Gly Tyr Arg Pro Lys Arg Ala Val Asn Cys Phe Met
 65                  70                  75                  80

CAA TGG GCT GCA CAG CCG GAA AAT AAC CTG ACA AAG GAA AGT TAT TAT       288
Gln Trp Ala Ala Gln Pro Glu Asn Asn Leu Thr Lys Glu Ser Tyr Tyr
                 85                  90                  95

CCC AAT ATT GAC CGA ACT GAG ATG ATT TCA AAA GGA TAC GTG GCT TCA       336
Pro Asn Ile Asp Arg Thr Glu Met Ile Ser Lys Gly Tyr Val Ala Ser
            100                 105                 110

AAA TCA AGC CAT AGC CGC GGC AGT GCC ATT GAT CTT ACG CTT TAT CGA       384
Lys Ser Ser His Ser Arg Gly Ser Ala Ile Asp Leu Thr Leu Tyr Arg
        115                 120                 125

TTA GAC ACG GGT GAG CTT GTA CCA ATG GGG AGC CGA TTT GAT TTT ATG       432
Leu Asp Thr Gly Glu Leu Val Pro Met Gly Ser Arg Phe Asp Phe Met
    130                 135                 140

GAT GAA CGC TCT CAT CAT GCG GCA AAT GGA ATA TCA TGC AAT GAA GCG       480
Asp Glu Arg Ser His His Ala Ala Asn Gly Ile Ser Cys Asn Glu Ala
145                 150                 155                 160

CAA AAT CGC AGA CGT TTG CGC TCC ATC ATG GAA AAC AGT GGG TTT GAA       528
Gln Asn Arg Arg Arg Leu Arg Ser Ile Met Glu Asn Ser Gly Phe Glu
```

```
            165                 170                 175

GCA TAT AGC CTC GAA TGG TGG CAC TAT GTA TTA AGA GAC GAA CCA TAC       576
Ala Tyr Ser Leu Glu Trp Trp His Tyr Val Leu Arg Asp Glu Pro Tyr
            180                 185                 190

CCC AAT AGC TAT TTT GAT TTC CCC GTT AAA                               606
Pro Asn Ser Tyr Phe Asp Phe Pro Val Lys
        195                 200
```

(2) INFORMATION FOR SEQ ID NO:6:

(i) SEQUENCE CHARACTERISTICS:
(A) LENGTH: 202 amino acids
(B) TYPE: amino acid
(D) TOPOLOGY: linear (ii) MOLECULE TYPE: protein (xi) SEQUENCE DESCRIPTION: SEQ ID NO:6:

```
Met Glu Ile Gly Phe Thr Phe Leu Asp Glu Ile Val His Gly Val Arg
  1               5                  10                  15

Trp Asp Ala Lys Tyr Ala Thr Trp Asp Asn Phe Thr Gly Lys Pro Val
             20                  25                  30

Asp Gly Tyr Glu Val Asn Arg Ile Val Gly Thr Tyr Glu Leu Ala Glu
         35                  40                  45

Ser Leu Leu Lys Ala Lys Glu Leu Ala Ala Thr Gln Gly Tyr Gly Leu
     50                  55                  60

Leu Leu Trp Asp Gly Tyr Arg Pro Lys Arg Ala Val Asn Cys Phe Met
 65                  70                  75                  80

Gln Trp Ala Ala Gln Pro Glu Asn Asn Leu Thr Lys Glu Ser Tyr Tyr
                 85                  90                  95

Pro Asn Ile Asp Arg Thr Glu Met Ile Ser Lys Gly Tyr Val Ala Ser
            100                 105                 110

Lys Ser Ser His Ser Arg Gly Ser Ala Ile Asp Leu Thr Leu Tyr Arg
        115                 120                 125

Leu Asp Thr Gly Glu Leu Val Pro Met Gly Ser Arg Phe Asp Phe Met
    130                 135                 140

Asp Glu Arg Ser His His Ala Ala Asn Gly Ile Ser Cys Asn Glu Ala
145                 150                 155                 160

Gln Asn Arg Arg Arg Leu Arg Ser Ile Met Glu Asn Ser Gly Phe Glu
                165                 170                 175

Ala Tyr Ser Leu Glu Trp Trp His Tyr Val Leu Arg Asp Glu Pro Tyr
            180                 185                 190

Pro Asn Ser Tyr Phe Asp Phe Pro Val Lys
        195                 200
```

(2) INFORMATION FOR SEQ ID NO:7:

(i) SEQUENCE CHARACTERISTICS:
(A) LENGTH: 1347 base pairs
(B) TYPE: nucleic acid
(C) STRANDEDNESS: unknown
(D) TOPOLOGY: unknown (ii) MOLECULE TYPE: DNA (genomic)

(ix) FEATURE:
(A) NAME/KEY: CDS
(B) LOCATION: 215..1243

(xi) SEQUENCE DESCRIPTION: SEQ ID NO:7:

```
GAGCTCTTCC TTCAACGCAC TTCTGTACCA AGAGTTGTTG TCCATTTGAT CACTAACAAT     60
```

-continued

```
AGCTTCCCCT GCTTTCTTCA AGCCCTTTGT CATAAAATCG TTAGATTTTC ATCATAAAAA    120

TACGAGAAAG ACAACAGGAA GACCGCAAAT TTTCTTTTCT TTTCCTAGGT ACACTGAATG    180

TAACCTTAAA AGAAAAAAGG AAAGGAAGAA AATG ATG AAA AAA ATT GCC GTT       232
                                      Met Lys Lys Ile Ala Val
                                        1               5

TTA TTT GGA GGG AAT TCT CCA GAA TAC TCA GTG TCA CTA ACC TCA GCA      280
Leu Phe Gly Gly Asn Ser Pro Glu Tyr Ser Val Ser Leu Thr Ser Ala
             10                  15                  20

GCA AGT GTG ATC CAA GCT ATT GAC CCG CTG AAA TAT GAA GTA ATG ACC      328
Ala Ser Val Ile Gln Ala Ile Asp Pro Leu Lys Tyr Glu Val Met Thr
        25                  30                  35

ATT GGC ATC GCA CCA ACA ATG GAT TGG TAT TGG TAT CAA GGA AAC CTC      376
Ile Gly Ile Ala Pro Thr Met Asp Trp Tyr Trp Tyr Gln Gly Asn Leu
    40                  45                  50

GCG AAT GTT CGC AAT GAT ACT TGG CTA GAA GAT CAC AAA AAC TGT CAC      424
Ala Asn Val Arg Asn Asp Thr Trp Leu Glu Asp His Lys Asn Cys His
 55                  60                  65                  70

CAG CTG ACT TTT TCT AGC CAA GGA TTT ATA TTA GGA GAA AAA CGA ATC      472
Gln Leu Thr Phe Ser Ser Gln Gly Phe Ile Leu Gly Glu Lys Arg Ile
                 75                  80                  85

GTC CCT GAT GTC CTC TTT CCA GTC TTG CAT GGG AAG TAT GGC GAG GAT      520
Val Pro Asp Val Leu Phe Pro Val Leu His Gly Lys Tyr Gly Glu Asp
             90                  95                 100

GGC TGT ATC CAA GGA CTG CTT GAA CTA ATG AAC CTG CCT TAT GTT GGT      568
Gly Cys Ile Gln Gly Leu Leu Glu Leu Met Asn Leu Pro Tyr Val Gly
        105                 110                 115

TGC CAT GTC GCT GCC TCC GCA TTA TGT ATG AAC AAA TGG CTC TTG CAT      616
Cys His Val Ala Ala Ser Ala Leu Cys Met Asn Lys Trp Leu Leu His
    120                 125                 130

CAA CTT GCT GAT ACC ATG GGA ATC GCT AGT GCT CCC ACT TTG CTT TTA      664
Gln Leu Ala Asp Thr Met Gly Ile Ala Ser Ala Pro Thr Leu Leu Leu
135                 140                 145                 150

TCC CGC TAT GAA AAC GAT CCT GCC ACA ATC GAT CGT TTT ATT CAA GAC      712
Ser Arg Tyr Glu Asn Asp Pro Ala Thr Ile Asp Arg Phe Ile Gln Asp
                155                 160                 165

CAT GGA TTC CCG ATC TTT ATC AAG CCG AAT GAA GCC GGT TCT TCA AAA      760
His Gly Phe Pro Ile Phe Ile Lys Pro Asn Glu Ala Gly Ser Ser Lys
            170                 175                 180

GGG ATC ACA AAA GTA ACT GAC AAA ACA GCG CTC CAA TCT GCA TTA ACG      808
Gly Ile Thr Lys Val Thr Asp Lys Thr Ala Leu Gln Ser Ala Leu Thr
        185                 190                 195

ACT GCT TTT GCT TAC GGT TCT ACT GTG TTG ATC CAA AAG GCG ATA GCG      856
Thr Ala Phe Ala Tyr Gly Ser Thr Val Leu Ile Gln Lys Ala Ile Ala
    200                 205                 210

GGT ATT GAA ATT GGC TGC GGC ATC TTA GGA AAT GAG CAA TTG ACG ATT      904
Gly Ile Glu Ile Gly Cys Gly Ile Leu Gly Asn Glu Gln Leu Thr Ile
215                 220                 225                 230

GGT GCT TGT GAT GCG ATT TCT CTT GTC GAC GGT TTT TTT GAT TTT GAA      952
Gly Ala Cys Asp Ala Ile Ser Leu Val Asp Gly Phe Phe Asp Phe Glu
                235                 240                 245

GAG AAA TAC CAA TTA ATC AGC GCC ACG ATC ACT GTC CCA GCA CCA TTG     1000
Glu Lys Tyr Gln Leu Ile Ser Ala Thr Ile Thr Val Pro Ala Pro Leu
            250                 255                 260

CCT CTC GCG CTT GAA TCA CAG ATC AAG GAG CAG GCA CAG CTG CTT TAT     1048
Pro Leu Ala Leu Glu Ser Gln Ile Lys Glu Gln Ala Gln Leu Leu Tyr
        265                 270                 275

CGA AAC TTG GGA TTG ACG GGT CTG GCT CGA ATC GAT TTT TTC GTC ACC     1096
Arg Asn Leu Gly Leu Thr Gly Leu Ala Arg Ile Asp Phe Phe Val Thr
```

-continued

```
    280                 285                 290

AAT CAA GGA GCG ATT TAT TTA AAC GAA ATC AAC ACC ATG CCG GGA TTT      1144
Asn Gln Gly Ala Ile Tyr Leu Asn Glu Ile Asn Thr Met Pro Gly Phe
295                 300                 305                 310

ACT GGG CAC TCC CGC TAC CCA GCT ATG ATG GCG GAA GTC GGG TTA TCC      1192
Thr Gly His Ser Arg Tyr Pro Ala Met Met Ala Glu Val Gly Leu Ser
                315                 320                 325

TAC GAA ATA TTA GTA GAG CAA TTG ATT GCA CTG GCA GAG GAG GAC AAA      1240
Tyr Glu Ile Leu Val Glu Gln Leu Ile Ala Leu Ala Glu Glu Asp Lys
            330                 335                 340

CGA TGAACACATT ACAATTGATC AATAAAAACC ATCCATTGAA AAAAAATCAA           1293
Arg

GAGCCCCCGC ACTTAGTGCT AGCTCCTTTT AGCGATCACG ATGTTTACCT GCAG          1347
```

(2) INFORMATION FOR SEQ ID NO:8:

(i) SEQUENCE CHARACTERISTICS:
(A) LENGTH: 343 amino acids
(B) TYPE: amino acid
(D) TOPOLOGY: linear (ii) MOLECULE TYPE: protein (xi) SEQUENCE DESCRIPTION: SEQ ID NO:8:

```
Met Lys Lys Ile Ala Val Leu Phe Gly Gly Asn Ser Pro Glu Tyr Ser
  1               5                  10                  15

Val Ser Leu Thr Ser Ala Ala Ser Val Ile Gln Ala Ile Asp Pro Leu
             20                  25                  30

Lys Tyr Glu Val Met Thr Ile Gly Ile Ala Pro Thr Met Asp Trp Tyr
         35                  40                  45

Trp Tyr Gln Gly Asn Leu Ala Asn Val Arg Asn Asp Thr Trp Leu Glu
     50                  55                  60

Asp His Lys Asn Cys His Gln Leu Thr Phe Ser Ser Gln Gly Phe Ile
 65                  70                  75                  80

Leu Gly Glu Lys Arg Ile Val Pro Asp Val Leu Phe Pro Val Leu His
                 85                  90                  95

Gly Lys Tyr Gly Glu Asp Gly Cys Ile Gln Gly Leu Leu Glu Leu Met
            100                 105                 110

Asn Leu Pro Tyr Val Gly Cys His Val Ala Ala Ser Ala Leu Cys Met
        115                 120                 125

Asn Lys Trp Leu Leu His Gln Leu Ala Asp Thr Met Gly Ile Ala Ser
    130                 135                 140

Ala Pro Thr Leu Leu Leu Ser Arg Tyr Glu Asn Asp Pro Ala Thr Ile
145                 150                 155                 160

Asp Arg Phe Ile Gln Asp His Gly Phe Pro Ile Phe Ile Lys Pro Asn
                165                 170                 175

Glu Ala Gly Ser Ser Lys Gly Ile Thr Lys Val Thr Asp Lys Thr Ala
            180                 185                 190

Leu Gln Ser Ala Leu Thr Thr Ala Phe Ala Tyr Gly Ser Thr Val Leu
        195                 200                 205

Ile Gln Lys Ala Ile Ala Gly Ile Glu Ile Gly Cys Gly Ile Leu Gly
    210                 215                 220

Asn Glu Gln Leu Thr Ile Gly Ala Cys Asp Ala Ile Ser Leu Val Asp
225                 230                 235                 240

Gly Phe Phe Asp Phe Glu Glu Lys Tyr Gln Leu Ile Ser Ala Thr Ile
                245                 250                 255
```

-continued

```
Thr Val Pro Ala Pro Leu Pro Leu Ala Leu Glu Ser Gln Ile Lys Glu
            260                 265                 270

Gln Ala Gln Leu Leu Tyr Arg Asn Leu Gly Leu Thr Gly Leu Ala Arg
        275                 280                 285

Ile Asp Phe Phe Val Thr Asn Gln Gly Ala Ile Tyr Leu Asn Glu Ile
    290                 295                 300

Asn Thr Met Pro Gly Phe Thr Gly His Ser Arg Tyr Pro Ala Met Met
305                 310                 315                 320

Ala Glu Val Gly Leu Ser Tyr Glu Ile Leu Val Glu Gln Leu Ile Ala
                325                 330                 335

Leu Ala Glu Glu Asp Lys Arg
            340
```

(2) INFORMATION FOR SEQ ID NO:9:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

```
GGNGARGAYG GNWSNHTNCA RGGN                                            24
```

(2) INFORMATION FOR SEQ ID NO:10:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:10:

```
AAYACNHTNC CNGGNTTYAC                                                 20
```

(2) INFORMATION FOR SEQ ID NO:11:

(i) SEQUENCE CHARACTERISTICS:
(A) LENGTH: 693 base pairs
(B) TYPE: nucleic acid
(C) STRANDEDNESS: unknown
(D) TOPOLOGY: linear (ii) MOLECULE TYPE: DNA (genomic)

(ix) FEATURE:
(A) NAME/KEY: CDS
(B) LOCATION: 1..693

(xi) SEQUENCE DESCRIPTION: SEQ ID NO:11:

```
ATG AGC GAT AAA ATA CTT ATT GTG GAT GAT GAA CAT GAA ATT GCC GAT       48
Met Ser Asp Lys Ile Leu Ile Val Asp Asp Glu His Glu Ile Ala Asp
  1               5                  10                  15

TTG GTT GAA TTA TAC TTA AAA AAC GAG AAT TAT ACG GTT TTC AAA TAC       96
Leu Val Glu Leu Tyr Leu Lys Asn Glu Asn Tyr Thr Val Phe Lys Tyr
             20                  25                  30

TAT ACC GCC AAA GAA GCA TTG GAA TGT ATA GAC AAG TCT GAG ATT GAC      144
Tyr Thr Ala Lys Glu Ala Leu Glu Cys Ile Asp Lys Ser Glu Ile Asp
         35                  40                  45

CTT GCC ATA TTG GAC ATC ATG CTT CCC GGC ACA AGC GGC CTT ACT ATC      192
Leu Ala Ile Leu Asp Ile Met Leu Pro Gly Thr Ser Gly Leu Thr Ile
```

-continued

```
     50                  55                  60

TGT CAA AAA ATA AGG GAC AAG CAC ACC TAT CCG ATT ATC ATG CTG ACC      240
Cys Gln Lys Ile Arg Asp Lys His Thr Tyr Pro Ile Ile Met Leu Thr
 65                  70                  75                  80

GGG AAA GAT ACA GAG GTA GAT AAA ATT ACA GGG TTA ACA ATC GGC GCG      288
Gly Lys Asp Thr Glu Val Asp Lys Ile Thr Gly Leu Thr Ile Gly Ala
                 85                  90                  95

GAT GAT TAT ATA ACG AAG CCC TTT CGC CCA CTG GAG TTA ATT GCT CGG      336
Asp Asp Tyr Ile Thr Lys Pro Phe Arg Pro Leu Glu Leu Ile Ala Arg
            100                 105                 110

GTA AAG GCC CAG TTG CGC CGA TAC AAA AAA TTC AGT GGA GTA AAG GAG      384
Val Lys Ala Gln Leu Arg Arg Tyr Lys Lys Phe Ser Gly Val Lys Glu
        115                 120                 125

CAG AAC GAA AAT GTT ATC GTC CAC TCC GGC CTT GTC ATT AAT GTT AAC      432
Gln Asn Glu Asn Val Ile Val His Ser Gly Leu Val Ile Asn Val Asn
    130                 135                 140

ACC CAT GAG TGT TAT CTG AAC GAG AAG CAG TTA TCC CTT ACT CCC ACC      480
Thr His Glu Cys Tyr Leu Asn Glu Lys Gln Leu Ser Leu Thr Pro Thr
145                 150                 155                 160

GAG TTT TCA ATA CTG CGA ATC CTC TGT GAA AAC AAG GGG AAT GTG GTT      528
Glu Phe Ser Ile Leu Arg Ile Leu Cys Glu Asn Lys Gly Asn Val Val
                165                 170                 175

AGC TCC GAG CTG CTA TTT CAT GAG ATA TGG GGC GAC GAA TAT TTC AGC      576
Ser Ser Glu Leu Leu Phe His Glu Ile Trp Gly Asp Glu Tyr Phe Ser
            180                 185                 190

AAG AGC AAC AAC ACC ATC ACC GTG CAT ATC CGG CAT TTG CGC GAA AAA      624
Lys Ser Asn Asn Thr Ile Thr Val His Ile Arg His Leu Arg Glu Lys
        195                 200                 205

ATG AAC GAC ACC ATT GAT AAT CCG AAA TAT ATA AAA ACG GTA TGG GGG      672
Met Asn Asp Thr Ile Asp Asn Pro Lys Tyr Ile Lys Thr Val Trp Gly
    210                 215                 220

GTT GGT TAT AAA ATT GAA AAA                                          693
Val Gly Tyr Lys Ile Glu Lys
225                 230
```

(2) INFORMATION FOR SEQ ID NO:12:

(i) SEQUENCE CHARACTERISTICS:
(A) LENGTH: 231 amino acids
(B) TYPE: amino acid
(D) TOPOLOGY: linear (ii) MOLECULE TYPE: protein (xi) SEQUENCE DESCRIPTION: SEQ ID NO:12:

```
Met Ser Asp Lys Ile Leu Ile Val Asp Asp Glu His Glu Ile Ala Asp
  1               5                  10                  15

Leu Val Glu Leu Tyr Leu Lys Asn Glu Asn Tyr Thr Val Phe Lys Tyr
             20                  25                  30

Tyr Thr Ala Lys Glu Ala Leu Glu Cys Ile Asp Lys Ser Glu Ile Asp
         35                  40                  45

Leu Ala Ile Leu Asp Ile Met Leu Pro Gly Thr Ser Gly Leu Thr Ile
     50                  55                  60

Cys Gln Lys Ile Arg Asp Lys His Thr Tyr Pro Ile Ile Met Leu Thr
 65                  70                  75                  80

Gly Lys Asp Thr Glu Val Asp Lys Ile Thr Gly Leu Thr Ile Gly Ala
                 85                  90                  95

Asp Asp Tyr Ile Thr Lys Pro Phe Arg Pro Leu Glu Leu Ile Ala Arg
            100                 105                 110
```

-continued

```
Val Lys Ala Gln Leu Arg Arg Tyr Lys Lys Phe Ser Gly Val Lys Glu
        115                 120                 125

Gln Asn Glu Asn Val Ile Val His Ser Gly Leu Val Ile Asn Val Asn
    130                 135                 140

Thr His Glu Cys Tyr Leu Asn Glu Lys Gln Leu Ser Leu Thr Pro Thr
145                 150                 155                 160

Glu Phe Ser Ile Leu Arg Ile Leu Cys Glu Asn Lys Gly Asn Val Val
                165                 170                 175

Ser Ser Glu Leu Leu Phe His Glu Ile Trp Gly Asp Glu Tyr Phe Ser
            180                 185                 190

Lys Ser Asn Asn Thr Ile Thr Val His Ile Arg His Leu Arg Glu Lys
        195                 200                 205

Met Asn Asp Thr Ile Asp Asn Pro Lys Tyr Ile Lys Thr Val Trp Gly
    210                 215                 220

Val Gly Tyr Lys Ile Glu Lys
225                 230
```

(2) INFORMATION FOR SEQ ID NO:13:

(i) SEQUENCE CHARACTERISTICS:
(A) LENGTH: 1152 base pairs
(B) TYPE: nucleic acid
(C) STRANDEDNESS: unknown
(D) TOPOLOGY: linear (ii) MOLECULE TYPE: DNA (genomic)

(ix) FEATURE:
(A) NAME/KEY: CDS
(B) LOCATION: 1..1152

(xi) SEQUENCE DESCRIPTION: SEQ ID NO:13:

```
TTG GTT ATA AAA TTG AAA AAT AAA AAA AAC GAC TAT TCC AAA CTA GAA       48
Leu Val Ile Lys Leu Lys Asn Lys Lys Asn Asp Tyr Ser Lys Leu Glu
  1               5                  10                  15

CGA AAA CTT TAC ATG TAT ATC GTT GCA ATT GTT GTG GTA GCA ATT GTA       96
Arg Lys Leu Tyr Met Tyr Ile Val Ala Ile Val Val Val Ala Ile Val
             20                  25                  30

TTC GTG TTG TAT ATT CGT TCA ATG ATC CGA GGG AAA CTT GGG GAT TGG      144
Phe Val Leu Tyr Ile Arg Ser Met Ile Arg Gly Lys Leu Gly Asp Trp
         35                  40                  45

ATC TTA AGT ATT TTG GAA AAC AAA TAT GAC TTA AAT CAC CTG GAC GCG      192
Ile Leu Ser Ile Leu Glu Asn Lys Tyr Asp Leu Asn His Leu Asp Ala
     50                  55                  60

ATG AAA TTA TAT CAA TAT TCC ATA CGG AAC AAT ATA GAT ATC TTT ATT      240
Met Lys Leu Tyr Gln Tyr Ser Ile Arg Asn Asn Ile Asp Ile Phe Ile
 65                  70                  75                  80

TAT GTG GCG ATT GTC ATT AGT ATT CTT ATT CTA TGT CGC GTC ATG CTT      288
Tyr Val Ala Ile Val Ile Ser Ile Leu Ile Leu Cys Arg Val Met Leu
                 85                  90                  95

TCA AAA TTC GCA AAA TAC TTT GAC GAG ATA AAT ACC GGC ATT GAT GTA      336
Ser Lys Phe Ala Lys Tyr Phe Asp Glu Ile Asn Thr Gly Ile Asp Val
            100                 105                 110

CTT ATT CAG AAC GAA GAT AAA CAA ATT GAG CTT TCT GCG GAA ATG GAT      384
Leu Ile Gln Asn Glu Asp Lys Gln Ile Glu Leu Ser Ala Glu Met Asp
        115                 120                 125

GTT ATG GAA CAA AAG CTC AAC ACA TTA AAA CGG ACT CTG GAA AAG CGA      432
Val Met Glu Gln Lys Leu Asn Thr Leu Lys Arg Thr Leu Glu Lys Arg
    130                 135                 140

GAG CAG GAT GCA AAG CTG GCC GAA CAA AGA AAA AAT GAC GTT GTT ATG      480
Glu Gln Asp Ala Lys Leu Ala Glu Gln Arg Lys Asn Asp Val Val Met
```

-continued

```
145                 150                 155                 160

TAC TTG GCG CAC GAT ATT AAA ACG CCC CTT ACA TCC ATT ATC GGT TAT      528
Tyr Leu Ala His Asp Ile Lys Thr Pro Leu Thr Ser Ile Ile Gly Tyr
                165                 170                 175

TTG AGC CTG CTT GAC GAG GCT CCA GAC ATG CCG GTA GAT CAA AAG GCA      576
Leu Ser Leu Leu Asp Glu Ala Pro Asp Met Pro Val Asp Gln Lys Ala
            180                 185                 190

AAG TAT GTG CAT ATC ACG TTG GAC AAA GCG TAT CGA CTC GAA CAG CTA      624
Lys Tyr Val His Ile Thr Leu Asp Lys Ala Tyr Arg Leu Glu Gln Leu
        195                 200                 205

ATC GAC GAG TTT TTT GAG ATT ACA CGG TAT AAC CTA CAA ACG ATA ACG      672
Ile Asp Glu Phe Phe Glu Ile Thr Arg Tyr Asn Leu Gln Thr Ile Thr
    210                 215                 220

CTA ACA AAA ACG CAC ATA GAC CTA TAC TAT ATG CTG GTG CAG ATG ACC      720
Leu Thr Lys Thr His Ile Asp Leu Tyr Tyr Met Leu Val Gln Met Thr
225                 230                 235                 240

GAT GAA TTT TAT CCT CAG CTT TCC GCA CAT GGA AAA CAG GCG GTT ATT      768
Asp Glu Phe Tyr Pro Gln Leu Ser Ala His Gly Lys Gln Ala Val Ile
                245                 250                 255

CAC GCC CCC GAG GAT CTG ACC GTG TCC GGC GAC CCT GAT AAA CTC GCG      816
His Ala Pro Glu Asp Leu Thr Val Ser Gly Asp Pro Asp Lys Leu Ala
            260                 265                 270

AGA GTC TTT AAC AAC ATT TTG AAA AAC GCC GCT GCA TAC AGT GAG GAT      864
Arg Val Phe Asn Asn Ile Leu Lys Asn Ala Ala Ala Tyr Ser Glu Asp
        275                 280                 285

AAC AGC ATC ATT GAC ATT ACC GCG GGC CTC TCC GGG GAT GTG GTG TCA      912
Asn Ser Ile Ile Asp Ile Thr Ala Gly Leu Ser Gly Asp Val Val Ser
    290                 295                 300

ATC GAA TTC AAG AAC ACT GGA AGC ATC CCA AAA GAT AAG CTA GCT GCC      960
Ile Glu Phe Lys Asn Thr Gly Ser Ile Pro Lys Asp Lys Leu Ala Ala
305                 310                 315                 320

ATA TTT GAA AAG TTC TAT AGG CTG GAC AAT GCT CGT TCT TCC GAT ACG     1008
Ile Phe Glu Lys Phe Tyr Arg Leu Asp Asn Ala Arg Ser Ser Asp Thr
                325                 330                 335

GGT GGC GCG GGA CTT GGA TTG GCG ATT GCA AAA GAA ATT ATT GTT CAG     1056
Gly Gly Ala Gly Leu Gly Leu Ala Ile Ala Lys Glu Ile Ile Val Gln
            340                 345                 350

CAT GGA GGG CAG ATT TAC GCG GAA AGC AAT GAT AAC TAT ACG ACG TTT     1104
His Gly Gly Gln Ile Tyr Ala Glu Ser Asn Asp Asn Tyr Thr Thr Phe
        355                 360                 365

AGG GTA GAG CTT CCA GCG ATG CCA GAC TTG GTT GAT AAA AGG AGG TCC     1152
Arg Val Glu Leu Pro Ala Met Pro Asp Leu Val Asp Lys Arg Arg Ser
    370                 375                 380
```

(2) INFORMATION FOR SEQ ID NO:14:

(i) SEQUENCE CHARACTERISTICS:
 (A) LENGTH: 384 amino acids
 (B) TYPE: amino acid
 (D) TOPOLOGY: linear (ii) MOLECULE TYPE: protein (xi) SEQUENCE DESCRIPTION: SEQ ID NO:14:

```
Leu Val Ile Lys Leu Lys Asn Lys Lys Asn Asp Tyr Ser Lys Leu Glu
  1               5                  10                  15

Arg Lys Leu Tyr Met Tyr Ile Val Ala Ile Val Val Val Ala Ile Val
             20                  25                  30

Phe Val Leu Tyr Ile Arg Ser Met Ile Arg Gly Lys Leu Gly Asp Trp
         35                  40                  45
```

-continued

```
Ile Leu Ser Ile Leu Glu Asn Lys Tyr Asp Leu Asn His Leu Asp Ala
     50                  55                  60

Met Lys Leu Tyr Gln Tyr Ser Ile Arg Asn Asn Ile Asp Ile Phe Ile
 65                  70                  75                  80

Tyr Val Ala Ile Val Ile Ser Ile Leu Ile Leu Cys Arg Val Met Leu
                 85                  90                  95

Ser Lys Phe Ala Lys Tyr Phe Asp Glu Ile Asn Thr Gly Ile Asp Val
            100                 105                 110

Leu Ile Gln Asn Glu Asp Lys Gln Ile Glu Leu Ser Ala Glu Met Asp
        115                 120                 125

Val Met Glu Gln Lys Leu Asn Thr Leu Lys Arg Thr Leu Glu Lys Arg
    130                 135                 140

Glu Gln Asp Ala Lys Leu Ala Glu Gln Arg Lys Asn Asp Val Val Met
145                 150                 155                 160

Tyr Leu Ala His Asp Ile Lys Thr Pro Leu Thr Ser Ile Ile Gly Tyr
                165                 170                 175

Leu Ser Leu Leu Asp Glu Ala Pro Asp Met Pro Val Asp Gln Lys Ala
            180                 185                 190

Lys Tyr Val His Ile Thr Leu Asp Lys Ala Tyr Arg Leu Glu Gln Leu
        195                 200                 205

Ile Asp Glu Phe Phe Glu Ile Thr Arg Tyr Asn Leu Gln Thr Ile Thr
    210                 215                 220

Leu Thr Lys Thr His Ile Asp Leu Tyr Tyr Met Leu Val Gln Met Thr
225                 230                 235                 240

Asp Glu Phe Tyr Pro Gln Leu Ser Ala His Gly Lys Gln Ala Val Ile
                245                 250                 255

His Ala Pro Glu Asp Leu Thr Val Ser Gly Asp Pro Asp Lys Leu Ala
            260                 265                 270

Arg Val Phe Asn Asn Ile Leu Lys Asn Ala Ala Ala Tyr Ser Glu Asp
        275                 280                 285

Asn Ser Ile Ile Asp Ile Thr Ala Gly Leu Ser Gly Asp Val Val Ser
    290                 295                 300

Ile Glu Phe Lys Asn Thr Gly Ser Ile Pro Lys Asp Lys Leu Ala Ala
305                 310                 315                 320

Ile Phe Glu Lys Phe Tyr Arg Leu Asp Asn Ala Arg Ser Ser Asp Thr
                325                 330                 335

Gly Gly Ala Gly Leu Gly Leu Ala Ile Ala Lys Glu Ile Ile Val Gln
            340                 345                 350

His Gly Gly Gln Ile Tyr Ala Glu Ser Asn Asp Asn Tyr Thr Thr Phe
        355                 360                 365

Arg Val Glu Leu Pro Ala Met Pro Asp Leu Val Asp Lys Arg Arg Ser
    370                 375                 380
```

(2) INFORMATION FOR SEQ ID NO:15:

(i) SEQUENCE CHARACTERISTICS:
(A) LENGTH: 7225 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO:15:

```
AAGCTTTTCT TTTTGCTCAT TTGTTAGAGA TTTACTAACC GTATTAAATA GCTTCTTTTC      60

AGCCATTGCC CTTGCTTCCC ACACCATTCT TTCAAGTGTA GTGATAGCAG GCAGTATAAT     120
```

-continued

```
TTTGTTTTTT CTTAGAAAAT CTATGCATTC ATGCAGTAGA TGAATGGCAT CACCATTTTC    180
CAAAGCTAAT TGATGAAGGT ACTTAAATGT CATTCGATAT TCACTCAGGG TAAAAGTTAC    240
AAAGTCGTAT TCACTTCGAA TTTCTTTCAA ATGATCCCAA AGTGTATTTT CCCTTTGAGG    300
ATAATGATCA AGCGAGGATG GACTAACACC AATCTGTTTC GATATATATT GTATGACCGA    360
ATCTGGGATG CTTTTGATAT GAGTGTATGG CCAACCGGGA TACCGAAGAA CAGCTAATTG    420
AACAGCAAAT CCTAAACGGT TTTCTTCCCT CCTTCGCTTA TTAACTATTT CTAAATCCCG    480
TTTGGAAAAA GTGAAGTAGG TCCCCAGTAT CCATTCATCT TCAGGGATTT GCATAAAAGC    540
CTGTCTCTGT TCCGGTGTAA GCAATTCTCT ACCTCTCGCA ATTTTCATTC AGTATCATTC    600
CATTTCTGTA TTTTCAATTT ATTAGTTCAA TTATATATCA ATAGAGTGTA CTCTATTGAT    660
ACAAATGTAG TAGACTGATA AAATCATAGT TAAGAGCGTC TCATAAGACT TGTCTCAAAA    720
ATGAGGTGAT ATTTTGCGGA AAATCGGTTA TATTCGTGTC AGTTCGACTA ACCAGAATCC    780
TTCAAGACAA TTTCAGCAGT TGAACGAGAT CGGAATGGAT ATTATATAAA GAGAAAGTTT    840
CAGGAGCAAC AAAGGATCGC GAGCAACTTC AAAAAGTGTT AGACGATTTA CAGGAAGATG    900
ACATCATTTA TGTTACAGAC TTAACTCGAA TCACTCGTAG TACACAAGAT CTATTTGAAT    960
TAATCGATAA CATACGAGAT AAAAAGGCAA GTTTAAAATC ACTAAAAGAT ACATGGCTTG   1020
ATTTATCAGA AGATAATCCA TACAGCCAAT TCTTAATTAC TGTAATGGCT GGTGTTAACC   1080
AATTAGAGCG AGATCTTATT CGGATGAGAC AACGTGAAGG GATTGAATTG GCTAAGAAAG   1140
AAGGAAAGTT TAAAGGTCGA TTAAAGAAGT ATCATAAAAA TCACGCAGGA ATGAATTATG   1200
CGGAAAGCTA TATAAAGAAG GAAATATGAC TGTAAATCAA ATTTGTGAAA TTACTAATGT   1260
ATCTAGGGCT TCATTATACA GGAAATTATC AGAAGTGAAT AATTAGCCAT TCTGTATTCC   1320
GCTAATGGGC AATATTTTTA AAGAAGAAAA GGAAACTATA AAATATTAAC AGCCTCCTAG   1380
CGATGCCGAA AAGCCCTTTG ATAAAAAAAG AATCATCATC TTAAGAAATT CTTAGTCATT   1440
TATTATGTAA ATGCTTATAA ATTCGGCCCT ATAATCTGAT AAATTATTAA GGGCAAACTT   1500
ATGTGAAAGG GTGATAACTA TGAGCGATAA AATACTTATT GTGGATGATG AACATGAAAT   1560
TGCCGATTTG GTTGAATTAT ACTTAAAAAA CGAGAATTAT ACGGTTTTCA AATACTATAC   1620
CGCCAAAGAA GCATTGGAAT GTATAGACAA GTCTGAGATT GACCTTGCCA TATTGGACAT   1680
CATGCTTCCC GGCACAAGCG GCCTTACTAT CTGTCAAAAA ATAAGGGACA AGCACACCTA   1740
TCCGATTATC ATGCTGACCG GGAAAGATAC AGAGGTAGAT AAAATTACAG GGTTAACAAT   1800
CGGCGCGGAT GATTATATAA CGAAGCCCTT TCGCCCACTG GAGTTAATTG CTCGGGTAAA   1860
GGCCCAGTTG CGCCGATACA AAAAATTCAG TGGAGTAAAG GAGCAGAACG AAAATGTTAT   1920
CGTCCACTCC GGCCTTGTCA TTAATGTTAA CACCCATGAG TGTTATCTGA ACGAGAAGCA   1980
GTTATCCCTT ACTCCCACCG AGTTTTCAAT ACTGCGAATC CTCTGTGAAA ACAAGGGGAA   2040
TGTGGTTAGC TCCGAGCTGC TATTTCATGA GATATGGGGC GACGAATATT TCAGCAAGAG   2100
CAACAACACC ATCACCGTGC ATATCCGGCA TTTGCGCGAA AAAATGAACG ACACCATTGA   2160
TAATCCGAAA TATATAAAAA CGGTATGGGG GGTTGGTTAT AAAATTGAAA AATAAAAAAA   2220
ACGACTATTC CAAACTAGAA CGAAAACTTT ACATGTATAT CGTTGCAATT GTTGTGGTAG   2280
CAATTGTATT CGTGTTGTAT ATTCGTTCAA TGATCCGAGG GAAACTTGGG GATTGGATCT   2340
TAAGTATTTT GGAAAACAAA TATGACTTAA ATCACCTGGA CGCGATGAAA TTATATCAAT   2400
ATTCCATACG GAACAATATA GATATCTTTA TTTATGTGGC GATTGTCATT AGTATTCTTA   2460
```

-continued

```
TTCTATGTCG CGTCATGCTT TCAAAATTCG CAAAATACTT TGACGAGATA AATACCGGCA   2520
TTGATGTACT TATTCAGAAC GAAGATAAAC AAATTGAGCT TTCTGCGGAA ATGGATGTTA   2580
TGGAACAAAA GCTCAACACA TTAAAACGGA CTCTGGAAAA GCGAGAGCAG GATGCAAAGC   2640
TGGCCGAACA AAGAAAAAAT GACGTTGTTA TGTACTTGGC GCACGATATT AAAACGCCCC   2700
TTACATCCAT TATCGGTTAT TTGAGCCTGC TTGACGAGGC TCCAGACATG CCGGTAGATC   2760
AAAAGGCAAA GTATGTGCAT ATCACGTTGG ACAAAGCGTA TCGACTCGAA CAGCTAATCG   2820
ACGAGTTTTT TGAGATTACA CGGTATAACC TACAAACGAT AACGCTAACA AAAACGCACA   2880
TAGACCTATA CTATATGCTG GTGCAGATGA CCGATGAATT TTATCCTCAG CTTTCCGCAC   2940
ATGGAAAACA GGCGGTTATT CACGCCCCCG AGGATCTGAC CGTGTCCGGC GACCCTGATA   3000
AACTCGCGAG AGTCTTTAAC AACATTTTGA AAAACGCCGC TGCATACAGT GAGGATAACA   3060
GCATCATTGA CATTACCGCG GGCCTCTCCG GGGATGTGGT GTCAATCGAA TTCAAGAACA   3120
CTGGAAGCAT CCCAAAAGAT AAGCTAGCTG CCATATTTGA AAAGTTCTAT AGGCTGGACA   3180
ATTCTCGTTC TTCCGATACG GGTGGCGCGG GACTTGGATT GGCGATTGCA AAAGAAATTA   3240
TTGTTCAGCA TGGAGGGCAG ATTTACGCGG AAAGCTATGA TAACTATACG ACGTTTAGGG   3300
TAGAGCTTCC AGCGATGCCA GACTTGGTTG ATAAAAGGAG GTCCTAAGAG ATGTATATAA   3360
TTTTTTAGGA AAATCTCAAG GTTATCTTTA CTTTTTCTTA GGAAATTAAC AATTTAATAT   3420
TAAGAAACGG CTCGTTCTTA CACGGTAGAC TTAATACCGT AAGAACGAGC CGTTTTCGTT   3480
CTTCAGAGAA AGATTTGACA AGATTACCAT TGGCATCCCC GTTTTATTTG GTGCCTTTCA   3540
CAGAAAGGGT TGGTCTTAAT TATGAATAAC ATCGGCATTA CTGTTTATGG ATGTGAGCAG   3600
GATGAGGCAG ATGCATTCCA TGCTCTTTCG CCTCGCTTTG GCGTTATGGC AACGATAATT   3660
AACGCCAACG TGTCGGAATC CAACGCCAAA TCCGCGCCTT TCAATCAATG TATCAGTGTG   3720
GGACATAAAT CAGAGATTTC CGCCTCTATT CTTCTTGCGC TGAAGAGAGC CGGTGTGAAA   3780
TATATTTCTA CCCGAAGCAT CGGCTGCAAT CATATAGATA CAACTGCTGC TAAGAGAATG   3840
GGCATCACTG TCGACAATGT GGCGTACTCG CCGGATAGCG TTGCCGATTA TACTATGATG   3900
CTAATTCTTA TGGCAGTACG CAACGTAAAA TCGATTGTGC GCTCTGTGGA AAAACATGAT   3960
TTCAGGTTGG ACAGCGACCG TGGCAAGGTA CTCAGCGACA TGACAGTTGG TGTGGTGGGA   4020
ACGGGCCAGA TAGGCAAAGC GGTTATTGAG CGGCTGCGAG GATTTGGATG TAAAGTGTTG   4080
GCTTATAGTC GCAGCCGAAG TATAGAGGTA AACTATGTAC CGTTTGATGA GTTGATGCAA   4140
AATAGCGATA TCGTTACGCT TCATGTGCCG CTCAATACGG ATACGCACTA TATTATCAGC   4200
CACGAACAAA TACAGAGAAT GAAGCAAGGA GCATTTCTTA TCAATACTGG GCGCGGTCCA   4260
CTTGTAGATA CCTATGAGTT GGTTAAAGCA TTAGAAAACG GAAACTGGG CGGTGCCGCA    4320
TTGGATGTAT TGGAAGGAGA GGAAGAGTTT TTCTACTCTG ATTGCACCCA AAAACCAATT   4380
GATAATCAAT TTTTACTTAA ACTTCAAAGA ATGCCTAACG TGATAATCAC ACCGCATACG   4440
GCCTATTATA CCGAGCAAGC GTTGCGTGAT ACCGTTGAAA AAACCATTAA AAACTGTTTG   4500
GATTTTGAAA GGAGACAGGA GCATGAATAG AATAAAAGTT GCAATACTGT TTGGGGGTTG   4560
CTCAGAGGAG CATGACGTAT CGGTAAAATC TGCAATAGAG ATAGCCGCTA ACATTAATAA   4620
AGAAAAATAC GAGCCGTTAT ACATTGGAAT TACGAAATCT GGTGTATGGA AAATGTGCGA   4680
AAAACCTTGC GCGGAATGGG AAAACGACAA TTGCTATTCA GCTGTACTCT CGCCGGATAA   4740
AAAAATGCAC GGATTACTTG TTAAAAAGAA CCATGAATAT GAAATCAACC ATGTTGATGT   4800
AGCATTTTCA GCTTTGCATG GCAAGTCAGG TGAAGATGGA TCCATACAAG GTCTGTTTGA   4860
```

-continued

```
ATTGTCCGGT ATCCCTTTTG TAGGCTGCGA TATTCAAAGC TCAGCAATTT GTATGGACAA   4920
ATCGTTGACA TACATCGTTG CGAAAAATGC TGGGATAGCT ACTCCCGCCT TTTGGGTTAT   4980
TAATAAAGAT GATAGGCCGG TGGCAGCTAC GTTTACCTAT CCTGTTTTTG TTAAGCCGGC   5040
GCGTTCAGGC TCATCCTTCG GTGTGAAAAA AGTCAATAGC GCGGACGAAT TGGACTACGC   5100
AATTGAATCG GCAAGACAAT ATGACAGCAA AATCTTAATT GAGCAGGCTG TTTCGGGCTG   5160
TGAGGTCGGT TGTGCGGTAT TGGGAAACAG TGCCGCGTTA GTTGTTGGCG AGGTGGACCA   5220
AATCAGGCTG CAGTACGGAA TCTTTCGTAT TCATCAGGAA GTCGAGCCGG AAAAAGGCTC   5280
TGAAAACGCA GTTATAACCG TTCCCGCAGA CCTTTCAGCA GAGGAGCGAG GACGGATACA   5340
GGAAACGGCA AAAAAAATAT ATAAAGCGCT CGGCTGTAGA GGTCTAGCCC GTGTGGATAT   5400
GTTTTTACAA GATAACGGCC GCATTGTACT GAACGAAGTC AATACTCTGC CCGGTTTCAC   5460
GTCATACAGT CGTTATCCCC GTATGATGGC CGCTGCAGGT ATTGCACTTC CCGAACTGAT   5520
TGACCGCTTG ATCGTATTAG CGTTAAAGGG GTGATAAGCA TGGAAATAGG ATTTACTTTT   5580
TTAGATGAAA TAGTACACGG TGTTCGTTGG GACGCTAAAT ATGCCACTTG GGATAATTTC   5640
ACCGGAAAAC CGGTTGACGG TTATGAAGTA AATCGCATTG TAGGGACATA CGAGTTGGCT   5700
GAATCGCTTT TGAAGGCAAA AGAACTGGCT GCTACCCAAG GGTACGGATT GCTTCTATGG   5760
GACGGTTACC GTCCTAAGCG TGCTGTAAAC TGTTTTATGC AATGGGCTGC ACAGCCGGAA   5820
AATAACCTGA CAAAGGAAAG TTATTATCCC AATATTGACC GAACTGAGAT GATTTCAAAA   5880
GGATACGTGG CTTCAAAATC AAGCCATAGC CGCGGCAGTG CCATTGATCT TACGCTTTAT   5940
CGATTAGACA CGGGTGAGCT TGTACCAATG GGGAGCCGAT TTGATTTTAT GGATGAACGC   6000
TCTCATCATG CGGCAAATGG AATATCATGC AATGAAGCGC AAAATCGCAG ACGTTTGCGC   6060
TCCATCATGG AAAACAGTGG GTTTGAAGCA TATAGCCTCG AATGGTGGCA CTATGTATTA   6120
AGAGACGAAC CATACCCCAA TAGCTATTTT GATTTCCCCG TTAAATAAAC TTTTAACCGT   6180
TGCACGGACA AACTATATAA GCTAACTCTT TCGGCAGGAA ACCCGACGTA TGTAACTGGT   6240
TCTTAGGGAA TTTATATATA GTAGATAGTA TTGAAGATGT AAGGCAGAGC GATATTGCGG   6300
TCATTATCTG CGTGCGCTGC GGCAAGATAG CCTGATAATA AGACTGATCG CATAGAGGGG   6360
TGGTATTTCA CACCGCCCAT TGTCAACAGG CAGTTCAGCC TCGTTAAATT CAGCATGGGT   6420
ATCACTTATG AAAATTCATC TACATTGGTG ATAATAGTAA ATCCAGTAGG GCGAAATAAT   6480
TGACTGTAAT TTACGGGGCA AAACGGCACA ATCTCAAACG AGATTGTGCC GTTTAAGGGG   6540
AAGATTCTAG AAATATTTCA TACTTCCAAC TATATAGTTA AGGAGGAGAC TGAAAATGAA   6600
GAAGTTGTTT TTTTTATTGT TATTGTTATT CTTAATATAC TTAGGTTATG ACTACGTTAA   6660
TGAAGCACTG TTTTCTCAGG AAAAAGTCGA ATTTCAAAAT TATGATCAAA ATCCCAAAGA   6720
ACATTTAGAA AATAGTGGGA CTTCTGAAAA TACCCAAGAG AAAACAATTA CAGAAGAACA   6780
GGTTTATCAA GGAAATCTGC TATTAATCAA TAGTAAATAT CCTGTTCGCC AAGAAGTGTG   6840
AAGTCAGATA TCGTGAATTT ATCTAAACAT GACGAATTAA TAAATGGATA CGGGTTGCTT   6900
GATAGTAATA TTTATATGTC AAAAGAAATA GCACAAAAAT TTTCAGAGAT GGTCAATGAT   6960
GCTGTAAAGG GTGGCGTTAG TCATTTTATT ATTAATAGTG GCTATCGAGA CTTTGATGAG   7020
CAAAGTGTGC TTTACCAAGA AATGGGGGCT GAGTATGCCT TACCAGCAGG TTATAGTGAG   7080
CATAATTCAG GTTTATCACT AGATGTAGGA TCAAGCTTGA CGAAAATGGA ACGAGCCCCT   7140
GAAGGAAAGT GGATAGAAGA AAATGCTTGG AAATACGGGT TCATTTTACG TTATCCAGAG   7200
```

-continued

GACAAAACAG AGTTAACAGG AATTC 7225

(2) INFORMATION FOR SEQ ID NO:16:

(i) SEQUENCE CHARACTERISTICS:
(A) LENGTH: 10851 base pairs
(B) TYPE: nucleic acid
(C) STRANDEDNESS: double
(D) TOPOLOGY: unknown (ii) MOLECULE TYPE: DNA (genomic)

(xi) SEQUENCE DESCRIPTION: SEQ ID NO:16:

GGGGTAGCGT CAGGAAAATG CGGATTTACA ACGCTAAGCC TATTTTCCTG ACGAATCCCT 60

CGTTTTTAAC AACGTTAAGA AAGTTTTAGT GGTCTTAAAG AATTTAATGA GACTACTTTC 120

TCTGAGTTAA AATGGTATTC TCCTAGTAAA TTAATATGTT CCCAACCTAA GGGCGACATA 180

TGGTGTAACA AATCTTCATT AAAGCTACCT GTCCGTTTTT TATATTCAAC TGCTGTTGTT 240

AGGTGGAGAG TATTCCAAAT ACTTATAGCA TTGATAATTA TGTTTAAAGC ACTGGCTCTT 300

TGCAATTGAT GCTGTATGGT GCGTTCTCTA AGCTCACCTT GTTTTCCGAA GAAAATAGCT 360

CTTGCCAATC CATTCATGGC TTCTCCTTTA TTCAATCCTC TTTGTATTTT TCTTCTTAAT 420

GATTCATCCG ATATATAATT CAAAATAAAG ATCGTTTTTT CTATTCGGCC CATCTCACGT 480

AAGGCTGTAG CTAAGCTGTT TTGTCTTGAA TAGGAACCTA GCTTCCCCAT AATAAGGGAT 540

GCTGAAACTG TTCCCTCCCT TATAGAATGA GCTAATCGCA AAACATCCTC ATAATTTTCT 600

TTAATGACCT TTGTATTTAT TTGTCCACGT AAAATGGCTT CTAGTTTTGG ATACTCACTT 660

GCTTTATCTA TCGTAAATAA TTTTGAGTCC GATAAATCCC TTATTCTTGG GGCAAATTTA 720

AATCCTAATA AATGAGTCAG TCCGAATATT TGGTCAGTGT AACCGGCAGT GTCTGTATAA 780

TGTTCCTCTA TGTTTAGATC CGTCTCATGA TGTAACAAAC CATCCAAAAC ATGAATCGCA 840

TCTCTTGAAT TAGTATGAAT AATCTTTGTG TAGTAAGAAG AGAATTGATC ACTTGTAAAT 900

CGGTAGATGG TGGCTCCTTT TCCAGTTCCA TAATGTGGAT TTGCATCTGC ATGTAGTGAT 960

GAAACACCTA GCTGCATTCT CATACCATCT GACGAAGATG TTGTACCGTC GCCCCAATAG 1020

AAAGGCAATT GTAATTTATG ATGAAAGTTT ACTAATATGG CTTGGGCTTT ATTCATGGCA 1080

TCTTCATACA TGCGCCATTG AGATACATTG GCTAGTTGCT TATATGTAAG TCCGGGTGTG 1140

GCTTCGGCCA TCTTGCTCAA GCCAATATTC ATTCCCATTC CTAAAAGGGC AGCCATGATA 1200

ATGATTGTTT CTTCCTTATC TGGTTTTCGA TTATTGGAAG CATGAGTGAA TTGCTCATGA 1260

AATCCTGTTA TATGGGCCAC ATCCATGAGT AAATCAGTTA ATTTTATTCT TGGTAGCATC 1320

TGATAAAGGC TTGCACTAAA TTTTTTTGCT TCTTCTGGAA CATCTTTTTC TAAGCGTGCA 1380

AGTGATAGCT TTCCTTTTTC AAGAGAAACC CCATCTAACT TATTGGAATT GGCAGCTAAC 1440

CACTTTAACC TTTCATTAAA GCTGCTGGTT CTCTCCGTTA TATAATCTTC GAATGATAAA 1500

CTAACTGATA ATCTCGTATT CCCCTTCGAT TGATTCCATG TATCTTCCGA AAACAAATAT 1560

TCCTCAAAAT CCCTATATTG TCTGCTGCCA ACAATGGAAA CATCTCCTGC CCGAACATGC 1620

TCCCGAAGTT CTGTTAAAAC AGCCATTTCA TAGTAATGAC GATTAATTGT TGTACCATCA 1680

TCCTCGTATA AATGTCTTTT CCATCGTTTT GAAATAAAAT CCACAGGTGA GTCATCAGGC 1740

ACTTTTCGCT TTCCAGATTC GTTCATTCCT CGGATAATCT CAACAGCTTG TAAAAGTGGC 1800

TCATTTGCCT TTGTAGAATG AAATTCCAAT ACTCTTAATA GCGTTGGCGT ATATTTTCTT 1860

AGTGAATAAA ACCGTTTTTG CAGTAAGTCT AAATAATCAT AGTCGGCAGG ACGTGCAAGT 1920

-continued

```
TCCTGAGCCT CTTCTACTGA AGAGACAAAG GTATTCCATT CAATAACCGA TTCTAAAACC   1980
TTAAAAACGT CTAATTTTTC CTCTCTTGCT TTAATTAATG CTTGTCCGAT GTTCGTAAAG   2040
TGTATAACTT TCTCATTTAG CTTTTTACCG TTTTGTTTCT GGATTTCCTC TTGAGCCTTA   2100
CGACCTTTTG ATAACAAACT AAGTATTTGC CTATCATGAA TTTCAAACGC TTTATCCGTT   2160
AGCTCCTGAG TAAGTTGTAA TAAATAGATG GTTAATATCG AATAACGTTT ATTTTCTTGA   2220
AAGTCACGGA ATGCATACGG CTCGTATCTT GAGCCTAAGC GAGACAGCTG CAACAGGCGG   2280
TTACGGTGCA AATGACTAAT TTGCACTGTT TCTAAATCCA TTCCTCGTAT GTATTCGAGT   2340
CGTTCTATTA TTTTTAGAAA AGTTTCGGGT GAAGGATGAC CCGGTGGCTC TTTTAACCAA   2400
CCCAATATCG TTTTATTGGA TTCGGATGGA TGCTGCGAGG TAATAATCCC TTCAAGCTTT   2460
TCTTTTTGCT CATTTGTTAG AGATTTACTA ACCGTATTAA ATAGCTTCTT TTCAGCCATT   2520
GCCCTTGCTT CCCACACCAT TCTTTCAAGT GTAGTGATAG CAGGCAGTAT AATTTTGTTT   2580
TTTCTTAGAA AATCTATGCA TTCATGCAGT AGATGAATGG CATCACCATT TTCCAAAGCT   2640
AATTGATGAA GGTACTTAAA TGTCATTCGA TATTCACTCA GGGTAAAAGT TACAAAGTCG   2700
TATTCACTTC GAATTTCTTT CAAATGATCC CAAAGTGTAT TTTCCCTTTG AGGATAATGA   2760
TCAAGCGAGG ATGGACTAAC ACCAATCTGT TTCGATATAT ATTGTATGAC CGAATCTGGG   2820
ATGCTTTTGA TATGAGTGTA TGGCCAACCG GGATACCGAA GAACAGCTAA TTGAACAGCA   2880
AATCCTAAAC GGTTTTCTTC CCTCCTTCGC TTATTAACTA TTTCTAAATC CCGTTTGGAA   2940
AAAGTGAAGT AGGTCCCCAG TATCCATTCA TCTTCAGGGA TTTGCATAAA AGCCTGTCTC   3000
TGTTCCGGTG TAAGCAATTC TCTACCTCTC GCAATTTTCA TTCAGTATCA TTCCATTTCT   3060
GTATTTTCAA TTTATTAGTT CAATTATATA TCAATAGAGT GTACTCTATT GATACAAATG   3120
TAGTAGACTG ATAAAATCAT AGTTAAGAGC GTCTCATAAG ACTTGTCTCA AAAATGAGGT   3180
GATATTTTGC GGAAAATCGG TTATATTCGT GTCAGTTCGA CTAACCAGAA TCCTTCAAGA   3240
CAATTTCAGC AGTTGAACGA GATCGGAATG GATATTATAT ATGAAGAGAA AGTTTCAGGA   3300
GCAACAAAGG ATCGCGAGCA ACTTCAAAAA GTGTTAGACG ATTTACAGGA AGATGACATC   3360
ATTTATGTTA CAGACTTAAC TCGAATCACT CGTAGTACAC AAGATCTATT TGAATTAATC   3420
GATAACATAC GAGATAAAAA GGCAAGTTTA AAATCACTAA AAGATACATG GCTTGATTTA   3480
TCAGAAGATA ATCCATACAG CCAATTCTTA ATTACTGTAA TGGCTGGTGT TAACCAATTA   3540
GAGCGAGATC TTATTCGGAT GAGACAACGT GAAGGGATTG AATTGGCTAA GAAAGAAGGA   3600
AAGTTTAAAG GTCGATTAAA GAAGTATCAT AAAAATCACG CAGGAATGAA TTATGCGGTA   3660
AAGCTATATA AAGAAGGAAA TATGACTGTA AATCAAATTT GTGAAATTAC TAATGTATCT   3720
AGGGCTTCAT TATACAGGAA ATTATCAGAA GTGAATAATT AGCCATTCTG TATTCCGCTA   3780
ATGGGCAATA TTTTTAAAGA AGAAAAGGAA ACTATAAAAT ATTAACAGCC TCCTAGCGAT   3840
GCCGAAAAGC CCTTTGATAA AAAAAGAATC ATCATCTTAA GAAATTCTTA GTCATTTATT   3900
ATGTAAATGC TTATAAATTC GGCCCTATAA TCTGATAAAT TATTAAGGGC AAACTTATGT   3960
GAAAGGGTGA TAACTATGAG CGATAAAATA CTTATTGTGG ATGATGAACA TGAAATTGCC   4020
GATTTGGTTG AATTATACTT AAAAAACGAG AATTATACGG TTTTCAAATA CTATACCGCC   4080
AAAGAAGCAT TGGAATGTAT AGACAAGTCT GAGATTGACC TTGCCATATT GGACATCATG   4140
CTTCCCGGCA CAAGCGGCCT TACTATCTGT CAAAAAATAA GGGACAAGCA CACCTATCCG   4200
ATTATCATGC TGACCGGGAA AGATACAGAG GTAGATAAAA TTACAGGGTT AACAATCGGC   4260
GCGGATGATT ATATAACGAA GCCCTTTCGC CCACTGGAGT TAATTGCTCG GGTAAAGGCC   4320
```

-continued

```
CAGTTGCGCC GATACAAAAA ATTCAGTGGA GTAAAGGAGC AGAACGAAAA TGTTATCGTC   4380
CACTCCGGCC TTGTCATTAA TGTTAACACC CATGAGTGTT ATCTGAACGA GAAGCAGTTA   4440
TCCCTTACTC CCACCGAGTT TTCAATACTG CGAATCCTCT GTGAAAACAA GGGGAATGTG   4500
GTTAGCTCCG AGCTGCTATT TCATGAGATA TGGGGCGACG AATATTTCAG CAAGAGCAAC   4560
AACACCATCA CCGTGCATAT CCGGCATTTG CGCGAAAAAA TGAACGACAC CATTGATAAT   4620
CCGAAATATA TAAAAACGGT ATGGGGGGTT GGTTATAAAA TTGAAAAATA AAAAAAACGA   4680
CTATTCCAAA CTAGAACGAA AACTTTACAT GTATATCGTT GCAATTGTTG TGGTAGCAAT   4740
TGTATTCGTG TTGTATATTC GTTCAATGAT CCGAGGGAAA CTTGGGGATT GGATCTTAAG   4800
TATTTTGGAA AACAAATATG ACTTAAATCA CCTGGACGCG ATGAAATTAT ATCAATATTC   4860
CATACGGAAC AATATAGATA TCTTTATTTA TGTGGCGATT GTCATTAGTA TTCTTATTCT   4920
ATGTCGCGTC ATGCTTTCAA AATTCGCAAA ATACTTTGAC GAGATAAATA CCGGCATTGA   4980
TGTACTTATT CAGAACGAAG ATAAACAAAT TGAGCTTTCT GCGGAAATGG ATGTTATGGA   5040
ACAAAAGCTC AACACATTAA AACGGACTCT GGAAAAGCGA GAGCAGGATG CAAAGCTGGC   5100
CGAACAAAGA AAAAATGACG TTGTTATGTA CTTGGCGCAC GATATTAAAA CGCCCCTTAC   5160
ATCCATTATC GGTTATTTGA GCCTGCTTGA CGAGGCTCCA GACATGCCGG TAGATCAAAA   5220
GGCAAAGTAT GTGCATATCA CGTTGGACAA AGCGTATCGA CTCGAACAGC TAATCGACGA   5280
GTTTTTTGAG ATTACACGGT ATAACCTACA AACGATAACG CTAACAAAAA CGCACATAGA   5340
CCTATACTAT ATGCTGGTGC AGATGACCGA TGAATTTTAT CCTCAGCTTT CCGCACATGG   5400
AAAACAGGCG GTTATTCACG CCCCCGAGGA TCTGACCGTG TCCGGCGACC CTGATAAACT   5460
CGCGAGAGTC TTTAACAACA TTTTGAAAAA CGCCGCTGCA TACAGTGAGG ATAACAGCAT   5520
CATTGACATT ACCGCGGGCC TCTCCGGGGA TGTGGTGTCA ATCGAATTCA AGAACACTGG   5580
AAGCATCCCA AAAGATAAGC TAGCTGCCAT ATTTGAAAAG TTCTATAGGC TGGACAATGC   5640
TCGTTCTTCC GATACGGGTG GCGCGGGACT TGGATTGGCG ATTGCAAAAG AAATTATTGT   5700
TCAGCATGGA GGGCAGATTT ACGCGGAAAG CAATGATAAC TATACGACGT TTAGGGTAGA   5760
GCTTCCAGCG ATGCCAGACT TGGTTGATAA AAGGAGGTCC TAAGAGATGT ATATAATTTT   5820
TTAGGAAAAT CTCAAGGTTA TCTTTACTTT TTCTTAGGAA ATTAACAATT TAATATTAAG   5880
AAACGGCTCG TTCTTACACG GTAGACTTAA TACCGTAAGA ACGAGCCGTT TTCGTTCTTC   5940
AGAGAAAGAT TTGACAAGAT TACCATTGGC ATCCCCGTTT TATTTGGTGC CTTTCACAGA   6000
AAGGGTTGGT CTTAATTATG AATAACATCG GCATTACTGT TTATGGATGT GAGCAGGATG   6060
AGGCAGATGC ATTCCATGCT CTTTCGCCTC GCTTTGGCGT TATGGCAACG ATAATTAACG   6120
CCAACGTGTC GGAATCCAAC GCCAAATCCG CGCCTTTCAA TCAATGTATC AGTGTGGGAC   6180
ATAAATCAGA GATTTCCGCC TCTATTCTTC TTGCGCTGAA GAGAGCCGGT GTGAAATATA   6240
TTTCTACCCG AAGCATCGGC TGCAATCATA TAGATACAAC TGCTGCTAAG AGAATGGGCA   6300
TCACTGTCGA CAATGTGGCG TACTCGCCGG ATAGCGTTGC CGATTATACT ATGATGCTAA   6360
TTCTTATGGC AGTACGCAAC GTAAAATCGA TTGTGCGCTC TGTGGAAAAA CATGATTTCA   6420
GGTTGGACAG CGACCGTGGC AAGGTACTCA GCGACATGAC AGTTGGTGTG GTGGGAACGG   6480
GCCAGATAGG CAAAGCGGTT ATTGAGCGGC TGCGAGGATT TGGATGTAAA GTGTTGGCTT   6540
ATAGTCGCAG CCGAAGTATA GAGGTAAACT ATGTACCGTT TGATGAGTTG CTGCAAAATA   6600
GCGATATCGT TACGCTTCAT GTGCCGCTCA ATACGGATAC GCACTATATT ATCAGCCACG   6660
```

-continued

```
AACAAATACA GAGAATGAAG CAAGGAGCAT TTCTTATCAA TACTGGGCGC GGTCCACTTG   6720

TAGATACCTA TGAGTTGGTT AAAGCATTAG AAAACGGGAA ACTGGGCGGT GCCGCATTGG   6780

ATGTATTGGA AGGAGAGGAA GAGTTTTTCT ACTCTGATTG CACCCAAAAA CCAATTGATA   6840

ATCAATTTTT ACTTAAACTT CAAAGAATGC CTAACGTGAT AATCACACCG CATACGGCCT   6900

ATTATACCGA GCAAGCGTTG CGTGATACCG TTGAAAAAAC CATTAAAAAC TGTTTGGATT   6960

TTGAAAGGAG ACAGGAGCAT GAATAGAATA AAAGTTGCAA TACTGTTTGG GGGTTGCTCA   7020

GAGGAGCATG ACGTATCGGT AAAATCTGCA ATAGAGATAG CCGCTAACAT TAATAAAGAA   7080

AAATACGAGC CGTTATACAT TGGAATTACG AAATCTGGTG TATGGAAAAT GTGCGAAAAA   7140

CCTTGCGCGG AATGGGAAAA CGACAATTGC TATTCAGCTG TACTCTCGCC GGATAAAAAA   7200

ATGCACGGAT TACTTGTTAA AAAGAACCAT GAATATGAAA TCAACCATGT TGATGTAGCA   7260

TTTTCAGCTT TGCATGGCAA GTCAGGTGAA GATGGATCCA TACAAGGTCT GTTTGAATTG   7320

TCCGGTATCC CTTTTGTAGG CTGCGATATT CAAAGCTCAG CAATTTGTAT GGACAAATCG   7380

TTGACATACA TCGTTGCGAA AAATGCTGGG ATAGCTACTC CCGCCTTTTG GGTTATTAAT   7440

AAAGATGATA GGCCGGTGGC AGCTACGTTT ACCTATCCTG TTTTTGTTAA GCCGGCGCGT   7500

TCAGGCTCAT CCTTCGGTGT GAAAAAAGTC AATAGCGCGG ACGAATTGGA CTACGCAATT   7560

GAATCGGCAA GACAATATGA CAGCAAAATC TTAATTGAGC AGGCTGTTTC GGGCTGTGAG   7620

GTCGGTTGTG CGGTATTGGG AAACAGTGCC GCGTTAGTTG TTGGCGAGGT GGACCAAATC   7680

AGGCTGCAGT ACGGAATCTT TCGTATTCAT CAGGAAGTCG AGCCGGAAAA AGGCTCTGAA   7740

AACGCAGTTA TAACCGTTCC CGCAGACCTT TCAGCAGAGG AGCGAGGACG GATACAGGAA   7800

ACGGCAAAAA AAATATATAA AGCGCTCGGC TGTAGAGGTC TAGCCCGTGT GGATATGTTT   7860

TTACAAGATA ACGGCCGCAT TGTACTGAAC GAAGTCAATA CTCTGCCCGG TTTCACGTCA   7920

TACAGTCGTT ATCCCCGTAT GATGGCCGCT GCAGGTATTG CACTTCCCGA ACTGATTGAC   7980

CGCTTGATCG TATTAGCGTT AAAGGGGTGA TAAGCATGGA AATAGGATTT ACTTTTTTAG   8040

ATGAAATAGT ACACGGTGTT CGTTGGGACG CTAAATATGC CACTTGGGAT AATTTCACCG   8100

GAAAACCGGT TGACGGTTAT GAAGTAAATC GCATTGTAGG GACATACGAG TTGGCTGAAT   8160

CGCTTTTGAA GGCAAAAGAA CTGGCTGCTA CCCAAGGGTA CGGATTGCTT CTATGGGACG   8220

GTTACCGTCC TAAGCGTGCT GTAAACTGTT TTATGCAATG GGCTGCACAG CCGGAAAATA   8280

ACCTGACAAA GGAAAGTTAT TATCCCAATA TTGACCGAAC TGAGATGATT TCAAAAGGAT   8340

ACGTGGCTTC AAAATCAAGC CATAGCCGCG GCAGTGCCAT TGATCTTACG CTTTATCGAT   8400

TAGACACGGG TGAGCTTGTA CCAATGGGGA GCCGATTTGA TTTTATGGAT GAACGCTCTC   8460

ATCATGCGGC AAATGGAATA TCATGCAATG AAGCGCAAAA TCGCAGACGT TTGCGCTCCA   8520

TCATGGAAAA CAGTGGGTTT GAAGCATATA GCCTCGAATG GTGGCACTAT GTATTAAGAG   8580

ACGAACCATA CCCCAATAGC TATTTTGATT TCCCCGTTAA ATAAACTTTT AACCGTTGCA   8640

CGGACAAACT ATATAAGCTA ACTCTTTCGG CAGGAAACCC GACGTATGTA ACTGGTTCTT   8700

AGGGAATTTA TATATAGTAG ATAGTATTGA AGATGTAAGG CAGAGCGATA TTGCGGTCAT   8760

TATCTGCGTG CGCTGCGGCA AGATAGCCTG ATAATAAGAC TGATCGCATA GAGGGGTGGT   8820

ATTTCACACC GCCCATTGTC AACAGGCAGT TCAGCCTCGT TAAATTCAGC ATGGGTATCA   8880

CTTATGAAAA TTCATCTACA TTGGTGATAA TAGTAAATCC AGTAGGGCGA AATAATTGAC   8940

TGTAATTTAC GGGGCAAAAC GGCACAATCT CAAACGAGAT TGTGCCGTTT AAGGGGAAGA   9000

TTCTAGAAAT ATTTCATACT TCCAACTATA TAGTTAAGGA GGAGACTGAA AATGAAGAAG   9060
```

-continued

```
TTGTTTTTTT TATTGTTATT GTTATTCTTA ATATACTTAG GTTATGACTA CGTTAATGAA   9120

GCACTGTTTT CTCAGGAAAA AGTCGAATTT CAAAATTATG ATCAAAATCC CAAAGAACAT   9180

TTAGAAAATA GTGGGACTTC TGAAAATACC CAAGAGAAAA CAATTACAGA AGAACAGGTT   9240

TATCAAGGAA ATCTGCTATT AATCAATAGT AAATATCCTG TTCGCCAAGA AAGTGTGAAG   9300

TCAGATATCG TGAATTTATC TAAACATGAC GAATTAATAA ATGGATACGG GTTGCTTGAT   9360

AGTAATATTT ATATGTCAAA AGAAATAGCA CAAAAATTTT CAGAGATGGT CAATGATGCT   9420

GTAAAGGGTG GCGTTAGTCA TTTTATTATT AATAGTGGCT ATCGAGACTT TGATGAGCAA   9480

AGTGTGCTTT ACCAAGAAAT GGGGGCTGAG TATGCCTTAC CAGCAGGTTA TAGTGAGCAT   9540

AATTCAGGTT TATCACTAGA TGTAGGATCA AGCTTGACGA AAATGGAACG AGCCCCTGAA   9600

GGAAAGTGGA TAGAAGAAAA TGCTTGGAAA TACGGGTTCA TTTTACGTTA TCCAGAGGAC   9660

AAAACAGAGT TAACAGGAAT TCAATATGAA CCATGGCATA TTCGCTATGT TGGTTTACCA   9720

CATAGTGCGA TTATGAAAGA AAAGAATTTC GTTCTCGAGG AATATATGGA TTACCTAAAA   9780

GAAGAAAAAA CCATTTCTGT TAGTGTAAAT GGGGAAAAAT ATGAGATCTT TTATTATCCT   9840

GTTACTAAAA ATACCACCAT TCATGTGCCG ACTAATCTTC GTTATGAGAT ATCAGGAAAC   9900

AATATAGACG GTGTAATTGT GACAGTGTTT CCCGGATCAA CACATACTAA TTCAAGGAGG   9960

TAAGGATGGC GGAATGAAAC CAACGAAATT AATGAACAGC ATTATTGTAC TAGCACTTTT  10020

GGGGTAACGT TAGCTTTTTA ATTTAAAACC CACGTTAACT AGGACATTGC TATACTAATG  10080

ATACAACTTA AACAAAAGAA TTAGAGGAAA TTATATTGGG AAAAATATTA TCTAGAGGAT  10140

TGCTAGCTTT ATATTTAGTG ACACTAATCT GGTTAGTGTT ATTCAAATTA CAATACAATA  10200

TTTTATCAGT ATTTAATTAT CATCAAAGAA GTCTTAACTT GACTCCATTT ACTGCTACTG  10260

GGAATTTCAG AGAGATGATA GATAATGTTA TAATCTTTAT TCCATTTGGC TTGCTTTTGA  10320

ATGTCAATTT TAAAGAAATC GGATTTTTAC CTAAGTTTGC TTTTGTACTG GTTTTAAGTC  10380

TTACTTTTGA AATAATTCAA TTTATCTTCG CTATTGGAGC GACAGACATA ACAGATGTAA  10440

TTACAAATAC TGTTGGAGGC TTTCTTGGAC TGAAATTATA TGGTTTAAGC AATAAGCATA  10500

TGAATCAAAA AAAATTAGAC AGAGTTATTA TTTTTGTAGG TATACTTTTG CTCGTATTAT  10560

TGCTCGTTTA CCGTACCCAT TTAAGAATAA ATTACGTGTA AGATGTCTAA ATCAAGCAAT  10620

CTGATCTTTC ATACACATAA AGATATTGAA TGAATTGGAT TAGATGGAAA ACGGGATGTG  10680

GGGAAACTCG CCCGTAGGTG TGAAGTGAGG GGAAAACCGG TGATAAAGTA AAAAGCTTAC  10740

CTAACACTAT AGTAACAAAG AAAGCCCAAT TATCAATTTT AGTGCTGAGG AATTGGTCTC  10800

TTTAATAAAT TTCCTTAACG TTGTAAATCC GCATTTTCCT GACGGTACCC C           10851
```

(2) INFORMATION FOR SEQ ID NO:17:

(i) SEQUENCE CHARACTERISTICS:
(A) LENGTH: 2667 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO:17:

```
CAAGATTACC ATTGGCATCC CCGTTTTATT TGGTGCCTTT CACAGAAAGG GTTGGTCTTA     60

ATTATGAATA ACATCGGCAT TACTGTTTAT GGATGTGAGC AGGATGAGGC AGATGCATTC    120

CATGCTCTTT CGCCTCGCTT TGGCGTTATG GCAACGATAA TTAACGCCAA CGTGTCGGAA    180
```

-continued

```
TCCAACGCCA AATCCGCGCC TTTCAATCAA TGTATCAGTG TGGGACATAA ATCAGAGATT    240
TCCGCCTCTA TTCTTCTTGC GCTGAAGAGA GCCGGTGTGA AATATATTTC TACCCGAAGC    300
ATCGGCTGCA ATCATATAGA TACAACTGCT GCTAAGAGAA TGGGCATCAC TGTCGACAAT    360
GTGGCGTACT CGCCGGATAG CGTTGCCGAT TATACTATGA TGCTAATTCT TATGGCAGTA    420
CGCAACGTAA AATCGATTGT GCGCTCTGTG GAAAAACATG ATTTCAGGTT GGACAGCGAC    480
CGTGGCAAGG TACTCAGCGA CATGACAGTT GGTGTGGTGG GAACGGGCCA GATAGGCAAA    540
GCGGTTATTG AGCGGCTGCG AGGATTTGGA TGTAAAGTGT TGGCTTATAG TCGCAGCCGA    600
AGTATAGAGG TAAACTATGT ACCGTTTGAT GAGTTGATGC AAAATAGCGA TATCGTTACG    660
CTTCATGTGC CGCTCAATAC GGATACGCAC TATATTATCA GCCACGAACA AATACAGAGA    720
ATGAAGCAAG GAGCATTTCT TATCAATACT GGGCGCGGTC CACTTGTAGA TACCTATGAG    780
TTGGTTAAAG CATTAGAAAA CGGGAAACTG GGCGGTGCCG CATTGGATGT ATTGGAAGGA    840
GAGGAAGAGT TTTTCTACTC TGATTGCACC CAAAAACCAA TTGATAATCA ATTTTTACTT    900
AAACTTCAAA GAATGCCTAA CGTGATAATC ACACCGCATA CGGCCTATTA TACCGAGCAA    960
GCGTTGCGTG ATACCGTTGA AAAAACCATT AAAAACTGTT TGGATTTTGA AAGGAGACAG   1020
GAGCATGAAT AGAATAAAAG TTGCAATACT GTTTGGGGGT TGCTCAGAGG AGCATGACGT   1080
ATCGGTAAAA TCTGCAATAG AGATAGCCGC TAACATTAAT AAAGAAAAAT ACGAGCCGTT   1140
ATACATTGGA ATTACGAAAT CTGGTGTATG GAAAATGTGC GAAAAACCTT GCGCGGAATG   1200
GGAAAACGAC AATTGCTATT CAGCTGTACT CTCGCCGGAT AAAAAAATGC ACGGATTACT   1260
TGTTAAAAAG AACCATGAAT ATGAAATCAA CCATGTTGAT GTAGCATTTT CAGCTTTGCA   1320
TGGCAAGTCA GGTGAAGATG GATCCATACA AGGTCTGTTT GAATTGTCCG GTATCCCTTT   1380
TGTAGGCTGC GATATTCAAA GCTCAGCAAT TTGTATGGAC AAATCGTTGA CATACATCGT   1440
TGCGAAAAAT GCTGGGATAG CTACTCCCGC CTTTTGGGTT ATTAATAAAG ATGATAGGCC   1500
GGTGGCAGCT ACGTTTACCT ATCCTGTTTT TGTTAAGCCG GCGCGTTCAG GCTCATCCTT   1560
CGGTGTGAAA AAAGTCAATA GCGCGGACGA ATTGGACTAC GCAATTGAAT CGGCAAGACA   1620
ATATGACAGC AAAATCTTAA TTGAGCAGGC TGTTTCGGGC TGTGAGGTCG GTTGTGCGGT   1680
ATTGGGAAAC AGTGCCGCGT TAGTTGTTGG CGAGGTGGAC CAAATCAGGC TGCAGTACGG   1740
AATCTTTCGT ATTCATCAGG AAGTCGAGCC GGAAAAAGGC TCTGAAAACG CAGTTATAAC   1800
CGTTCCCGCA GACCTTTCAG CAGAGGAGCG AGGACGGATA CAGGAAACGG CAAAAAAAAT   1860
ATATAAAGCG CTCGGCTGTA GAGGTCTAGC CCGTGTGGAT ATGTTTTTAC AAGATAACGG   1920
CCGCATTGTA CTGAACGAAG TCAATACTCT GCCCGGTTTC ACGTCATACA GTCGTTATCC   1980
CCGTATGATG GCCGCTGCAG GTATTGCACT TCCCGAACTG ATTGACCGCT TGATCGTATT   2040
AGCGTTAAAG GGGTGATAAG CATGGAAATA GGATTTACTT TTTTAGATGA AATAGTACAC   2100
GGTGTTCGTT GGGACGCTAA ATATGCCACT TGGGATAATT TCACCGGAAA ACCGGTTGAC   2160
GGTTATGAAG TAAATCGCAT TGTAGGGACA TACGAGTTGG CTGAATCGCT TTTGAAGGCA   2220
AAAGAACTGG CTGCTACCCA AGGGTACGGA TTGCTTCTAT GGGACGGTTA CCGTCCTAAG   2280
CGTGCTGTAA ACTGTTTTAT GCAATGGGCT GCACAGCCGG AAAATAACCT GACAAAGGAA   2340
AGTTATTATC CCAATATTGA CCGAACTGAG ATGATTTCAA AAGGATACGT GGCTTCAAAA   2400
TCAAGCCATA GCCGCGGCAG TGCCATTGAT CTTACGCTTT ATCGATTAGA CACGGGTGAG   2460
CTTGTACCAA TGGGGAGCCG ATTTGATTTT ATGGATGAAC GCTCTCATCA TGCGGCAAAT   2520
```

-continued

```
GGAATATCAT GCAATGAAGC GCAAAATCGC AGACGTTTGC GCTCCATCAT GGAAAACAGT   2580

GGGTTTGAAG CATATAGCCT CGAATGGTGG CACTATGTAT TAAGAGACGA ACCATACCCC   2640

AATAGCTATT TTGATTTCCC CGTTAAA                                       2667
```

(2) INFORMATION FOR SEQ ID NO:18:

(i) SEQUENCE CHARACTERISTICS:
(A) LENGTH: 2964 base pairs
(B) TYPE: nucleic acid
(C) STRANDEDNESS: unknown
(D) TOPOLOGY: linear (ii) MOLECULE TYPE: DNA (genomic)

(ix) FEATURE:
(A) NAME/KEY: CDS
(B) LOCATION: 1..2964

(xi) SEQUENCE DESCRIPTION: SEQ ID NO:18:

```
ATG AAA ATT GCG AGA GGT AGA GAA TTG CTT ACA CCG GAA CAG AGA CAG       48
Met Lys Ile Ala Arg Gly Arg Glu Leu Leu Thr Pro Glu Gln Arg Gln
  1               5                  10                  15

GCT TTT ATG CAA ATC CCT GAA GAT GAA TGG ATA CTG GGG ACC TAC TTC       96
Ala Phe Met Gln Ile Pro Glu Asp Glu Trp Ile Leu Gly Thr Tyr Phe
             20                  25                  30

ACT TTT TCC AAA CGG GAT TTA GAA ATA GTT AAT AAG CGA AGG AGG GAA      144
Thr Phe Ser Lys Arg Asp Leu Glu Ile Val Asn Lys Arg Arg Arg Glu
         35                  40                  45

GAA AAC CGT TTA GGA TTT GCT GTT CAA TTA GCT GTT CTT CGG TAT CCC      192
Glu Asn Arg Leu Gly Phe Ala Val Gln Leu Ala Val Leu Arg Tyr Pro
     50                  55                  60

GGT TGG CCA TAC ACT CAT ATC AAA AGC ATC CCA GAT TCG GTC ATA CAA      240
Gly Trp Pro Tyr Thr His Ile Lys Ser Ile Pro Asp Ser Val Ile Gln
 65                  70                  75                  80

TAT ATA TCG AAA CAG ATT GGT GTT AGT CCA TCC TCG CTT GAT CAT TAT      288
Tyr Ile Ser Lys Gln Ile Gly Val Ser Pro Ser Ser Leu Asp His Tyr
                 85                  90                  95

CCT CAA AGG GAA AAT ACA CTT TGG GAT CAT TTG AAA GAA ATT CGA AGT      336
Pro Gln Arg Glu Asn Thr Leu Trp Asp His Leu Lys Glu Ile Arg Ser
            100                 105                 110

GAA TAC GAC TTT GTA ACT TTT ACC CTG AGT GAA TAT CGA ATG ACA TTT      384
Glu Tyr Asp Phe Val Thr Phe Thr Leu Ser Glu Tyr Arg Met Thr Phe
        115                 120                 125

AAG TAC CTT CAT CAA TTA GCT TTG GAA AAT GGT GAT GCC ATT CAT CTA      432
Lys Tyr Leu His Gln Leu Ala Leu Glu Asn Gly Asp Ala Ile His Leu
    130                 135                 140

CTG CAT GAA TGC ATA GAT TTT CTA AGA AAA AAC AAA ATT ATA CTG CCT      480
Leu His Glu Cys Ile Asp Phe Leu Arg Lys Asn Lys Ile Ile Leu Pro
145                 150                 155                 160

GCT ATC ACT ACA CTT GAA AGA ATG GTG TGG GAA GCA AGG GCA ATG GCT      528
Ala Ile Thr Thr Leu Glu Arg Met Val Trp Glu Ala Arg Ala Met Ala
                165                 170                 175

GAA AAG AAG CTA TTT AAT ACG GTT AGT AAA TCT CTA ACA AAT GAG CAA      576
Glu Lys Lys Leu Phe Asn Thr Val Ser Lys Ser Leu Thr Asn Glu Gln
            180                 185                 190

AAA GAA AAG CTT GAA GGG ATT ATT ACC TCG CAG CAT CCA TCC GAA TCC      624
Lys Glu Lys Leu Glu Gly Ile Ile Thr Ser Gln His Pro Ser Glu Ser
        195                 200                 205

AAT AAA ACG ATA TTG GGT TGG TTA AAA GAG CCA CCG GGT CAT CCT TCA      672
Asn Lys Thr Ile Leu Gly Trp Leu Lys Glu Pro Pro Gly His Pro Ser
    210                 215                 220
```

-continued

```
CCC GAA ACT TTT CTA AAA ATA ATA GAA CGA CTC GAA TAC ATA CGA GGA      720
Pro Glu Thr Phe Leu Lys Ile Ile Glu Arg Leu Glu Tyr Ile Arg Gly
225                 230                 235                 240

ATG GAT TTA GAA ACA GTG CAA ATT AGT CAT TTG CAC CGT AAC CGC CTG      768
Met Asp Leu Glu Thr Val Gln Ile Ser His Leu His Arg Asn Arg Leu
                245                 250                 255

TTG CAG CTG TCT CGC TTA GGC TCA AGA TAC GAG CCG TAT GCA TTC CGT      816
Leu Gln Leu Ser Arg Leu Gly Ser Arg Tyr Glu Pro Tyr Ala Phe Arg
            260                 265                 270

GAC TTT CAA GAA AAT AAA CGT TAT TCG ATA TTA ACC ATC TAT TTA TTA      864
Asp Phe Gln Glu Asn Lys Arg Tyr Ser Ile Leu Thr Ile Tyr Leu Leu
        275                 280                 285

CAA CTT ACT CAG GAG CTA ACG GAT AAA GCG TTT GAA ATT CAT GAT AGG      912
Gln Leu Thr Gln Glu Leu Thr Asp Lys Ala Phe Glu Ile His Asp Arg
    290                 295                 300

CAA ATA CTT AGT TTG TTA TCA AAA GGT CGT AAG GCT CAA GAG GAA ATC      960
Gln Ile Leu Ser Leu Leu Ser Lys Gly Arg Lys Ala Gln Glu Glu Ile
305                 310                 315                 320

CAG AAA CAA AAC GGT AAA AAG CTA AAT GAG AAA GTT ATA CAC TTT ACG     1008
Gln Lys Gln Asn Gly Lys Lys Leu Asn Glu Lys Val Ile His Phe Thr
                325                 330                 335

AAC ATC GGA CAA GCA TTA ATT AAA GCA AGA GAG GAA AAA TTA GAC GTT     1056
Asn Ile Gly Gln Ala Leu Ile Lys Ala Arg Glu Glu Lys Leu Asp Val
            340                 345                 350

TTT AAG GTT TTA GAA TCG GTT ATT GAA TGG AAT ACC TTT GTC TCT TCA     1104
Phe Lys Val Leu Glu Ser Val Ile Glu Trp Asn Thr Phe Val Ser Ser
        355                 360                 365

GTA GAA GAG GCT CAG GAA CTT GCA CGT CCT GCC GAC TAT GAT TAT TTA     1152
Val Glu Glu Ala Gln Glu Leu Ala Arg Pro Ala Asp Tyr Asp Tyr Leu
    370                 375                 380

GAC TTA CTG CAA AAA CGG TTT TAT TCA CTA AGA AAA TAT ACG CCA ACG     1200
Asp Leu Leu Gln Lys Arg Phe Tyr Ser Leu Arg Lys Tyr Thr Pro Thr
385                 390                 395                 400

CTA TTA AGA GTA TTG GAA TTT CAT TCT ACA AAG GCA AAT GAG CCA CTT     1248
Leu Leu Arg Val Leu Glu Phe His Ser Thr Lys Ala Asn Glu Pro Leu
                405                 410                 415

TTA CAA GCT GTT GAG ATT ATC CGA GGA ATG AAC GAA TCT GGA AAG CGA     1296
Leu Gln Ala Val Glu Ile Ile Arg Gly Met Asn Glu Ser Gly Lys Arg
            420                 425                 430

AAA GTG CCT GAT GAC TCA CCT GTG GAT TTT ATT TCA AAA CGA TGG AAA     1344
Lys Val Pro Asp Asp Ser Pro Val Asp Phe Ile Ser Lys Arg Trp Lys
        435                 440                 445

AGA CAT TTA TAC GAG GAT GAT GGT ACA ACA ATT AAT CGT CAT TAC TAT     1392
Arg His Leu Tyr Glu Asp Asp Gly Thr Thr Ile Asn Arg His Tyr Tyr
    450                 455                 460

GAA ATG GCT GTT TTA ACA GAA CTT CGG GAG CAT GTT CGG GCA GGA GAT     1440
Glu Met Ala Val Leu Thr Glu Leu Arg Glu His Val Arg Ala Gly Asp
465                 470                 475                 480

GTT TCC ATT GTT GGC AGC AGA CAA TAT AGG GAT TTT GAG GAA TAT TTG     1488
Val Ser Ile Val Gly Ser Arg Gln Tyr Arg Asp Phe Glu Glu Tyr Leu
                485                 490                 495

TTT TCG GAA GAT ACA TGG AAT CAA TCG AAG GGG AAT ACG AGA TTA TCA     1536
Phe Ser Glu Asp Thr Trp Asn Gln Ser Lys Gly Asn Thr Arg Leu Ser
            500                 505                 510

GTT AGT TTA TCA TTC GAA GAT TAT ATA ACG GAG AGA ACC AGC AGC TTT     1584
Val Ser Leu Ser Phe Glu Asp Tyr Ile Thr Glu Arg Thr Ser Ser Phe
        515                 520                 525

AAT GAA AGG TTA AAG TGG TTA GCT GCC AAT TCC AAT AAG TTA GAT GGG     1632
Asn Glu Arg Leu Lys Trp Leu Ala Ala Asn Ser Asn Lys Leu Asp Gly
    530                 535                 540
```

-continued

```
GTT TCT CTT GAA AAA GGA AAG CTA TCA CTT GCA CGC TTA GAA AAA GAT     1680
Val Ser Leu Glu Lys Gly Lys Leu Ser Leu Ala Arg Leu Glu Lys Asp
545                 550                 555                 560

GTT CCA GAA GAA GCA AAA AAA TTT AGT GCA AGC CTT TAT CAG ATG CTA     1728
Val Pro Glu Glu Ala Lys Lys Phe Ser Ala Ser Leu Tyr Gln Met Leu
                565                 570                 575

CCA AGA ATA AAA TTA ACT GAT TTA CTC ATG GAT GTG GCC CAT ATA ACA     1776
Pro Arg Ile Lys Leu Thr Asp Leu Leu Met Asp Val Ala His Ile Thr
            580                 585                 590

GGA TTT CAT GAG CAA TTC ACT CAT GCT TCC AAT AAT CGA AAA CCA GAT     1824
Gly Phe His Glu Gln Phe Thr His Ala Ser Asn Asn Arg Lys Pro Asp
        595                 600                 605

AAG GAA GAA ACA ATC ATT ATC ATG GCT GCC CTT TTA GGA ATG GGA ATG     1872
Lys Glu Glu Thr Ile Ile Ile Met Ala Ala Leu Leu Gly Met Gly Met
    610                 615                 620

AAT ATT GGC TTG AGC AAG ATG GCC GAA GCC ACA CCC GGA CTT ACA TAT     1920
Asn Ile Gly Leu Ser Lys Met Ala Glu Ala Thr Pro Gly Leu Thr Tyr
625                 630                 635                 640

AAG CAA CTA GCC AAT GTA TCT CAA TGG CGC ATG TAT GAA GAT GCC ATG     1968
Lys Gln Leu Ala Asn Val Ser Gln Trp Arg Met Tyr Glu Asp Ala Met
                645                 650                 655

AAT AAA GCC CAA GCC ATA TTA GTA AAC TTT CAT CAT AAA TTA CAA TTG     2016
Asn Lys Ala Gln Ala Ile Leu Val Asn Phe His His Lys Leu Gln Leu
            660                 665                 670

CCT TTC TAT TGG GGC GAC GGT ACA ACA TCT TCG TCA GAT GGT ATG AGA     2064
Pro Phe Tyr Trp Gly Asp Gly Thr Thr Ser Ser Ser Asp Gly Met Arg
        675                 680                 685

ATG CAG CTA GGT GTT TCA TCA CTA CAT GCA GAT GCA AAT CCA CAT TAT     2112
Met Gln Leu Gly Val Ser Ser Leu His Ala Asp Ala Asn Pro His Tyr
    690                 695                 700

GGA ACT GGA AAA GGA GCC ACC ATC TAC CGA TTT ACA AGT GAT CAA TTC     2160
Gly Thr Gly Lys Gly Ala Thr Ile Tyr Arg Phe Thr Ser Asp Gln Phe
705                 710                 715                 720

TCT TCT TAC TAC ACA AAG ATT ATT CAT ACT AAT TCA AGA GAT GCG ATT     2208
Ser Ser Tyr Tyr Thr Lys Ile Ile His Thr Asn Ser Arg Asp Ala Ile
                725                 730                 735

CAT GTT TTG GAT GGT TTG TTA CAT CAT GAG ACG GAT CTA AAC ATA GAG     2256
His Val Leu Asp Gly Leu Leu His His Glu Thr Asp Leu Asn Ile Glu
            740                 745                 750

GAA CAT TAT ACA GAC ACT GCC GGT TAC ACT GAC CAA ATA TTC GGA CTG     2304
Glu His Tyr Thr Asp Thr Ala Gly Tyr Thr Asp Gln Ile Phe Gly Leu
        755                 760                 765

ACT CAT TTA TTA GGA TTT AAA TTT GCC CCA AGA ATA AGG GAT TTA TCG     2352
Thr His Leu Leu Gly Phe Lys Phe Ala Pro Arg Ile Arg Asp Leu Ser
    770                 775                 780

GAC TCA AAA TTA TTT ACG ATA GAT AAA GCA AGT GAG TAT CCA AAA CTA     2400
Asp Ser Lys Leu Phe Thr Ile Asp Lys Ala Ser Glu Tyr Pro Lys Leu
785                 790                 795                 800

GAA GCC ATT TTA CGT GGA CAA ATA AAT ACA AAG GTC ATT AAA GAA AAT     2448
Glu Ala Ile Leu Arg Gly Gln Ile Asn Thr Lys Val Ile Lys Glu Asn
                805                 810                 815

TAT GAG GAT GTT TTG CGA TTA GCT CAT TCT ATA AGG GAG GGA ACA GTT     2496
Tyr Glu Asp Val Leu Arg Leu Ala His Ser Ile Arg Glu Gly Thr Val
            820                 825                 830

TCA GCA TCC CTT ATT ATG GGG AAG CTA GGT TCC TAT TCA AGA CAA AAC     2544
Ser Ala Ser Leu Ile Met Gly Lys Leu Gly Ser Tyr Ser Arg Gln Asn
        835                 840                 845

AGC TTA GCT ACA GCC TTA CGT GAG ATG GGC CGA ATA GAA AAA ACG ATC     2592
Ser Leu Ala Thr Ala Leu Arg Glu Met Gly Arg Ile Glu Lys Thr Ile
```

-continued

```
    850                 855                 860

TTT ATT TTG AAT TAT ATA TCG GAT GAA TCA TTA AGA AGA AAA ATA CAA     2640
Phe Ile Leu Asn Tyr Ile Ser Asp Glu Ser Leu Arg Arg Lys Ile Gln
865                 870                 875                 880

AGA GGA TTG AAT AAA GGA GAA GCC ATG AAT GGA TTG GCA AGA GCT ATT     2688
Arg Gly Leu Asn Lys Gly Glu Ala Met Asn Gly Leu Ala Arg Ala Ile
                885                 890                 895

TTC TTC GGA AAA CAA GGT GAG CTT AGA GAA CGC ACC ATA CAG CAT CAA     2736
Phe Phe Gly Lys Gln Gly Glu Leu Arg Glu Arg Thr Ile Gln His Gln
            900                 905                 910

TTG CAA AGA GCC AGT GCT TTA AAC ATA ATT ATC AAT GCT ATA AGT ATT     2784
Leu Gln Arg Ala Ser Ala Leu Asn Ile Ile Ile Asn Ala Ile Ser Ile
        915                 920                 925

TGG AAT ACT CTC CAC CTA ACA ACA GCA GTT GAA TAT AAA AAA CGG ACA     2832
Trp Asn Thr Leu His Leu Thr Thr Ala Val Glu Tyr Lys Lys Arg Thr
    930                 935                 940

GGT AGC TTT AAT GAA GAT TTG TTA CAC CAT ATG TCG CCC TTA GGT TGG     2880
Gly Ser Phe Asn Glu Asp Leu Leu His His Met Ser Pro Leu Gly Trp
945                 950                 955                 960

GAA CAT ATT AAT TTA CTA GGA GAA TAC CAT TTT AAC TCA GAG AAA GTA     2928
Glu His Ile Asn Leu Leu Gly Glu Tyr His Phe Asn Ser Glu Lys Val
                965                 970                 975

GTC TCA TTA AAT TCT TTA AGA CCA CTA AAA CTT TCT                     2964
Val Ser Leu Asn Ser Leu Arg Pro Leu Lys Leu Ser
            980                 985
```

(2) INFORMATION FOR SEQ ID NO:19:

(i) SEQUENCE CHARACTERISTICS:
(A) LENGTH: 988 amino acids
(B) TYPE: amino acid
(D) TOPOLOGY: linear (ii) MOLECULE TYPE: protein (xi) SEQUENCE DESCRIPTION: SEQ ID NO:19:

```
Met Lys Ile Ala Arg Gly Arg Glu Leu Leu Thr Pro Glu Gln Arg Gln
  1               5                  10                  15

Ala Phe Met Gln Ile Pro Glu Asp Glu Trp Ile Leu Gly Thr Tyr Phe
             20                  25                  30

Thr Phe Ser Lys Arg Asp Leu Glu Ile Val Asn Lys Arg Arg Arg Glu
         35                  40                  45

Glu Asn Arg Leu Gly Phe Ala Val Gln Leu Ala Val Leu Arg Tyr Pro
     50                  55                  60

Gly Trp Pro Tyr Thr His Ile Lys Ser Ile Pro Asp Ser Val Ile Gln
 65                  70                  75                  80

Tyr Ile Ser Lys Gln Ile Gly Val Ser Pro Ser Ser Leu Asp His Tyr
                 85                  90                  95

Pro Gln Arg Glu Asn Thr Leu Trp Asp His Leu Lys Glu Ile Arg Ser
            100                 105                 110

Glu Tyr Asp Phe Val Thr Phe Thr Leu Ser Glu Tyr Arg Met Thr Phe
        115                 120                 125

Lys Tyr Leu His Gln Leu Ala Leu Glu Asn Gly Asp Ala Ile His Leu
    130                 135                 140

Leu His Glu Cys Ile Asp Phe Leu Arg Lys Asn Lys Ile Ile Leu Pro
145                 150                 155                 160

Ala Ile Thr Thr Leu Glu Arg Met Val Trp Glu Ala Arg Ala Met Ala
                165                 170                 175
```

-continued

```
Glu Lys Lys Leu Phe Asn Thr Val Ser Lys Ser Leu Thr Asn Glu Gln
            180                 185                 190

Lys Glu Lys Leu Glu Gly Ile Ile Thr Ser Gln His Pro Ser Glu Ser
        195                 200                 205

Asn Lys Thr Ile Leu Gly Trp Leu Lys Glu Pro Pro Gly His Pro Ser
    210                 215                 220

Pro Glu Thr Phe Leu Lys Ile Ile Glu Arg Leu Glu Tyr Ile Arg Gly
225                 230                 235                 240

Met Asp Leu Glu Thr Val Gln Ile Ser His Leu His Arg Asn Arg Leu
                245                 250                 255

Leu Gln Leu Ser Arg Leu Gly Ser Arg Tyr Glu Pro Tyr Ala Phe Arg
            260                 265                 270

Asp Phe Gln Glu Asn Lys Arg Tyr Ser Ile Leu Thr Ile Tyr Leu Leu
        275                 280                 285

Gln Leu Thr Gln Glu Leu Thr Asp Lys Ala Phe Glu Ile His Asp Arg
    290                 295                 300

Gln Ile Leu Ser Leu Leu Ser Lys Gly Arg Lys Ala Gln Glu Glu Ile
305                 310                 315                 320

Gln Lys Gln Asn Gly Lys Lys Leu Asn Glu Lys Val Ile His Phe Thr
                325                 330                 335

Asn Ile Gly Gln Ala Leu Ile Lys Ala Arg Glu Glu Lys Leu Asp Val
            340                 345                 350

Phe Lys Val Leu Glu Ser Val Ile Glu Trp Asn Thr Phe Val Ser Ser
        355                 360                 365

Val Glu Glu Ala Gln Glu Leu Ala Arg Pro Ala Asp Tyr Asp Tyr Leu
    370                 375                 380

Asp Leu Leu Gln Lys Arg Phe Tyr Ser Leu Arg Lys Tyr Thr Pro Thr
385                 390                 395                 400

Leu Leu Arg Val Leu Glu Phe His Ser Thr Lys Ala Asn Glu Pro Leu
                405                 410                 415

Leu Gln Ala Val Glu Ile Ile Arg Gly Met Asn Glu Ser Gly Lys Arg
            420                 425                 430

Lys Val Pro Asp Asp Ser Pro Val Asp Phe Ile Ser Lys Arg Trp Lys
        435                 440                 445

Arg His Leu Tyr Glu Asp Asp Gly Thr Thr Ile Asn Arg His Tyr Tyr
    450                 455                 460

Glu Met Ala Val Leu Thr Glu Leu Arg Glu His Val Arg Ala Gly Asp
465                 470                 475                 480

Val Ser Ile Val Gly Ser Arg Gln Tyr Arg Asp Phe Glu Glu Tyr Leu
                485                 490                 495

Phe Ser Glu Asp Thr Trp Asn Gln Ser Lys Gly Asn Thr Arg Leu Ser
            500                 505                 510

Val Ser Leu Ser Phe Glu Asp Tyr Ile Thr Glu Arg Thr Ser Ser Phe
        515                 520                 525

Asn Glu Arg Leu Lys Trp Leu Ala Ala Asn Ser Asn Lys Leu Asp Gly
    530                 535                 540

Val Ser Leu Glu Lys Gly Lys Leu Ser Leu Ala Arg Leu Glu Lys Asp
545                 550                 555                 560

Val Pro Glu Glu Ala Lys Lys Phe Ser Ala Ser Leu Tyr Gln Met Leu
                565                 570                 575

Pro Arg Ile Lys Leu Thr Asp Leu Leu Met Asp Val Ala His Ile Thr
            580                 585                 590

Gly Phe His Glu Gln Phe Thr His Ala Ser Asn Asn Arg Lys Pro Asp
```

-continued

```
        595                 600                 605

Lys Glu Glu Thr Ile Ile Ile Met Ala Ala Leu Leu Gly Met Gly Met
    610                 615                 620

Asn Ile Gly Leu Ser Lys Met Ala Glu Ala Thr Pro Gly Leu Thr Tyr
625                 630                 635                 640

Lys Gln Leu Ala Asn Val Ser Gln Trp Arg Met Tyr Glu Asp Ala Met
                645                 650                 655

Asn Lys Ala Gln Ala Ile Leu Val Asn Phe His His Lys Leu Gln Leu
            660                 665                 670

Pro Phe Tyr Trp Gly Asp Gly Thr Thr Ser Ser Ser Asp Gly Met Arg
        675                 680                 685

Met Gln Leu Gly Val Ser Ser Leu His Ala Asp Ala Asn Pro His Tyr
    690                 695                 700

Gly Thr Gly Lys Gly Ala Thr Ile Tyr Arg Phe Thr Ser Asp Gln Phe
705                 710                 715                 720

Ser Ser Tyr Tyr Thr Lys Ile Ile His Thr Asn Ser Arg Asp Ala Ile
                725                 730                 735

His Val Leu Asp Gly Leu Leu His His Glu Thr Asp Leu Asn Ile Glu
            740                 745                 750

Glu His Tyr Thr Asp Thr Ala Gly Tyr Thr Asp Gln Ile Phe Gly Leu
        755                 760                 765

Thr His Leu Leu Gly Phe Lys Phe Ala Pro Arg Ile Arg Asp Leu Ser
    770                 775                 780

Asp Ser Lys Leu Phe Thr Ile Asp Lys Ala Ser Glu Tyr Pro Lys Leu
785                 790                 795                 800

Glu Ala Ile Leu Arg Gly Gln Ile Asn Thr Lys Val Ile Lys Glu Asn
                805                 810                 815

Tyr Glu Asp Val Leu Arg Leu Ala His Ser Ile Arg Glu Gly Thr Val
            820                 825                 830

Ser Ala Ser Leu Ile Met Gly Lys Leu Gly Ser Tyr Ser Arg Gln Asn
        835                 840                 845

Ser Leu Ala Thr Ala Leu Arg Glu Met Gly Arg Ile Glu Lys Thr Ile
    850                 855                 860

Phe Ile Leu Asn Tyr Ile Ser Asp Glu Ser Leu Arg Arg Lys Ile Gln
865                 870                 875                 880

Arg Gly Leu Asn Lys Gly Glu Ala Met Asn Gly Leu Ala Arg Ala Ile
                885                 890                 895

Phe Phe Gly Lys Gln Gly Glu Leu Arg Glu Arg Thr Ile Gln His Gln
            900                 905                 910

Leu Gln Arg Ala Ser Ala Leu Asn Ile Ile Ile Asn Ala Ile Ser Ile
        915                 920                 925

Trp Asn Thr Leu His Leu Thr Thr Ala Val Glu Tyr Lys Lys Arg Thr
    930                 935                 940

Gly Ser Phe Asn Glu Asp Leu Leu His His Met Ser Pro Leu Gly Trp
945                 950                 955                 960

Glu His Ile Asn Leu Leu Gly Glu Tyr His Phe Asn Ser Glu Lys Val
                965                 970                 975

Val Ser Leu Asn Ser Leu Arg Pro Leu Lys Leu Ser
            980                 985
```

(2) INFORMATION FOR SEQ ID NO:20:

(i) SEQUENCE CHARACTERISTICS:
(A) LENGTH: 573 base pairs (B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..573

(xi) SEQUENCE DESCRIPTION: SEQ ID NO:20:

```
TTG CGG AAA ATC GGT TAT ATT CGT GTC AGT TCG ACT AAC CAG AAT CCT       48
Leu Arg Lys Ile Gly Tyr Ile Arg Val Ser Ser Thr Asn Gln Asn Pro
  1               5                  10                  15

TCA AGA CAA TTT CAG CAG TTG AAC GAG ATC GGA ATG GAT ATT ATA TAT       96
Ser Arg Gln Phe Gln Gln Leu Asn Glu Ile Gly Met Asp Ile Ile Tyr
             20                  25                  30

GAA GAG AAA GTT TCA GGA GCA ACA AAG GAT CGC GAG CAA CTT CAA AAA      144
Glu Glu Lys Val Ser Gly Ala Thr Lys Asp Arg Glu Gln Leu Gln Lys
         35                  40                  45

GTG TTA GAC GAT TTA CAG GAA GAT GAC ATC ATT TAT GTT ACA GAC TTA      192
Val Leu Asp Asp Leu Gln Glu Asp Asp Ile Ile Tyr Val Thr Asp Leu
     50                  55                  60

ACT CGA ATC ACT CGT AGT ACA CAA GAT CTA TTT GAA TTA ATC GAT AAC      240
Thr Arg Ile Thr Arg Ser Thr Gln Asp Leu Phe Glu Leu Ile Asp Asn
 65                  70                  75                  80

ATA CGA GAT AAA AAG GCA AGT TTA AAA TCA CTA AAA GAT ACA TGG CTT      288
Ile Arg Asp Lys Lys Ala Ser Leu Lys Ser Leu Lys Asp Thr Trp Leu
                 85                  90                  95

GAT TTA TCA GAA GAT AAT CCA TAC AGC CAA TTC TTA ATT ACT GTA ATG      336
Asp Leu Ser Glu Asp Asn Pro Tyr Ser Gln Phe Leu Ile Thr Val Met
            100                 105                 110

GCT GGT GTT AAC CAA TTA GAG CGA GAT CTT ATT CGG ATG AGA CAA CGT      384
Ala Gly Val Asn Gln Leu Glu Arg Asp Leu Ile Arg Met Arg Gln Arg
        115                 120                 125

GAA GGG ATT GAA TTG GCT AAG AAA GAA GGA AAG TTT AAA GGT CGA TTA      432
Glu Gly Ile Glu Leu Ala Lys Lys Glu Gly Lys Phe Lys Gly Arg Leu
    130                 135                 140

AAG AAG TAT CAT AAA AAT CAC GCA GGA ATG AAT TAT GCG GTA AAG CTA      480
Lys Lys Tyr His Lys Asn His Ala Gly Met Asn Tyr Ala Val Lys Leu
145                 150                 155                 160

TAT AAA GAA GGA AAT ATG ACT GTA AAT CAA ATT TGT GAA ATT ACT AAT      528
Tyr Lys Glu Gly Asn Met Thr Val Asn Gln Ile Cys Glu Ile Thr Asn
                165                 170                 175

GTA TCT AGG GCT TCA TTA TAC AGG AAA TTA TCA GAA GTG AAT AAT          573
Val Ser Arg Ala Ser Leu Tyr Arg Lys Leu Ser Glu Val Asn Asn
            180                 185                 190
```

(2) INFORMATION FOR SEQ ID NO:21:

(i) SEQUENCE CHARACTERISTICS:
(A) LENGTH: 191 amino acids
(B) TYPE: amino acid
(D) TOPOLOGY: linear (ii) MOLECULE TYPE: protein (xi) SEQUENCE DESCRIPTION: SEQ ID NO:21:

```
Leu Arg Lys Ile Gly Tyr Ile Arg Val Ser Ser Thr Asn Gln Asn Pro
  1               5                  10                  15

Ser Arg Gln Phe Gln Gln Leu Asn Glu Ile Gly Met Asp Ile Ile Tyr
             20                  25                  30

Glu Glu Lys Val Ser Gly Ala Thr Lys Asp Arg Glu Gln Leu Gln Lys
```

-continued

```
        35                  40                  45

Val Leu Asp Asp Leu Gln Glu Asp Asp Ile Ile Tyr Val Thr Asp Leu
     50                  55                  60

Thr Arg Ile Thr Arg Ser Thr Gln Asp Leu Phe Glu Leu Ile Asp Asn
 65                  70                  75                  80

Ile Arg Asp Lys Lys Ala Ser Leu Lys Ser Leu Lys Asp Thr Trp Leu
                 85                  90                  95

Asp Leu Ser Glu Asp Asn Pro Tyr Ser Gln Phe Leu Ile Thr Val Met
            100                 105                 110

Ala Gly Val Asn Gln Leu Glu Arg Asp Leu Ile Arg Met Arg Gln Arg
        115                 120                 125

Glu Gly Ile Glu Leu Ala Lys Lys Glu Gly Lys Phe Lys Gly Arg Leu
    130                 135                 140

Lys Lys Tyr His Lys Asn His Ala Gly Met Asn Tyr Ala Val Lys Leu
145                 150                 155                 160

Tyr Lys Glu Gly Asn Met Thr Val Asn Gln Ile Cys Glu Ile Thr Asn
                165                 170                 175

Val Ser Arg Ala Ser Leu Tyr Arg Lys Leu Ser Glu Val Asn Asn
            180                 185                 190
```

(2) INFORMATION FOR SEQ ID NO:22:

(i) SEQUENCE CHARACTERISTICS:
(A) LENGTH: 909 base pairs
(B) TYPE: nucleic acid
(C) STRANDEDNESS: unknown
(D) TOPOLOGY: linear (ii) MOLECULE TYPE: DNA (genomic)

(ix) FEATURE:
(A) NAME/KEY: CDS
(B) LOCATION: 1..909

(xi) SEQUENCE DESCRIPTION: SEQ ID NO:22:

```
ATG AAG AAG TTG TTT TTT TTA TTG TTA TTG TTA TTC TTA ATA TAC TTA       48
Met Lys Lys Leu Phe Phe Leu Leu Leu Leu Leu Phe Leu Ile Tyr Leu
  1               5                  10                  15

GGT TAT GAC TAC GTT AAT GAA GCA CTG TTT TCT CAG GAA AAA GTC GAA       96
Gly Tyr Asp Tyr Val Asn Glu Ala Leu Phe Ser Gln Glu Lys Val Glu
             20                  25                  30

TTT CAA AAT TAT GAT CAA AAT CCC AAA GAA CAT TTA GAA AAT AGT GGG      144
Phe Gln Asn Tyr Asp Gln Asn Pro Lys Glu His Leu Glu Asn Ser Gly
        35                  40                  45

ACT TCT GAA AAT ACC CAA GAG AAA ACA ATT ACA GAA GAA CAG GTT TAT      192
Thr Ser Glu Asn Thr Gln Glu Lys Thr Ile Thr Glu Glu Gln Val Tyr
     50                  55                  60

CAA GGA AAT CTG CTA TTA ATC AAT AGT AAA TAT CCT GTT CGC CAA GAA      240
Gln Gly Asn Leu Leu Leu Ile Asn Ser Lys Tyr Pro Val Arg Gln Glu
 65                  70                  75                  80

AGT GTG AAG TCA GAT ATC GTG AAT TTA TCT AAA CAT GAC GAA TTA ATA      288
Ser Val Lys Ser Asp Ile Val Asn Leu Ser Lys His Asp Glu Leu Ile
                 85                  90                  95

AAT GGA TAC GGG TTG CTT GAT AGT AAT ATT TAT ATG TCA AAA GAA ATA      336
Asn Gly Tyr Gly Leu Leu Asp Ser Asn Ile Tyr Met Ser Lys Glu Ile
            100                 105                 110

GCA CAA AAA TTT TCA GAG ATG GTC AAT GAT GCT GTA AAG GGT GGC GTT      384
Ala Gln Lys Phe Ser Glu Met Val Asn Asp Ala Val Lys Gly Gly Val
        115                 120                 125

AGT CAT TTT ATT ATT AAT AGT GGC TAT CGA GAC TTT GAT GAG CAA AGT      432
```

-continued

```
Ser His Phe Ile Ile Asn Ser Gly Tyr Arg Asp Phe Asp Glu Gln Ser
    130                 135                 140

GTG CTT TAC CAA GAA ATG GGG GCT GAG TAT GCC TTA CCA GCA GGT TAT       480
Val Leu Tyr Gln Glu Met Gly Ala Glu Tyr Ala Leu Pro Ala Gly Tyr
145                 150                 155                 160

AGT GAG CAT AAT TCA GGT TTA TCA CTA GAT GTA GGA TCA AGC TTG ACG       528
Ser Glu His Asn Ser Gly Leu Ser Leu Asp Val Gly Ser Ser Leu Thr
                165                 170                 175

AAA ATG GAA CGA GCC CCT GAA GGA AAG TGG ATA GAA GAA AAT GCT TGG       576
Lys Met Glu Arg Ala Pro Glu Gly Lys Trp Ile Glu Glu Asn Ala Trp
            180                 185                 190

AAA TAC GGG TTC ATT TTA CGT TAT CCA GAG GAC AAA ACA GAG TTA ACA       624
Lys Tyr Gly Phe Ile Leu Arg Tyr Pro Glu Asp Lys Thr Glu Leu Thr
        195                 200                 205

GGA ATT CAA TAT GAA CCA TGG CAT ATT CGC TAT GTT GGT TTA CCA CAT       672
Gly Ile Gln Tyr Glu Pro Trp His Ile Arg Tyr Val Gly Leu Pro His
    210                 215                 220

AGT GCG ATT ATG AAA GAA AAG AAT TTC GTT CTC GAG GAA TAT ATG GAT       720
Ser Ala Ile Met Lys Glu Lys Asn Phe Val Leu Glu Glu Tyr Met Asp
225                 230                 235                 240

TAC CTA AAA GAA GAA AAA ACC ATT TCT GTT AGT GTA AAT GGG GAA AAA       768
Tyr Leu Lys Glu Glu Lys Thr Ile Ser Val Ser Val Asn Gly Glu Lys
                245                 250                 255

TAT GAG ATC TTT TAT TAT CCT GTT ACT AAA AAT ACC ACC ATT CAT GTG       816
Tyr Glu Ile Phe Tyr Tyr Pro Val Thr Lys Asn Thr Thr Ile His Val
            260                 265                 270

CCG ACT AAT CTT CGT TAT GAG ATA TCA GGA AAC AAT ATA GAC GGT GTA       864
Pro Thr Asn Leu Arg Tyr Glu Ile Ser Gly Asn Asn Ile Asp Gly Val
        275                 280                 285

ATT GTG ACA GTG TTT CCC GGA TCA ACA CAT ACT AAT TCA AGG AGG           909
Ile Val Thr Val Phe Pro Gly Ser Thr His Thr Asn Ser Arg Arg
    290                 295                 300
```

(2) INFORMATION FOR SEQ ID NO:23:

(i) SEQUENCE CHARACTERISTICS:
(A) LENGTH: 303 amino acids
(B) TYPE: amino acid
(D) TOPOLOGY: linear (ii) MOLECULE TYPE: protein (xi) SEQUENCE DESCRIPTION: SEQ ID NO:23:

```
Met Lys Lys Leu Phe Phe Leu Leu Leu Leu Leu Phe Leu Ile Tyr Leu
  1               5                  10                  15

Gly Tyr Asp Tyr Val Asn Glu Ala Leu Phe Ser Gln Glu Lys Val Glu
            20                  25                  30

Phe Gln Asn Tyr Asp Gln Asn Pro Lys Glu His Leu Glu Asn Ser Gly
        35                  40                  45

Thr Ser Glu Asn Thr Gln Glu Lys Thr Ile Thr Glu Glu Gln Val Tyr
     50                  55                  60

Gln Gly Asn Leu Leu Leu Ile Asn Ser Lys Tyr Pro Val Arg Gln Glu
 65                  70                  75                  80

Ser Val Lys Ser Asp Ile Val Asn Leu Ser Lys His Asp Glu Leu Ile
                 85                  90                  95

Asn Gly Tyr Gly Leu Leu Asp Ser Asn Ile Tyr Met Ser Lys Glu Ile
            100                 105                 110

Ala Gln Lys Phe Ser Glu Met Val Asn Asp Ala Val Lys Gly Gly Val
        115                 120                 125
```

-continued

```
Ser His Phe Ile Ile Asn Ser Gly Tyr Arg Asp Phe Asp Glu Gln Ser
    130                 135                 140

Val Leu Tyr Gln Glu Met Gly Ala Glu Tyr Ala Leu Pro Ala Gly Tyr
145                 150                 155                 160

Ser Glu His Asn Ser Gly Leu Ser Leu Asp Val Gly Ser Ser Leu Thr
                165                 170                 175

Lys Met Glu Arg Ala Pro Glu Gly Lys Trp Ile Glu Glu Asn Ala Trp
            180                 185                 190

Lys Tyr Gly Phe Ile Leu Arg Tyr Pro Glu Asp Lys Thr Glu Leu Thr
        195                 200                 205

Gly Ile Gln Tyr Glu Pro Trp His Ile Arg Tyr Val Gly Leu Pro His
    210                 215                 220

Ser Ala Ile Met Lys Glu Lys Asn Phe Val Leu Glu Glu Tyr Met Asp
225                 230                 235                 240

Tyr Leu Lys Glu Glu Lys Thr Ile Ser Val Ser Val Asn Gly Glu Lys
                245                 250                 255

Tyr Glu Ile Phe Tyr Tyr Pro Val Thr Lys Asn Thr Thr Ile His Val
            260                 265                 270

Pro Thr Asn Leu Arg Tyr Glu Ile Ser Gly Asn Asn Ile Asp Gly Val
        275                 280                 285

Ile Val Thr Val Phe Pro Gly Ser Thr His Thr Asn Ser Arg Arg
    290                 295                 300
```

(2) INFORMATION FOR SEQ ID NO:24:

(i) SEQUENCE CHARACTERISTICS:
(A) LENGTH: 483 base pairs
(B) TYPE: nucleic acid
(C) STRANDEDNESS: unknown
(D) TOPOLOGY: linear (ii) MOLECULE TYPE: DNA (genomic)

(ix) FEATURE:
(A) NAME/KEY: CDS
(B) LOCATION: 1..483

(xi) SEQUENCE DESCRIPTION: SEQ ID NO:24:

```
TTG GGA AAA ATA TTA TCT AGA GGA TTG CTA GCT TTA TAT TTA GTG ACA       48
Leu Gly Lys Ile Leu Ser Arg Gly Leu Leu Ala Leu Tyr Leu Val Thr
  1               5                  10                  15

CTA ATC TGG TTA GTG TTA TTC AAA TTA CAA TAC AAT ATT TTA TCA GTA       96
Leu Ile Trp Leu Val Leu Phe Lys Leu Gln Tyr Asn Ile Leu Ser Val
            20                  25                  30

TTT AAT TAT CAT CAA AGA AGT CTT AAC TTG ACT CCA TTT ACT GCT ACT      144
Phe Asn Tyr His Gln Arg Ser Leu Asn Leu Thr Pro Phe Thr Ala Thr
        35                  40                  45

GGG AAT TTC AGA GAG ATG ATA GAT AAT GTT ATA ATC TTT ATT CCA TTT      192
Gly Asn Phe Arg Glu Met Ile Asp Asn Val Ile Ile Phe Ile Pro Phe
     50                  55                  60

GGC TTG CTT TTG AAT GTC AAT TTT AAA GAA ATC GGA TTT TTA CCT AAG      240
Gly Leu Leu Leu Asn Val Asn Phe Lys Glu Ile Gly Phe Leu Pro Lys
 65                  70                  75                  80

TTT GCT TTT GTA CTG GTT TTA AGT CTT ACT TTT GAA ATA ATT CAA TTT      288
Phe Ala Phe Val Leu Val Leu Ser Leu Thr Phe Glu Ile Ile Gln Phe
                 85                  90                  95

ATC TTC GCT ATT GGA GCG ACA GAC ATA ACA GAT GTA ATT ACA AAT ACT      336
Ile Phe Ala Ile Gly Ala Thr Asp Ile Thr Asp Val Ile Thr Asn Thr
            100                 105                 110

GTT GGA GGC TTT CTT GGA CTG AAA TTA TAT GGT TTA AGC AAT AAG CAT      384
```

-continued

```
Val Gly Gly Phe Leu Gly Leu Lys Leu Tyr Gly Leu Ser Asn Lys His
        115                 120                 125

ATG AAT CAA AAA AAA TTA GAC AGA GTT ATT ATT TTT GTA GGT ATA CTT      432
Met Asn Gln Lys Lys Leu Asp Arg Val Ile Ile Phe Val Gly Ile Leu
    130                 135                 140

TTG CTC GTA TTA TTG CTC GTT TAC CGT ACC CAT TTA AGA ATA AAT TAC      480
Leu Leu Val Leu Leu Leu Val Tyr Arg Thr His Leu Arg Ile Asn Tyr
145                 150                 155                 160

GTG                                                                  483
Val
```

(2) INFORMATION FOR SEQ ID NO:25:

(i) SEQUENCE CHARACTERISTICS:
(A) LENGTH: 161 amino acids
(B) TYPE: amino acid
(D) TOPOLOGY: linear (ii) MOLECULE TYPE: protein (xi) SEQUENCE DESCRIPTION: SEQ ID NO:25:

```
Leu Gly Lys Ile Leu Ser Arg Gly Leu Leu Ala Leu Tyr Leu Val Thr
  1               5                  10                  15

Leu Ile Trp Leu Val Leu Phe Lys Leu Gln Tyr Asn Ile Leu Ser Val
             20                  25                  30

Phe Asn Tyr His Gln Arg Ser Leu Asn Leu Thr Pro Phe Thr Ala Thr
        35                  40                  45

Gly Asn Phe Arg Glu Met Ile Asp Asn Val Ile Ile Phe Ile Pro Phe
     50                  55                  60

Gly Leu Leu Leu Asn Val Asn Phe Lys Glu Ile Gly Phe Leu Pro Lys
 65                  70                  75                  80

Phe Ala Phe Val Leu Val Leu Ser Leu Thr Phe Glu Ile Ile Gln Phe
                 85                  90                  95

Ile Phe Ala Ile Gly Ala Thr Asp Ile Thr Asp Val Ile Thr Asn Thr
            100                 105                 110

Val Gly Gly Phe Leu Gly Leu Lys Leu Tyr Gly Leu Ser Asn Lys His
        115                 120                 125

Met Asn Gln Lys Lys Leu Asp Arg Val Ile Ile Phe Val Gly Ile Leu
    130                 135                 140

Leu Leu Val Leu Leu Leu Val Tyr Arg Thr His Leu Arg Ile Asn Tyr
145                 150                 155                 160

Val
```

(2) INFORMATION FOR SEQ ID NO:26:

(i) SEQUENCE CHARACTERISTICS:
(A) LENGTH: 18 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO:26:

```
ATGCTCCTGT CTCCTTTC                                                   18
```

(2) INFORMATION FOR SEQ ID NO:27:

(i) SEQUENCE CHARACTERISTICS:
(A) LENGTH: 2296 amino acids
(B) TYPE: amino acid (D) TOPOLOGY: linear (ii) MOLECULE TYPE: protein (xi) SEQUENCE DESCRIPTION: SEQ ID NO:27:

```
Lys Leu Phe Phe Leu Leu Ile Cys Arg Phe Thr Asn Arg Ile Lys Leu
1               5                   10                  15

Leu Phe Ser His Cys Pro Cys Phe Pro His His Ser Phe Lys Cys Ser
            20                  25                  30

Asp Ser Arg Gln Tyr Asn Phe Val Phe Ser Lys Ile Tyr Ala Phe Met
        35                  40                  45

Gln Met Asn Gly Ile Thr Ile Phe Gln Ser Leu Met Lys Val Leu Lys
    50                  55                  60

Cys His Ser Ile Phe Thr Gln Gly Lys Ser Tyr Lys Val Val Phe Thr
65                  70                  75                  80

Ser Asn Phe Phe Gln Met Ile Pro Lys Cys Ile Phe Pro Leu Arg Ile
                85                  90                  95

Met Ile Lys Arg Gly Trp Thr Asn Thr Asn Leu Phe Arg Tyr Ile Leu
            100                 105                 110

Tyr Asp Arg Ile Trp Asp Ala Phe Asp Met Ser Val Trp Pro Thr Gly
        115                 120                 125

Ile Pro Lys Asn Ser Leu Asn Ser Lys Ser Thr Val Phe Phe Pro Pro
    130                 135                 140

Ser Leu Ile Asn Tyr Phe Ile Pro Phe Gly Lys Ser Glu Val Gly Pro
145                 150                 155                 160

Gln Tyr Pro Phe Ile Phe Arg Asp Leu His Lys Ser Leu Ser Leu Phe
                165                 170                 175

Arg Cys Lys Gln Phe Ser Thr Ser Arg Asn Phe His Ser Val Ser Phe
            180                 185                 190

His Phe Cys Ile Phe Asn Leu Leu Val Gln Leu Tyr Ile Asn Arg Val
        195                 200                 205

Tyr Ser Ile Asp Thr Asn Val Val Asp Asn His Ser Glu Arg Leu Ile
    210                 215                 220

Arg Leu Val Ser Lys Met Arg Tyr Phe Ala Glu Asn Arg Leu Tyr Ser
225                 230                 235                 240

Cys Gln Phe Asp Pro Glu Ser Phe Lys Thr Ile Ser Ala Val Glu Arg
                245                 250                 255

Asp Arg Asn Gly Tyr Tyr Ile Lys Arg Lys Phe Gln Glu Gln Gln Arg
            260                 265                 270

Ile Ala Ser Asn Phe Lys Lys Cys Thr Ile Tyr Arg Lys Met Thr Ser
        275                 280                 285

Phe Met Leu Gln Thr Leu Glu Ser Leu Val Val His Lys Ile Tyr Leu
    290                 295                 300

Asn Ser Ile Thr Tyr Glu Ile Lys Arg Gln Val Asn His Lys Ile His
305                 310                 315                 320

Gly Leu Ile Tyr Gln Lys Ile Ile His Thr Ala Asn Ser Leu Leu Trp
                325                 330                 335

Leu Val Leu Thr Asn Ser Glu Ile Leu Phe Gly Asp Asn Val Lys Gly
            340                 345                 350

Leu Asn Trp Leu Arg Lys Lys Glu Ser Leu Lys Val Asp Arg Ser Ile
        355                 360                 365

Ile Lys Ile Thr Gln Glu Ile Met Arg Arg Lys Leu Tyr Lys Glu Gly
    370                 375                 380

Asn Met Thr Val Asn Gln Ile Cys Glu Ile Thr Asn Val Ser Arg Ala
```

-continued

```
385                 390                 395                 400

Ser Leu Tyr Arg Lys Leu Ser Glu Val Asn Asn Pro Phe Cys Ile Pro
                405                 410                 415

Leu Met Gly Asn Ile Phe Lys Glu Glu Lys Glu Thr Ile Lys Tyr Gln
            420                 425                 430

Pro Pro Ser Asp Ala Glu Lys Pro Phe Asp Lys Lys Arg Ile Ile Ile
        435                 440                 445

Leu Arg Asn Ser Ser Phe Ile Met Met Leu Ile Asn Ser Ala Leu Ser
    450                 455                 460

Asp Lys Leu Leu Arg Ala Asn Leu Cys Glu Arg Val Ile Thr Met Ser
465                 470                 475                 480

Asp Lys Ile Leu Ile Val Asp Asp Glu His Glu Ile Ala Asp Leu Val
                485                 490                 495

Glu Leu Tyr Leu Lys Asn Glu Asn Tyr Thr Val Phe Lys Tyr Tyr Thr
            500                 505                 510

Ala Lys Glu Ala Leu Glu Cys Ile Asp Lys Ser Glu Ile Asp Leu Ala
        515                 520                 525

Ile Leu Asp Ile Met Leu Pro Gly Thr Ser Gly Leu Thr Ile Cys Gln
    530                 535                 540

Lys Ile Arg Asp Lys His Thr Tyr Pro Ile Ile Met Leu Thr Gly Lys
545                 550                 555                 560

Asp Thr Glu Val Asp Lys Ile Thr Gly Leu Thr Ile Gly Ala Asp Asp
                565                 570                 575

Tyr Ile Thr Lys Pro Phe Arg Pro Leu Glu Leu Ile Ala Arg Val Lys
            580                 585                 590

Ala Gln Leu Arg Arg Tyr Lys Lys Phe Ser Gly Val Lys Glu Gln Asn
        595                 600                 605

Glu Asn Val Ile Val His Ser Gly Leu Val Ile Asn Val Asn Thr His
    610                 615                 620

Glu Cys Tyr Leu Asn Glu Lys Gln Leu Ser Leu Thr Pro Thr Glu Phe
625                 630                 635                 640

Ser Ile Leu Arg Ile Leu Cys Glu Asn Lys Gly Asn Val Val Ser Ser
                645                 650                 655

Glu Leu Leu Phe His Glu Ile Trp Gly Asp Glu Tyr Phe Ser Lys Ser
            660                 665                 670

Asn Asn Thr Ile Thr Val His Ile Arg His Leu Arg Glu Lys Met Asn
        675                 680                 685

Asp Thr Ile Asp Asn Pro Lys Tyr Ile Lys Thr Val Trp Gly Val Gly
    690                 695                 700

Tyr Lys Ile Glu Lys Lys Lys Arg Leu Phe Gln Thr Arg Thr Lys Thr
705                 710                 715                 720

Leu His Val Tyr Arg Cys Asn Cys Cys Gly Ser Asn Cys Ile Arg Val
                725                 730                 735

Val Tyr Ser Phe Asn Asp Pro Arg Glu Thr Trp Gly Leu Asp Leu Lys
            740                 745                 750

Tyr Phe Gly Lys Gln Ile Leu Lys Ser Pro Gly Arg Asp Glu Ile Ile
        755                 760                 765

Ser Ile Phe His Thr Glu Gln Tyr Arg Tyr Leu Tyr Leu Cys Gly Asp
    770                 775                 780

Cys His Tyr Ser Tyr Ser Met Ser Arg His Ala Phe Lys Ile Arg Lys
785                 790                 795                 800

Ile Leu Arg Asp Lys Tyr Arg His Cys Thr Tyr Ser Glu Arg Arg Thr
                805                 810                 815
```

-continued

```
Asn Ala Phe Cys Gly Asn Gly Cys Tyr Gly Thr Lys Ala Gln His Ile
            820                 825                 830

Lys Thr Asp Ser Gly Lys Ala Arg Ala Gly Cys Lys Ala Gly Arg Thr
        835                 840                 845

Lys Lys Lys Arg Cys Tyr Val Leu Gly Ala Arg Tyr Asn Ala Pro Tyr
    850                 855                 860

Ile His Tyr Arg Leu Phe Glu Pro Ala Arg Gly Ser Arg His Ala Gly
865                 870                 875                 880

Arg Ser Lys Gly Lys Val Cys Ala Tyr His Val Gly Gln Ser Val Ser
                885                 890                 895

Thr Arg Thr Ala Asn Arg Arg Val Phe Asp Tyr Thr Val Pro Thr Asn
            900                 905                 910

Asp Asn Ala Asn Lys Asn Ala His Arg Pro Ile Leu Tyr Ala Gly Ala
        915                 920                 925

Asp Asp Arg Ile Leu Ser Ser Ala Phe Arg Thr Trp Lys Thr Gly Gly
    930                 935                 940

Tyr Ser Arg Pro Arg Gly Ser Asp Arg Val Arg Arg Pro Thr Arg Glu
945                 950                 955                 960

Ser Leu Gln His Phe Glu Lys Arg Arg Cys Ile Gln Gly Gln His His
                965                 970                 975

His Tyr Arg Gly Pro Leu Arg Gly Cys Gly Val Asn Arg Ile Gln Glu
            980                 985                 990

His Trp Lys His Pro Lys Arg Ala Ser Cys His Ile Lys Val Leu Ala
        995                 1000                1005

Gly Gln Phe Ser Phe Phe Arg Tyr Gly Trp Arg Gly Thr Trp Ile Gly
    1010                1015                1020

Asp Cys Lys Arg Asn Tyr Cys Ser Ala Trp Arg Ala Asp Leu Arg Gly
1025                1030                1035                1040

Lys Leu Leu Tyr Asp Val Gly Arg Ala Ser Ser Asp Ala Arg Leu Gly
                1045                1050                1055

Lys Glu Val Leu Arg Asp Val Tyr Asn Phe Leu Gly Lys Ser Gln Gly
            1060                1065                1070

Tyr Leu Tyr Phe Phe Leu Gly Asn Gln Phe Asn Ile Lys Lys Arg Leu
        1075                1080                1085

Val Leu Thr Arg Thr Tyr Arg Lys Asn Glu Pro Phe Ser Phe Phe Arg
    1090                1095                1100

Glu Arg Phe Asp Lys Ile Thr Ile Gly Ile Pro Val Leu Phe Gly Ala
1105                1110                1115                1120

Phe His Arg Lys Gly Trp Ser Leu Ile Thr Ser Ala Leu Leu Phe Met
                1125                1130                1135

Asp Val Ser Arg Met Arg Gln Met His Ser Met Leu Phe Arg Leu Ala
            1140                1145                1150

Leu Ala Leu Trp Gln Arg Leu Thr Pro Thr Cys Arg Asn Pro Thr Pro
        1155                1160                1165

Asn Pro Arg Leu Ser Ile Asn Val Ser Val Trp Asp Ile Asn Gln Arg
    1170                1175                1180

Phe Pro Pro Leu Phe Phe Leu Arg Arg Glu Pro Val Asn Ile Phe Leu
1185                1190                1195                1200

Pro Glu Ala Ser Ala Ala Ile Ile Ile Gln Leu Leu Leu Arg Glu Trp
                1205                1210                1215

Ala Ser Leu Ser Thr Met Trp Arg Thr Arg Arg Ile Ala Leu Pro Ile
            1220                1225                1230
```

-continued

```
Ile Leu Cys Phe Leu Trp Gln Tyr Ala Thr Asn Arg Leu Cys Ala Leu
        1235                1240                1245

Trp Lys Asn Met Ile Ser Gly Trp Thr Ala Thr Val Ala Arg Tyr Ser
    1250                1255                1260

Ala Thr Gln Leu Val Trp Trp Glu Arg Ala Arg Ala Lys Arg Leu Leu
1265                1270                1275                1280

Ser Gly Cys Glu Asp Leu Asp Val Lys Cys Trp Leu Ile Val Ala Ala
                1285                1290                1295

Glu Val Arg Thr Met Tyr Arg Leu Met Ser Cys Cys Lys Ile Ala Ile
            1300                1305                1310

Ser Leu Arg Phe Met Cys Arg Ser Ile Arg Ile Arg Thr Ile Leu Ser
        1315                1320                1325

Ala Thr Asn Lys Tyr Arg Glu Ser Lys Glu His Phe Leu Ser Ile Leu
    1330                1335                1340

Gly Ala Val His Leu Ile Pro Met Ser Trp Leu Lys His Lys Thr Gly
1345                1350                1355                1360

Asn Trp Ala Val Pro His Trp Met Tyr Trp Lys Glu Arg Lys Ser Phe
                1365                1370                1375

Ser Thr Leu Ile Ala Pro Lys Asn Gln Leu Ile Ile Asn Phe Tyr Leu
            1380                1385                1390

Asn Phe Lys Glu Cys Leu Thr Ser His Arg Ile Arg Pro Ile Ile Pro
        1395                1400                1405

Ser Lys Arg Cys Val Ile Pro Leu Lys Lys Pro Leu Lys Thr Val Trp
    1410                1415                1420

Ile Leu Lys Gly Asp Arg Ser Met Asn Arg Ile Lys Val Ala Ile Leu
1425                1430                1435                1440

Phe Gly Gly Cys Ser Glu Glu His Asp Val Ser Val Lys Ser Ala Ile
                1445                1450                1455

Glu Ile Ala Ala Asn Ile Asn Lys Glu Lys Tyr Glu Pro Leu Tyr Ile
            1460                1465                1470

Gly Ile Thr Lys Ser Gly Val Trp Lys Met Cys Glu Lys Pro Cys Ala
        1475                1480                1485

Glu Trp Glu Asn Asp Asn Cys Tyr Ser Ala Val Leu Ser Pro Asp Lys
    1490                1495                1500

Lys Met His Gly Leu Leu Val Lys Lys Asn His Glu Tyr Glu Ile Asn
1505                1510                1515                1520

His Val Asp Val Ala Phe Ser Ala Leu His Gly Lys Ser Gly Glu Asp
                1525                1530                1535

Gly Ser Ile Gln Gly Leu Phe Glu Leu Ser Gly Ile Pro Phe Val Gly
            1540                1545                1550

Cys Asp Ile Gln Ser Ser Ala Ile Cys Met Asp Lys Ser Leu Thr Tyr
        1555                1560                1565

Ile Val Ala Lys Asn Ala Gly Ile Ala Thr Pro Ala Phe Trp Val Ile
    1570                1575                1580

Asn Lys Asp Asp Arg Pro Val Ala Ala Thr Phe Thr Tyr Pro Val Phe
1585                1590                1595                1600

Val Lys Pro Ala Arg Ser Gly Ser Ser Phe Gly Val Lys Lys Val Asn
                1605                1610                1615

Ser Ala Asp Glu Leu Asp Tyr Ala Ile Glu Ser Ala Arg Gln Tyr Asp
            1620                1625                1630

Ser Lys Ile Leu Ile Glu Gln Ala Val Ser Gly Cys Glu Val Gly Cys
        1635                1640                1645

Ala Val Leu Gly Asn Ser Ala Ala Leu Val Val Gly Glu Val Asp Gln
```

-continued

```
    1650                1655                1660

Ile Arg Leu Gln Tyr Gly Ile Phe Arg Ile His Gln Glu Val Glu Pro
1665                1670                1675                1680

Glu Lys Gly Ser Glu Asn Ala Val Ile Thr Val Pro Ala Asp Leu Ser
                1685                1690                1695

Ala Glu Glu Arg Gly Arg Ile Gln Glu Thr Ala Lys Lys Ile Tyr Lys
            1700                1705                1710

Ala Leu Gly Cys Arg Gly Leu Ala Arg Val Asp Met Phe Leu Gln Asp
        1715                1720                1725

Asn Gly Arg Ile Val Leu Asn Glu Val Asn Thr Leu Pro Gly Phe Thr
    1730                1735                1740

Ser Tyr Ser Arg Tyr Pro Arg Met Met Ala Ala Ala Gly Ile Ala Leu
1745                1750                1755                1760

Pro Glu Leu Ile Asp Arg Leu Ile Val Leu Ala Leu Lys Gly Ala Trp
                1765                1770                1775

Lys Asp Leu Leu Phe Met Lys Tyr Thr Val Phe Val Gly Thr Leu Asn
            1780                1785                1790

Met Pro Leu Gly Ile Ile Ser Pro Glu Asn Arg Leu Thr Val Met Lys
        1795                1800                1805

Ile Ala Leu Gly His Thr Ser Trp Leu Asn Arg Phe Arg Gln Lys Asn
    1810                1815                1820

Trp Leu Leu Pro Lys Gly Thr Asp Cys Phe Tyr Gly Thr Val Thr Val
1825                1830                1835                1840

Leu Ser Val Leu Thr Val Leu Cys Asn Gly Leu His Ser Arg Lys Ile
                1845                1850                1855

Thr Gln Arg Lys Val Ile Ile Pro Ile Leu Thr Glu Leu Arg Phe Gln
            1860                1865                1870

Lys Asp Thr Trp Leu Gln Asn Gln Ala Ile Ala Ala Ala Val Pro Leu
        1875                1880                1885

Ile Leu Arg Phe Ile Asp Thr Arg Val Ser Leu Tyr Gln Trp Gly Ala
    1890                1895                1900

Asp Leu Ile Leu Trp Met Asn Ala Leu Ile Met Arg Gln Met Glu Tyr
1905                1910                1915                1920

His Ala Met Lys Arg Lys Ile Ala Asp Val Cys Ala Pro Ser Trp Lys
                1925                1930                1935

Thr Val Gly Leu Lys His Ile Ala Ser Asn Gly Gly Thr Met Tyr Glu
            1940                1945                1950

Thr Asn His Thr Pro Ile Ala Ile Leu Ile Ser Pro Leu Asn Lys Leu
        1955                1960                1965

Leu Thr Val Ala Arg Thr Asn Tyr Ile Ser Leu Phe Arg Gln Glu Thr
    1970                1975                1980

Arg Arg Met Leu Val Leu Arg Glu Phe Ile Tyr Ser Arg Tyr Arg Cys
1985                1990                1995                2000

Lys Ala Glu Arg Tyr Cys Gly His Tyr Leu Arg Ala Leu Arg Gln Asp
                2005                2010                2015

Ser Leu Ile Ile Arg Leu Ile Ala Arg Gly Gly Ile Ser His Arg Pro
            2020                2025                2030

Leu Ser Thr Gly Ser Ser Ala Ser Leu Asn Ser Ala Trp Val Ser Leu
        2035                2040                2045

Met Lys Ile His Leu His Trp Ile Gln Gly Glu Ile Ile Asp Cys Asn
    2050                2055                2060

Leu Arg Gly Lys Thr Ala Gln Ser Gln Thr Arg Leu Cys Arg Leu Arg
2065                2070                2075                2080
```

-continued

```
Gly Arg Phe Lys Tyr Phe Ile Leu Pro Thr Ile Leu Arg Arg Arg Leu
                2085                2090                2095

Lys Met Lys Lys Leu Phe Phe Leu Leu Leu Leu Leu Phe Leu Ile Tyr
            2100                2105                2110

Leu Gly Tyr Asp Tyr Val Asn Glu Ala Leu Phe Ser Gln Glu Lys Val
        2115                2120                2125

Glu Phe Gln Asn Tyr Asp Gln Asn Pro Lys Glu His Leu Glu Asn Ser
    2130                2135                2140

Gly Thr Ser Glu Asn Thr Gln Glu Lys Thr Ile Thr Glu Glu Gln Val
2145                2150                2155                2160

Tyr Gln Gly Asn Leu Leu Leu Ile Asn Ser Lys Tyr Pro Val Arg Gln
                2165                2170                2175

Glu Val Ser Gln Ile Ser Ile Tyr Leu Asn Met Thr Asn Met Asp Thr
            2180                2185                2190

Gly Cys Leu Ile Val Ile Phe Ile Cys Gln Lys Lys His Lys Asn Phe
        2195                2200                2205

Gln Arg Trp Ser Met Met Leu Arg Val Ala Leu Val Ile Leu Leu Leu
    2210                2215                2220

Ile Val Ala Ile Glu Thr Leu Met Ser Lys Val Cys Phe Thr Lys Lys
2225                2230                2235                2240

Trp Gly Leu Ser Met Pro Tyr Gln Gln Val Ile Val Ser Ile Ile Gln
                2245                2250                2255

Val Tyr His Met Asp Gln Ala Arg Lys Trp Asn Glu Pro Leu Lys Glu
            2260                2265                2270

Ser Gly Lys Lys Met Leu Gly Asn Thr Gly Ser Phe Tyr Val Ile Gln
        2275                2280                2285

Arg Thr Lys Gln Ser Gln Glu Phe
    2290                2295
```

(2) INFORMATION FOR SEQ ID NO:28:

(i) SEQUENCE CHARACTERISTICS:
(A) LENGTH: 2254 amino acids
(B) TYPE: amino acid
(D) TOPOLOGY: linear (ii) MOLECULE TYPE: protein (xi) SEQUENCE DESCRIPTION: SEQ ID NO:28:

```
Ser Phe Ser Phe Cys Ser Phe Val Arg Asp Leu Leu Thr Val Leu Asn
1               5                   10                  15

Ser Phe Phe Ser Ala Ile Ala Leu Ala Ser His Thr Ile Leu Ser Ser
            20                  25                  30

Val Val Ile Ala Gly Ser Ile Ile Leu Phe Phe Leu Arg Lys Ser Met
        35                  40                  45

His Ser Cys Ser Arg Met Ala Ser Pro Phe Ser Lys Ala Asn Arg Tyr
    50                  55                  60

Leu Asn Val Ile Arg Tyr Ser Leu Arg Val Lys Val Thr Lys Ser Tyr
65                  70                  75                  80

Ser Leu Arg Ile Ser Phe Lys Ser Gln Ser Val Phe Ser Leu Gly Ser
                85                  90                  95

Ser Glu Asp Gly Leu Thr Pro Ile Cys Phe Asp Ile Tyr Cys Met Thr
            100                 105                 110

Glu Ser Gly Met Leu Leu Ile Val Tyr Gly Gln Pro Gly Tyr Arg Arg
        115                 120                 125
```

-continued

```
Thr Ala Asn Thr Ala Asn Pro Lys Arg Phe Ser Ser Leu Leu Arg Leu
    130                 135                 140

Leu Thr Ile Ser Lys Ser Arg Leu Glu Lys Val Lys Val Pro Ser Ile
145                 150                 155                 160

His Ser Ser Ser Gly Ile Cys Ile Lys Ala Cys Leu Cys Ser Gly Val
                165                 170                 175

Ser Asn Ser Leu Pro Leu Ala Ile Phe Ile Gln Tyr His Ser Ile Ser
            180                 185                 190

Val Phe Ser Ile Tyr Phe Asn Tyr Ile Ser Ile Glu Cys Thr Leu Leu
        195                 200                 205

Ile Gln Met Thr Asp Lys Ile Ile Val Lys Ser Val Ser Asp Leu Ser
    210                 215                 220

Gln Lys Gly Asp Ile Leu Arg Lys Ile Gly Tyr Ile Arg Val Ser Ser
225                 230                 235                 240

Thr Asn Gln Asn Pro Ser Arg Gln Phe Gln Gln Leu Asn Glu Ile Gly
                245                 250                 255

Met Asp Ile Ile Arg Glu Ser Phe Arg Ser Asn Lys Gly Ser Arg Ala
            260                 265                 270

Thr Ser Lys Ser Val Arg Arg Phe Thr Gly Arg His His Leu Cys Tyr
        275                 280                 285

Arg Leu Asn Ser Asn His Ser Tyr Thr Arg Ser Ile Ile Asn Arg His
    290                 295                 300

Thr Arg Lys Gly Lys Phe Lys Ile Thr Lys Arg Tyr Met Ala Phe Ile
305                 310                 315                 320

Arg Arg Ser Ile Gln Pro Ile Leu Asn Tyr Cys Asn Gly Trp Cys Pro
                325                 330                 335

Ile Arg Ala Arg Ser Tyr Ser Asp Glu Thr Thr Arg Asp Ile Gly Glu
            340                 345                 350

Arg Arg Lys Val Arg Ser Ile Lys Glu Val Ser Lys Ser Arg Arg Asn
        355                 360                 365

Glu Leu Cys Gly Glu Ser Tyr Ile Lys Lys Glu Ile Leu Ile Lys Phe
    370                 375                 380

Val Lys Leu Leu Met Tyr Leu Gly Leu His Tyr Thr Gly Asn Tyr Gln
385                 390                 395                 400

Lys Ile Ile Ser His Ser Val Phe Arg Trp Ala Ile Phe Leu Lys Lys
                405                 410                 415

Lys Arg Lys Leu Asn Ile Asn Ser Leu Leu Ala Met Pro Lys Ser Pro
            420                 425                 430

Leu Ile Lys Lys Glu Ser Ser Ser Glu Ile Leu Ser His Leu Leu Cys
        435                 440                 445

Lys Cys Leu Ile Arg Pro Tyr Asn Leu Ile Asn Tyr Gly Gln Thr Tyr
    450                 455                 460

Val Lys Gly Leu Ala Ile Lys Tyr Leu Leu Trp Met Met Asn Met Lys
465                 470                 475                 480

Leu Pro Ile Trp Leu Asn Tyr Thr Lys Thr Arg Ile Ile Arg Phe Ser
                485                 490                 495

Asn Thr Ile Pro Pro Lys Lys His Trp Asn Val Thr Ser Leu Arg Leu
            500                 505                 510

Thr Leu Pro Tyr Trp Thr Ser Cys Phe Pro Ala Gln Ala Ala Leu Leu
        515                 520                 525

Ser Val Lys Lys Gly Thr Ser Thr Pro Ile Arg Leu Ser Cys Pro Gly
    530                 535                 540

Lys Ile Gln Arg Ile Lys Leu Gln Gly Gln Ser Ala Arg Met Ile Ile
```

-continued

```
545                 550                 555                 560

Arg Ser Pro Phe Ala His Trp Ser Leu Leu Gly Arg Pro Ser Cys Ala
                565                 570                 575

Asp Thr Lys Asn Ser Val Glu Arg Ser Arg Thr Lys Met Leu Ser Ser
            580                 585                 590

Thr Pro Ala Leu Ser Leu Met Leu Thr Pro Met Ser Val Ile Thr Arg
        595                 600                 605

Ser Ser Tyr Pro Leu Leu Pro Pro Ser Phe Gln Tyr Cys Glu Ser Ser
    610                 615                 620

Val Lys Thr Arg Gly Met Trp Leu Ala Pro Ser Cys Tyr Phe Met Arg
625                 630                 635                 640

Tyr Gly Ala Thr Asn Ile Ser Ala Arg Ala Thr Thr Pro Ser Pro Cys
                645                 650                 655

Ile Ser Gly Ile Cys Ala Lys Lys Thr Thr Pro Leu Ile Ile Arg Asn
            660                 665                 670

Ile Lys Arg Tyr Gly Gly Leu Val Ile Lys Leu Lys Asn Lys Lys Asn
        675                 680                 685

Asp Tyr Ser Lys Leu Glu Arg Lys Leu Tyr Met Tyr Ile Val Ala Ile
    690                 695                 700

Val Val Val Ala Ile Val Phe Val Leu Tyr Ile Arg Ser Met Ile Arg
705                 710                 715                 720

Gly Lys Leu Gly Asp Trp Ile Leu Ser Ile Leu Glu Asn Lys Tyr Asp
                725                 730                 735

Leu Asn His Leu Asp Ala Met Lys Leu Tyr Gln Tyr Ser Ile Arg Asn
            740                 745                 750

Asn Ile Asp Ile Phe Ile Tyr Val Ala Ile Val Ile Ser Ile Leu Ile
        755                 760                 765

Leu Cys Arg Val Met Leu Ser Lys Phe Ala Lys Tyr Phe Asp Glu Ile
    770                 775                 780

Asn Thr Gly Ile Asp Val Leu Ile Gln Asn Glu Asp Lys Gln Ile Glu
785                 790                 795                 800

Leu Ser Ala Glu Met Asp Val Met Glu Gln Lys Leu Asn Thr Leu Lys
                805                 810                 815

Arg Thr Leu Glu Lys Arg Glu Gln Asp Ala Lys Leu Ala Glu Gln Arg
            820                 825                 830

Lys Asn Asp Val Val Met Tyr Leu Ala His Asp Ile Lys Thr Pro Leu
        835                 840                 845

Thr Ser Ile Ile Gly Tyr Leu Ser Leu Leu Asp Glu Ala Pro Asp Met
    850                 855                 860

Pro Val Asp Gln Lys Ala Lys Tyr Val His Ile Thr Leu Asp Lys Ala
865                 870                 875                 880

Tyr Arg Leu Glu Gln Leu Ile Asp Glu Phe Phe Glu Ile Thr Arg Tyr
                885                 890                 895

Asn Leu Gln Thr Ile Thr Leu Thr Lys Thr His Ile Asp Leu Tyr Tyr
            900                 905                 910

Met Leu Val Gln Met Thr Asp Glu Phe Tyr Pro Gln Leu Ser Ala His
        915                 920                 925

Gly Lys Gln Ala Val Ile His Ala Pro Glu Asp Leu Thr Val Ser Gly
    930                 935                 940

Asp Pro Asp Lys Leu Ala Arg Val Phe Asn Asn Ile Leu Lys Asn Ala
945                 950                 955                 960

Ala Ala Tyr Ser Glu Asp Asn Ser Ile Ile Asp Ile Thr Ala Gly Leu
                965                 970                 975
```

-continued

```
Ser Gly Asp Val Val Ser Ile Glu Phe Lys Asn Thr Gly Ser Ile Pro
            980                 985                 990

Lys Asp Lys Leu Ala Ala Ile Phe Glu Lys Phe Tyr Arg Leu Asp Asn
        995                 1000                1005

Ser Arg Ser Ser Asp Thr Gly Gly Ala Gly Leu Gly Leu Ala Ile Ala
    1010                1015                1020

Lys Glu Ile Ile Val Gln His Gly Gly Gln Ile Tyr Ala Glu Ser Tyr
1025                1030                1035                1040

Asp Asn Tyr Thr Thr Phe Arg Val Glu Leu Pro Ala Met Pro Asp Leu
                1045                1050                1055

Val Asp Lys Arg Arg Ser Glu Met Tyr Ile Ile Phe Glu Asn Leu Lys
            1060                1065                1070

Val Ile Phe Thr Phe Ser Glu Ile Asn Asn Leu Ile Leu Arg Asn Gly
        1075                1080                1085

Ser Phe Leu His Gly Arg Leu Asn Thr Val Arg Thr Ser Arg Phe Arg
    1090                1095                1100

Ser Ser Glu Lys Asp Leu Thr Arg Leu Pro Leu Ala Ser Pro Phe Tyr
1105                1110                1115                1120

Leu Val Pro Phe Thr Glu Arg Val Gly Leu Asn Tyr Glu His Arg His
                1125                1130                1135

Tyr Cys Leu Trp Met Ala Gly Gly Arg Cys Ile Pro Cys Ser Phe Ala
            1140                1145                1150

Ser Leu Trp Arg Tyr Gly Asn Asp Asn Arg Gln Arg Val Gly Ile Gln
        1155                1160                1165

Arg Gln Ile Arg Ala Phe Gln Ser Met Tyr Gln Cys Gly Thr Ile Arg
    1170                1175                1180

Asp Phe Arg Leu Tyr Ser Ser Cys Ala Glu Glu Ser Arg Cys Glu Ile
1185                1190                1195                1200

Tyr Phe Tyr Pro Lys His Arg Leu Gln Ser Tyr Arg Tyr Asn Cys Cys
                1205                1210                1215

Glu Asn Gly His His Cys Arg Gln Cys Gly Val Leu Ala Gly Arg Cys
            1220                1225                1230

Arg Leu Tyr Tyr Asp Ala Asn Ser Tyr Gly Ser Thr Gln Arg Lys Ile
        1235                1240                1245

Asp Cys Ala Leu Cys Gly Lys Thr Phe Gln Val Gly Gln Arg Pro Trp
    1250                1255                1260

Gln Gly Thr Gln Arg His Asp Ser Trp Cys Gly Gly Asn Gly Pro Asp
1265                1270                1275                1280

Arg Gln Ser Gly Tyr Ala Ala Ala Arg Ile Trp Met Ser Val Gly Leu
                1285                1290                1295

Ser Gln Pro Lys Tyr Arg Gly Lys Leu Cys Thr Val Val Ala Ala Lys
            1300                1305                1310

Arg Tyr Arg Tyr Ala Ser Cys Ala Ala Gln Tyr Gly Tyr Ala Leu Tyr
        1315                1320                1325

Tyr Gln Pro Arg Thr Asn Thr Glu Asn Glu Ala Arg Ser Ile Ser Tyr
    1330                1335                1340

Gln Tyr Trp Ala Arg Ser Thr Cys Arg Tyr Leu Val Gly Ser Ile Arg
1345                1350                1355                1360

Lys Arg Glu Thr Gly Arg Cys Arg Ile Gly Cys Ile Gly Arg Arg Gly
                1365                1370                1375

Arg Val Phe Leu Leu Leu His Pro Lys Thr Asn Ser Ile Phe Thr Thr
            1380                1385                1390
```

-continued

```
Ser Lys Asn Ala Arg Asp Asn His Thr Ala Tyr Gly Leu Leu Tyr Arg
        1395                1400                1405

Ala Ser Val Ala Tyr Arg Lys Asn His Lys Leu Phe Gly Phe Lys Glu
    1410                1415                1420

Thr Gly Ala Ile Glu Lys Leu Gln Tyr Cys Leu Gly Val Ala Gln Arg
1425                1430                1435                1440

Ser Met Thr Tyr Arg Asn Leu Gln Arg Pro Leu Thr Leu Ile Lys Lys
                1445                1450                1455

Asn Thr Ser Arg Tyr Thr Leu Glu Leu Arg Asn Leu Val Tyr Gly Lys
            1460                1465                1470

Cys Ala Lys Asn Leu Ala Arg Asn Gly Lys Thr Thr Ile Ala Ile Gln
        1475                1480                1485

Leu Tyr Ser Arg Arg Ile Lys Lys Cys Thr Asp Tyr Leu Leu Lys Arg
    1490                1495                1500

Thr Met Asn Met Lys Ser Thr Met Leu Met His Phe Gln Leu Cys Met
1505                1510                1515                1520

Ala Ser Gln Val Lys Met Asp Pro Tyr Lys Val Cys Leu Asn Cys Pro
                1525                1530                1535

Val Ser Leu Leu Ala Ala Ile Phe Lys Ala Gln Gln Phe Val Trp Thr
            1540                1545                1550

Asn Arg His Thr Ser Leu Arg Lys Met Leu Gly Leu Leu Pro Pro Phe
        1555                1560                1565

Gly Leu Leu Ile Lys Met Ile Gly Arg Trp Gln Leu Arg Leu Pro Ile
    1570                1575                1580

Leu Phe Leu Leu Ser Arg Arg Val Gln Ala His Pro Ser Val Lys Lys
1585                1590                1595                1600

Ser Ile Ala Arg Thr Asn Trp Thr Thr Gln Leu Asn Arg Gln Asp Asn
                1605                1610                1615

Met Thr Ala Lys Ser Leu Ser Arg Leu Phe Arg Ala Val Arg Ser Val
            1620                1625                1630

Val Arg Tyr Trp Glu Thr Val Pro Arg Leu Leu Ala Arg Trp Thr Lys
        1635                1640                1645

Ser Gly Cys Ser Thr Glu Ser Phe Val Phe Ile Arg Lys Ser Ser Arg
    1650                1655                1660

Lys Lys Ala Leu Lys Thr Gln Leu Pro Phe Pro Gln Thr Phe Gln Gln
1665                1670                1675                1680

Arg Ser Glu Asp Gly Tyr Arg Lys Arg Gln Lys Lys Tyr Ile Lys Arg
                1685                1690                1695

Ser Ala Val Glu Val Pro Val Trp Ile Cys Phe Tyr Lys Ile Thr Ala
            1700                1705                1710

Ala Leu Tyr Thr Lys Ser Ile Leu Cys Pro Val Ser Arg His Thr Val
        1715                1720                1725

Val Ile Pro Val Trp Pro Leu Gln Val Leu His Phe Pro Asn Leu Thr
    1730                1735                1740

Ala Ser Tyr Arg Arg Gly Asp Lys His Gly Asn Arg Ile Tyr Phe Phe
1745                1750                1755                1760

Arg Asn Ser Thr Arg Cys Ser Leu Gly Arg Ile Cys His Leu Gly Phe
                1765                1770                1775

His Arg Lys Thr Gly Arg Leu Ser Lys Ser His Cys Arg Asp Ile Arg
            1780                1785                1790

Val Gly Ile Ala Phe Glu Gly Lys Arg Thr Gly Cys Tyr Pro Arg Val
        1795                1800                1805

Arg Ile Ala Ser Met Gly Arg Leu Pro Ser Ala Cys Cys Lys Leu Phe
```

-continued

```
    1810                1815                1820

Tyr Ala Met Gly Cys Thr Ala Gly Lys Pro Asp Lys Gly Lys Leu Leu
1825                1830                1835                1840

Ser Gln Tyr Pro Asn Asp Asp Phe Lys Arg Ile Arg Gly Phe Lys Ile
                1845                1850                1855

Lys Pro Pro Arg Gln Cys His Ser Tyr Ala Leu Ser Ile Arg His Gly
            1860                1865                1870

Ala Cys Thr Asn Gly Glu Pro Ile Phe Tyr Gly Thr Leu Ser Ser Cys
        1875                1880                1885

Gly Lys Trp Asn Ile Met Gln Ser Ala Lys Ser Gln Thr Phe Ala Leu
    1890                1895                1900

His His Gly Lys Gln Trp Val Ser Ile Pro Arg Met Val Ala Leu Cys
1905                1910                1915                1920

Ile Lys Arg Arg Thr Ile Pro Gln Leu Phe Phe Pro Arg Ile Asn Phe
                1925                1930                1935

Pro Leu His Gly Gln Thr Ile Ala Asn Ser Phe Gly Arg Lys Pro Asp
            1940                1945                1950

Val Cys Asn Trp Phe Leu Gly Asn Leu Tyr Ile Val Asp Ser Ile Glu
        1955                1960                1965

Asp Val Arg Gln Ser Asp Ile Ala Val Ile Ile Cys Val Arg Cys Gly
    1970                1975                1980

Lys Ile Ala Asp Ser His Arg Gly Val Val Phe His Thr Ala His Cys
1985                1990                1995                2000

Gln Gln Ala Val Gln Pro Arg Ile Gln His Gly Tyr His Leu Lys Phe
                2005                2010                2015

Ile Tyr Ile Gly Asp Asn Ser Lys Ser Ser Arg Ala Lys Leu Thr Val
            2020                2025                2030

Ile Tyr Gly Ala Lys Arg His Asn Leu Lys Arg Asp Cys Ala Val Gly
        2035                2040                2045

Glu Asp Ser Arg Asn Ile Ser Tyr Phe Gln Leu Tyr Ser Gly Gly Asp
    2050                2055                2060

Lys Arg Ser Cys Phe Phe Tyr Cys Tyr Cys Tyr Ser Tyr Thr Val Met
2065                2070                2075                2080

Thr Thr Leu Met Lys His Cys Phe Leu Arg Lys Lys Ser Asn Phe Lys
                2085                2090                2095

Ile Met Ile Lys Ile Pro Lys Asn Ile Lys Ile Val Gly Leu Leu Lys
            2100                2105                2110

Ile Pro Lys Arg Lys Gln Leu Gln Lys Asn Arg Phe Ile Lys Glu Ile
        2115                2120                2125

Cys Tyr Ser Ile Val Asn Ile Leu Phe Ala Lys Lys Cys Glu Val Arg
    2130                2135                2140

Tyr Arg Glu Phe Ile Thr Arg Ile Asn Lys Trp Ile Arg Val Ala Tyr
2145                2150                2155                2160

Leu Tyr Val Lys Arg Asn Ser Thr Lys Ile Phe Arg Asp Gly Gln Cys
                2165                2170                2175

Cys Lys Gly Trp Arg Ser Phe Tyr Tyr Trp Leu Ser Arg Leu Ala Lys
            2180                2185                2190

Cys Ala Leu Pro Arg Asn Gly Gly Val Cys Leu Thr Ser Arg Leu Ala
        2195                2200                2205

Phe Arg Phe Ile Thr Arg Cys Arg Ile Lys Leu Asp Glu Asn Gly Thr
    2210                2215                2220

Ser Pro Arg Lys Val Asp Arg Arg Lys Cys Leu Glu Ile Arg Val His
2225                2230                2235                2240
```

```
Phe Thr Leu Ser Arg Gly Gln Asn Arg Val Asn Arg Asn Ser
                2245                2250
```

(2) INFORMATION FOR SEQ ID NO:29:

(i) SEQUENCE CHARACTERISTICS:
(A) LENGTH: 2291 amino acids
(B) TYPE: amino acid
(D) TOPOLOGY: linear (ii) MOLECULE TYPE: protein (xi) SEQUENCE DESCRIPTION: SEQ ID NO:29:

```
Ala Phe Leu Phe Ala His Leu Leu Glu Ile Tyr Pro Tyr Ile Ala Ser
1               5                   10                  15

Phe Gln Pro Leu Pro Leu Leu Pro Thr Pro Phe Phe Gln Val Gln Ala
            20                  25                  30

Val Phe Cys Phe Phe Leu Glu Asn Leu Cys Ile His Ala Val Asp Glu
        35                  40                  45

Trp His His His Phe Pro Lys Leu Ile Asp Glu Gly Thr Met Ser Phe
    50                  55                  60

Asp Ile His Ser Gly Lys Leu Gln Ser Arg Ile His Phe Glu Phe Leu
65                  70                  75                  80

Ser Asn Asp Pro Lys Val Tyr Phe Pro Phe Glu Asp Asn Asp Gln Ala
                85                  90                  95

Arg Met Asp His Gln Ser Val Ser Ile Tyr Ile Val Pro Asn Leu Gly
            100                 105                 110

Cys Phe Tyr Glu Cys Met Ala Asn Arg Asp Thr Glu Glu Gln Leu Ile
        115                 120                 125

Glu Gln Gln Ile Leu Asn Gly Phe Leu Pro Ser Phe Ala Tyr Leu Phe
    130                 135                 140

Leu Asn Pro Val Trp Lys Lys Ser Arg Ser Pro Val Ser Ile His Leu
145                 150                 155                 160

Gln Gly Phe Ala Lys Pro Val Ser Val Pro Val Ala Ile Leu Tyr Leu
                165                 170                 175

Ser Gln Phe Ser Phe Ser Ile Ile Pro Phe Leu Tyr Phe Gln Phe Ile
            180                 185                 190

Ser Ser Ile Ile Tyr Gln Ser Val Leu Tyr Tyr Lys Cys Ser Arg Leu
        195                 200                 205

Ile Lys Ser Leu Arg Ala Ser His Lys Thr Cys Leu Lys Asn Glu Val
    210                 215                 220

Ile Phe Cys Gly Lys Ser Val Ile Phe Val Ser Val Arg Leu Thr Arg
225                 230                 235                 240

Ile Leu Gln Asp Asn Phe Ser Ser Thr Arg Ser Glu Trp Ile Leu Tyr
                245                 250                 255

Lys Glu Lys Val Ser Gly Ala Thr Lys Asp Arg Glu Gln Leu Gln Lys
            260                 265                 270

Val Leu Asp Asp Leu Gln Glu Asp Asp Ile Ile Tyr Val Thr Asp Leu
        275                 280                 285

Thr Arg Ile Thr Arg Ser Thr Gln Asp Leu Phe Glu Leu Ile Asp Asn
    290                 295                 300

Ile Arg Asp Lys Lys Ala Ser Leu Lys Ser Leu Lys Asp Thr Trp Leu
305                 310                 315                 320

Asp Leu Ser Glu Asp Asn Pro Tyr Ser Gln Phe Leu Ile Thr Val Met
                325                 330                 335
```

-continued

```
Ala Gly Val Asn Gln Leu Glu Arg Asp Leu Ile Arg Met Arg Gln Arg
            340                 345                 350

Glu Gly Ile Glu Leu Ala Lys Lys Glu Gly Lys Phe Lys Gly Arg Leu
        355                 360                 365

Lys Lys Tyr His Lys Asn His Ala Gly Met Asn Tyr Ala Ala Lys Ala
    370                 375                 380

Ile Arg Arg Lys Tyr Asp Cys Lys Ser Asn Leu Asn Tyr Cys Ile Gly
385                 390                 395                 400

Phe Ile Ile Gln Glu Ile Ile Arg Ser Glu Leu Ala Ile Leu Tyr Ser
                405                 410                 415

Ala Asn Gly Gln Tyr Phe Arg Arg Lys Gly Asn Tyr Lys Ile Leu Thr
            420                 425                 430

Ala Ser Arg Cys Arg Lys Ala Leu Lys Lys Asn His His Leu Lys Lys
        435                 440                 445

Phe Leu Val Ile Tyr Tyr Val Asn Ala Tyr Lys Phe Gly Pro Ile Ile
    450                 455                 460

Ile Ile Lys Gly Lys Leu Met Lys Gly Asp Asn Tyr Glu Arg Asn Thr
465                 470                 475                 480

Tyr Cys Gly Thr Asn Cys Arg Phe Gly Ile Ile Leu Lys Lys Arg Glu
                485                 490                 495

Leu Tyr Gly Phe Gln Ile Leu Tyr Arg Gln Arg Ser Ile Gly Met Tyr
            500                 505                 510

Arg Gln Val Asp Pro Cys His Ile Gly His His Ala Ser Arg His Lys
        515                 520                 525

Arg Pro Tyr Tyr Leu Ser Lys Asn Lys Gly Gln Ala His Leu Ser Asp
    530                 535                 540

Tyr His Ala Asp Arg Glu Arg Tyr Arg Gly Arg Asn Tyr Arg Val Asn
545                 550                 555                 560

Asn Arg Arg Gly Leu Tyr Asn Glu Ala Leu Ser Pro Thr Gly Val Asn
                565                 570                 575

Cys Ser Gly Lys Gly Pro Val Ala Pro Ile Gln Lys Ile Gln Trp Ser
            580                 585                 590

Lys Gly Ala Glu Arg Lys Cys Tyr Arg Pro Leu Arg Pro Cys His Cys
        595                 600                 605

His Pro Val Leu Ser Glu Arg Glu Ala Val Ile Pro Tyr Ser His Arg
    610                 615                 620

Val Phe Asn Thr Ala Asn Pro Leu Lys Gln Gly Glu Cys Gly Leu Arg
625                 630                 635                 640

Ala Ala Ile Ser Asp Met Gly Arg Arg Ile Phe Gln Gln Glu Gln Gln
                645                 650                 655

His His His Arg Ala Tyr Pro Ala Phe Ala Arg Lys Asn Glu Arg His
            660                 665                 670

His Ser Glu Ile Tyr Lys Asn Gly Met Gly Gly Trp Leu Asn Lys Ile
        675                 680                 685

Lys Lys Thr Thr Ile Pro Asn Asn Glu Asn Phe Thr Cys Ile Ser Leu
    690                 695                 700

Gln Leu Leu Trp Gln Leu Tyr Ser Cys Cys Ile Phe Val Gln Ser Glu
705                 710                 715                 720

Gly Asn Leu Gly Ile Gly Ser Val Phe Trp Lys Thr Asn Met Thr Ile
                725                 730                 735

Thr Trp Thr Arg Asn Tyr Ile Asn Ile Pro Tyr Gly Thr Ile Ile Ser
            740                 745                 750

Leu Phe Met Trp Arg Leu Ser Leu Val Phe Leu Phe Tyr Val Ala Ser
```

-continued

```
        755                 760                 765

Cys Phe Gln Asn Ser Gln Asn Thr Leu Thr Arg Ile Pro Ala Leu Met
    770                 775                 780

Tyr Leu Phe Arg Thr Lys Ile Asn Lys Leu Ser Phe Leu Arg Lys Trp
785                 790                 795                 800

Met Leu Trp Asn Lys Ser Ser Thr His Asn Gly Leu Trp Lys Ser Glu
                805                 810                 815

Ser Arg Met Gln Ser Trp Pro Asn Lys Glu Lys Met Thr Leu Leu Cys
            820                 825                 830

Thr Trp Arg Thr Ile Leu Lys Arg Pro Leu His Pro Leu Ser Val Ile
        835                 840                 845

Ala Cys Leu Thr Arg Leu Gln Thr Cys Arg Ile Lys Arg Gln Ser Met
    850                 855                 860

Cys Ile Ser Arg Trp Thr Lys Arg Ile Asp Ser Asn Ser Ser Thr Ser
865                 870                 875                 880

Phe Leu Arg Leu His Gly Ile Thr Tyr Lys Arg Arg Gln Lys Arg Thr
                885                 890                 895

Thr Tyr Thr Ile Cys Trp Cys Arg Pro Met Asn Phe Ile Leu Ser Phe
            900                 905                 910

Pro His Met Glu Asn Arg Arg Leu Phe Thr Pro Pro Arg Ile Pro Cys
        915                 920                 925

Pro Ala Thr Leu Ile Asn Ser Arg Glu Ser Leu Thr Thr Phe Lys Thr
    930                 935                 940

Pro Leu His Thr Val Arg Ile Thr Ala Ser Leu Thr Leu Pro Arg Ala
945                 950                 955                 960

Ser Pro Gly Met Trp Cys Gln Ser Asn Ser Arg Thr Leu Glu Ala Ser
                965                 970                 975

Gln Lys Ile Ser Leu Pro Tyr Leu Lys Ser Ser Ile Gly Trp Thr Ile
            980                 985                 990

Leu Val Leu Pro Ile Arg Val Ala Arg Asp Leu Asp Trp Arg Leu Gln
        995                 1000                1005

Lys Lys Leu Leu Phe Ser Met Glu Gly Arg Phe Thr Arg Lys Ala Met
    1010                1015                1020

Ile Thr Ile Arg Arg Leu Gly Ser Phe Gln Arg Cys Gln Thr Trp Leu
1025                1030                1035                1040

Ile Lys Gly Gly Pro Lys Arg Cys Ile Phe Phe Arg Lys Ile Ser Arg
                1045                1050                1055

Leu Ser Leu Leu Phe Leu Arg Lys Leu Thr Ile Tyr Glu Thr Ala Arg
            1060                1065                1070

Ser Tyr Thr Val Asp Leu Ile Pro Glu Arg Ala Val Phe Val Leu Gln
        1075                1080                1085

Arg Lys Ile Gln Asp Tyr His Trp His Pro Arg Phe Ile Trp Cys Leu
    1090                1095                1100

Ser Gln Lys Gly Leu Val Leu Ile Met Asn Asn Ile Gly Ile Thr Val
1105                1110                1115                1120

Tyr Gly Cys Glu Gln Asp Glu Ala Asp Ala Phe His Ala Leu Ser Pro
                1125                1130                1135

Arg Phe Gly Val Met Ala Thr Ile Ile Asn Ala Asn Val Ser Glu Ser
            1140                1145                1150

Asn Ala Lys Ser Ala Pro Phe Asn Gln Cys Ile Ser Val Gly His Lys
        1155                1160                1165

Ser Glu Ile Ser Ala Ser Ile Leu Leu Ala Leu Lys Arg Ala Gly Val
    1170                1175                1180
```

-continued

```
Lys Tyr Ile Ser Thr Arg Ser Ile Gly Cys Asn His Ile Asp Thr Thr
1185                1190                1195                1200

Ala Ala Lys Arg Met Gly Ile Thr Val Asp Asn Val Ala Tyr Ser Pro
                1205                1210                1215

Asp Ser Val Ala Asp Tyr Thr Met Met Leu Ile Leu Met Ala Val Arg
            1220                1225                1230

Asn Val Lys Ser Ile Val Arg Ser Val Glu Lys His Asp Phe Arg Leu
        1235                1240                1245

Asp Ser Asp Arg Gly Lys Val Leu Ser Asp Met Thr Val Gly Val Val
    1250                1255                1260

Gly Thr Gly Gln Ile Gly Lys Ala Val Ile Glu Arg Leu Arg Gly Phe
1265                1270                1275                1280

Gly Cys Lys Val Leu Ala Tyr Ser Arg Ser Arg Ser Ile Glu Val Asn
                1285                1290                1295

Tyr Val Pro Phe Asp Glu Leu Leu Gln Asn Ser Asp Ile Val Thr Leu
            1300                1305                1310

His Val Pro Leu Asn Thr Asp Thr His Tyr Ile Ile Ser His Glu Gln
        1315                1320                1325

Ile Gln Arg Met Lys Gln Gly Ala Phe Leu Ile Asn Thr Gly Arg Gly
    1330                1335                1340

Pro Leu Val Asp Thr Tyr Glu Leu Val Lys Ala Leu Glu Asn Gly Lys
1345                1350                1355                1360

Leu Gly Gly Ala Ala Leu Asp Val Leu Glu Gly Glu Glu Glu Phe Phe
                1365                1370                1375

Tyr Ser Asp Cys Thr Gln Lys Pro Ile Asp Asn Gln Phe Leu Leu Lys
            1380                1385                1390

Leu Gln Arg Met Pro Asn Val Ile Ile Thr Pro His Thr Ala Tyr Tyr
        1395                1400                1405

Thr Glu Gln Ala Leu Arg Asp Thr Val Glu Lys Thr Ile Lys Asn Cys
    1410                1415                1420

Leu Asp Phe Glu Arg Arg Gln Glu His Glu Asn Lys Ser Cys Asn Thr
1425                1430                1435                1440

Val Trp Gly Leu Leu Arg Gly Ala Arg Ile Gly Lys Ile Cys Asn Arg
                1445                1450                1455

Asp Ser Arg His Arg Lys Ile Arg Ala Val Ile His Trp Asn Tyr Glu
            1460                1465                1470

Ile Trp Cys Met Glu Asn Val Arg Lys Thr Leu Arg Gly Met Gly Lys
        1475                1480                1485

Arg Gln Leu Leu Phe Ser Cys Thr Leu Ala Gly Lys Asn Ala Arg Ile
    1490                1495                1500

Thr Cys Lys Glu Pro Ile Asn Gln Pro Cys Cys Ser Ile Phe Ser Phe
1505                1510                1515                1520

Ala Trp Gln Val Arg Arg Trp Ile His Thr Arg Ser Val Ile Val Arg
                1525                1530                1535

Tyr Pro Phe Cys Arg Leu Arg Tyr Ser Lys Leu Ser Asn Leu Tyr Gly
            1540                1545                1550

Gln Ile Val Asp Ile His Arg Cys Glu Lys Cys Trp Asp Ser Tyr Ser
        1555                1560                1565

Arg Leu Leu Gly Tyr Arg Ala Gly Gly Ser Tyr Val Tyr Leu Ser Cys
    1570                1575                1580

Phe Cys Ala Gly Ala Phe Arg Leu Ile Leu Arg Cys Glu Lys Ser Gln
1585                1590                1595                1600
```

-continued

```
Arg Gly Arg Ile Gly Leu Arg Asn Ile Gly Lys Thr Ile Gln Gln Asn
                1605                1610                1615

Leu Asn Ala Gly Cys Phe Gly Leu Gly Arg Leu Cys Gly Ile Gly Lys
            1620                1625                1630

Gln Cys Arg Val Ser Cys Trp Arg Gly Gly Pro Asn Gln Ala Ala Val
        1635                1640                1645

Arg Asn Leu Ser Tyr Ser Ser Gly Ser Arg Ala Gly Lys Arg Leu Lys
    1650                1655                1660

Arg Ser Tyr Asn Arg Ser Arg Arg Pro Phe Ser Arg Gly Ala Arg Thr
1665                1670                1675                1680

Asp Thr Gly Asn Gly Lys Lys Asn Ile Ser Ala Arg Leu Arg Ser Ser
                1685                1690                1695

Pro Cys Gly Tyr Val Phe Thr Arg Arg Pro His Cys Thr Glu Arg Ser
            1700                1705                1710

Gln Tyr Ser Ala Arg Phe His Val Ile Gln Ser Leu Ser Pro Tyr Asp
        1715                1720                1725

Gly Arg Cys Arg Tyr Cys Thr Ser Arg Thr Asp Pro Leu Asp Arg Ile
    1730                1735                1740

Ser Val Lys Gly Val Ile Ser Met Glu Ile Gly Phe Thr Phe Leu Asp
1745                1750                1755                1760

Glu Ile Val His Gly Val Arg Trp Asp Ala Lys Tyr Ala Thr Trp Asp
                1765                1770                1775

Asn Phe Thr Gly Lys Pro Val Asp Gly Tyr Glu Val Asn Arg Ile Val
            1780                1785                1790

Gly Thr Tyr Glu Leu Ala Glu Ser Leu Leu Lys Ala Lys Glu Leu Ala
        1795                1800                1805

Ala Thr Gln Gly Tyr Gly Leu Leu Leu Trp Asp Gly Tyr Arg Pro Lys
    1810                1815                1820

Arg Ala Val Asn Cys Phe Met Gln Trp Ala Ala Gln Pro Glu Asn Asn
1825                1830                1835                1840

Leu Thr Lys Glu Ser Tyr Tyr Pro Asn Ile Asp Arg Thr Glu Met Ile
                1845                1850                1855

Ser Lys Gly Tyr Val Ala Ser Lys Ser Ser His Ser Arg Gly Ser Ala
            1860                1865                1870

Ile Asp Leu Thr Leu Tyr Arg Leu Asp Thr Gly Glu Leu Val Pro Met
        1875                1880                1885

Gly Ser Arg Phe Asp Phe Met Asp Glu Arg Ser His His Ala Ala Asn
    1890                1895                1900

Gly Ile Ser Cys Asn Glu Ala Gln Asn Arg Arg Arg Leu Arg Ser Ile
1905                1910                1915                1920

Met Glu Asn Ser Gly Phe Glu Ala Tyr Ser Leu Glu Trp Trp His Tyr
                1925                1930                1935

Val Leu Arg Asp Glu Pro Tyr Pro Asn Ser Tyr Phe Asp Phe Pro Val
            1940                1945                1950

Lys Thr Phe Asn Arg Cys Thr Asp Lys Leu Tyr Lys Leu Thr Leu Ser
        1955                1960                1965

Ala Gly Asn Pro Thr Tyr Val Thr Gly Ser Gly Ile Tyr Ile Ile Val
    1970                1975                1980

Leu Lys Met Gly Arg Ala Ile Leu Arg Ser Leu Ser Ala Cys Ala Ala
1985                1990                1995                2000

Ala Arg Pro Asp Asn Lys Thr Asp Arg Ile Glu Gly Trp Tyr Phe Thr
                2005                2010                2015

Pro Pro Ile Val Asn Arg Gln Phe Ser Leu Val Lys Phe Ser Met Gly
```

-continued

```
            2020                2025                2030

Ile Thr Tyr Glu Asn Ser Ser Thr Leu Val Ile Ile Val Asn Pro Val
        2035                2040                2045

Gly Arg Asn Asn Leu Phe Thr Gly Gln Asn Gly Thr Ile Ser Asn Glu
    2050                2055                2060

Ile Val Pro Phe Lys Gly Lys Ile Leu Glu Ile Phe His Thr Ser Asn
2065                2070                2075                2080

Tyr Ile Val Lys Glu Glu Thr Glu Asn Glu Glu Val Val Phe Phe Ile
                2085                2090                2095

Val Ile Val Ile Leu Asn Ile Leu Arg Leu Leu Arg Ser Thr Val Phe
            2100                2105                2110

Ser Gly Lys Ser Arg Ile Ser Lys Leu Ser Lys Ser Gln Arg Thr Phe
        2115                2120                2125

Arg Lys Trp Asp Phe Lys Tyr Pro Arg Glu Asn Asn Tyr Arg Arg Thr
    2130                2135                2140

Gly Leu Ser Arg Lys Ser Ala Ile Asn Gln Ile Ser Cys Ser Pro Arg
2145                2150                2155                2160

Ser Val Lys Ser Asp Ile Val Asn Leu Ser Lys His Asp Glu Leu Ile
                2165                2170                2175

Asn Gly Tyr Gly Leu Leu Asp Ser Asn Ile Tyr Met Ser Lys Glu Ile
            2180                2185                2190

Ala Gln Lys Phe Ser Glu Met Val Asn Asp Ala Val Lys Gly Gly Val
        2195                2200                2205

Ser His Phe Ile Ile Asn Ser Gly Tyr Arg Asp Phe Asp Glu Gln Ser
    2210                2215                2220

Val Leu Tyr Gln Glu Met Gly Ala Glu Tyr Ala Leu Pro Ala Gly Tyr
2225                2230                2235                2240

Ser Glu His Asn Ser Gly Leu Ser Leu Asp Val Gly Ser Ser Leu Thr
                2245                2250                2255

Lys Met Glu Arg Ala Pro Glu Gly Lys Trp Ile Glu Glu Asn Ala Trp
            2260                2265                2270

Lys Tyr Gly Phe Ile Leu Arg Tyr Pro Glu Asp Lys Thr Glu Leu Thr
        2275                2280                2285

Gly Ile Gln
    2290
```

(2) INFORMATION FOR SEQ ID NO:30:

(i) SEQUENCE CHARACTERISTICS:
- (A) LENGTH: 3190 base pairs
- (B) TYPE: nucleic acid
- (C) STRANDEDNESS: double
- (D) TOPOLOGY: linear (ii) MOLECULE TYPE: DNA (genomic)

(xi) SEQUENCE DESCRIPTION: SEQ ID NO:30:

```
CAAAATATCA CCTCATTTTT GAGACAAGTC TTATGAGACG CTCTTAACTA TGATTTTATC     60

AGTCTACTAC ATTTGTATCA ATAGAGTACA CTCTATTGAT ATATAATTGA ACTAATAAAT    120

TGAAAATACA GAAATGGAAT GATACTGAAA TGAAAATTGC GAGAGGTAGA GAATTGCTTA    180

CACCGGAACA GAGACAGGCT TTTATGCAAA TCCCTGAAGA TGAATGGATA CTGGGGACCT    240

ACTTCACTTT TTCCAAACGG GATTTAGAAA TAGTTAATAA GCGAAGGAGG GAAGAAAACC    300

GTTTAGGATT TGCTGTTCAA TTAGCTGTTC TTCGGTATCC CGGTTGGCCA TACACTCATA    360

TCAAAAGCAT CCCAGATTCG GTCATACAAT ATATATCGAA ACAGATTGGT GTTAGTCCAT    420
```

-continued

```
CCTCGCTTGA TCATTATCCT CAAAGGGAAA ATACACTTTG GGATCATTTG AAAGAAATTC    480
GAAGTGAATA CGACTTTGTA ACTTTTACCC TGAGTGAATA TCGAATGACA TTTAAGTACC    540
TTCATCAATT AGCTTTGGAA AATGGTGATG CCATTCATCT ACTGCATGAA TGCATAGATT    600
TTCTAAGAAA AAACAAAATT ATACTGCCTG CTATCACTAC ACTTGAAAGA ATGGTGTGGG    660
AAGCAAGGGC AATGGCTGAA AAGAAGCTAT TTAATACGGT TAGTAAATCT CTAACAAATG    720
AGCAAAAAGA AAAGCTTGAA GGGATTATTA CCTCGCAGCA TCCATCCGAA TCCAATAAAA    780
CGATATTGGG TTGGTTAAAA GAGCCACCGG GTCATCCTTC ACCCGAAACT TTTCTAAAAA    840
TAATAGAACG ACTCGAATAC ATACGAGGAA TGGATTTAGA AACAGTGCAA ATTAGTCATT    900
TGCACCGTAA CCGCCTGTTG CAGCTGTCTC GCTTAGGCTC AAGATACGAG CCGTATGCAT    960
TCCGTGACTT TCAAGAAAAT AAACGTTATT CGATATTAAC CATCTATTTA TTACAACTTA   1020
CTCAGGAGCT AACGGATAAA GCGTTTGAAA TTCATGATAG GCAAATACTT AGTTTGTTAT   1080
CAAAAGGTCG TAAGGCTCAA GAGGAAATCC AGAAACAAAA CGGTAAAAAG CTAAATGAGA   1140
AAGTTATACA CTTTACGAAC ATCGGACAAG CATTAATTAA AGCAAGAGAG GAAAAATTAG   1200
ACGTTTTTAA GGTTTTAGAA TCGGTTATTG AATGGAATAC CTTTGTCTCT TCAGTAGAAG   1260
AGGCTCAGGA ACTTGCACGT CCTGCCGACT ATGATTATTT AGACTTACTG CAAAAACGGT   1320
TTTATTCACT AAGAAAATAT ACGCCAACGC TATTAAGAGT ATTGGAATTT CATTCTACAA   1380
AGGCAAATGA GCCACTTTTA CAAGCTGTTG AGATTATCCG AGGAATGAAC GAATCTGGAA   1440
AGCGAAAAGT GCCTGATGAC TCACCTGTGG ATTTTATTTC AAAACGATGG AAAAGACATT   1500
TATACGAGGA TGATGGTACA ACAATTAATC GTCATTACTA TGAAATGGCT GTTTTAACAG   1560
AACTTCGGGA GCATGTTCGG GCAGGAGATG TTTCCATTGT TGGCAGCAGA CAATATAGGG   1620
ATTTTGAGGA ATATTTGTTT TCGGAAGATA CATGGAATCA ATCGAAGGGG AATACGAGAT   1680
TATCAGTTAG TTTATCATTC GAAGATTATA TAACGGAGAG AACCAGCAGC TTTAATGAAA   1740
GGTTAAAGTG GTTAGCTGCC AATTCCAATA AGTTAGATGG GGTTTCTCTT GAAAAAGGAA   1800
AGCTATCACT TGCACGCTTA GAAAAAGATG TTCCAGAAGA AGCAAAAAAA TTTAGTGCAA   1860
GCCTTTATCA GATGCTACCA AGAATAAAAT TAACTGATTT ACTCATGGAT GTGGCCCATA   1920
TAACAGGATT TCATGAGCAA TTCACTCATG CTTCCAATAA TCGAAAACCA GATAAGGAAG   1980
AAACAATCAT TATCATGGCT GCCCTTTTAG GAATGGGAAT GAATATTGGC TTGAGCAAGA   2040
TGGCCGAAGC CACACCCGGA CTTACATATA AGCAACTAGC CAATGTATCT CAATGGCGCA   2100
TGTATGAAGA TGCCATGAAT AAAGCCCAAG CCATATTAGT AAACTTTCAT CATAAATTAC   2160
AATTGCCTTT CTATTGGGGC GACGGTACAA CATCTTCGTC AGATGGTATG AGAATGCAGC   2220
TAGGTGTTTC ATCACTACAT GCAGATGCAA ATCCACATTA TGGAACTGGA AAAGGAGCCA   2280
CCATCTACCG ATTTACAAGT GATCAATTCT CTTCTTACTA CACAAAGATT ATTCATACTA   2340
ATTCAAGAGA TGCGATTCAT GTTTTGGATG GTTTGTTACA TCATGAGACG GATCTAAACA   2400
TAGAGGAACA TTATACAGAC ACTGCCGGTT ACACTGACCA AATATTCGGA CTGACTCATT   2460
TATTAGGATT TAAATTTGCC CCAAGAATAA GGGATTTATC GGACTCAAAA TTATTTACGA   2520
TAGATAAAGC AAGTGAGTAT CCAAAACTAG AAGCCATTTT ACGTGGACAA ATAAATACAA   2580
AGGTCATTAA AGAAAATTAT GAGGATGTTT TGCGATTAGC TCATTCTATA AGGGAGGGAA   2640
CAGTTTCAGC ATCCCTTATT ATGGGGAAGC TAGGTTCCTA TTCAAGACAA AACAGCTTAG   2700
CTACAGCCTT ACGTGAGATG GGCCGAATAG AAAAAACGAT CTTTATTTTG AATTATATAT   2760
```

-continued

```
CGGATGAATC ATTAAGAAGA AAAATACAAA GAGGATTGAA TAAAGGAGAA GCCATGAATG   2820

GATTGGCAAG AGCTATTTTC TTCGGAAAAC AAGGTGAGCT TAGAGAACGC ACCATACAGC   2880

ATCAATTGCA AAGAGCCAGT GCTTTAAACA TAATTATCAA TGCTATAAGT ATTTGGAATA   2940

CTCTCCACCT AACAACAGCA GTTGAATATA AAAAACGGAC AGGTAGCTTT AATGAAGATT   3000

TGTTACACCA TATGTCGCCC TTAGGTTGGG AACATATTAA TTTACTAGGA GAATACCATT   3060

TTAACTCAGA GAAAGTAGTC TCATTAAATT CTTTAAGACC ACTAAAACTT TCTTAACGTT   3120

GTTAAAAACG AGGGATTCGT CAGGAAAATA GGCTTAGCGT TGTAAATCCG CATTTTCCTG   3180

ACGCTACCCC                                                          3190
```

(2) INFORMATION FOR SEQ ID NO:31:

(i) SEQUENCE CHARACTERISTICS:
(A) LENGTH: 1347 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO:31:

```
GAGCTCTTCC TTCAACGCAC TTCTGTACCA AGAGTTGTTG TCCATTTGAT CACTAACAAT     60

AGCTTCCCCT GCTTTCTTCA AGCCCTTTGT CATAAAATCG TTAGATTTTC ATCATAAAAA    120

TACGAGAAAG ACAACAGGAA GACCGCAAAT TTTCTTTTCT TTTCCTAGGT ACACTGAATG    180

TAACCTTAAA AGAAAAAAGG AAAGGAAGAA AATGATGAAA AAAATTGCCG TTTTATTTGG    240

AGGGAATTCT CCAGAATACT CAGTGTCACT AACCTCAGCA GCAAGTGTGA TCCAAGCTAT    300

TGACCCGCTG AAATATGAAG TAATGACCAT TGGCATCGCA CCAACAATGG ATTGGTATTG    360

GTATCAAGGA AACCTCGCGA ATGTTCGCAA TGATACTTGG CTAGAAGATC ACAAAAACTG    420

TCACCAGCTG ACTTTTTCTA GCCAAGGATT TATATTAGGA GAAAAACGAA TCGTCCCTGA    480

TGTCCTCTTT CCAGTCTTGC ATGGGAAGTA TGGCGAGGAT GGCTGTATCC AAGGACTGCT    540

TGAACTAATG AACCTGCCTT ATGTTGGTTG CCATGTCGCT GCCTCCGCAT TATGTATGAA    600

CAAATGGCTC TTGCATCAAC TTGCTGATAC CATGGGAATC GCTAGTGCTC CCACTTTGCT    660

TTTATCCCGC TATGAAAACG ATCCTGCCAC AATCGATCGT TTTATTCAAG ACCATGGATT    720

CCCGATCTTT ATCAAGCCGA ATGAAGCCGG TTCTTCAAAA GGGATCACAA AAGTAACTGA    780

CAAAACAGCG CTCCAATCTG CATTAACGAC TGCTTTTGCT TACGGTTCTA CTGTGTTGAT    840

CCAAAAGGCG ATAGCGGGTA TTGAAATTGG CTGCGGCATC TTAGGAAATG AGCAATTGAC    900

GATTGGTGCT TGTGATGCGA TTTCTCTTGT CGACGGTTTT TTTGATTTTG AAGAGAAATA    960

CCAATTAATC AGCGCCACGA TCACTGTCCC AGCACCATTG CCTCTCGCGC TTGAATCACA   1020

GATCAAGGAG CAGGCACAGC TGCTTTATCG AAACTTGGGA TTGACGGGTC TGGCTCGAAT   1080

CGATTTTTTC GTCACCAATC AAGGAGCGAT TTATTTAAAC GAAATCAACA CCATGCCGGG   1140

ATTTACTGGG CACTCCCGCT ACCCAGCTAT GATGGCGGAA GTCGGGTTAT CCTACGAAAT   1200

ATTAGTAGAG CAATTGATTG CACTGGCAGA GGAGGACAAA CGATGAACAC ATTACAATTG   1260

ATCAATAAAA ACCATCCATT GAAAAAAAAT CAAGAGCCCC CGCACTTAGT GCTAGCTCCT   1320

TTTAGCGATC ACGATGTTTA CCTGCAG                                       1347
```

(2) INFORMATION FOR SEQ ID NO:32:

(i) SEQUENCE CHARACTERISTICS:

(A) LENGTH: 364 amino acids
(B) TYPE: amino acid
(D) TOPOLOGY: linear (ii) MOLECULE TYPE: protein (xi) SEQUENCE DESCRIPTION: SEQ ID NO:32:

```
Met Glu Lys Leu Arg Val Gly Ile Val Gly Gly Gly Lys Ser Ala Glu
1               5                   10                  15

His Glu Val Ser Leu Gln Ser Ala Lys Asn Ile Val Asp Ala Ile Asp
            20                  25                  30

Lys Ser Arg Phe Asp Val Val Leu Leu Gly Ile Asp Lys Gln Gly Gln
        35                  40                  45

Trp His Val Ser Asp Ala Ser Asn Tyr Leu Leu Asn Ala Asp Asp Pro
    50                  55                  60

Ala His Ile Ala Leu Arg Pro Ser Ala Thr Ser Leu Ala Gln Val Pro
65                  70                  75                  80

Gly Lys His Glu His Gln Leu Ile Asp Ala Gln Asn Gly Gln Pro Leu
                85                  90                  95

Pro Thr Val Asp Val Ile Phe Pro Ile Val His Gly Thr Leu Gly Glu
            100                 105                 110

Asp Gly Ser Leu Gln Gly Met Leu Arg Val Ala Asn Leu Pro Phe Val
        115                 120                 125

Gly Ser Asp Val Leu Ala Ser Ala Ala Cys Met Asp Lys Asp Val Thr
    130                 135                 140

Lys Arg Leu Leu Arg Asp Ala Gly Leu Asn Ile Ala Pro Phe Ile Thr
145                 150                 155                 160

Leu Thr Arg Ala Asn Arg His Asn Ile Ser Phe Ala Glu Val Glu Ser
                165                 170                 175

Lys Leu Gly Leu Pro Leu Phe Val Lys Pro Ala Asn Gln Gly Ser Ser
            180                 185                 190

Val Gly Val Ser Lys Val Thr Ser Glu Glu Gln Tyr Ala Thr Ala Val
        195                 200                 205

Ala Leu Ala Phe Glu Phe Asp His Lys Val Ile Val Glu Gln Gly Ile
    210                 215                 220

Lys Gly Arg Glu Ile Glu Cys Ala Val Leu Gly Asn Asp Asn Pro Gln
225                 230                 235                 240

Ala Ser Thr Cys Gly Glu Ile Val Leu Thr Ser Asp Phe Tyr Ala Tyr
                245                 250                 255

Asp Thr Lys Tyr Ile Asp Glu Asp Gly Ala Lys Val Val Val Pro Ala
            260                 265                 270

Ala Ile Ala Pro Glu Ile Asn Asp Lys Ile Arg Ala Ile Ala Val Gln
        275                 280                 285

Ala Tyr Gln Thr Leu Gly Cys Ala Gly Met Ala Arg Val Asp Val Phe
    290                 295                 300

Leu Thr Pro Glu Asn Glu Val Val Ile Asn Glu Ile Asn Thr Leu Pro
305                 310                 315                 320

Gly Phe Thr Asn Ile Ser Met Tyr Pro Lys Leu Trp Gln Ala Ser Gly
                325                 330                 335

Leu Gly Tyr Thr Asp Leu Ile Thr Arg Leu Ile Glu Leu Ala Leu Glu
            340                 345                 350

Arg His Ala Ala Asn Asn Ala Leu Lys Thr Thr Met
        355                 360
```

(2) INFORMATION FOR SEQ ID NO:33:

(i) SEQUENCE CHARACTERISTICS:
(A) LENGTH: 306 amino acids
(B) TYPE: amino acid
(D) TOPOLOGY: linear (ii) MOLECULE TYPE: protein (xi) SEQUENCE DESCRIPTION: SEQ ID NO:33:

```
Met Thr Asp Lys Ile Ala Val Leu Leu Gly Gly Thr Ser Ala Glu Arg
1               5                   10                  15

Glu Val Ser Leu Asn Ser Gly Ala Ala Val Leu Ala Gly Leu Arg Glu
            20                  25                  30

Gly Gly Ile Asp Ala Tyr Pro Val Asp Pro Lys Glu Val Asp Val Thr
        35                  40                  45

Gln Leu Lys Ser Met Gly Phe Gln Lys Val Phe Ile Ala Leu His Gly
    50                  55                  60

Arg Gly Gly Glu Asp Gly Thr Leu Gln Gly Met Leu Glu Leu Met Gly
65                  70                  75                  80

Leu Pro Tyr Thr Gly Ser Gly Val Met Ala Ser Ala Leu Ser Met Asp
                85                  90                  95

Lys Leu Arg Ser Lys Leu Leu Trp Gln Gly Ala Gly Leu Pro Val Ala
            100                 105                 110

Pro Trp Val Ala Leu Thr Arg Ala Glu Phe Glu Lys Gly Leu Ser Asp
        115                 120                 125

Lys Gln Leu Ala Glu Ile Ser Ala Leu Gly Leu Pro Val Ile Val Lys
    130                 135                 140

Pro Ser Arg Glu Gly Ser Ser Val Gly Met Ser Lys Val Val Ala Glu
145                 150                 155                 160

Asn Ala Leu Gln Asp Ala Leu Arg Leu Ala Phe Gln His Asp Glu Glu
                165                 170                 175

Val Leu Ile Glu Lys Trp Leu Ser Gly Pro Glu Phe Thr Val Ala Ile
            180                 185                 190

Leu Gly Glu Glu Ile Leu Pro Ser Ile Arg Ile Gln Pro Ser Gly Thr
        195                 200                 205

Phe Tyr Asp Tyr Glu Ala Lys Tyr Leu Ser Asp Glu Thr Gln Tyr Phe
    210                 215                 220

Cys Pro Ala Gly Leu Glu Ala Ser Gln Glu Ala Asn Leu Gln Ala Leu
225                 230                 235                 240

Val Leu Lys Ala Trp Thr Thr Leu Gly Cys Lys Gly Trp Gly Arg Ile
                245                 250                 255

Asp Val Met Leu Asp Ser Asp Gly Gln Phe Tyr Leu Leu Glu Ala Asn
            260                 265                 270

Thr Ser Pro Gly Met Thr Ser His Ser Leu Val Pro Met Ala Ala Arg
        275                 280                 285

Gln Ala Gly Met Ser Phe Ser Gln Leu Val Val Arg Ile Leu Glu Leu
    290                 295                 300

Ala Asp
305
```

(2) INFORMATION FOR SEQ ID NO:34:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:34:

Leu Phe Pro Met Val Ile
1 5

(2) INFORMATION FOR SEQ ID NO:35:

(i) SEQUENCE CHARACTERISTICS:
(A) LENGTH: 5 amino acids
(B) TYPE: amino acid
(D) TOPOLOGY: linear (ii) MOLECULE TYPE: peptide (xi) SEQUENCE DESCRIPTION: SEQ ID NO:35:

Ser Thr Gln Asn Cys
1 5

(2) INFORMATION FOR SEQ ID NO:36:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:36:

Gly Glu Asp Gly Ser Ile Gln Gly
1 5

(2) INFORMATION FOR SEQ ID NO:37:

(i) SEQUENCE CHARACTERISTICS:
(A) LENGTH: 7 amino acids
(B) TYPE: amino acid
(D) TOPOLOGY: linear (ii) MOLECULE TYPE: peptide (xi) SEQUENCE DESCRIPTION: SEQ ID NO:37:

Asn Thr Leu Pro Gly Phe Thr
1 5

(2) INFORMATION FOR SEQ ID NO:38:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:38:

Gly Glu Asp Gly Thr Leu Gln Gly
1 5

(2) INFORMATION FOR SEQ ID NO:39:

(i) SEQUENCE CHARACTERISTICS:
(A) LENGTH: 7 amino acids
(B) TYPE: amino acid
(D) TOPOLOGY: linear (ii) MOLECULE TYPE: peptide (xi) SEQUENCE DESCRIPTION: SEQ ID NO:39:

Asn Thr Ser Pro Gly Met Thr

```
1               5

(2) INFORMATION FOR SEQ ID NO:40:

     (i) SEQUENCE CHARACTERISTICS:
          (A) LENGTH: 259 amino acids
          (B) TYPE: amino acid
          (D) TOPOLOGY: linear

    (ii) MOLECULE TYPE: protein

     (v) FRAGMENT TYPE: internal

    (vi) ORIGINAL SOURCE:
          (A) ORGANISM: E. faecium
          (B) STRAIN: BM4147

    (xi) SEQUENCE DESCRIPTION: SEQ ID NO:40:

Glu Met Asp Val Met Glu Gln Lys Leu Asn Thr Leu Lys Arg Thr Leu
1               5                   10                  15

Glu Lys Arg Glu Gln Asp Ala Lys Leu Ala Glu Gln Arg Lys Asn Asp
            20                  25                  30

Val Val Met Tyr Leu Ala His Asp Ile Lys Thr Pro Leu Thr Ser Ile
        35                  40                  45

Ile Gly Tyr Leu Ser Leu Leu Asp Glu Ala Pro Asp Met Pro Val Asp
    50                  55                  60

Gln Lys Ala Lys Tyr Val His Ile Thr Leu Asp Lys Ala Tyr Arg Leu
65                  70                  75                  80

Glu Gln Leu Ile Asp Glu Phe Phe Glu Ile Thr Arg Tyr Asn Leu Gln
                85                  90                  95

Thr Ile Thr Leu Thr Lys Thr His Ile Asp Leu Tyr Tyr Met Leu Val
            100                 105                 110

Gln Met Thr Asp Glu Phe Tyr Pro Gln Leu Ser Ala His Gly Lys Gln
        115                 120                 125

Ala Val Ile His Ala Pro Glu Asp Leu Thr Val Ser Gly Asp Pro Asp
    130                 135                 140

Lys Leu Ala Arg Val Phe Asn Asn Ile Leu Lys Asn Ala Ala Ala Tyr
145                 150                 155                 160

Ser Glu Asp Asn Ser Ile Ile Asp Ile Thr Ala Gly Leu Ser Gly Asp
                165                 170                 175

Val Val Ser Ile Glu Phe Lys Asn Thr Gly Ser Ile Pro Lys Asp Lys
            180                 185                 190

Leu Ala Ala Ile Phe Glu Lys Phe Tyr Arg Leu Asp Asn Ala Arg Ser
        195                 200                 205

Ser Asp Thr Gly Gly Ala Gly Leu Gly Leu Ala Ile Ala Lys Glu Ile
    210                 215                 220

Ile Val Gln His Gly Gly Gln Ile Tyr Ala Glu Ser Asn Asp Asn Tyr
225                 230                 235                 240

Thr Thr Phe Arg Val Glu Leu Pro Ala Met Pro Asp Leu Val Asp Lys
                245                 250                 255

Arg Arg Ser


(2) INFORMATION FOR SEQ ID NO:41:

     (i) SEQUENCE CHARACTERISTICS:
          (A) LENGTH: 256 amino acids
          (B) TYPE: amino acid
          (D) TOPOLOGY: linear

    (ii) MOLECULE TYPE: protein
```

(v) FRAGMENT TYPE: internal (vi) ORIGINAL SOURCE:
(A) ORGANISM: Escherichia coli (xi) SEQUENCE DESCRIPTION: SEQ ID NO:41:

```
Glu Ile Arg Val Met Pro Tyr Thr His Lys Gln Leu Leu Met Val Ala
1               5                   10                  15

Arg Asp Val Thr Gln Met His Gln Leu Glu Gly Ala Arg Arg Asn Phe
            20                  25                  30

Phe Ala Asn Val Ser His Glu Leu Arg Thr Pro Leu Thr Val Leu Gln
        35                  40                  45

Gly Tyr Leu Glu Met Met Asn Glu Gln Pro Leu Glu Gly Ala Val Arg
    50                  55                  60

Glu Lys Ala Leu His Thr Met Arg Glu Gln Thr Gln Arg Met Glu Gly
65                  70                  75                  80

Leu Val Lys Gln Leu Leu Thr Leu Ser Lys Ile Glu Ala Ala Pro Thr
                85                  90                  95

His Leu Leu Asn Glu Lys Val Asp Val Pro Met Met Leu Arg Val Val
            100                 105                 110

Glu Arg Glu Ala Gln Thr Leu Ser Gln Lys Lys Gln Thr Phe Thr Phe
        115                 120                 125

Glu Ile Asp Asn Gly Leu Lys Val Ser Gly Asn Glu Asp Gln Leu Arg
    130                 135                 140

Ser Ala Ile Ser Asn Leu Val Tyr Asn Ala Val Asn His Thr Pro Glu
145                 150                 155                 160

Gly Thr His Ile Thr Val Arg Trp Gln Arg Val Pro His Gly Ala Glu
                165                 170                 175

Phe Ser Val Glu Asp Asn Gly Pro Gly Ile Ala Pro Glu His Ile Pro
            180                 185                 190

Arg Leu Thr Glu Arg Phe Tyr Arg Val Asp Lys Ala Arg Ser Arg Gln
        195                 200                 205

Thr Gly Gly Ser Gly Leu Gly Leu Ala Ile Val Lys His Ala Val Asn
    210                 215                 220

His His Glu Ser Arg Leu Asn Ile Glu Ser Thr Val Gly Lys Gly Thr
225                 230                 235                 240

Arg Phe Ser Phe Val Ile Pro Glu Arg Leu Ile Ala Lys Asn Ser Asp
                245                 250                 255
```

(2) INFORMATION FOR SEQ ID NO:42:

(i) SEQUENCE CHARACTERISTICS:
(A) LENGTH: 241 amino acids
(B) TYPE: amino acid
(D) TOPOLOGY: linear (ii) MOLECULE TYPE: protein (v) FRAGMENT TYPE: internal (vi) ORIGINAL SOURCE:
(A) ORGANISM: Escherichia coli (xi) SEQUENCE DESCRIPTION: SEQ ID NO:42:

```
Ala Ser Glu Val Arg Ser Val Thr Arg Ala Phe Asn His Met Ala Ala
1               5                   10                  15

Gly Val Lys Gln Leu Ala Asp Asp Arg Thr Leu Leu Met Ala Gly Val
            20                  25                  30
```

-continued

```
Ser His Asp Leu Arg Thr Pro Leu Thr Arg Ile Arg Leu Ala Thr Glu
        35                  40                  45

Met Met Ser Glu Gln Asp Gly Tyr Leu Ala Glu Ser Ile Asn Lys Asp
    50                  55                  60

Ile Glu Glu Cys Asn Ala Ile Ile Glu Gln Phe Ile Asp Tyr Leu Arg
65                  70                  75                  80

Thr Gly Gln Glu Met Pro Met Glu Met Ala Asp Leu Asn Ala Val Leu
                85                  90                  95

Gly Glu Val Ile Ala Ala Glu Ser Gly Tyr Glu Arg Glu Ile Glu Thr
            100                 105                 110

Ala Leu Tyr Pro Gly Ser Ile Glu Val Lys Met His Pro Leu Ser Ile
        115                 120                 125

Lys Arg Ala Val Ala Asn Met Val Val Asn Ala Ala Arg Tyr Gly Asn
    130                 135                 140

Gly Trp Ile Lys Val Ser Ser Gly Thr Glu Pro Asn Arg Ala Trp Phe
145                 150                 155                 160

Gln Val Glu Asp Asp Gly Pro Gly Ile Ala Pro Glu Gln Arg Lys His
                165                 170                 175

Leu Phe Gln Pro Phe Val Arg Gly Asp Ser Ala Arg Thr Ile Ser Gly
            180                 185                 190

Thr Gly Leu Gly Leu Ala Ile Val Gln Arg Ile Val Asp Asn His Asn
        195                 200                 205

Gly Met Leu Glu Leu Gly Thr Ser Glu Arg Gly Gly Leu Ser Ile Arg
    210                 215                 220

Ala Trp Leu Pro Val Pro Val Thr Arg Ala Gln Gly Thr Thr Lys Glu
225                 230                 235                 240

Gly
```

(2) INFORMATION FOR SEQ ID NO:43:

(i) SEQUENCE CHARACTERISTICS:
(A) LENGTH: 231 amino acids
(B) TYPE: amino acid
(D) TOPOLOGY: linear (ii) MOLECULE TYPE: protein (vi) ORIGINAL SOURCE:
(A) ORGANISM: E. faecium
(B) STRAIN: BM4147

(xi) SEQUENCE DESCRIPTION: SEQ ID NO:43:

```
Met Ser Asp Lys Ile Leu Ile Val Asp Asp Glu His Glu Ile Ala Asp
1               5                   10                  15

Leu Val Glu Leu Tyr Leu Lys Asn Glu Asn Tyr Thr Val Phe Lys Tyr
            20                  25                  30

Tyr Thr Ala Lys Glu Ala Leu Glu Cys Ile Asp Lys Ser Glu Ile Asp
        35                  40                  45

Leu Ala Ile Leu Asp Ile Met Leu Pro Gly Thr Ser Gly Leu Thr Ile
    50                  55                  60

Cys Gln Lys Ile Arg Asp Lys His Thr Tyr Pro Ile Ile Met Leu Thr
65                  70                  75                  80

Gly Lys Asp Thr Glu Val Asp Lys Ile Thr Gly Leu Thr Ile Gly Ala
                85                  90                  95

Asp Asp Tyr Ile Thr Lys Pro Phe Arg Pro Leu Glu Leu Ile Ala Arg
            100                 105                 110

Val Lys Ala Gln Leu Arg Arg Tyr Lys Lys Phe Ser Gly Val Lys Glu
```

```
        115                 120                 125

Gln Asn Glu Asn Val Ile Val His Ser Gly Leu Val Ile Asn Val Asn
    130                 135                 140

Thr His Glu Cys Tyr Leu Asn Glu Lys Gln Leu Ser Leu Thr Pro Thr
145                 150                 155                 160

Glu Phe Ser Ile Leu Arg Ile Leu Cys Glu Asn Lys Gly Asn Val Val
                165                 170                 175

Ser Ser Glu Leu Leu Phe His Glu Ile Trp Gly Asp Glu Tyr Phe Ser
            180                 185                 190

Lys Ser Asn Asn Thr Ile Thr Val His Ile Arg His Leu Arg Glu Lys
        195                 200                 205

Met Asn Asp Thr Ile Asp Asn Pro Lys Tyr Ile Lys Thr Val Trp Gly
    210                 215                 220

Val Gly Tyr Lys Ile Glu Lys
225                 230
```

(2) INFORMATION FOR SEQ ID NO:44:

(i) SEQUENCE CHARACTERISTICS:
(A) LENGTH: 239 amino acids
(B) TYPE: amino acid
(D) TOPOLOGY: linear (ii) MOLECULE TYPE: protein (vi) ORIGINAL SOURCE:
(A) ORGANISM: Escherichia coli (xi) SEQUENCE DESCRIPTION: SEQ ID NO:44:

```
Met Gln Glu Asn Tyr Lys Ile Leu Val Val Asp Asp Asp Met Arg Leu
1               5                   10                  15

Arg Ala Leu Leu Glu Arg Tyr Leu Thr Glu Gln Gly Phe Gln Val Arg
            20                  25                  30

Ser Val Ala Asn Ala Glu Gln Met Asp Arg Leu Leu Thr Arg Glu Ser
        35                  40                  45

Phe His Leu Met Val Leu Asp Leu Met Leu Pro Gly Glu Asp Gly Leu
    50                  55                  60

Ser Ile Cys Arg Arg Leu Arg Ser Gln Ser Asn Pro Met Pro Ile Ile
65                  70                  75                  80

Met Val Thr Ala Lys Gly Glu Glu Val Asp Arg Ile Val Gly Leu Glu
                85                  90                  95

Ile Gly Ala Asp Asp Tyr Ile Pro Lys Pro Phe Asn Pro Arg Glu Leu
            100                 105                 110

Leu Ala Arg Ile Arg Ala Val Leu Arg Arg Gln Ala Asn Glu Leu Pro
        115                 120                 125

Gly Ala Pro Ser Gln Glu Glu Ala Val Ile Ala Phe Gly Lys Phe Lys
    130                 135                 140

Leu Asn Leu Gly Thr Arg Glu Met Phe Arg Glu Asp Glu Pro Met Pro
145                 150                 155                 160

Leu Thr Ser Gly Glu Phe Ala Val Leu Lys Ala Leu Val Ser His Pro
                165                 170                 175

Arg Glu Pro Ile Ser Arg Asp Lys Leu Met Asn Leu Ala Arg Gly Arg
            180                 185                 190

Glu Tyr Ser Ala Met Glu Arg Ser Ile Asp Val Gln Ile Ser Arg Leu
        195                 200                 205

Arg Arg Met Val Glu Glu Asp Pro Ala His Pro Arg Tyr Ile Gln Thr
    210                 215                 220
```

-continued

```
Val Trp Gly Leu Gly Tyr Val Phe Val Pro Asp Gly Ser Lys Ala
225                 230                 235
```

(2) INFORMATION FOR SEQ ID NO:45:

(i) SEQUENCE CHARACTERISTICS:
(A) LENGTH: 229 amino acids
(B) TYPE: amino acid
(D) TOPOLOGY: linear (ii) MOLECULE TYPE: protein (vi) ORIGINAL SOURCE:
(A) ORGANISM: Escherichia coli (xi) SEQUENCE DESCRIPTION: SEQ ID NO:45:

```
Met Ala Arg Arg Ile Leu Val Val Glu Asp Glu Ala Pro Ile Arg Glu
1               5                   10                  15

Met Val Cys Phe Val Leu Glu Gln Asn Gly Phe Gln Pro Val Glu Ala
            20                  25                  30

Glu Asp Tyr Asp Ser Ala Val Asn Gln Leu Asn Glu Pro Trp Pro Asp
        35                  40                  45

Leu Ile Leu Leu Asp Trp Met Leu Pro Gly Gly Ser Gly Ile Gln Phe
    50                  55                  60

Ile Lys His Leu Lys Arg Glu Ser Met Thr Arg Asp Ile Pro Val Val
65                  70                  75                  80

Met Leu Thr Ala Arg Gly Glu Glu Glu Asp Arg Val Arg Gly Leu Glu
                85                  90                  95

Thr Gly Ala Asp Asp Tyr Ile Thr Lys Pro Phe Ser Pro Lys Glu Leu
            100                 105                 110

Val Ala Arg Ile Lys Ala Val Met Arg Arg Ile Ser Pro Met Ala Val
        115                 120                 125

Glu Glu Val Ile Glu Met Gln Gly Leu Ser Leu Asp Pro Thr Ser His
    130                 135                 140

Arg Val Met Ala Gly Glu Glu Pro Leu Glu Met Gly Pro Thr Glu Phe
145                 150                 155                 160

Lys Leu Leu His Phe Phe Met Thr His Pro Glu Arg Val Tyr Ser Arg
                165                 170                 175

Glu Gln Leu Leu Asn His Val Trp Gly Thr Asn Val Tyr Val Glu Asp
            180                 185                 190

Arg Thr Val Asp Val His Ile Arg Arg Leu Arg Lys Ala Leu Glu Pro
        195                 200                 205

Gly Gly His Asp Arg Met Val Gln Thr Val Arg Gly Thr Gly Tyr Arg
    210                 215                 220

Phe Ser Thr Arg Phe
225
```

(2) INFORMATION FOR SEQ ID NO:46:

(i) SEQUENCE CHARACTERISTICS:
(A) LENGTH: 129 amino acids
(B) TYPE: amino acid
(D) TOPOLOGY: linear (ii) MOLECULE TYPE: protein (vi) ORIGINAL SOURCE:
(A) ORGANISM: Escherichia coli (xi) SEQUENCE DESCRIPTION: SEQ ID NO:46:

-continued

```
Met Ala Asp Lys Glu Leu Lys Phe Leu Val Val Asp Asp Phe Ser Thr
1               5                   10                  15

Met Arg Arg Ile Val Arg Asn Leu Leu Lys Glu Leu Cys Phe Asn Asn
            20                  25                  30

Val Glu Glu Ala Glu Asp Gly Val Asp Ala Leu Asn Lys Leu Gln Ala
        35                  40                  45

Gly Gly Phe Gly Phe Ile Ile Ser Asp Trp Asn Met Pro Asn Met Asp
    50                  55                  60

Gly Leu Glu Leu Leu Lys Thr Ile Arg Ala Asp Ser Ala Met Ser Ala
65                  70                  75                  80

Leu Pro Val Leu Met Val Thr Ala Glu Ala Lys Lys Glu Asn Ile Ile
                85                  90                  95

Ala Ala Ala Gln Ala Gly Ala Ser Gly Tyr Val Val Lys Pro Phe Thr
            100                 105                 110

Ala Ala Thr Leu Glu Glu Lys Leu Asn Lys Ile Phe Glu Lys Leu Gly
        115                 120                 125

Met
```

(2) INFORMATION FOR SEQ ID NO:47:

(i) SEQUENCE CHARACTERISTICS:
(A) LENGTH: 9 amino acids
(B) TYPE: amino acid
(D) TOPOLOGY: linear (ii) MOLECULE TYPE: peptide (v) FRAGMENT TYPE: N-terminal (vi) ORIGINAL SOURCE:
(A) ORGANISM: E. faecium
(B) STRAIN: BM4147

(xi) SEQUENCE DESCRIPTION: SEQ ID NO:47:

```
Met Asn Arg Ile Lys Val Ala Ile Leu
1               5
```

(2) INFORMATION FOR SEQ ID NO:48:

(i) SEQUENCE CHARACTERISTICS:
(A) LENGTH: 10 base pairs
(B) TYPE: nucleic acid
(C) STRANDEDNESS: unknown
(D) TOPOLOGY: linear (ii) MOLECULE TYPE: DNA (genomic)

(ix) FEATURE:
(A) NAME/KEY: RBS
(B) LOCATION: 1..10

(xi) SEQUENCE DESCRIPTION: SEQ ID NO:48:

```
TGAAAGGAGA                                                         10
```

(2) INFORMATION FOR SEQ ID NO:49:

(i) SEQUENCE CHARACTERISTICS:
(A) LENGTH: 10 base pairs
(B) TYPE: nucleic acid
(C) STRANDEDNESS: unknown
(D) TOPOLOGY: linear (ii) MOLECULE TYPE: RNA (genomic)

(xi) SEQUENCE DESCRIPTION: SEQ ID NO:49:

-continued

UCUUUCCUCC 10

(2) INFORMATION FOR SEQ ID NO:50:

(i) SEQUENCE CHARACTERISTICS:
(A) LENGTH: 23 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO:50:

GCTGCAGATA AAAATTTAGG AGG 23

(2) INFORMATION FOR SEQ ID NO:51:

(i) SEQUENCE CHARACTERISTICS:
(A) LENGTH: 24 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO:51:

CGCATGCTAT TATAAAAGCC AGTC 24

(2) INFORMATION FOR SEQ ID NO:52:

(i) SEQUENCE CHARACTERISTICS:
(A) LENGTH: 10 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO:52:

TGAAAGGGTG 10

(2) INFORMATION FOR SEQ ID NO:53:

(i) SEQUENCE CHARACTERISTICS:
(A) LENGTH: 21 base pairs
(B) TYPE: nucleic acid
(C) STRANDEDNESS: unknown
(D) TOPOLOGY: linear (ii) MOLECULE TYPE: rRNA (vi) ORIGINAL SOURCE:
(A) ORGANISM: B. subtilis (xi) SEQUENCE DESCRIPTION: SEQ ID NO:53:

GGGGGGTTGG NNNNNNNNTT G 21

(2) INFORMATION FOR SEQ ID NO:54:

(i) SEQUENCE CHARACTERISTICS:
(A) LENGTH: 19 base pairs
(B) TYPE: nucleic acid
(C) STRANDEDNESS: unknown
(D) TOPOLOGY: linear (ii) MOLECULE TYPE: rRNA (vi) ORIGINAL SOURCE:
(A) ORGANISM: B. subtilis -continued (xi) SEQUENCE DESCRIPTION: SEQ ID NO:54:

AGAACGAAAA NNNNNNATG 19

POLYPEPTIDES IMPLICATED IN THE EXPRESSION OF RESISTANCE TO GLYCOPEPTIDES, IN PARTICULAR IN GRAM-POSITIVE BACTERIA, NUCLEOTIDE SEQUENCE CODING FOR THESE POLYPEPTIDES AND USE FOR DIAGNOSIS

This Application is a Divisional of application Ser. No. 08/980,357, filed on Nov. 28, 1997, now allowed, which is a Divisional of application Ser. No. 08/286,819 filed on Aug. 5, 1994, now U.S. Pat. No. 5,871,910, which is a Continuation of application Ser. No. 08/174,682 filed on Dec. 28, 1993, abandoned, which is a Continuation of application Ser. No. 07/917,146 filed on Aug. 10, 1992, abandoned, which is a National Stage Application of PCT/FR91/00855 Oct. 29, 1991, abandoned.

The invention relates to the polypeptides associated with the expression of resistance to antibiotics of the glycopeptide family, in particular in Gram-positive bacteria, in particular in the family of the Gram-positive cocci. The invention also relates to a nucleotide sequence coding for these polypeptides. It also relates to the use of these polypeptides and their nucleotide sequence as agents for the in vitro detection of resistance to glycopeptides. Among the Gram-positive cocci, the invention relates most particularly to the enterococci, the streptococci and the staphylococci which are of particular importance for the implementation of the invention.

The glycopeptides, which include vancomycin and teicoplanin are antibiotics which inhibit the synthesis of the bacterial cell wall. These antibiotics are very much used for the treatment of severe infections due to Gram-positive cocci (enterococci, streptococci and staphylococci), in particular in the light of allergy and resistance to the penicillins. In spite of long clinical usage of vancomycin, this antibiotic has remained active towards almost all of the strains up to 1986, the date at which the first resistant strains were isolated. Since then, resistance to the glycopeptides has been detected by many microbiologists in Europe and in the United States, in particular in strains isolated from immunodepressive patients, making necessary a systematic evaluation of the sensitivity of the microbes in hospital environments.

The activity of the glycopeptides depends on the formation of a complex between the antibiotic and the precursors of the peptidoglycan, more than on the direct interaction with enzymes of cell wall metabolism. In particular, it has been observed that the glycopeptides bind to the terminal D-alanyl-D-alanine residues (D-ala-D-ala) of the precursors of the peptidoglycan.

The recent emergence of resistance to the glycopeptides, in particular in the enterococci, has led to certain results being obtained with regard to knowledge of the factors conferring this resistance.

For example it has been observed in a particular strain of enterococci, *Enterococcus faecium* BM4147, that the determinant of resistance to the glycopeptides is localized on a plasmid of 34 kb, the plasmid pIP816. This determinant has been cloned in *E. coli* (Brisson Noel et al., 1990, Antimicrob Agents Chemother 34, 924–927).

According to the results hitherto obtained, the resistance to the glycopeptides is associated with the production of a protein of molecular weight of about 40 kDa, the synthesis of this protein being induced by sub-inhibitory concentrations of certain glycopeptides such as vancomycin.

By carrying out a more detailed study of the resistance of certain strains of Gram-positive cocci towards glycopeptides, in particular vancomycin or teicoplanin, the inventors have observed that this resistance might be linked to the expression of several proteins or polypeptides encoded in sequences usually borne by plasmids in the resistant strains. The recent results obtained by the inventors also make it possible to distinguish the genes coding for two phenotypes of resistance, on the one hand strains highly resistant to the glycopeptides, and, on the other, strains with a low level of resistance.

By strain with a high level of resistance is meant a strain of bacteria, in particular a strain of Gram-positive cocci, for which the minimal inhibitory concentrations (MIC) of vancomycin and teichoplanin are higher than 32 and 8 μg/ml, respectively. The MIC of vancomycin towards strains with low-level resistance are included between 16 and 32 μg/ml. These strains are apparently sensitive to teicoplanin.

The inventors have isolated and purified, among the components necessary for the expression of the resistance to the glycopeptides, a particular protein designated VANA or VanA which exhibits a certain homology with D-alanine-D-alanine ligases. VanA is nonetheless functionally distinct from the ligases.

In principle, a gene sequence will be designated by "van . . . " and an amino acid sequence by "Van . . . ".

The invention relates to polypeptides or proteins implicated in the expression of resistance to antibiotics of the glycopeptide family and, in particular, to vancomycin and/or teicoplanin as well as to the nucleotide sequences coding for such complexes.

The invention also relates to nucleotide probes which can be used for the detection of resistance to the glycopeptides, in particular by means of the polymerase chain reaction (PCR), or by tests involving antibodies.

The invention relates to a composition of polypeptides, characterized in that it contains at least one protein or part of a protein selected from the amino acid sequences identified in the list of the sequences as SEQ ID NO 2 (VanH), SEQ ID NO 4 (VanA), SEQ ID NO 6 (VanX) or SEQ ID NO 8 (VanC), or any protein or part of a protein recognized by the antibodies directed against VanH, VanA, VanX or VanC, or any protein or part of a protein encoded in a sequence hybridizing with one of the nucleotide sequences identified in the list of the sequences as SEQ ID NO 1, SEQ ID NO 3, SEQ ID NO 5 or SEQ ID NO 7 or with one of the following sequences V1 (SEQ ID NO:9) or V2 (SEQ ID NO:10) under stringent or only slightly stringent conditions:

```
V1 : GGX GAA GAT GGX TCX TTX CAA GGX
           G   C     AG  C     G
                         A

V2 : AAT ACX ATX CCX GGX TTT AC
       C     T             C
             C
```

A first particular composition according to the invention implicated in the expression of the resistance to the glycopeptides is characterized in that it comprises at least 3 proteins or any part of one or more of these proteins necessary to confer to Gram-positive bacteria the resistance to antibiotics of the glycopeptide family, in particular to vancomycin and/or teicoplanin or to promote this resistance, in particular in strains of the family of the Gram-positive cocci, these proteins or parts of proteins being a) recognized by antibodies directed against one of the sequences identified in the list of the sequences as SEQ ID NO 2, SEQ ID NO 4, SEQ ID NO 6, b) or encoded in genes containing a sequence identified as SEQ ID NO 1, SEQ ID NO 3 or SEQ ID NO 5 or hybridizing with one of these sequences or its complementary sequence or with the sequences V1 (SEQ ID NO:9) or V2, (SEQ ID NO:10) under stringent or only slightly stringent conditions.

These sequences are also designated, respectively, by ORF3, ORF1 containing the gene VanH, vanA (or ORF2); they characterize the proteins responsible for resistance as obtained from the strain *Enterococcus faecium* BM4147 described by Leclerq et al (N. Engl. J. Med. 319:157–161).

Another protein, VanC, (SEQ ID NO:8) related to the D-Ala-D-Ala ligases but of different specificity has been characterized in *Enterococcus gallinarum* BM4173; the vanC gene (SEQ ID NO:7) possesses domains having sufficient homology with the vanA gene for probes corresponding to defined regions of vanA to make possible its detection.

*E. gallinarum* is a constitutive isolate resistant to low levels of vancomycin (Dutka-Malen et al., Antimicrob. Agents Chemother 34 (1990b) 1875–1879).

By the expression "polypeptides" is meant any sequence of amino acids constituting proteins or being of a size less than that of a protein.

The stringent conditions mentioned above are defined according to the usual conditions pertaining to the hybridization of nucleotide sequences. As an example, in the case of the sequences which hybridize with the sequence of the vanA gene (SEQ ID NO 1) it will be possible to apply the following conditions:

for hybridization under conditions of high stringency:
 a reaction temperature of 65° C. overnight in a solution containing 0.1% SDS, 0.7% skimmed milk powder, 6×SSC (1×SSC=0.15 M NaCl and 0.015 M sodium citrate at pH=7.0)
 washes at 65° C. in 2×SSC=0.1% SDS;
for hybridization under slightly stringent conditions, the hybridization temperature is 60° C. overnight and the temperature of the washings is 45° C.

The expression of resistance to glycopeptides may be expressed by the persistence of an infection due to microbes usually sensitive to the glycopeptides.

A polypeptide or a protein is necessary for the expression of resistance to the glycopeptides, if its absence makes the strain which contains this polypeptide or this protein more sensitive to the glycopeptides and if this polypeptide or protein is not present in sensitive strains.

Different levels of resistance to the glycopeptides exist in the strains of Gram-positive cocci, in particular.

According to a preferred embodiment of the invention, the polypeptides included in the composition defined above correspond to the combination of the proteins identified in the list of the sequences as SEQ ID NO 2 (VanH), SEQ ID NO 4 (VanA), SEQ ID NO 6 (VanX).

The inventors have thus observed that the expression of resistance to the glycopeptides in Gram-positive bacteria requires the expression of at least three proteins or of polypeptides derived from these proteins.

According to a first particular embodiment of the invention, the polypeptides of the composition are also characterized in that the amino acid sequences necessary for the expression of resistance to antibiotics of the glycopeptide family are under the control of regulatory elements, in particular of the proteins corresponding to the sequences designated by SEQ ID NO 12 and SEQ ID NO 14 in the list of the sequences, and which correspond to a regulatory sequence R and to a sensor sequence S, respectively.

VanS and VanR constitute a two-component regulatory system, VanR being an activator of transcription and VanS stimulating the transcription dependent on VanR. VanS is capable of modulating the level of phosphorylation of VanR in response to the vancomycin present in the external medium and is thus involved in the control of the transcription of the genes for resistance to vancomycin.

These regulatory sequences are in particular capable of increasing the level of resistance, to the extent to which they promote the expression of the proteins responsible for resistance comprised in the polypeptides of the invention.

According to another advantageous embodiment of the invention, the polypeptides of the above composition are encoded in the sequence SEQ ID NO 15 identified in the list of the sequences, which represents the sequence coding for the 5 proteins previously described.

Another sequence according to the invention is designated by SEQ ID NO 16 which contains the sequence SEQ ID NO 15 as well as a sequence upstream from SEQ ID NO 15 coding for a transposase (encoded in the (–) strand of the sequence, and a sequence downstream from SEQ ID NO 6 corresponding to the genes vanY and vanZ and at each end reverse repeated sequences of 38 bp. SEQ ID NO 16 constitutes a transposon, the genes of which are implicated at different levels in the establishment of resistance to the glycopeptides.

The invention also relates to the purified proteins belonging to the composition and to the polypeptides described previously. In particular, the invention relates to the purified protein VanA, characterized in that it corresponds to the amino acid sequence SEQ ID NO 4 in the list of the sequences or a protein VanC, encoded in a gene capable of hybridizing with the vanA gene.

The protein VanA contains 343 amino acids and has a calculated molecular mass of 37400 Da. The protein VanC contains 343 amino acids and has a calculated molecular mass of 37504 Da.

Other interesting proteins in the framework of the invention correspond to the sequences identified as SEQ ID NO 2 (VanH), SEQ ID NO 6 (VanX), SEQ ID NO 12 (VanR), SEQ ID NO 14 (VanS) in the list of the sequences.

The sequence identified by the abbreviation SEQ ID NO 1 contains the protein VanH encoded in the gene vanH, this protein contains 322 amino acids and begins with a methionine. This protein is an enzyme implicated in the synthesis of the peptidoglycan and has a molecular mass of 35,754 kDA. VanH exhibits some similarities to dehydrogenases which catalyze the $NAD^+$-dependent oxidation of 2-hydroxy-carboxylic acids to form the corresponding 2-keto-carboxylic acids. In fact, the VanH protein might use $NADP^+$ rather than $NAD^+$. The VanH protein also contains several residues of reactive sites which probably participate directly in the binding of the substrate and in catalysis. VanH might be implicated in the synthesis of a substrate of the ligase VanA. This substrate of VanA might be a D-α-hydroxy-carboxylic acid, which might be condensed by VanA with D-alanine in the place of a D-amino acid, which might affect the binding of the precursor of the peptidoglycan with vancomycin, as a result of the loss of a hydrogen bond because one of the hydrogen bonds formed between vancomycin and N-acetyl-D-Ala-D-Ala occurs with the NH group of the terminal D-alanine residue. Let it be recalled that "Ala" is the abbreviation for "alanine".

The inventors have been able to detect some interactions between the proteins VanA and VanH and have in particular been able to describe the following: the nature of the VanA protein (D-alanine: D-alanine ligase with reduced specificity for its substrate) which has made possible resistance to glycopeptides, implies the biosynthesis by VanA of a novel compound different from D-Ala-D-Ala, a peptide which may be incorporated into the peptidoglycans but which is not recognized by vancomycin. In particular the observation of similarities between the product of the vanH gene and the D-specific α-keto-acid reductases has made it possible to determine that this compound cannot be a D-amino acid but is a D hydroxy acid, which when it is bound to D-alanine by VanH, can generate the novel depsipeptide precursor of the peptidoglycan.

The invention also relates to any combination of these different proteins in a resistance complex, as well as to hybrid proteins comprising one or several of the above proteins, or part of these proteins, in combination with a defined amino acid sequence.

Also included in the framework of the invention are nucleotide sequences coding for one of the amino acid sequences described above.

A particular sequence is the nucleotide sequence of about 7.3 kb, corresponding to the HindIII-EcoRI restriction fragment, such as that obtained starting from the plasmid pIP816 described in the publication of Leclerq et al—1988, cited above.

This sequence of 7.3 kb comprises the nucleotide sequence coding for the 3 resistance proteins and the 2 regulatory proteins referred to above. This coding sequence is included in an internal BglII-XbaI fragment. It also comprises a part of the sequences coding for the transposase and the resolvase.

The invention also relates to any nucleotide fragment comprising the above-mentioned restriction fragment as well as any part of the HindIII-EcoRI fragment, in particular the EcoRI-XbaI fragment of about 3.4 kb coding for the 3 resistance proteins or the EcoRV-SacII fragment of about 1.7 kb coding for VanA or also HindIII-EcoRI fragment of about 3.3 kb coding for the 2 regulatory proteins VanR and VanS.

Another definition of a nucleotide sequence of the invention corresponds to a nucleotide fragment containing the following restriction sites in the following order, such as obtained starting from pIP816 mentioned above:

HindIII, BglII, BglII, EcoRI, BamHI, XbaI, EcoRI.

Another nucleotide sequence according to the invention is characterized in that it corresponds to a sequence selected from the sequences identified as SEQ ID NO 15, SEQ ID NO 17, or SEQ ID NO 16, or in that it includes this sequence or any part of this sequence, or also any sequence or part of the sequence of the complementary DNA or any sequence of RNA corresponding to one of these DNAs, capable,

- either of constituting a hybridization probe for the detection of resistance to antibiotics of the glycopeptide family, in particular to vancomycin and/or teicoplanin in particular in strains of the family of the Gram-positive cocci,
- or of coding for a sequence necessary or associated with the expression of resistance to antibiotics of the glycopeptide family, in particular to vancomycin and/or teicoplanin., in particular in strains of the family of the Gram-positive cocci.

The sequence SEQ ID NO 17 codes for the 3 resistance proteins VanH, VanA and VanX.

Figure 7A:
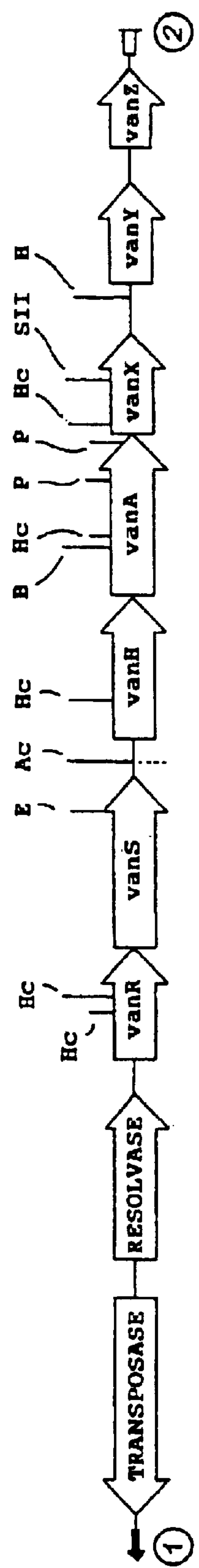

The sequence SEQ ID NO 16 includes a transposon shown in FIG. 7*a*; this transposon contains the genes necessary for the expression of resistance to the glycopeptides as well as the genes associated with this resistance implicated, for example, in the regulation of the expression of the genes necessary to produce the resistance phenotype or implicated in the amount of resistance polypeptide produced.

A specific sequence corresponding to the above definition is one of the following sequences:

```
  (SEQ ID NO:9)

V1 : GGX GAA GAT GGX TCX TTX CAA GGX

         G   C     AG  C     G

or                     A

  (SEQ ID NO:10)

V2 : AAT ACX ATX CCX GGX TTT AC

      C     T           T

            C
```

V1 and V2 make possible the constitution of probes, if necessary, in combination with other nucleotides, depending on the degree of specificity desired in order to detect vanA and vanC and may also be used as primers in polymerase chain reactions.

Other preferred nucleotide sequences are the sequences SEQ ID NO 1, SEQ ID NO 3, SEQ ID NO 5, SEQ ID NO 7, SEQ ID 18 (transposase), SEQ ID NO 20 (resolvase), SEQ ID NO 22 (vanY), SEQ ID NO 24 (vanZ), SEQ ID NO 11 (vanR), SEQ ID NO 13 (vanS) or a variant of one of these sequences provided that it codes for a protein having immunological and/or functional properties similar to those of the proteins encoded in the sequences SEQ ID NO 1 (vanA), SEQ ID NO 3 (vanH), SEQ ID NO 5 (vanX), or SEQ ID NO 7 (vanC), SEQ ID NO 18 (transposase), SEQ ID NO 20 (resolvase), SEQ ID NO 22 (vanY), SEQ ID NO 24 (vanZ), SEQ ID NO 11 (vanR), SEQ ID NO 13 (vanS) or in that it makes possible the detection of strains resistant to antibiotics of the glycopeptide family.

Variants include all of the fragments of the sequences having the following properties.

These sequences code for the resistance proteins VanH, VanA and VanX.

The nucleotide sequence designated by SEQ ID NO 1 corresponds to a DNA fragment of 1029 bp situated between the ATG codon at position 377 and the TGA codon at position 1406 on the plasmid pAT214 (FIG. 6).

The invention also relates to a nucleotide sequence coding for the sequence SEQ ID NO 15 corresponding to the sequence coding for the 5 proteins (2 regulatory proteins and 3 resistance proteins), and also comprising the flanking sequences associated with these coding sequences, or comprising this sequence.

Also included in the framework of the invention is a sequence modified with respect to SEQ ID NO 15, characterized in that it lacks the flanking sequences. These flanking sequences are the sequences shown in the following pages and defined as follows:

- sequence upstream from the sequence coding for R: between the bases 1 and 1476 of the sequence shown in FIG. 5,
- sequence between the sequence coding for the sensor protein S and ORF1: between the bases 3347 and 3500 of the sequence shown in FIG. 5,
- sequence downstream from the sequence coding for ORF3: between the bases 6168 and 7227 of the sequence shown in FIG. 5.

The sequence designated by SEQ ID NO 15 is also characterized by the fragment bearing the restriction sites in the following order:

BglIII-EcoRI-BamHI-EcoRI

Figure 3A:
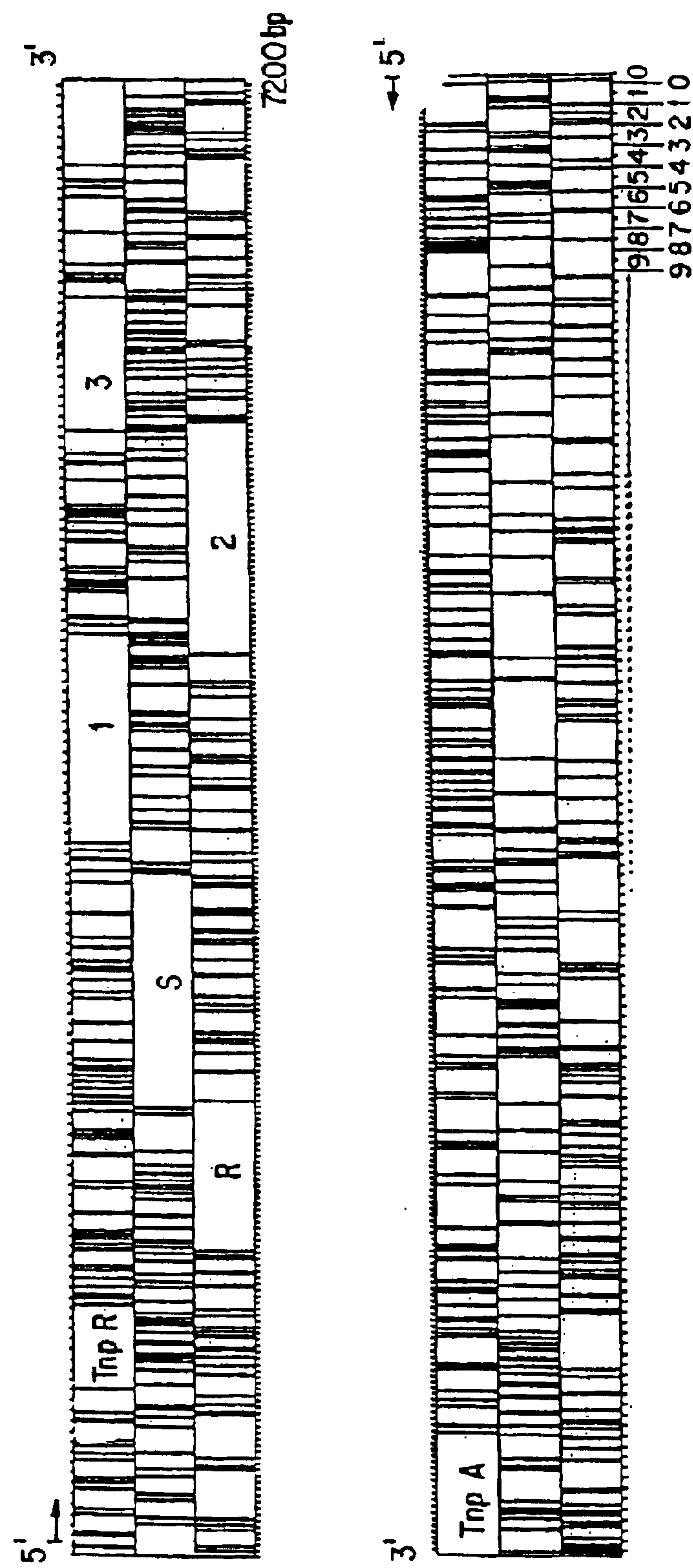
Figure 3B:
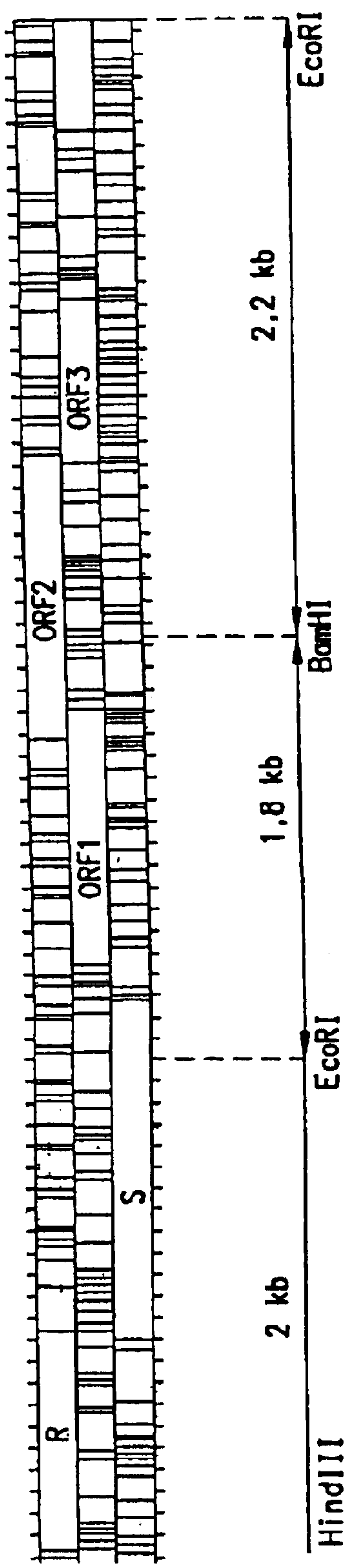

The location of the regulatory proteins and the resistance proteins is shown in FIG. 3.

The inventors have identified upstream and downstream from the genes vanR, vanS, vanH, vanA and vanX, which are necessary for or associated with the expression of resistance to glycopeptides at a given level, genes coding for a transposase and a resolvase (upstream from the group previously mentioned) and genes vanY and vanZ, downstream from this group. The genes for the transposase and resolvase might be implicated in transposition functions and the vanY gene coding for a D,D-carboxy peptidase might be implicated in the metabolism of the peptidoglycan, and might contribute to resistance to the glycopeptides in *E. faecium* BM4147 even though vanR, vanS, vanH, vanA and vanX borne by a plasmid in a high number of copies, alone confer a high level of resistance.

Let it be noted that the sequence coding for the transposase (SEQ ID NO:18) is located on the (−) strand of the sequence ID NO 16 which codes for vanR, vanS, vanH, vanA, vanX, vanY, vanZ and the resolvase.

The invention relates not only to the DNA sequences identified in the list of the sequences but also to the complementary DNA sequences and the corresponding RNA sequences. The invention concerns in addition sequences which are equivalent to the former, either in terms of expression of proteins, polypeptides or their fragments described above, or in terms of the capacity to detect, for example by chain polymerization procedures, strains of Gram-positive bacteria exhibiting resistance to antibiotics of the glycopeptide family such as vancomycin or teicoplanin.

Recombinant sequences characterized in that they comprise one of the above nucleotide sequences also form part of the invention.

The invention also relates to a recombinant vector characterized in that it includes one of the above nucleotide sequences at a site inessential for its replication, under the control of regulatory elements likely to be implemented in the expression of the resistance to antibiotics of the glycopeptide family, in particular to vancomycin or teicoplanin, in a defined host.

Particularly advantageous recombinant vectors for the implementation of the invention are the following vectors: pAT214 containing the EcoRV-SacII fragment of 1761 bp containing a nucleotide sequence coding for the VanA protein; in these vectors the sequences of the invention are advantageously placed under the control of promoters such as the lac promoter.

The invention also relates to a recombinant cell host containing a nucleotide sequence such as that previously described or a vector such as that described above under conditions which make possible the expression of resistance to antibiotics of the glycopeptide family, in particular resistance to vancomycin and/or this host being for example selected from the bacteria, in particular the Gram-positive cocci.

In certain applications it is also possible to use yeasts, fungi, insect or mammalian cells.

The invention also relates to a nucleotide probe characterized in that it is capable of hybridizing with a sequence previously described, this probe being labelled if necessary. These probes may or may not be specific for the proteins of resistance to glycopeptides.

Labels which can be used for the requirements of the invention are the known radioactive labels as well as other labels such as enzymatic labels or chemoluminescent labels.

Probes thus labelled may be used in hybridization tests in order to detect resistance to glycopeptides in Gram-positive bacteria. In this case, conditions of low stringency will be used.

Nucleotide probes according to the invention may be characterized in that they are specific in Gram-positive bacteria for the sequences coding for a resistance protein to the glycopeptides, in particular to vancomycin and/or teicoplanin these probes being in addition universal among these sequences.

By these specific probes is meant any oligonucleotide hybridizing with a nucleotide sequence coding for one of the proteins according to the invention, such as described in the preceding pages, and not exhibiting a cross hybridization reaction or amplification reaction (PCR) with sequences present in all of the sensitive strains.

The universal character of the oligonucleotide which can be used in PCR is defined by their capacity to promote specifically the amplification of a nucleotide sequence implicated in resistance in any one strain of Gram-positive bacteria, resistant to the antibiotics of the glycopeptide family.

The size of the nucleotide probes according to the invention may vary depending on the use desired. For the oligonucleotides which are used in PCR, recourse will be had to fragments of a length which is usual in this procedure. In order to construct probes, it is possible to take any part of the sequences of the invention, for example probe fragments of 200 nucleotides.

According to a particular embodiment of the invention, a nucleotide probe is selected for its specificity towards a nucleotide sequence coding for a protein necessary for the expression in Gram-positive bacteria of a high level of resistance to antibiotics of the glycopeptide family, in particular to vancomycin and teicoplanin.

As examples, useful probes may be selected from the intragenic part of the vanA gene.

Other useful probes for carrying out the invention are characterized by their universal character, according to the preceding definition, but are not specific for the resistance genes. They may also be used as primers in PCR, and are for example:

```
  (SEQ ID NO:9)
V1 : GGX GAA GAT GGX TCX TTX CAA GGX
           G   C     AG   C     G
                          A
  (SEQ ID NO:10)
V2 : AAT ACX ATX CCX GGX TTT AC
       C     T             C
             C
```

V1 and V2 hybridize with vanA and vanC and are capable of leading to the detection of proteins associated with resistance to glycopeptides in other micro-organisms.

Other particular probes of the invention have the specific character of a nucleotide sequence coding for a protein necessary for the expression in Gram-positive bacteria of a low level of resistance to antibiotics of the glycopeptide family, in particular to vancomycin in Gram-positive bacteria.

It should also be mentioned that oligonucleotide probes which might be derived from the sequence of the vanA gene coding for the VanA protein may be used indiscriminately to detect high-level or low-level resistance.

In a particularly preferred manner, a probe of the invention is characterized in that it hybridizes with a chromosomal or non-chromosomal nucleotide sequence of a Gram-positive strain resistant to glycopeptides, in particular to vancomycin and/or teicoplanin, in particular in that it hybridizes with a chromosomal or non-chromosomal nucleotide sequence of a strain of Gram-positive cocci, for example an enterococcal strain and preferably *E. faecium* 4147 or *E. gallinarum.*

In order to distinguish strains with a high level of resistance from strains with a low level of resistance it is possible to carry out a hybridization test using conditions of high stringency.

The oligonucleotides of the invention may be obtained from the sequences of the invention by cutting with restriction enzymes, or by chemical synthesis according to the standard methods.

Furthermore, the invention relates to polyclonal or monoclonal antibodies, characterized in that they recognize the polypeptide(s) described above or an amino acid sequence described above.

These antibodies may be obtained according to standard methods for antibody production. In particular, in the case of the preparation of monoclonal antibodies, recourse will be had to the method of Köhler and Milstein according to which monoclonal antibodies are prepared by cell fusion between myeloma cells and mouse spleen cells previously immunized with a polypeptide or a composition according to the invention, in conformity with the standard procedure.

The antibodies of the invention can advantageously be used for the detection of the presence of proteins characteristic of resistance to the glycopeptides, in particular to vancomycin and teicoplanin.

Particularly useful antibodies are polyclonal or monoclonal antibodies directed against the protein VanA or VanC. Such antibodies advantageously make it possible to detect strains of bacteria, in particular Gram-positive cocci, exhibiting high-level resistance to the antibiotics of the glycopeptide family. If necessary, a step entailing lysis of the cells of the sample undergoing detection is performed prior to the placing in contact of the sample with the antibodies.

In order to carry out this detection, recourse will advantageously be had to antibodies labelled for example with a radioactive substance or other type of label.

Hence, tests for the detection in Gram-positive bacteria of resistance to the glycopeptides, in particular tests making use of the ELISA procedures, are included in the framework of the invention.

A kit for the in vitro diagnosis of the presence of Gram-positive strains, resistant to the glycopeptides, in particular to vancomycin and/or teicoplanin, these strains belonging in particular to the Gram-positive cocci for example enterococci, for example *E. faecium* or *E. gallinarum* is characterized in that it comprises:

- antibodies corresponding to the above definition, labelled if necessary,
- a reagent for the detection of an immunological reaction of the antigen-antibody type,
- if necessary, reagents to effect the lysis of the cells of the sample to be tested.

Furthermore, the agents developed by the inventors offer the very useful advantage of being suitable for the development of a rapid and reliable test or kit for the detection of Gram-positive strains resistant to the glycopeptides by means of the polymerase chain reaction (PCR). Such a test makes it possible to improve the sensitivity of the existing tests which remain rather unreliable and, in certain cases, may make possible the detection of all of the representatives of the family of the genes coding for resistance proteins to the glycopeptides in Gram-positive bacteria.

The carrying out of a test by means of the method of amplification of the genes of these proteins is done by the PCR procedure or by the RPCR procedure (RPCR: abbreviation for reverse polymerase chain reaction).

The RPCR technique makes possible the amplification of the $NH_2$ and COOH terminal regions of the genes it is desired to detect.

Some specific primers make it possible to amplify the genes of the strains with low-level resistance. These primers are selected, for example, from the sequence coding for the resistance protein VanA.

As examples, the following sequences can be used as primers for the preparation of probes for the detection of an amplification by means of the PCR or RPCR method.

```
  (SEQ ID NO:9)

V1 : GGX GAA GAT GGX TCX TTX CAA GGX

           G   C      AG  C     G

                          A

  (SEQ ID NO:10)

V2 : AAT ACX ATX CCX GGX TTT AC

          C  T             C

             C
```

X represents one of the bases A, T, C or G or also corresponds in all cases to inosine.

Naturally, the invention relates to the complementary probes of the oligonucleotides previously described as well as possibly to the RNA probes which correspond to them.

A kit for the in vitro diagnosis of the presence of strains of Gram-positive bacteria resistant to the glycopeptides, in particular resistant to vancomycin and/or teicoplanin these strains belonging in particular to the Gram-positive cocci, in particular that they are strains of enterococci, for example *E. faecium* or *E. gallinarum*, is characterized in that it contains:

- a nucleotide probe complying with the above specifications and if necessary,
- oligonucleoside triphosphates in an amount sufficient to make possible the amplification of the desired sequence,
- a hybridization buffer,
- a DNA polymerization agent.

The invention also relates to a procedure for the in vitro detection of the presence of Gram-positive strains resistant to the glycopeptides, in particular to vancomycin and/or teicoplanin these strains belonging in particular to the family of the Gram-positive cocci, in particular in that they are strains of enterococci, for example *E. faecium* or *E. gallinarum*, characterized in that it comprises:

a) the placing of a biological sample likely to contain the resistant strains in contact with a primer constituted by a nucleotide sequence described above, or any part of a sequence previously described, capable of hybridizing with a desired nucleotide sequence necessary for the expression of resistance to the glycopeptides, this sequence being used as matrix in the presence of the 4 different nucleoside triphosphates and a polymerization agent under conditions of hybridization such that for each nucleotide sequence which has hybridized with a primer, an elongation product of each primer complementary to the matrix is synthesized, b) the separation of the matrix from the elongation product obtained, this latter then also being capable of behaving as a matrix, c) the repetition of step a) so as to produce a detectable amount of the desired nucleotide sequences, d) the detection of the product of amplification of the nucleotide sequences.

The detection of the elongation products of the desired sequence may be carried out by a probe identical with the primers used to carry out the PCR or RPCR procedure, or also by a probe different from these primers, this probe being labelled if necessary.

Details relating to the implementation of the PCR procedures may be obtained from the patent applications EP 0229701 and EP 0200362.

Other advantages and characteristics of the invention will become apparent in the examples which follow and from the figures.

FIGURES

FIG. 1 electrophoresis on SDS-polyacrylamide gel (SDS-PAGE) of the proteins of the membrane fractions line 1 and line 4, molecular weight standards; line 2, *E. faecium* BM4147 placed in culture in the absence of vancomycin; line 3, BM4147 placed in culture in the presence of 10 μg/ml of vancomycin. The head of the arrow indicates the position of the VanA protein.

FIG. 2:

FIG. 2A Restriction maps of the inserts of the plasmids pAT213 and pAT214. The vector and the DNA insert are distinguished by light and dark segments, respectively. The open arrow represents the vanA gene.

FIG. 2B Strategy for the nucleotide sequencing of the insert of 1761 bp in the plasmid pAT214. The arrows indicate the direction and extent of the sequencing reactions by the dideoxy method. The synthetic oligonucleotide primer (5' ATGCTCCTGTCTCCTTTC 3' OH) (SEQ ID NO:27) is complementary to the sequence between the positions 361 and 378. Only the pertinent restriction sites are given.

FIG. 3: position of the sequences R, S, ORF1, ORF2, ORF3.

FIG. 4: representation of SEQ ID NO 15.

FIG. 5: representation of SEQ ID NO 15 and the corresponding protein. (SEQ ID NOS:27, 28 and 29).

FIG. 6: sequence of the vanA gene and the corresponding protein.

FIG. 7:

(A): Localization of the genes vanR, vanS, vanes, vanA, vanX, vanY, vanZ of the gene for the transposase and of the gene for the resolvase as well as the repeated reverse terminal sequences of 38 bp at the end of the transposon.

Mapping of the plasmids. (B) Polylinker pAT29 and derivatives constructed in this study. The arrow labelled P2 indicates the position and orientation of the P2 promoter of aphA-3 (Caillaud et al., 1987, Mol. Gen. Genet. 207:509–513). (C) Insert pAT80. The white rectangles indicate the DNA of pAT29 but they are not shown to scale. The rectangles terminating in an arrow indicate the coding sequences. The arrows shown in vertical and horizontal full lines indicate the position and orientation, respectively, of the apha-1 gene in the derivatives of pAT80. Restriction sites: Ac, AccI; B, BamHI; Bg, BglII; Bs, BssHII; E, EcoRI; H, HindIII; Hc, HincII; K, KpnI; P, PstI; S, SmaI; SI, SacI, SII, SacII; Sa, SalI; Sp, SphI; Xb, XbaI. (D) Inserts in pAT86, pAT87, pAT88 and pAT89. The inserts are shown by full lines and the corresponding vectors are indicated in parentheses.

Figures 7B, 7C, 7D:
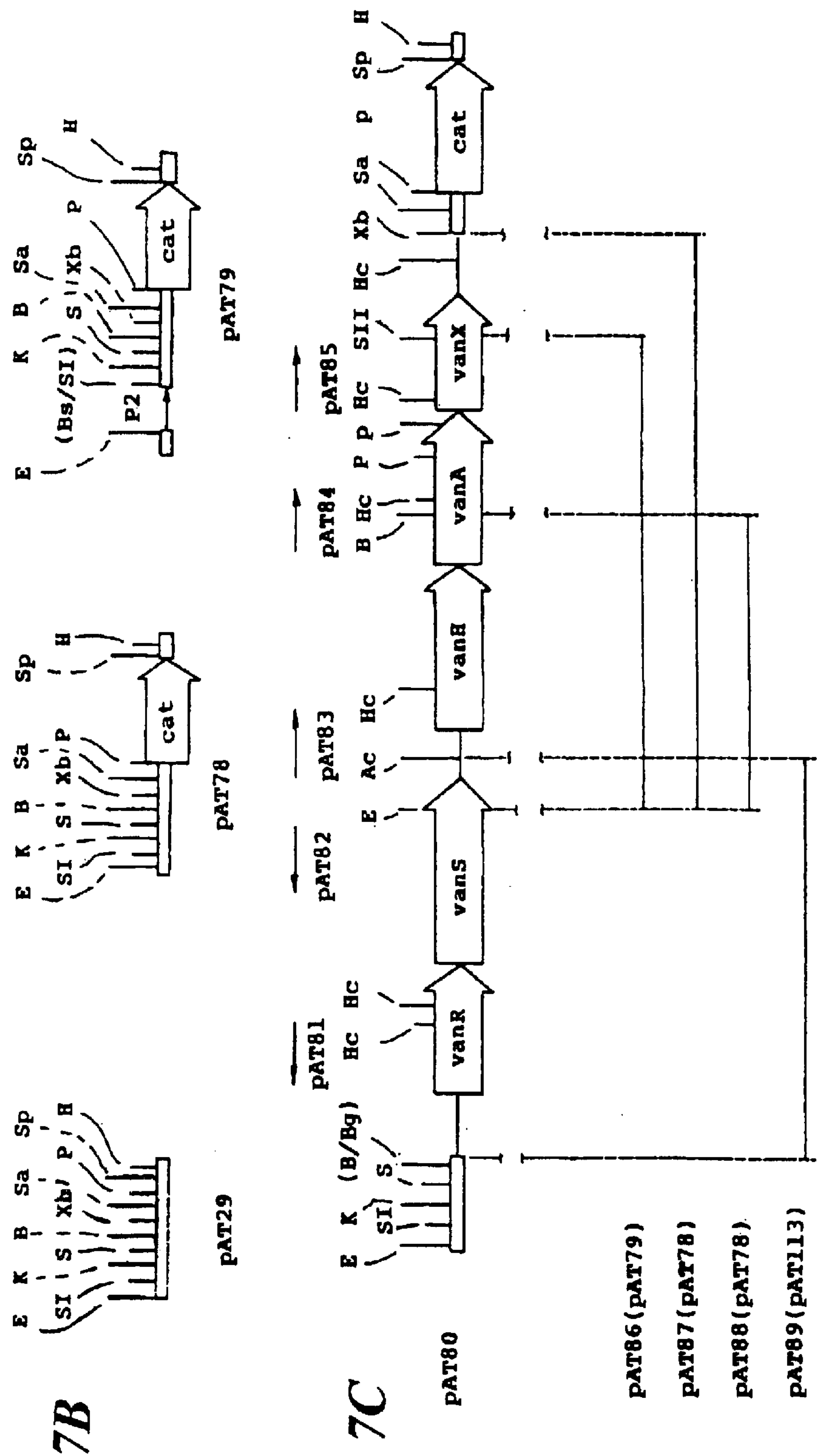

FIGS. 8 A–W: nucleotide sequence of the transposon shown in FIG. 7 and amino acid sequence of the corresponding proteins. The nucleotide sequence is shown for the (+) strand and for the (−) strand (corresponding to the complementary sequence of the (+) strand for the positions 1 to 3189) on which the coding sequence of the transposase is located.

FIGS. 9 A–C: Nucleotide sequence of the SacI-PstI fragment of 1347 bp of the plasmid pAT216 containing the vanC gene. The numbering starts at the first base G of the SacI restriction site. The potential RBS sequence upstream from the initiation codon ATG of translation at position 215 is underlined. The STOP codon (TGA) is indicated by *. The region coding for the vanC and the deduced amino acid sequence are indicated in bold characters. Sequential overlapping clones were generated by restriction fragments of subcloning of pAT216 in the bacteriophage M13 mp10 (Amersham, England). The universal primer (New England Biolabs Beverly Mass.) was used to sequence the insert in the recombinant phages. The sequencing was performed by the enzymatic dideoxy nucleotide method (Sanger et al., 1977 PNAS 74: 5463–5467) by using the T7 DNA polymerase (Sequenase US B CORP, Cleveland, Ohio) and [$\alpha$-$^{35}$S] dATP (Amersham, England). The reaction products were loaded onto 6% denaturing polyacrylamide gels.

FIG. 10: alignment of the amino acid sequence of VanC (SEQ ID NO:8), VanA (SEQ ID NO:4), Dd1A (SEQ ID NO:32) and Dd1B (SEQ ID NO:33). The identical (I) amino acids and the conservative (C) substitutions in the 4 sequences are indicated in the alignment. In order to classify the conservative substitutions, the amino acids were grouped as follows: RK, LFPMV1 (SEQ ID NO:34), STQNC (SEQ ID NO:35), AGW, H, ED AND Y. The regions of high homology corresponding to the domains 1, 2, 3 and 4 are underlined. The sequences corresponding to the peptides of 1 and 2 are indicated by the arrows.

Figure 11:
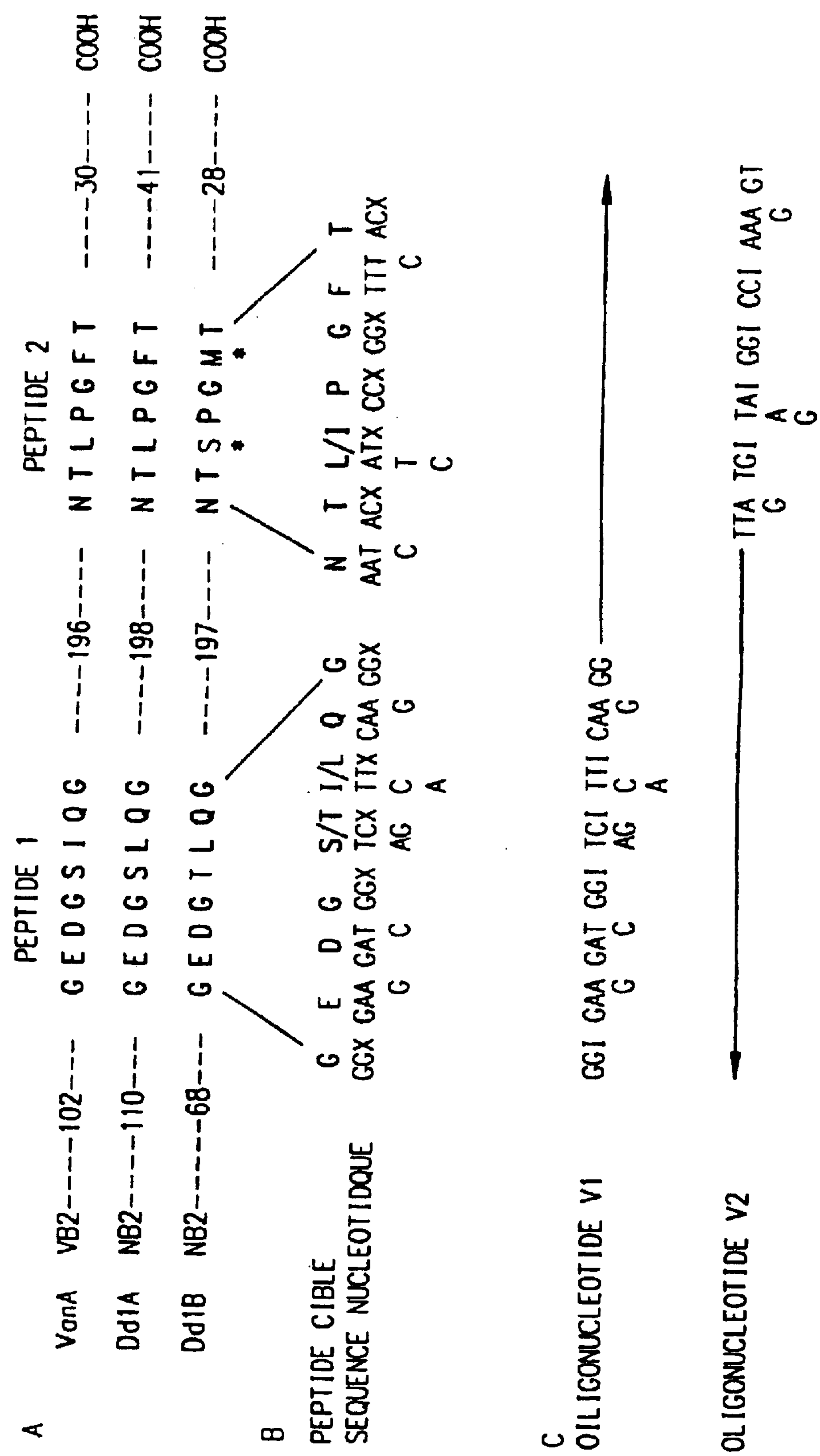

FIG. 11: description of the oligonucleotides V1 (SEQ ID NO:9) and V2 (SEQ ID NO:10) (A): Amino acid sequence of the peptides 1 (SEQ ID NO:36) and 2 (SEQ ID NO:37) of VanA and of the D-Ala-D-Ala ligases (SEQ ID NOS:36–39). The number of amino acids between the N-terminus and peptide 1, between the peptides 1 and 2 and the peptide 2 and the C-terminus is indicated. The identical amino acids between at least 2 of the 3 sequences are indicated in bold characters.

FIG. 11B: Target peptides (SEQ ID NO:36–39) and deduced nucleotide sequence. X represents any base of the DNA. Peptide 2 in Dd1B (SEQ ID NO:39) differs from the target peptide at 2 positions (*).

FIG. 11C: Nucleotide sequence of V1 (SEQ ID NO:9) and V2 (SEQ ID NO:10). Alternate nucleotides and deoxyinosine (I) which may correspond to any base in the DNA, were used at the positions at which the nucleotide sequences coding for the target peptides vary. The arrows indicate the direction of DNA synthesis. The oligonucleotides were synthesized by the methoxy-phosphoramidite method with a Biosystem DNA 380B machine (Applied Biosystem, Foster City, Calif.). The DNA was isolated from bacterial lysates by extraction with hexadecyl trimethyl ammonium bromide (Inst. biotechnologies, Inc., New Haven, Colo.) (Le Bouguénec et al., 1990, J. Bacteriol. 172:727–734) and used as matrix for the amplification by means of PCR with a controlled heating system "Intelligent Heating Block" IBH101 (Hybarid Ltd., GB) according to the description of Mabilat et al. (1990, Plasmid 23:27–34). The amplification products were revealed by electrophoresis on a 0.8% gel, after staining with ethidium bromide.

Figure 12:
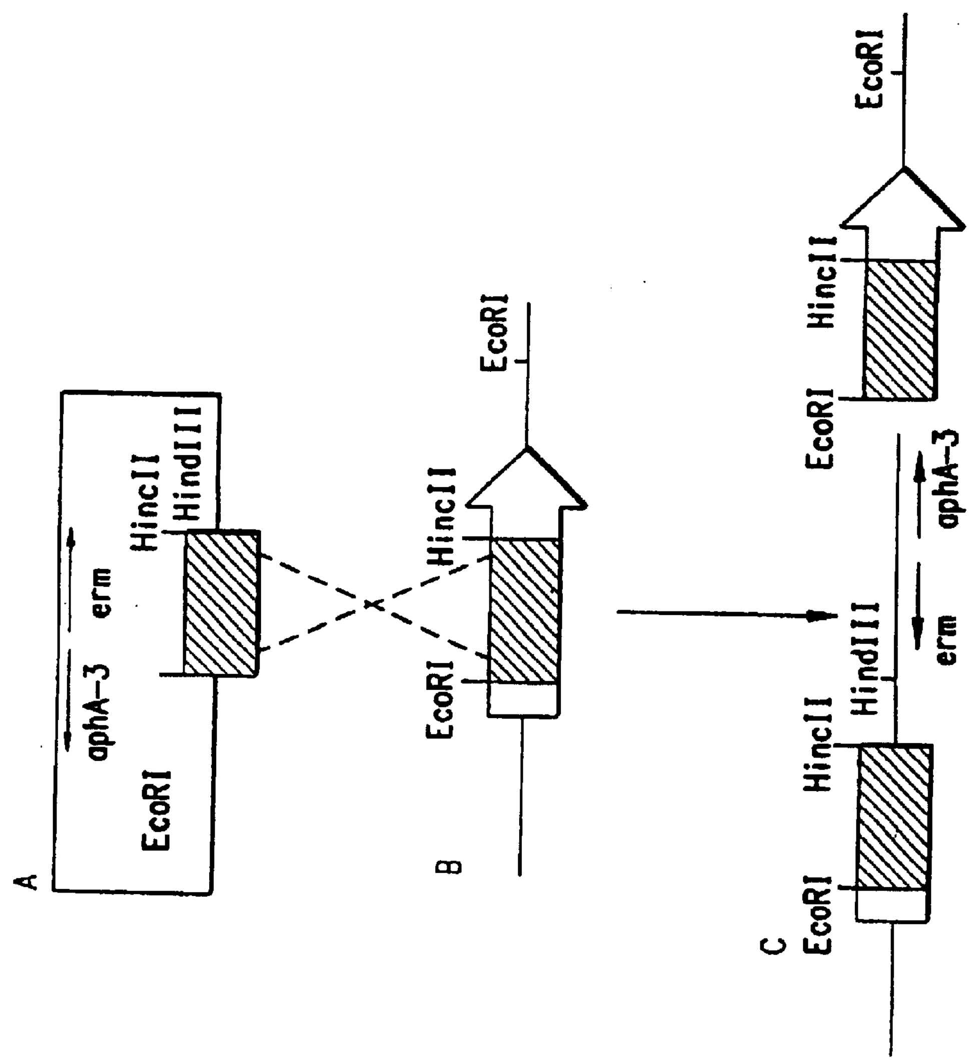

FIG. 12: Inactivation by insertion of vanC. The vanC gene is shown by an open arrow and the internal EcoRI-HincII fragment of 690 bp is hatched. The DNA of pAT114 is shown by a thin line; the chromosomal DNA of PM4174 by a thick line; the arrows indicate the genes for resistance to the antibiotics: aphA-3 is the gene coding for the 3'-aminoglycoside phosphotransferase; erm is the gene coding for the $ER^R$ methyl transferase.

FIG. 12A: The plasmid pAT217 was constructed by ligation of the EcoRI-HincII fragment of pAT216 to the suicide vector pAT114 (Trieu-Cuot et al., 1991, Gene 106:21–27), digested with EcoRI and SmaI.

FIG. 12B: vanC region of the chromosomal DNA of BM4174.

FIG. 12C: vanC region after integration of pAT217.

Figure 13:
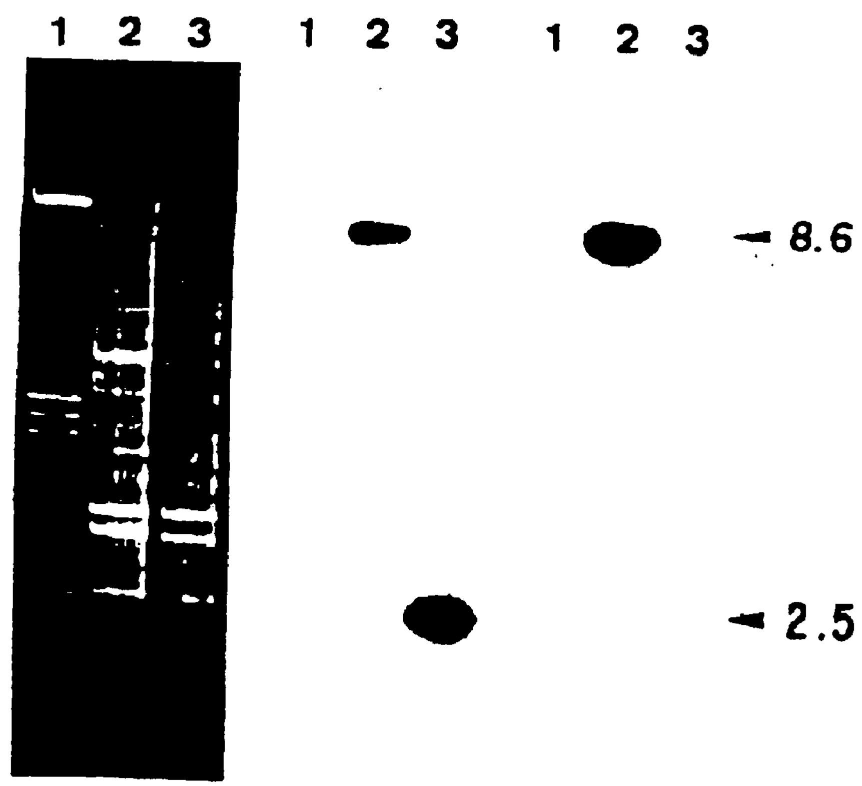

FIG. 13: Southern blot analysis of the integration of pAT217 into the vanC gene of BM4174.

(left hand side): Total DNA of BM4175 (line 2) and BM4174 (line 3) digested with EcoRI and resolved by means of electrophoresis on a 1% agarose gel. The DNA of the bacteriophage lambda digested with PstI was used as molecular mass standard (line 1). The DNA was transferred under vacuum to a Nytran membrane (Schleicher and Schül, Germany) by using a Trans-Vac TE80 apparatus (Höfer Scientific Instruments, San Francisco, Calif.) and bound to the membrane through the intermediary of UV light. The hybridization was carried out with the probe C (Middle) or the probe aphA-3 specific for pAT114 (Lambert et al., 1985, Annales de l'Institut Pasteur/Microbiol. 136(b): 135–150).

(right hand side): the probes were labelled with $^{32}P$ by nick translation. The molecular masses (kb) are indicated.

FIG. 14: alignment of the deduced amino acid sequences of VanS derived from *E. faecium* BM147 (SEQ ID NO:40) and of PhoR (SEQ ID NO:41) and EnvZ (SEQ ID NO:42) from *E. coli*. The numbers on the left refer to the position of the first amino acid in the alignment. The numbers on the right refer to the position of the last amino acid of the corresponding line. The identical amino acids are placed in boxes. The dotted lines indicate gaps introduced in order to optimize their similarity. The dashes indicate the positions of the amino acid residues conserved in other HPK. The histidine residues in bold characters in section 1 are potential sites of auto-phosphorylation.

FIG. 15: alignment of the deduced amino acid sequences of VanR from *E. faecium* BM4147(SEQ ID NO:43), OmpR (SEQ ID NO:44) and PhoB (SEQ ID NO:45) from E. coli as that of CheY from *Salmonella* typhimurium (SEQ ID NO:46). The numbers on the right indicate the position of the last amino acid of the corresponding line. The identical amino acids are placed in boxes. The dotted lines indicate the gaps introduced in order to optimize the homologies. The residues in bold characters correspond to the amino acids strongly conserved in the effector domains of other RR. The aspartic acid residue 57 of CheY is phosphorylated by the HPK associated with CheA.

I—Identification of VanA

Materials and Methods for the Identification and Characterization of the VanA Gene Bacterial Strains and Plasmids The origin of the plasmids used is given in the table below.

| Strain or plasmid | Source or reference |
|---|---|
| *Escherichia coli* | |
| JM83 | Messing (1979) |
| AR1062 | Rambach and Hogness (1977) |
| JM103 | Hannshan (1983) |
| ST640 | Lugtenberg and van Schijndel van-Dam (1973) |
| *Enterococcus faecium* | |
| BM4147 | Leclercq et al (1988) |
| Plasmid pUC18 | Norrander et al (1983) |
| pAT213 | Brisson-Noel et al (1990) |
| pAT214 | Described in this text |

Preparation of the Enterococcal Membranes

*Enterococcus faecium* BM4147 was cultivated in 500 ml of heart-brain broth (BHI broth medium) until the optical density ($OD_{600}$) reached 0.7. Induction was effected with 10 μg/ml of vancomycin (Eli Lilly Indianapolis Ind.). The subsequent steps were performed at 4° C. The cells were recovered by centrifugation for 10 minutes at 6000 g, washed with a TE buffer (0.01 M TRIS-HCl, 0.002 M EDTA, pH 7.0) and lysed by glass beads (100 μm in diameter) in a Braun apparatus for 2 minutes. The cell debris were separated by centrifugation for 10 minutes at 6000 g. The membranes were collected by centrifugation for 1 hour at 65000 g and resuspended in 0.5 ml of TE buffer.

Preparation of the Minicells

Plasmids were introduced by transformation into the strain *E. coli* AR1062 prepared in the form of bacterial vesicles. The bacterial vesicles were recovered on sucrose gradients and the proteins were labelled with 50 μCi of [$^{35}S$]-L-methionine (Amersham, Great Britain) according to the method of Rambach and Hogness (1977, P.N.A.S. USA, 74; 5041–5045).

Preparation of the Membrane Fractions and the Cytoplasmic Fractions of *E. coli*

*E. coli* JM83 and strains derived from it were placed in culture in BHI medium until an optical density ($OD_{600}$) of 0.7 was attained, washed and suspended in a TE buffer. The cell suspension was treated by sonication (ultrasound) for 20 seconds at doses of 50 W in a cell fragmentation apparatus in a Branson B7 sonication apparatus and the intact cells were removed by centrifugation for 10 minutes at 6000 g. The supernatant was fractionated into membrane and cytoplasmic fractions by means of centrifugation for 1 hour at 100,000 g.

Electrophoresis on SDS-polyacrylamide Gel (SDS-PAGE)

The proteins from the bacterial fractions were separated by means of SDS-PAGE on linear gradients of polyacrylamide gels (7.5%–15%) (Laemmli 1970, Nature 227: 680–685). The electrophoresis was carried out for 1 hour at 200 V, then for 3 hours at 350 V. The gels were stained with Coomassie blue. The proteins of the extracts were separated on 10% polyacrylamide gels and visualized by means of autoradiography.

Purification of the Protein Band and Determination of the N-Terminal Sequence

The proteins of the membrane fractions of an induced culture of *E. faecium* BM14147 were separated by means of SDS-PAGE. The gel was electrotransferred for 1 hour at 200 mA to a polyvinylidene difluoride membrane (Immobilon Transfer, Millipore) by using a transfer apparatus (Electrophoresis Unit LKB 2117 Multiphor II) in accordance with the instructions of the manufacturer. The transferred proteins were stained with Ponceau red. The portion of membrane bearing the protein of interest was excised, centered on a Teflon filter and placed in the cartridge of a sequencer (Sequencer Applied Biosystems model 470A). The protein was sequenced by means of the automated Edman degradation (1967, Eur. J. Biochem. 1; 80–81).

Construction of Plasmids

The plasmid pAT213 (Brisson-Noel et al., 1990, Antimicrob. Agents Chemother., 34; 924–927) consists of a EcoRI fragment of DNA of 4.0 kb of the enterococcal plasmid pIP816 cloned at the EcoRI site of a Gram-positive-Gram-negative shuttle vector pAT187 (Trieu-Cuot et al., 1987, FEMS Microbiol. Lett. 48; 289–294). In order to construct pAT214, the EcoRV-SacII DNA fragment of 1761 bp of pAT213 was purified, treated with the Klenow fragment of the DNA polymerase I of *E. coli* and ligated to the DNA of pUC18 which had previously been digested with SmaI and dephosphorylated (FIG. 2). The cloning (Maniatis et al., 1982 Cold Spring Harbor Laboratory Press) was carried out with restriction endonucleases (Boehringer Mannheim and Pharmacia), with the T4 DNA ligase (Pharmacia) and alkaline phosphatase (Pharmacia) according to the instructions of the manufacturer.

Subcloning in M13 and Nucleotide Sequence

The DNA restriction fragments were subcloned in the polylinker of the replicative forms of the derivatives mp18 and mp19 of the bacteriophage M13 (Norrander et al., 1983, Gene 26; 101–106), obtained from Pharmacia P-L Biochemicals. *E. coli* JM103 was transfected with recombinant phages and the single-stranded DNA was prepared. The nucleotide sequencing was carried out by the enzymatic di-deoxy nucleotide method (Sanger et al., 1977, P.N.A.S. USA 74; 5463–5467) by using a T7 DNA polymerase (Sequenase, United States Biochemical Corporation, Cleveland, Ohio) and [α-$^{35}$S] dATP (Amersham, Great Britain). The reaction products were revealed on 6% polyacrylamide gels containing a denaturing buffer.

Data-Processing Analysis and Data on the Sequence

The complete DNA sequence was assembled by using the computer programs DBCOMP and DBUTIL (Staden, 1980, Nucleic Acids Res 8; 3673–3694). The protein data bank PSEQIP of the Pasteur Institute was screened using an algorithm developed by Claverie (1984, Nucleic Acids Res 12; 397–407). The alignments between the pairs of amino acid sequences were constructed using the algorithm of Wilbur et al (1983, P.N.A.S. USA 80; 726–730). The statistical significance of the homology was evaluated with the algorithm of Lipman and Pearson (1985, Science 227; 1435–1440).

For each comparison 20 amino acid sequences were used to calculate the mean values and the standard deviations of the random results.

Genetic Complementation Tests

The plasmids were introduced by transformation into *E. coli* ST640, a temperature-sensitive mutant with an unmodified D-ala-D-ala ligase (Lugtenberg et al 1973, J. Bacteriol 110; 26–34). The transformants were selected at 30° C. on plates containing 100 μg/ml of ampicillin and the presence of the plasmid DNA of the expected size and the restriction maps were verified. Single colonies grown at 30° C. in BHI broth medium containing ampicillin were placed on a BHI agar medium containing both 100 μg/ml of ampicillin and 50 μM of isopropyl-1-thio-β-D-galacto-pyranoside (IPTG) and the plates were incubated at a permissive temperature of 30° C. and at a non-permissive temperature of 42° C. The complementation test was considered to be positive if the colonies were present after 18 hours of incubation at 42° C.

Results

Identification of the VanA Protein and its N-Terminal Sequence

The membrane fractions of the *E. faecium* BM4147 cells placed in culture, on the one hand, under conditions of induction, and, on the other, in the absence of induction, were analysed by means of SDS-PAGE. The sole difference which could be detected, related to the exposure to sub-inhibitory concentrations of vancomycin, was the marked intensification of a band which corresponded to a protein of an estimated molecular weight of about 40 kDa. In the induced cells and in the non-induced cells, the protein band represents the same protein because this band is absent from membranes of a derivative of BM4147 which has lost the pIP816 plasmid. The inducible protein, designated as VanA, was purified after SDS-PAGE and automated Edman degradation was carried out on a 50 pmol. sample. Nine amino acids of the N-terminal sequence of VanA were identified: Met Asn Arg Ile Lys Val Ala Ile Leu (SEQ ID NO:47).

Sub-Cloning of the VanA Gene

The insert of 4.0 kb of the plasmid pAT213 bears the determinant for resistance to the glycopeptides of *E. faecium* BM4147. Various restriction fragments of this insert were subcloned in pUC18 and the recombinant plasmids specific for vanA in *E. coli* were identified by SDS-PAGE analysis of the proteins of the cytoplasmic and membrane fractions or of the extracts of the bacterial vesicles. This approach was used since *E. coli* is intrinsically resistant to the glycopeptide. The EcoRV-SacII insert of the pAT214 plasmid (FIG. 2) codes for a unique polypeptide of 40 kDa which migrates together with VanA, derived from the membrane preparations of *E. faecium* BM4147.

Nucleotide Sequence of the Insert in pAT214 and Identification of the VanA Coding Sequence The nucleotide sequence of the EcoRV-SacII insert of 1761 bp in pAT214 was determined on both strands of the DNA according to the strategy described in FIG. 2. The location of the termination codons (TGA, TAA, TAG) in three reading frames on each DNA strand showed the presence of a unique open reading frame (ORF) which was sufficiently long to code for the VanA protein. This reading frame ORF is located between the TAA codon at position 281 and the TAG codon at position 1406. The amino acid sequence deduced for ORF was compared with that of the N-terminus of VanA. The nine amino acids identified by protein sequencing are encoded in the nucleotide sequence beginning with the ATG (methionine) codon at position 377 (FIG. 3). This codon for the initiation of translation is preceded by a sequence (TGAAAGGAGA)(SEQ ID NO:48) characteristic of a ribosomal binding site (RBS) in Gram-positive bacteria which is complementary to the 8 bases of the rRNA of the 16S subunit of *Bacillus subtilis* in its sequence (3' OH UCUUUCCUCC 5') (SEQ ID NO:49) (Moran et al., 1982, Mol. Gen. Genet. 186; 339–346). In this ORF, there is no other ATG or GTG initiation codon between the positions 281 and 377. The sequence of 1029 bp which extends from the ATG codon at position 377 to the TGA codon at position 1406 codes for a protein containing 343 amino acid residues. The calculated molecular weight of this protein is 37400 Da, which is in agreement with the estimation of 40 kDa obtained by SDS-PAGE analysis.

Homology of the Amino Acid Sequences of VanA and the D-ala-D-ala Ligase Enzymes

The screening of the protein data bank PSEQIP has shown the existence of a sequence homology between VanA and the D-ala-D-ala ligases of *E. coli* (ECOALA, Robinson et al., 1986, J. Bacteriol. 167; 809–817) and of *Salmonella typhimurium* (DALIG, Daub et al., 1988, Biochemistry 27; 3701–3708). The calculated percentage of homology between pairs of proteins was included between 28% and 36% for the identical amino acids and between 48% and 55% by taking into consideration homologous amino acids. VanA (SEQ ID NO:4) and DALIG are more closely related. The statistical significance of these similarities wa evaluated by aligning VANA and sequences containing the same composition of amino acids as DALIG or ECOALA (Lipman and Pearson, 1985, Science 227; 1435–1440).

Genetic Complementation Test for the Activity of D-ala-D-ala Ligase

The *E. coli* strain ST640 is a thermosensitive mutant exhibiting a deficient D-ala-D-ala ligase activity (Lugtenberg et al., 1973, J. Bacteriol. 113: 96–104). The plasmids pUC18 and pAT214 were introduced into *E. coli* ST640 by transformation. The strains ST640 and ST640 (pUC18) grew normally only at the permissive temperature (30° C.) whereas *E. coli* ST640 (pAT214) grew both at the permissive temperature and at the non-permissive temperature (42° C.).

This test shows that VANA is functionally related to the D-Ala-D-Ala ligases in *E. coli* and is probably capable of catalysing the same ligation reaction as DALIG.

II—VanS-VanR Two-Component Regulation System for the Control of the Synthesis of Depsipeptides of the Precursor of Peptidoglycans Materials and Methods Strains, Plasmids and Conditions of Culture The restriction fragments of pIP816 (Tra$^-$, Mob$^+$, Vm$^r$) were cloned in derivatives of the vector pAT29 which constitutes a shuttle vector between the Gram-positive and Gram-negative bacteria (oriR pAMβ1, oriR pUC, oriT RK2, spc, lacZ) (Trieu-Cuot et al., 1990, Nucleic Acids Res. 18:4296). This vector was constructed by the inventors and used to transform the strain *E. coli* JM103 ((lac-proAB), supE, thi, strA, sbcB15, endA, hspR4, F traD36, proAB, LacI$^q$, lacZ M15) (Messing et al., 1983, Methods Ezymol. 101:20–78). The plasmid DNA was prepared by an alkaline lysis protocol on a small scale (Sambrook et al., 1982, Molecular cloning, a laboratory manual. Cold Spring Harbor Laboratory, Cold Spring Harbor N.Y.) and introduced by electroporation (Cruz-Rodz A. L. et al., 1990, Mol. Gen. Genet. 224: 152–154) in *E. faecalis* JH2-2 (Fus$^R$, Rif$^R$) (Jacob A. E. et al., 1974, J. Bacteriol. 117: 360–372), by using a Gene Pulser apparatus (Bio-Rad Laboratories, Richmond, Calif.). The restriction profiles of the purified plasmids from *E. faecalis* and *E. coli* were compared in order to detect possible rearrangements of DNA.

The integrative plasmid pAT113 (Mob$^+$, Em$^R$, Km$^R$, oriR PACYC184, attTn1545, LacZ) (Trieu-Cuot et al., Gene 106: 21–27) carries the joined ends of the transposon Tn1545. This vector does not replicate in Gram-positive bacteria but is integrated into the chromosome of the host by illegitimate recombination mediated by the integrase of Tn1545 or of Tn916 (Trieu-Cuot et al. previously mentioned). The integrative plasmids were introduced into *E. faecalis* BM4148 (strain JH2-2::Tn916) by means of electroporation. This strain is modified by the transposon Tn917 described by Franque A. E. et al. (1981, J. Bacteriol. 145: 494–502).

The cultures were grown in brain-heart broth (BHI—Brain Heart Infusion Broth) or on agar at 37° C. The method of Steers et al (Antibiot. Chemother. Basel. 9: 307–311) was used to determine the minimal inhibitory concentrations (MICs) of the antibiotics on a Mueller-Hinton gelose agar medium.

Recombinant DNA Procedures

The cleavage of DNA with restriction endonucleases (Boehringer Mannheim and Pharmacia), the purification of the DNA restriction fragments from agarose gels, the conversion of the cohesive ends to blunt ends with the Klenow fragment of the DNA polymerase I of *E. coli* (Boehringer Mannheim), the dephosphorylation of the ends of the DNA with calf intestinal phosphatase (Boehringer Mannheim), the ligation of the DNA fragments with the T4 DNA ligase (Amersham) were carried out according to the standard methods of Sambrook et al (1982, Molecular Cloning, a Laboratory Manual. Cold Spring Harbor Laboratory. Cold Spring Harbor N.Y.).

Construction of Plasmids

The origin of the vectors and the inserts used for the recombinant plasmids constructed here is the following:

(i) vector pAT78 for the recognition of the promoter: the amplified DNA of the cat gene for chloramphenicol acetyltransferase of the plasmid pC194 of *Staphylococcus aureus* (Horinouchi et al., 1982, J. Bacteriol. 150: 815–825) was inserted between the PstI and SphI restriction sites of the shuttle vector pAT29. Amplification by means of the polymerase chain reaction was carried out by means of primers A1 and A2 which were synthesized by the methoxy phoshoramidite method (Mabilat et 1990 Plasmid 23: 27–34). The sequence of the primer A1 (SEQ ID NO:50) (5' G <u>CTGCAG</u>ATAAAAATTTAGGAGG) is composed of a PstI recognition site (underlined) and 18 bases (positions 6 to 23) of pC194 which include the ribosomal binding site (RBS; AGGAGG positions 18 to 23) of the cat gene. The sequence of the primer A2 (SEQ ID NO:51) (5' C<u>GCATGC</u>TATTATAAAA GCCAGTC) contains the SphI cleavage site (underlined) and is complementary (positions 8 to 24) to 17 bases at the 3' end of the cat gene. The triplet ATT at positions 9 to 11 correponds to the TAA stop codon of cat. The DNA fragments amplified with the primers A1 and A2 hence consist of an open reading frame (orf) and a ribosomal binding site for CAT (positions 1234 to 1912 according to the numbering of Horinouchi et al. (1982, J. Bacteriol. 150: 815–825) flanked by the PstI and SphI sites. The position 1234 is located at the interior of the loop of the secondary structure of the mRNA which blocks translation in the absence of chloramphenicol. Thus, the amplified sequence does not contain the cat promoter nor the sequence complementary to the RBS which is essential for the regulation of translation Ambulos, N. P. et al., 1984, Gene 28: 171–176).

(ii) expression vector pAT79: the ClaI-BssHII fragment of 243 bp bearing the P2 promoter of the aphA-3 gene of the enterococcal plasmid pJH1 (Caillaud et al., 1987, Mol. Gen. Genet. 207: 509–513) was inserted between the EcoRI and SacI restriction sites of pAT78.

(iii) plasmid pAT80 and its derivatives: the BglII-XbaI fragment of 5.5 kb of pIP816 was inserted between the BamHI and XbaI sites of pAT78. The resulting plasmid, designated as pAT80 was partially digested with HincII and ligated with the EcoRV fragment containing a gene related to the apha-I gene of the transposon Tn903 (Oka A. et al., 1981, J. Mol. Biol. 147:217–226. This fragment contains the aphA-I gene which codes for the 3'aminoglycoside phosphotransferase of type I conferring resistance to kanamycin. The insertion of aphAI was carried out at three different sites in pAT80, generating the plasmids pAT81, pAT83 and pAT85. The cassettes BamHI and EcoRI containing aphA-I were inserted at the BamHI (to form the plasmid pAT84) and EcoRI (to form the plasmid pAT82) sites of pAT80.

(iv) plasmids pAT86, pAT87, pAT88 and pAT89; the plasmid pAT86 was constructed by cloning the EcoRI-SacII fragment of 2.803 bp of pAT80 coding for VanH and VanA at a SmaI site of pAT79, pAT87 was obtained by inserting the EcoRI-XbaI fragment of 3.4 kb of pAT80 upstream from the cat gene of the detection vector of promoter pAT78. The plasmid pAT88 resulted from the ligation of pAT78 digested with EcoRI and BamHI to the EcoRI-BamHI fragment of 1.731 bp of pAT80. The BglII-AccI fragment (positions 1 to 2356) of pAT80 was inserted into the polylinker of the integrative vector pAT113, generating pAT89.

Sub-Cloning in M13 and Sequencing

The DNA restriction fragments were subcloned in a polylinker of replicative derivatives of the bacteriophage M13, these derivatives being called mp18 and mp19 (Norrander et al., 1983, Gene 26:101–106). *E. coli* JM103 was transfected with the recombinant phages and a single-stranded DNA was prepared. The sequencing of the nucleotides was carried out according to the conditions described by Sanger et al. (Proc. Natl. Acad. Sci. USA, 1977, 74: 5463–5467) by using the modified T7 DNA polymerase (Sequenase, United States, Biochemical Corporation Cleveland Ohio) and [$\alpha$-$^{35}$S] dATP (Amersham). The reaction products were resolved on gradient gels of polyacrylamide in a 6% buffer.

Enzymatic Test

The JH2-2 derivatives of *E. faecalis* were grown to an optical density $OD_{600}$ of 0.7 in a BHI broth supplemented with spectinomycin (300 $\mu$g/ml). The cells were treated with lysozyme, lysed by sonication and the cell debris were centrifuged for 45 minutes at 100,000 g according to the description given by Courvalin et al. (1978, Antimicrob. Agents Chemother. 13:716–725). The formation of 5-thio-2-nitrobenzoate was measured at 37° C. in the presence and in the absence of chloramphenicol and the specific CAT activity was expressed in micromole per minute and per milligram of proteins (Shaw et al., 1975, Methods Enzymol. 43:737–755).

Results

The vanH and vanA genes of pIP816 were cloned in a plasmid pAT79 under the control of the heterologous promoter P2 (Caillaud et al., 1987, Mol. Gen. Genet. 207:509–513) and the plasmid pAT86 formed did not confer resistance to vancomycin on the strain *E. faecalis* JH2-2. These genes are thus not sufficient for the synthesis of peptoglycan in the absence of the antibiotic. Different restriction fragments of pIP816 were cloned in the vector pAT78. The BglII-XbaI fragment of 5.5 kb of pAT80 is the smallest fragment obtained which conferred resistance to vancomycin.

Nucleotide Sequence of the VanR and VanS Genes

The sequence of the insert in pAT80 was determined on both strands of the DNA from the BglII site to the ATG initiation codon for the translation of VanH. Two open reading frames (orf) were detected within the sequence of 2475 bp: the first open reading frame extends from the nucleotide 386 to the nucleotide 1123; at position 431 a sequence characteristic of the RBS sequences in Gram-positive bacteria is found, 6 base pairs upstream from the ATG initiation codon for translation (<u>T</u>GAAAGGGT<u>G</u>) (SEQ ID NO:52); the other initiation codons for translation in this orf are not preceded by this type of sequence. The sequence of 693 bp extending from the ATG codon at position 431 to the TAA codon at position 1124 is capable of coding for a protein of 231 amino acids with a molecular mass of 26,612 Da which is designated as VanR.

In the case of the second open reading frame (from nucleotide 1089 to nucleotide 2255) the amino acid sequence deduced from the first initiation codon in phase (TTG at position 1104) would code for a protein of 384 amino acids having a molecular mass of 43,847 Da and designated as VanS. The TTG codon at position 1116 and the ATG codon at position 1164 are in-phase initiation codons for translation preceded by sequences with low complementarity with the 3'OH terminus of the 16S sub-unit of the rRNA of *B. subtilis* (G<u>G</u>GGG<u>G</u>TT<u>GG</u>-N8-TTG (SEQ ID NO:53) and <u>AGAA</u>C<u>G</u>A<u>A</u>AA-N6-ATG, (SEQ ID NO:54) respectively.

Between the last codon of vanS and the initiation codon ATG for the translation of vanH a sequence of 217 bp is to be observed which contains a repeated reverse sequence of 17 bp. This sequence does not function as a terminator of strong transcription.

The comparison of the sequences obtained with data bases has shown that the conserved amino acid residues identified by Stock et al. (1989, Microbiol. Rev. 53:450–490) in the kinase domain of 16 HPK (Histidine Protein Kinase) were detected in the C-terminal part of VanS. VanS (SEQ ID NO:14) possesses two groups of hydrophobic amino acids in the N-terminal region. The histidine residue 164 of VAnS is aligned with the residue His216 of PhoR (SEQ ID NO:14) (Makino et al., 1986, J. Mol. Biol. 192: 549–556) and His 243 of EnvZ (SEQ ID NO:42) (Comeau et al., 1985, 164:578–584) which are presumed sites of autophosphorylation in these proteins.

Similarly, the amino acids 1 to 122 of VanR (SEQ ID NO:12) exhibit similarities with the effector domains of response regulators RR. The aspartic acid 53 of VanR might be a phosphorylation site because this residue is aligned with Asp 57 of Che Y (SEQ ID NO:46) which is phosphorylated by HPK associated with CheA and corresponds to an invariant position in other proteins of the RR type (Stock et al previously mentioned). VanR might belong to the sub-class OmpR-PhoB of RR which activates the initiation of transcription mediated by the RNA polymerase containing the 70S factor of *E. coli* (Stock et al. previously mentioned).

Inactivation of the Van Genes by Insertion

Cassettes of resistance to kanamycin inserted in the group of van genes in the plasmid pAT80 have shown the following: the insertion in vanR suppresses resistance to vancomycin and chloramphenicol; VanR is an activator of transcription necessary for the expression of the genes for resistance to vancomycin. The inactivation of vanS leads to a two-fold reduction of the minimal inhibitory concentration (MIC) of chloramphenicol and to a three-fold reduction of the specific CAT activity but the minimal inhibitory concentration of vancomycin remains unchanged. Hence, VanS is necessary to produce a high level of transcription of the genes for resistance to vancomycin although it is not required for the expression of the phenotype of resistance to vancomycin.

Derivatives of pAT80 bearing insertions in vanH (pAT83), vanA (pAT84) or in the region 1.0 kb downstream from vanA (pAT85) have made it possible to obtain resistance to chloramphenicol but not to vancomycin. This dissociated phenotype corresponds to the inactivation of genes coding for enzymes which synthesize the depsipeptide precursors necessary for the assembly of the bacterial cell walls in the presence of vancomycin.

Downstream from the vanA gene the presence of an inactivated orf has been detected in pAT85 in the region of the sequence of 365 bp after the TGA codon of vanA and before the SacII site and this orf contains an in-phase ATG initiation codon preceded by a RBS-like sequence. This sequence codes for a protein necessary for resistance to the glycopeptide, designated as VanX and which comprises maximally about 330 amino acids.

Trans-Activation of the Transcription of the Van Genes

The integrative plasmid pAT89 coding for VanR and VanS was introduced into the chromosome of *E. faecalis* BM4138. The plasmid pAT87 bearing the genes vanH, vanA and vanX cloned upstream from the cat gene lacking the promoter for pAT78 conferred resistance to vancomycin on this strain but not to *E. faecalis*, JH2-2. The level of expression of the cat gene of pAT87 in the strains BM4138::pAT89 and JH2-2 indicated that VanR activates the transcription of the reporter gene localized at the 3' end of the group of van genes. Similar levels of CAT synthesis were observed for pAT88 which bears a transcription fusion between the 5' parts of vanA and the cat gene. These results show that in *E. faecalis* BM4138::pAT89 (pAT87) VanR and VanS encoded in the chromosome activate in a trans manner the transcription of vanA, vanH and vanX of pAT87 making possible the production of resistance to vancomycin.

Moreover, it has been observed that the expression of the gene was essentially constitutive when vanR and vanS were borne by a multicopy plasmid pAT80 and weakly inducible by vancomycin when the genes for the regulatory proteins were present on the chromosome of the host.

III—Characterization of the Sequence of the VanC Gene of *Enterococcus gallinarum* BM4174

Definition and Use of Universal Primers for the Amplification of Genes Coding for D-Ala-D-Ala Ligases and Related Proteins Implicated in Resistance to Vancomycin The protein VanA necessary for the expression of a high level of resistance to the glycopeptides in *E. faecium* BM4147 shares a similarity of about 28 to 36% as regards its amino acids with the D-Ala-D-Ala ligases of *E. coli* but possesses a different substrate specificity from that of these ligases. Peptides designated as 1 and 2 which are conserved in the sequences of the Dd1A and Dd1B ligases (Zawadzke, 1991 Biochemistry 30:1673–1682) of *E. coli* and in the protein VanA were selected in order to synthesize universal primers intended to amplify internal fragments of genes coding for D-Ala-D-Ala ligases or related enzymes. The peptide targets GEDG(S/T) (I/L)QG and NT(I/L)PGFT were translated back as is shown in Figure IV.1 in order to obtain degenerate oligonucleotides V1 and V2. As the peptides 1 and 2 of VanA, Dd1A and Dd1B are separated by amino acid sequences of similar length, the predicted size for the amplification product was about 640 bp.

Amplification by means of PCR with the DNA of *E. coli* JM83 and of *E. faecium* BM4147 made it possible to amplify products corresponding to the expected size which have then been purified and cloned in the bacteriophage M13 mp10 (Norrander et al., 1983, Gene 26:101–106). The sequencing of the insert obtained with *E. coli* JM83 has shown that the product of PCR was an internal fragment of dd1A. A probe generated starting from a recombinant phage obtained with the amplification fragment of BM4147 was used for the Southern blot analysis of a DNA of BM4147 and BM4147-1 which is a derivative of BM4147 sensitive to vancomycin and which lacks the plasmid pIP816 (Leclercq et al., 1988, N. Engl. J. Med. 319:157–161). The probe hybridized with the EcoRI DNA fragment of 4 kb from BM4147 but not with the DNA from *E. faecium* BM4147-1. As the vanA gene is borne by the EcoRI fragment of 4 kb from pIP816, these results indicate that the primers also make possible the amplification of B part of vanA. Thus the oligonucleotides V1 and V2 may amplify fragments of genes coding for different proteins related to the D-Ala-D-Ala ligases, and may do this in different species.

Amplification, Cloning and Sequencing of the VanC Gene

Amplification by means of PCR was carried out on the total DNA of *E. gallinarum* BM4174 and the amplification product obtained of about 640 bp was cloned in the bacteriophage M13 mp10. The single-stranded DNA isolated from the recombinant phage was used to construct a probe C (Hu et al., 1982, Gene 17:2171–2177). In Southern analysis the probe hybridized with a PstI fragment of 1.7 kb from BM4174 but not with the DNA of BM4147 and BM4147-1.

The DNA of BM4174 was digested with PstI and fragments of 1.5 and 2 kb were purified by electrophoresis on agarose gel and cloned in pUC18 (Norrander et al., 1983, mentioned previously). The recombinant plasmids were introduced into *E. coli* JM83 by transformation and screened by hybridization on colonies (Sambrook et al., 1989, Molecular cloning, a laboratory manual. Cold Spring Harbor Laboratory Press, Cold Spring Harbor, N.Y.) by using the probe C. A homology was detected with a transformant harbouring a plasmid called pAT216 which contained a PstI insert of 1.7 kb. The sequence of the SacI-PstI part of 1347 bp of the insert of pAT216 was determined on both strands of the DNA. The location of the termination codons in the three reading frames of each strand of DNA revealed the presence of an ORF phase located between the TGA codons at positions 47 and 1244. The initiation codon of transcription ATG at position 215 is preceded by a sequence GAAAGGAAGA characteristic of the RBS sequences complementary to the RNA of the 16S subunit of *B. subtilis* (Moran et al., 1982, Mol. Gen. Genet. 186:339–346). The sequence of 1029 bp which extends from the ATG codon at position 215 to the TGA codon at position 1244 might code for a protein of 343 amino acids having a calculated molecular mass of 37504 Da designated as VanC. A sequence homology was detected between VanC, VanA and the D-Ala-D-Ala ligases of *E. coli*. In particular, four domains of strong homology previously found between VanA and the D-Ala-D-Ala ligases of the enterobacteria are also present in VanC. The percentage of identical amino acids calculated for these proteins taken two at a time varied between 29 and 38%. The alignment of the four sequences revealed the presence of 57 invariant amino acids which include the conserved residues of the peptides 1 and 2 used to define the oligonucleotide probes V1 and V2.

Inactivation of the VanC Gene by Insertion

In order to evaluate the contribution of vanC to resistance to vancomycin in *E. gallinarum* BM4174, the vanC gene was inactivated by insertion. A EcoRI-HincII fragment of 690 bp, internal to vanC was cloned in pAT114 which does not replicate in Gram-positive bacteria. The resulting pAT217 plasmid was introduced into BM4174 by electroporation (Cruz-Rodz et al., 1990, Mol. Gen. Genet. 224:152–154) and the clones supposed to result from a homologous recombination leading to the integration of pAT217 into vanC were selected on erythromycin. The clone BM4175 was compared with BM4174 by Southern hybridization using the probe C and aphA-3 specific for pAT114. The two probes hybridized with the EcoRI fragment of 8.6 kb from BM4175. The probe C hybridized with a fragment of 2.5 kb from BM4174 whereas no signal was observed with the probe aphA-3. The results indicate that the plasmid pAT217 of 6.1 kb was integrated into the vanC gene. The determination of the minimal inhibitory concentration of vancomycin for BM4174 (16 mg/l) and BM4175 (2 mg/l) indicated that the inactivation by insertion in vanC abolishes resistance to vancomycin.

VanC is thus required for resistance to vancomycin. It may thus be supposed that this protein synthesizes a dipeptide or a depsipeptide which is incorporated into the precursors of peptidoglycans and is not recognized by vancomycin.

The sequences which are the object of the invention are given in the following pages after the list of the sequences containing the description of these sequences. In this list of the sequences, the proteins are identified with respect to the position of the nucleotide bases corresponding to the amino acids of the extremities of the proteins.

LIST OF THE SEQUENCES (contained in the sequences I (Ia, Ib), II presented below or in the sequence shown in FIG. 5).

Amino Acid Sequences

SEQ ID NO 2 (VanH): sequence of the first resistance protein, corresponding to the amino acid sequence of the open reading frame No. 3, starting at the base 3501 and terminating at the base 4529, containing the sequence coding for the vanH gene between the bases 3564 and 4529 with respect to the sequence shown in FIG. 5 or corresponding to the sequence between the positions of the nucleotides 6018 and 6983 of the sequence Ia.

SEQ ID NO 4 (VanA): sequence of the VanA protein, corresponding to the amino acid sequence of the open reading frame No. 1, starting at the base 4429 and terminating at the base 5553 with respect to the sequence shown in FIG. 5 or corresponding to the sequence between the positions of the nucleotides 6977 and 7807 of the sequence Ia.

SEQ ID NO 6 (VanX): sequence of the third resistance protein, corresponding to the amino acid sequence of the open reading frame No. 3, starting at the base 5526 and terminating at the base 6167 with respect to the sequence shown in FIG. 5 or corresponding to the sequence between the positions of the nucleotides 7816 and 8621 of the sequence Ia.

SEQ ID NO 12 (VanR) sequence of the regulatory protein R, corresponding to the amino acid sequence of the open reading frame No. 1, starting at the base 1477 and terminating at the base 2214 with respect to the sequence shown in FIG. 5 or corresponding to the sequence between the positions of the nucleotides 3976 and 4668 of the sequence Ia.

SEQ ID NO 14 (VanS): sequence of the sensor protein S, corresponding to the amino acid sequence of the open reading frame No. 2, starting at the base 2180 and terminating at the base 3346 with respect to the sequence shown in FIG. 5 or corresponding to the sequence between the positions of the nucleotides 4648 and 5800 of the sequence Ia.

SEQ ID NO 19: sequence of the transposase corresponding to the amino acids included between the nucleotides 150 and 3112 of the sequence Ib.

SEQ ID NO 21: sequence of the resolvase comprising the amino acids situated between the positions of the nucleotides 3187 and 3759 of the sequence Ia.

SEQ ID NO 23: VanY sequence comprising the amino acids situated between the positions of the nucleotides 9046 and 9960 of the sequence Ia.

SEQ ID NO 25: VanZ sequence comprising the amino acids situated between the positions of the nucleotides 10116 and 10598 of the sequence Ia.

SEQ ID NO 8: VanC amino acid sequence shown in list II.

Nucleotide Sequences

SEQ ID NO 15: nucleotide sequence containing the sequence coding for the 5 proteins as well as the flanking sequences, shown in FIG. 5.

SEQ ID NO 17: sequence containing the sequence coding for the 3 resistance proteins as well as the flanking sequences and starting at the base 3501 and terminating at the base 6167, shown in FIG. 5.

SEQ ID NO 1: sequence of the vanA gene, starting at the base 4429 and terminating at the base 5553 of the sequence shown in FIG. 5, or corresponding to the nucleotide sequence situated between the nucleotides 6977 and 7807 of the sequence Ia.

SEQ ID NO 1: sequence coding for the first resistance protein called VanH, starting at the base 3501 and terminating at the base 4529, in particular the sequence vanH, the coding sequence of which is located between the bases 3564 and 4529 of the sequence shown in FIG. 5, or corresponding to the nucleotide sequence situated between the nucleotides 6018 and 6983 of the sequence Ia.

SEQ ID NO 5: sequence coding for the third resistance protein VanX, starting at the base 5526 and terminating at the base 6167 of the sequence shown in FIG. 5, or corresponding to the nucleotide sequence situated between the nucleotides 7816 and 8621 of the sequence Ia.

SEQ ID NO 16: sequence of the transposon coding for the transposase, the resolvase, vanR, VAnS, VanH, VanA, VanX, VanY and VanZ and containing the repeated reverse sequence of 38 bp at its N- and C-termini and corresponding to the sequence Ia.

SEQ ID NO 18: sequence coding for the transposase, starting at the base 150 and terminating at the base 3112 of the sequence Ib.

SEQ ID NO 20: sequence coding for the resolvase, starting at the base 3187 and terminating at the base 3759 of the sequence Ia.

SEQ ID NO 22: sequence coding for VanY, starting at the base 9046 and terminating at the base 9960 of the sequence Ia.

SEQ ID NO 24: sequence coding for VanZ, starting at the base 10116 and terminating at the base 10598 of the sequence Ia.

SEQ ID NO 7: sequence coding for VanC, shown in the list II in relation to the protein VanC.

SEQ ID NO 16: complete sequence Ia of the transposon of *E. faecium*, starting at the base 1 and terminating at the base 10851.

SEQ ID NO 11: sequence coding for the protein VanR, starting at the base 3976 and terminating at the base 4668 of the sequence Ia.

SEQ ID NO 13: sequence coding for the protein VanS, starting at the base 4648 and terminating at the base 5800 of the sequence Ia.

I. Nucleotide sequence of the transposon and translation

Ia. (+) Strand

1 GGG GTA GCG TCA GGA AAA TGC GGA TTT ACA ACG CTA AGC CTA TTT TCC TGA CGA ATC CCT

61 CGT TTT TAA CAA CGT TAA GAA AGT TTT AGT GGT CTT AAA GAA TTT AAT GAG ACT ACT TTC

121 TCT GAG TTA AAA TGG TAT TCT CCT AGT AAA TTA ATA TGT TCC CAA CCT AAG GGC GAC ATA

181 TGG TGT AAC AAA TCT TCA TTA AAG CTA CCT GTC CGT TTT TTA TAT TCA ACT GCT GTT GTT

241 AGG TGG AGA GTA TTC CAA ATA CTT ATA GCA TTG ATA ATT ATG TTT AAA GCA CTG GCT CTT

301 TGC AAT TGA TGC TGT ATG GTG CGT TCT CTA AGC TCA CCT TGT TTT CCG AAG AAA ATA GCT

361 CTT GCC AAT CCA TTC ATG GCT TCT CCT TTA TTC AAT CCT CTT TGT ATT TTT CTT CTT AAT

421 GAT TCA TCC GAT ATA TAA TTC AAA ATA AAG ATC GTT TTT TCT ATT CGG CCC ATC TCA CGT

481 AAG GCT GTA GCT AAG CTG TTT TGT CTT GAA TAG GAA CCT AGC TTC CCC ATA ATA AGG GAT

541 GCT GAA ACT GTT CCC TCC CTT ATA GAA TGA GCT AAT CGC AAA ACA TCC TCA TAA TTT TCT

601 TTA ATG ACC TTT GTA TTT ATT TGT CCA CGT AAA ATG GCT TCT AGT TTT GGA TAC TCA CTT

661 GCT TTA TCT ATC GTA AAT AAT TTT GAG TCC GAT AAA TCC CTT ATT CTT GGG GCA AAT TTA

721 AAT CCT AAT AAA TGA GTC AGT CCG AAT ATT TGG TCA GTG TAA CCG GCA GTG TCT GTA TAA

781 TGT TCC TCT ATG TTT AGA TCC GTC TCA TGA TGT AAC AAA CCA TCC AAA ACA TGA ATC GCA

841 TCT CTT GAA TTA GTA TGA ATA ATC TTT GTG TAG TAA GAA GAG AAT TGA TCA CTT GTA AAT

901 CGG TAG ATG GTG GCT CCT TTT CCA GTT CCA TAA TGT GGA TTT GCA TCT GCA TGT AGT GAT

961 GAA ACA CCT AGC TGC ATT CTC ATA CCA TCT GAC GAA GAT GTT GTA CCG TCG CCC CAA TAG

1021 AAA GGC AAT TGT AAT TTA TGA TGA AAG TTT ACT AAT ATG GCT TGG GCT TTA TTC ATG GCA

1081 TCT TCA TAC ATG CGC CAT TGA GAT ACA TTG GCT AGT TGC TTA TAT GTA AGT CCG GGT GTG

1141 GCT TCG GCC ATC TTG CTC AAG CCA ATA TTC ATT CCC ATT CCT AAA AGG GCA GCC ATG ATA

1201 ATG ATT GTT TCT TCC TTA TCT GGT TTT CGA TTA TTG GAA GCA TGA GTG AAT TGC TCA TGA

1261 AAT CCT GTT ATA TGG GCC ACA TCC ATG AGT AAA TCA GTT AAT TTT ATT CTT GGT AGC ATC

1321 TGA TAA AGG CTT GCA CTA AAT TTT TTT GCT TCT TCT GGA ACA TCT TTT TCT AAG CGT GCA

1381 AGT GAT AGC TTT CCT TTT TCA AGA GAA ACC CCA TCT AAC TTA TTG GAA TTG GCA GCT AAC

1441 CAC TTT AAC CTT TCA TTA AAG CTG CTG GTT CTC TCC GTT ATA TAA TCT TCG AAT GAT AAA

1501 CTA ACT GAT AAT CTC GTA TTC CCC TTC GAT TGA TTC CAT GTA TCT TCC GAA AAC AAA TAT

1561 TCC TCA AAA TCC CTA TAT TGT CTG CTG CCA ACA ATG GAA ACA TCT CCT GCC CGA ACA TGC

1621 TCC CGA AGT TCT GTT AAA ACA GCC ATT TCA TAG TAA TGA CGA TTA ATT GTT GTA CCA TCA

1681 TCC TCG TAT AAA TGT CTT TTC CAT CGT TTT GAA ATA AAA TCC ACA GGT GAG TCA TCA GGC

1741 ACT TTT CGC TTT CCA GAT TCG TTC ATT CCT CGG ATA ATC TCA ACA GCT TGT AAA AGT GGC

1801 TCA TTT GCC TTT GTA GAA TGA AAT TCC AAT ACT CTT AAT AGC GTT GGC GTA TAT TTT CTT

1861 AGT GAA TAA AAC CGT TTT TGC AGT AAG TCT AAA TAA TCA TAG TCG GCA GGA CGT GCA AGT

1921 TCC TGA GCC TCT TCT ACT GAA GAG ACA AAG GTA TTC CAT TCA ATA ACC GAT TCT AAA ACC

1981 TTA AAA ACG TCT AAT TTT TCC TCT CTT GCT TTA ATT AAT GCT TGT CCG ATG TTC GTA AAG

2041 TGT ATA ACT TTC TCA TTT AGC TTT TTA CCG TTT TGT TTC TGG ATT TCC TCT TGA GCC TTA

2101 CGA CCT TTT GAT AAC AAA CTA AGT ATT TGC CTA TCA TGA ATT TCA AAC GCT TTA TCC GTT

2161 AGC TCC TGA GTA AGT TGT AAT AAA TAG ATG GTT AAT ATC GAA TAA CGT TTA TTT TCT TGA

2221 AAG TCA CGG AAT GCA TAC GGC TCG TAT CTT GAG CCT AAG CGA GAC AGC TGC AAC AGG CGG

-continued

I. Nucleotide sequence of the transposon and translation

```
2281 TTA CGG TGC AAA TGA CTA ATT TGC ACT GTT TCT AAA TCC ATT CCT CGT ATG TAT TCG AGT

2341 CGT TCT ATT ATT TTT AGA AAA GTT TCG GGT GAA GGA TGA CCC GGT GGC TCT TTT AAC CAA

2401 CCC AAT ATC GTT TTA TTG GAT TCG GAT GGA TGC TGC GAG GTA ATA ATC CCT TCA AGC TTT

2461 TCT TTT TGC TCA TTT GTT AGA GAT TTA CTA ACC GTA TTA AAT AGC TTC TTT TCA GCC ATT

2521 GCC CTT GCT TCC CAC ACC ATT CTT TCA AGT GTA GTG ATA GCA GGC AGT ATA ATT TTG TTT

2581 TTT CTT AGA AAA TCT ATG CAT TCA TGC AGT AGA TGA ATG GCA TCA CCA TTT TCC AAA GCT

2641 AAT TGA TGA AGG TAC TTA AAT GTC ATT CGA TAT TCA CTC AGG GTA AAA GTT ACA AAG TCG

2701 TAT TCA CTT CGA ATT TCT TTC AAA TGA TCC CAA AGT GTA TTT TCC CTT TGA GGA TAA TGA

2761 TCA AGC GAG GAT GGA CTA ACA CCA ATC TGT TTC GAT ATA TAT TGT ATG ACC GAA TCT GGG

2821 ATG CTT TTG ATA TGA GTG TAT GGC CAA CCG GGA TAC CGA AGA ACA GCT AAT TGA ACA GCA

2881 AAT CCT AAA CGG TTT TCT TCC CTC CTT CGC TTA TTA ACT ATT TCT AAA TCC CGT TTG GAA

2941 AAA GTG AAG TAG GTC CCC AGT ATC CAT TCA TCT TCA GGG ATT TGC ATA AAA GCC TGT CTC

3001 TGT TCC GGT GTA AGC AAT TCT CTA CCT CTC GCA ATT TTC ATT CAG TAT CAT TCC ATT TCT

3061 GTA TTT TCA ATT TAT TAG TTC AAT TAT ATA TCA ATA GAG TGT ACT CTA TTG ATA CAA ATG

3121 TAG TAG ACT GAT AAA ATC ATA GTT AAG AGC GTC TCA TAA GAC TTG TCT CAA AAA TGA GGT

3181         resolvase

            LEU ARG LYS ILE GLY TYR ILE ARG VAL SER SER THR ASN GLN ASN PRO SER ARG

     GAT ATT TTG CGG AAA ATC GGT TAT ATT CGT GTC AGT TCG ACT AAC CAG AAT CCT TCA AGA

3241 GLN PHE GLN GLN LEU ASN GLU ILE GLY MET ASP ILE ILE TYR GLU GLU LYS VAL SER GLY

     CAA TTT CAG CAG TTG AAC GAG ATC GGA ATG GAT ATT ATA TAT GAA GAG AAA GTT TCA GGA

3301 ALA THR LYS ASP ARG GLU GLN LEU GLN LYS VAL LEU ASP ASP LEU GLN GLU ASP ASP ILE

     GCA ACA AAG GAT CGC GAG CAA CTT CAA AAA GTG TTA GAC GAT TTA CAG GAA GAT GAC ATC

3361 ILE TYR VAL THR ASP LEU THR ARG ILE THR ARG SER THR GLN ASP LEU PHE GLU LEU ILE

     ATT TAT GTT ACA GAC TTA ACT CGA ATC ACT CGT AGT ACA CAA GAT CTA TTT GAA TTA ATC

3421 ASP ASN ILE ARG ASP LYS LYS ALA SER LEU LYS SER LEU LYS ASP THR TRP LEU ASP LEU

     GAT AAC ATA CGA GAT AAA AAG GCA AGT TTA AAA TCA CTA AAA GAT ACA TGG CTT GAT TTA

3481 SER GLU ASP ASN PRO TYR SER GLN PHE LEU ILE THR VAL MET ALA GLY VAL ASN GLN LEU

     TCA GAA GAT AAT CCA TAC AGC CAA TTC TTA ATT ACT GTA ATG GCT GGT GTT AAC CAA TTA

3541 GLU ARG ASP LEU ILE ARG MET ARG GLN ARG GLU GLY ILE GLU LEU ALA LYS LYS GLU GLY

     GAG CGA GAT CTT ATT CGG ATG AGA CAA CGT GAA GGG ATT GAA TTG GCT AAG AAA GAA GGA

3601 LYS PHE LYS GLY ARG LEU LYS LYS TYR HIS LYS ASN HIS ALA GLY MET ASN TYR ALA VAL

     AAG TTT AAA GGT CGA TTA AAG AAG TAT CAT AAA AAT CAC GCA GGA ATG AAT TAT GCG GTA

3661 LYS LEU TYR LYS GLU GLY ASN MET THR VAL ASN GLN ILE CYS GLU ILE THR ASN VAL SER

     AAG CTA TAT AAA GAA GGA AAT ATG ACT GTA AAT CAA ATT TGT GAA ATT ACT AAT GTA TCT

3721 ARG ALA SER LEU TYR ARG LYS LEU SER GLU VAL ASN ASN

     AGG GCT TCA TTA TAC AGG AAA TTA TCA GAA GTG AAT AAT TAG CCA TTC TGT ATT CCG CTA

3781 ATG GGC AAT ATT TTT AAA GAA GAA AAG GAA ACT ATA AAA TAT TAA CAG CCT CCT AGC GAT

3841 GCC GAA AAG CCC TTT GAT AAA AAA AGA ATC ATC ATC TTA AGA AAT TCT TAG TCA TTT ATT

3901 ATG TAA ATG CTT ATA AAT TCG GCC CTA TAA TCT GAT AAA TTA TTA AGG GCA AAC TTA TGT
```

-continued

| I. Nucleotide sequence of the transposon and translation |
|---|
| 3961 VanR MET SER ASP LYS ILE LEU ILE VAL ASP ASP GLU HIS GLU ILE ALA |
| GAA AGG GTG ATA ACT ATG AGC GAT AAA ATA CTT ATT GTG GAT GAT GAA CAT GAA ATT GCC |
| 4021 ASP LEU VAL GLU LEU TYR LEU LYS ASN GLU ASN TYR THR VAL PHE LYS TYR TYR THR ALA |
| GAT TTG GTT GAA TTA TAC TTA AAA AAC GAG AAT TAT ACG GTT TTC AAA TAC TAT ACC GCC |
| 4081 LYS GLU ALA LEU GLU CYS ILE ASP LYS SER GLU ILE ASP LEU ALA ILE LEU ASP ILE MET |
| AAA GAA GCA TTG GAA TGT ATA GAC AAG TCT GAG ATT GAC CTT GCC ATA TTG GAC ATC ATG |
| 4141 LEU PRO GLY THR SER GLY LEU THR ILE CYS GLN LYS ILE ARG ASP LYS HIS THR TYR PRO |
| CTT CCC GGC ACA AGC GGC CTT ACT ATC TGT CAA AAA ATA AGG GAC AAG CAC ACC TAT CCG |
| 4201 ILE ILE MET LEU THR GLY LYS ASP THR GLU VAL ASP LYS ILE THR GLY LEU THR ILE GLY |
| ATT ATC ATG CTG ACC GGG AAA GAT ACA GAG GTA GAT AAA ATT ACA GGG TTA ACA ATC GGC |
| 4261 ALA ASP ASP TYR ILE THR LYS PRO PHE ARG PRO LEU GLU LEU ILE ALA ARG VAL LYS ALA |
| GCG GAT GAT TAT ATA ACG AAG CCC TTT CGC CCA CTG GAG TTA ATT GCT CGG GTA AAG GCC |
| 4321 GLN LEU ARG ARG TYR LYS LYS PHE SER GLY VAL LYS GLU GLN ASN GLU ASN VAL ILE VAL |
| CAG TTG CGC CGA TAC AAA AAA TTC AGT GGA GTA AAG GAG CAG AAC GAA AAT GTT ATC GTC |
| 4381 HIS SER GLY LEU VAL ILE ASN VAL ASN THR HIS GLU CYS TYR LEU ASN GLU LYS GLN LEU |
| CAC TCC GGC CTT GTC ATT AAT GTT AAC ACC CAT GAG TGT TAT CTG AAC GAG AAG CAG TTA |
| 4441 SER LEU THR PRO THR GLU PHE SER ILE LEU ARG ILE LEU CYS GLU ASN LYS GLY ASN VAL |
| TCC CTT ACT CCC ACC GAG TTT TCA ATA CTG CGA ATC CTC TGT GAA AAC AAG GGG AAT GTG |
| 4501 VAL SER SER GLU LEU LEU PHE HIS GLU ILE TRP GLY ASP GLU TYR PHE SER LYS SER ASN |
| GTT AGC TCC GAG CTG CTA TTT CAT GAG ATA TGG GGC GAC GAA TAT TTC AGC AAG AGC AAC |
| 4561 ASN THR ILE THR VAL HIS ILE ARG HIS LEU ARG GLU LYS MET ASN ASP THR ILE ASP ASN |
| AAC ACC ATC ACC GTG CAT ATC CGG CAT TTG CGC GAA AAA ATG AAC GAC ACC ATT GAT AAT |
| 4621 PRO LYS TYR ILE LYS THR VAL TRP GLY VALGLYTYRLYSILEGLULYS |
| CCG AAA TAT ATA AAA ACG GTA TGG GGG GTTGGTTATAAAATTGAAAAAT AAA AAA AAC GAC |
| VanS LEUVALILELYSLEULYSASN LYS LYS ASN ASP |
| 4682 TYR SER LYS LEU GLU ARG LYS LEU TYR MET TYR ILE VAL ALA ILE VAL VAL VAL ALA ILE |
| TAT TCC AAA CTA GAA CGA AAA CTT TAC ATG TAT ATC GTT GCA ATT GTT GTG GTA GCA ATT |
| 4742 VAL PHE VAL LEU TYR ILE ARG SER MET ILE ARG GLY LYS LEU GLY ASP TRP ILE LEU SER |
| GTA TTC GTG TTG TAT ATT CGT TCA ATG ATC CGA GGG AAA CTT GGG GAT TGG ATC TTA AGT |
| 4802 ILE LEU GLU ASN LYS TYR ASP LEU ASN HIS LEU ASP ALA MET LYS LEU TYR GLN TYR SER |
| ATT TTG GAA AAC AAA TAT GAC TTA AAT CAC CTG GAC GCG ATG AAA TTA TAT CAA TAT TCC |
| 4862 ILE ARG ASN ASN ILE ASP ILE PHE ILE TYR VAL ALA ILE VAL ILE SER ILE LEU ILE LEU |
| ATA CGG AAC AAT ATA GAT ATC TTT ATT TAT GTG GCG ATT GTC ATT AGT ATT CTT ATT CTA |
| 4922 CYS ARG VAL MET LEU SER LYS PHE ALA LYS TYR PHE ASP GLU ILE ASN THR GLY ILE ASP |
| TGT CGC GTC ATG CTT TCA AAA TTC GCA AAA TAC TTT GAC GAG ATA AAT ACC GGC ATT GAT |
| 4982 VAL LEU ILE GLN ASN GLU ASP LYS GLN ILE GLU LEU SER ALA GLU MET ASP VAL MET GLU |
| GTA CTT ATT CAG AAC GAA GAT AAA CAA ATT GAG CTT TCT GCG GAA ATG GAT GTT ATG GAA |
| 5042 GLN LYS LEU ASN THR LEU LYS ARG THR LEU GLU LYS ARG GLU GLN ASP ALA LYS LEU ALA |

-continued

I. Nucleotide sequence of the transposon and translation

```
     CAA AAG CTC AAC ACA TTA AAA CGG ACT CTG GAA AAG CGA GAG CAG GAT GCA AAG CTG GCC
5102 GLU GLN ARG LYS ASN ASP VAL VAL MET TYR LEU ALA HIS ASP ILE LYS THR PRO LEU THR
     GAA CAA AGA AAA AAT GAC GTT GTT ATG TAC TTG GCG CAC GAT ATT AAA ACG CCC CTT ACA
5162 SER ILE ILE GLY TYR LEU SER LEU LEU ASP GLU ALA PRO ASP MET PRO VAL ASP GLN LYS
     TCC ATT ATC GGT TAT TTG AGC CTG CTT GAC GAG GCT CCA GAC ATG CCG GTA GAT CAA AAG
5222 ALA LYS TYR VAL HIS ILE THR LEU ASP LYS ALA TYR ARG LEU GLU GLN LEU ILE ASP GLU
     GCA AAG TAT GTG CAT ATC ACG TTG GAC AAA GCG TAT CGA CTC GAA CAG CTA ATC GAC GAG
5282 PHE PHE GLU ILE THR ARG TYR ASN LEU GLN THR ILE THR LEU THR LYS THR HIS ILE ASP
     TTT TTT GAG ATT ACA CGG TAT AAC CTA CAA ACG ATA ACG CTA ACA AAA ACG CAC ATA GAC
5342 LEU TYR TYR MET LEU VAL GLN MET THR ASP GLU PHE TYR PRO GLN LEU SER ALA HIS GLY
     CTA TAC TAT ATG CTG GTG CAG ATG ACC GAT GAA TTT TAT CCT CAG CTT TCC GCA CAT GGA
5402 LYS GLN ALA VAL ILE HIS ALA PRO GLU ASP LEU THR VAL SER GLY ASP PRO ASP LYS LEU
     AAA CAG GCG GTT ATT CAC GCC CCC GAG GAT CTG ACC GTG TCC GGC GAC CCT GAT AAA CTC
5462 ALA ARG VAL PHE ASN ASN ILE LEU LYS ASN ALA ALA ALA TYR SER GLU ASP ASN SER ILE
     GCG AGA GTC TTT AAC AAC ATT TTG AAA AAC GCC GCT GCA TAC AGT GAG GAT AAC AGC ATC
5522 ILE ASP ILE THR ALA GLY LEU SER GLY ASP VAL VAL SER ILE GLU PHE LYS ASN THR GLY
     ATT GAC ATT ACC GCG GGC CTC TCC GGG GAT GTG GTG TCA ATC GAA TTC AAG AAC ACT GGA
5582 SER ILE PRO LYS ASP LYS LEU ALA ALA ILE PHE GLU LYS PHE TYR ARG LEU ASP ASN ALA
     AGC ATC CCA AAA GAT AAG CTA GCT GCC ATA TTT GAA AAG TTC TAT AGG CTG GAC AAT GCT
5642 ARG SER SER ASP THR GLY GLY ALA GLY LEU GLY LEU ALA ILE ALA LYS GLU ILE ILE VAL
     CGT TCT TCC GAT ACG GGT GGC GCG GGA CTT GGA TTG GCG ATT GCA AAA GAA ATT ATT GTT
5702 GLN HIS GLY GLY GLN ILE TYR ALA GLU SER ASN ASP ASN TYR THR THR PHE ARG VAL GLU
     CAG CAT GGA GGG CAG ATT TAC GCG GAA AGC AAT GAT AAC TAT ACG ACG TTT AGG GTA GAG
5762 LEU PRO ALA MET PRO ASP LEU VAL ASP LYS ARG ARG SER
     CTT CCA GCG ATG CCA GAC TTG GTT GAT AAA AGG AGG TCC TAA GA GAT GTA TAT AAT TTT
5821 TTA GGA AAA TCT CAA GGT TAT CTT TAC TTT TTC TTA GGA AAT TAA CAA TTT AAT ATT AAG
5881 AAA CGG CTC GTT CTT ACA CGG TAG ACT TAA TAC CGT AAG AAC GAG CCG TTT TCG TTC TTC
5941 AGA GAA AGA TTT GAC AAG ATT ACC ATT GGC ATC CCC GTT TTA TTT GGT GCC TTT CAC AGA
6001        VanH         MET ASN ASN ILE GLY ILE THR VAL TYR GLY CYS  GLU GLN ASP GLU
     AAGGGTTGG TCT TAA TT ATG AAT AAC ATC GGC ATT ACT GTT TAT GGA TGT GAG CAG GAT GAG
6063 ALA ASP ALA PHE HIS ALA LEU SER PRO ARG PHE GLY VAL MET ALA THR ILE ILE ASN ALA
     GCA GAT GCA TTC CAT GCT CTT TCG CCT CGC TTT GGC GTT ATG GCA ACG ATA ATT AAC GCC
6123 ASN VAL SER GLU SER ASN ALA LYS SER ALA PRO PHE ASN GLN CYS ILE SER VAL GLY HIS
     AAC GTG TCG GAA TCC AAC GCC AAA TCC GCG CCT TTC AAT CAA TGT ATC AGT GTG GGA CAT
6183 LYS SER GLU ILE SER ALA SER ILE LEU LEU ALA LEU LYS ARG ALA GLY VAL LYS TYR ILE
     AAA TCA GAG ATT TCC GCC TCT ATT CTT CTT GCG CTG AAG AGA GCC GGT GTG AAA TAT ATT
6243 SER THR ARG SER ILE GLY CYS ASN HIS ILE ASP THR THR ALA ALA LYS ARG MET GLY ILE
     TCT ACC CGA AGC ATC GGC TGC AAT CAT ATA GAT ACA ACT GCT GCT AAG AGA ATG GGC ATC
6303 THR VAL ASP ASN VAL ALA TYR SER PRO ASP SER VAL ALA ASP TYR THR MET MET LEU ILE
```

-continued

I. Nucleotide sequence of the transposon and translation

```
     ACT GTC GAC AAT GTG GCG TAC TCG CCG GAT AGC GTT GCC GAT TAT ACT ATG ATG CTA ATT
6363 LEU MET ALA VAL ARG ASN VAL LYS SER ILE VAL ARG SER VAL GLU LYS HIS ASP PHE ARG
     CTT ATG GCA GTA CGC AAC GTA AAA TCG ATT GTG CGC TCT GTG GAA AAA CAT GAT TTC AGG
6423 LEU ASP SER ASP ARG GLY LYS VAL LEU SER ASP MET THR VAL GLY VAL VAL GLY THR GLY
     TTG GAC AGC GAC CGT GGC AAG GTA CTC AGC GAC ATG ACA GTT GGT GTG GTG GGA ACG GGC
6483 GLN ILE GLY LYS ALA VAL ILE GLU ARG LEU ARG GLY PHE GLY CYS LYS VAL LEU ALA TYR
     CAG ATA GGC AAA GCG GTT ATT GAG CGG CTG CGA GGA TTT GGA TGT AAA GTG TTG GCT TAT
6543 SER ARG SER ARG SER ILE GLU VAL ASN TYR VAL PRO PHE ASP GLU LEU LEU GLN ASN SER
     AGT CGC AGC CGA AGT ATA GAG GTA AAC TAT GTA CCG TTT GAT GAG TTG CTG CAA AAT AGC
6603 ASP ILE VAL THR LEU HIS VAL PRO LEU ASN THR ASP THR HIS TYR ILE ILE SER HIS GLU
     GAT ATC GTT ACG CTT CAT GTG CCG CTC AAT ACG GAT ACG CAC TAT ATT ATC AGC CAC GAA
6663 GLN ILE GLN ARG MET LYS GLN GLY ALA PHE LEU ILE ASN THR GLY ARG GLY PRO LEU VAL
     CAA ATA CAG AGA ATG AAG CAA GGA GCA TTT CTT ATC AAT ACT GGG CGC GGT CCA CTT GTA
6723 ASP THR TYR GLU LEU VAL LYS ALA LEU GLU ASN GLY LYS LEU GLY GLY ALA ALA LEU ASP
     GAT ACC TAT GAG TTG GTT AAA GCA TTA GAA AAC GGG AAA CTG GGC GGT GCC GCA TTG GAT
6783 VAL LEU GLU GLY GLU GLU GLU PHE PHE TYR SER ASP CYS THR GLN LYS PRO ILE ASP ASN
     GTA TTG GAA GGA GAG GAA GAG TTT TTC TAC TCT GAT TGC ACC CAA AAA CCA ATT GAT AAT
6843 GLN PHE LEU LEU LYS LEU GLN ARG MET PRO ASN VAL ILE ILE THR PRO HIS THR ALA TYR
     CAA TTT TTA CTT AAA CTT CAA AGA ATG CCT AAC GTG ATA ATC ACA CCG CAT ACG GCC TAT
6903 TYR THR GLU GLN ALA LEU ARG ASP THR VAL GLU LYS THR ILE LYS ASN CYS LEU ASP PHE
     TAT ACC GAG CAA GCG TTG CGT GAT ACC GTT GAA AAA ACC ATT AAA AAC TGT TTG GAT TTT
6963            VanA     METASN ARG ILE LYS VAL ALA ILE LEU PHE GLY  GLY CYS SER
     GAA AGG AGA CAG GAG CATGAAT AGA ATA AAA GTT GCA ATA CTG TTT GGG GGT TGC TCA
     GLU ARG ARG GLN GLU HISGLU
7021 GLU GLU HIS ASP VAL SER VAL LYS SER ALA ILE GLU ILE ALA ALA ASN ILE ASN LYS GLU
     GAG GAG CAT GAC GTA TCG GTA AAA TCT GCA ATA GAG ATA GCC GCT AAC ATT AAT AAA GAA
7081 LYS TYR GLU PRO LEU TYR ILE GLY ILE THR LYS SER GLY VAL TRP LYS MET CYS GLU LYS
     AAA TAC GAG CCG TTA TAC ATT GGA ATT ACG AAA TCT GGT GTA TGG AAA ATG TGC GAA AAA
7141 PRO CYS ALA GLU TRP GLU ASN ASP ASN CYS TYR SER ALA VAL LEU SER PRO ASP LYS LYS
     CCT TGC GCG GAA TGG GAA AAC GAC AAT TGC TAT TCA GCT GTA CTC TCG CCG GAT AAA AAA
7201 MET HIS GLY LEU LEU VAL LYS LYS ASN HIS GLU TYR GLU ILE ASN HIS VAL ASP VAL ALA
     ATG CAC GGA TTA CTT GTT AAA AAG AAC CAT GAA TAT GAA ATC AAC CAT GTT GAT GTA GCA
7261 PHE SER ALA LEU HIS GLY LYS SER GLY GLU ASP GLY SER ILE GLN GLY LEU PHE GLU LEU
     TTT TCA GCT TTG CAT GGC AAG TCA GGT GAA GAT GGA TCC ATA CAA GGT CTG TTT GAA TTG
7321 SER GLY ILE PRO PHE VAL GLY CYS ASP ILE GLN SER SER ALA ILE CYS MET ASP LYS SER
     TCC GGT ATC CCT TTT GTA GGC TGC GAT ATT CAA AGC TCA GCA ATT TGT ATG GAC AAA TCG
7381 LEU THR TYR ILE VAL ALA LYS ASN ALA GLY ILE ALA THR PRO ALA PHE TRP VAL ILE ASN
     TTG ACA TAC ATC GTT GCG AAA AAT GCT GGG ATA GCT ACT CCC GCC TTT TGG GTT ATT AAT
```

-continued

I. Nucleotide sequence of the transposon and translation

```
7441 LYS ASP ASP ARG PRO VAL ALA ALA THR PHE THR TYR PRO VAL PHE VAL LYS PRO ALA ARG
     AAA GAT GAT AGG CCG GTG GCA GCT ACG TTT ACC TAT CCT GTT TTT GTT AAG CCG GCG CGT
7501 SER GLY SER SER PHE GLY VAL LYS LYS VAL ASN SER ALA ASP GLU LEU ASP TYR ALA ILE
     TCA GGC TCA TCC TTC GGT GTG AAA AAA GTC AAT AGC GCG GAC GAA TTG GAC TAC GCA ATT
7561 GLU SER ALA ARG GLN TYR ASP SER LYS ILE LEU ILE GLU GLN ALA VAL SER GLY CYS GLU
     GAA TCG GCA AGA CAA TAT GAC AGC AAA ATC TTA ATT GAG CAG GCT GTT TCG GGC TGT GAG
7621 VAL GLY CYS ALA VAL LEU GLY ASN SER ALA ALA LEU VAL VAL GLY GLU VAL ASP GLN ILE
     GTC GGT TGT GCG GTA TTG GGA AAC AGT GCC GCG TTA GTT GTT GGC GAG GTG GAC CAA ATC
7681 ARG LEU GLN TYR GLY ILE PHE ARG ILE HIS GLN GLU VAL GLU PRO GLU LYS GLY SER GLU
     AGG CTG CAG TAC GGA ATC TTT CGT ATT CAT CAG GAA GTC GAG CCG GAA AAA GGC TCT GAA
7741 ASN ALA VAL ILE THR VAL PRO ALA ASP LEU SER ALA GLU GLU ARG GLY ARG ILE GLN GLU
     AAC GCA GTT ATA ACC GTT CCC GCA GAC CTT TCA GCA GAG GAG CGA GGA CGG ATA CAG GAA
7801 THR ALA LYS LYS ILE TYR LYS ALA LEU GLY CYS ARG GLY LEU ALA ARG VAL ASP MET PHE
     ACG GCA AAA AAA ATA TAT AAA GCG CTC GGC TGT AGA GGT CTA GCC CGT GTG GAT ATG TTT
7861 LEU GLN ASP ASN GLY ARG ILE VAL LEU ASN GLU VAL ASN THR LEU PRO GLY PHE THR SER
     TTA CAA GAT AAC GGC CGC ATT GTA CTG AAC GAA GTC AAT ACT CTG CCC GGT TTC ACG TCA
7921 TYR SER ARG TYR PRO ARG MET MET ALA ALA ALA GLY ILE ALA LEU PRO GLU LEU ILE ASP
     TAC AGT CGT TAT CCC CGT ATG ATG GCC GCT GCA GGT ATT GCA CTT CCC GAA CTG ATT GAC
7981 ARG LEU ILE VAL LEU ALA LEU LYS GLY
     CGC TTG ATC GTA TTA GCG TTA AAG GGG TGATAAGC ATG GAA ATA GGA TTT ACT TTT TTA GAT
                                         VanX    MET GLU ILE GLY PHE THR PHE  LEU ASP
8043 GLU ILE VAL HIS GLY VAL ARG TRP ASP ALA LYS TYR ALA THR TRP ASP ASN PHE THR GLY
     GAA ATA GTA CAC GGT GTT CGT TGG GAC GCT AAA TAT GCC ACT TGG GAT AAT TTC ACC GGA
8103 LYS PRO VAL ASP GLY TYR GLU VAL ASN ARG ILE VAL GLY THR TYR GLU LEU ALA GLU SER
     AAA CCG GTT GAC GGT TAT GAA GTA AAT CGC ATT GTA GGG ACA TAC GAG TTG GCT GAA TCG
8163 LEU LEU LYS ALA LYS GLU LEU ALA ALA THR GLN GLY TYR GLY LEU LEU LEU TRP ASP GLY
     CTT TTG AAG GCA AAA GAA CTG GCT GCT ACC CAA GGG TAC GGA TTG CTT CTA TGG GAC GGT
8223 TYR ARG PRO LYS ARG ALA VAL ASN CYS PHE MET GLN TRP ALA ALA GLN PRO GLU ASN ASN
     TAC CGT CCT AAG CGT GCT GTA AAC TGT TTT ATG CAA TGG GCT GCA CAG CCG GAA AAT AAC
8283 LEU THR LYS GLU SER TYR TYR PRO ASN ILE ASP ARG THR GLU MET ILE SER LYS GLY TYR
     CTG ACA AAG GAA AGT TAT TAT CCC AAT ATT GAC CGA ACT GAG ATG ATT TCA AAA GGA TAC
8343 VAL ALA SER LYS SER SER HIS SER ARG GLY SER ALA ILE ASP LEU THR LEU TYR ARG LEU
     GTG GCT TCA AAA TCA AGC CAT AGC CGC GGC AGT GCC ATT GAT CTT ACG CTT TAT CGA TTA
8403 ASP THR GLY GLU LEU VAL PRO MET GLY SER ARG PHE ASP PHE MET ASP GLU ARG SER HIS
     GAC ACG GGT GAG CTT GTA CCA ATG GGG AGC CGA TTT GAT TTT ATG GAT GAA CGC TCT CAT
8463 HIS ALA ALA ASN GLY ILE SER CYS ASN GLU ALA GLN ASN ARG ARG ARG LEU ARG SER ILE
     CAT GCG GCA AAT GGA ATA TCA TGC AAT GAA GCG CAA AAT CGC AGA CGT TTG CGC TCC ATC
8523 MET GLU ASN SER GLY PHE GLU ALA TYR SER LEU GLU TRP TRP HIS TYR VAL LEU ARG ASP
     ATG GAA AAC AGT GGG TTT GAA GCA TAT AGC CTC GAA TGG TGG CAC TAT GTA TTA AGA GAC
```

-continued

I. Nucleotide sequence of the transposon and translation

```
8583 GLU PRO TYR PRO ASN SER TYR PHE ASP PHE PRO VAL LYS
     GAA CCA TAC CCC AAT AGC TAT TTT GAT TTC CCC GTT AAA TAAA CTT TTA ACC GTT GCA
8641 CGG ACA AAC TAT ATA AGC TAA CTC TTT CGG CAG GAA ACC CGA CGT ATG TAA CTG GTT CTT
8701 AGG GAA TTT ATA TAT AGT AGA TAG TAT TGA AGA TGT AAG GCA GAG CGA TAT TGC GGT CAT
8761 TAT CTG CGT GCG CTG CGG CAA GAT AGC CTG ATA ATA AGA CTG ATC GCA TAG AGG GGT GGT
8821 ATT TCA CAC CGC CCA TTG TCA ACA GGC AGT TCA GCC TCG TTA AAT TCA GCA TGG GTA TCA
8881 CTT ATG AAA ATT CAT CTA CAT TGG TGA TAA TAG TAA ATC CAG TAG GGC GAA ATA ATT GAC
8941 TGT AAT TTA CGG GGC AAA ACG GCA CAA TCT CAA ACG AGA TTG TGC CGT TTA AGG GGA AGA
9001                                                                 VanY    MET LYS LYS
     TTC TAG AAA TAT TTC ATA CTT CCA ACT ATA TAG TTA AGG AGG AGA CTG AAA ATG AAG AAG
9061 LEU PHE PHE LEU LEU LEU LEU LEU PHE LEU ILE TYR LEU GLY TYR ASP TYR VAL ASN GLU
     TTG TTT TTT TTA TTG TTA TTG TTA TTC TTA ATA TAC TTA GGT TAT GAC TAC GTT AAT GAA
9121 ALA LEU PHE SER GLN GLU LYS VAL GLU PHE GLN ASN TYR ASP GLN ASN PRO LYS GLU HIS
     GCA CTG TTT TCT CAG GAA AAA GTC GAA TTT CAA AAT TAT GAT CAA AAT CCC AAA GAA CAT
9181 LEU GLU ASN SER GLY THR SER GLU ASN THR GLN GLU LYS THR ILE THR GLU GLU GLN VAL
     TTA GAA AAT AGT GGG ACT TCT GAA AAT ACC CAA GAG AAA ACA ATT ACA GAA GAA CAG GTT
9241 TYR GLN GLY ASN LEU LEU LEU ILE ASN SER LYS TYR PRO VAL ARG GLN GLU SER VAL LYS
     TAT CAA GGA AAT CTG CTA TTA ATC AAT AGT AAA TAT CCT GTT CGC CAA GAA AGT GTG AAG
9301 SER ASP ILE VAL ASN LEU SER LYS HIS ASP GLU LEU ILE ASN GLY TYR GLY LEU LEU ASP
     TCA GAT ATC GTG AAT TTA TCT AAA CAT GAC GAA TTA ATA AAT GGA TAC GGG TTG CTT GAT
9361 SER ASN ILE TYR MET SER LYS GLU ILE ALA GLN LYS PHE SER GLU MET VAL ASN ASP ALA
     AGT AAT ATT TAT ATG TCA AAA GAA ATA GCA CAA AAA TTT TCA GAG ATG GTC AAT GAT GCT
9421 VAL LYS GLY GLY VAL SER HIS PHE ILE ILE ASN SER GLY TYR ARG ASP PHE ASP GLU GLN
     GTA AAG GGT GGC GTT AGT CAT TTT ATT ATT AAT AGT GGC TAT CGA GAC TTT GAT GAG CAA
9481 SER VAL LEU TYR GLN GLU MET GLY ALA GLU TYR ALA LEU PRO ALA GLY TYR SER GLU HIS
     AGT GTG CTT TAC CAA GAA ATG GGG GCT GAG TAT GCC TTA CCA GCA GGT TAT AGT GAG CAT
9541 ASN SER GLY LEU SER LEU ASP VAL GLY SER SER LEU THR LYS MET GLU ARG ALA PRO GLU
     AAT TCA GGT TTA TCA CTA GAT GTA GGA TCA AGC TTG ACG AAA ATG GAA CGA GCC CCT GAA
9601 GLY LYS TRP ILE GLU GLU ASN ALA TRP LYS TYR GLY PHE ILE LEU ARG TYR PRO GLU ASP
     GGA AAG TGG ATA GAA GAA AAT GCT TGG AAA TAC GGG TTC ATT TTA CGT TAT CCA GAG GAC
9661 LYS THR GLU LEU THR GLY ILE GLN TYR GLU PRO TRP HIS ILE ARG TYR VAL GLY LEU PRO
     AAA ACA GAG TTA ACA GGA ATT CAA TAT GAA CCA TGG CAT ATT CGC TAT GTT GGT TTA CCA
9721 HIS SER ALA ILE MET LYS GLU LYS ASN PHE VAL LEU GLU GLU TYR MET ASP TYR LEU LYS
     CAT AGT GCG ATT ATG AAA GAA AAG AAT TTC GTT CTC GAG GAA TAT ATG GAT TAC CTA AAA
9781 GLU GLU LYS THR ILE SER VAL SER VAL ASN GLY GLU LYS TYR GLU ILE PHE TYR TYR PRO
     GAA GAA AAA ACC ATT TCT GTT AGT GTA AAT GGG GAA AAA TAT GAG ATC TTT TAT TAT CCT
9841 VAL THR LYS ASN THR THR ILE HIS VAL PRO THR ASN LEU ARG TYR GLU ILE SER GLY ASN
     GTT ACT AAA AAT ACC ACC ATT CAT GTG CCG ACT AAT CTT CGT TAT GAG ATA TCA GGA AAC
```

-continued

I. Nucleotide sequence of the transposon and translation

```
 9901 ASN ILE ASP GLY VAL ILE VAL THR VAL PHE PRO GLY SER THR HIS THR ASN SER ARG ARG

      AAT ATA GAC GGT GTA ATT GTG ACA GTG TTT CCC GGA TCA ACA CAT ACT AAT TCA AGG AGG

 9961 TAA GGA TGG CGG AAT GAA ACC AAC GAA ATT AAT GAA CAG CAT TAT TGT ACT AGC ACT TTT

10021 GGG GTA ACG TTA GCT TTT TAA TTT AAA ACC CAC GTT AAC TAG GAC ATT GCT ATA CTA ATG

10081                               VanZ     LEU GLY LYS ILE LEU SER  ARG GLY LEU

      ATA CAA CTT AAA CAA AAG AATTAGAGG AAA TTA TA TTG GGA AAA ATA TTA TCT AGA GGA TTG

10143 LEU ALA LEU TYR LEU VAL THR LEU ILE TRP LEU VAL LEU PHE LYS LEU GLN TYR ASN ILE

      CTA GCT TTA TAT TTA GTG ACA CTA ATC TGG TTA GTG TTA TTC AAA TTA CAA TAC AAT ATT

10203 LEU SER VAL PHE ASN TYR HIS GLN ARG SER LEU ASN LEU THR PRO PHE THR ALA THR GLY

      TTA TCA GTA TTT AAT TAT CAT CAA AGA AGT CTT AAC TTG ACT CCA TTT ACT GCT ACT GGG

10263 ASN PHE ARG GLU MET ILE ASP ASN VAL ILE ILE PHE ILE PRO PHE GLY LEU LEU LEU ASN

      AAT TTC AGA GAG ATG ATA GAT AAT GTT ATA ATC TTT ATT CCA TTT GGC TTG CTT TTG AAT

10323 VAL ASN PHE LYS GLU ILE GLY PHE LEU PRO LYS PHE ALA PHE VAL LEU VAL LEU SER LEU

      GTC AAT TTT AAA GAA ATC GGA TTT TTA CCT AAG TTT GCT TTT GTA CTG GTT TTA AGT CTT

10383 THR PHE GLU ILE ILE GLN PHE ILE PHE ALA ILE GLY ALA THR ASP ILE THR ASP VAL ILE

      ACT TTT GAA ATA ATT CAA TTT ATC TTC GCT ATT GGA GCG ACA GAC ATA ACA GAT GTA ATT

10443 THR ASN THR VAL GLY GLY PHE LEU GLY LEU LYS LEU TYR GLY LEU SER ASN LYS HIS MET

      ACA AAT ACT GTT GGA GGC TTT CTT GGA CTG AAA TTA TAT GGT TTA AGC AAT AAG CAT ATG

10503 ASN GLN LYS LYS LEU ASP ARG VAL ILE ILE PHE VAL GLY ILE LEU LEU LEU VAL LEU LEU

      AAT CAA AAA AAA TTA GAC AGA GTT ATT ATT TTT GTA GGT ATA CTT TTG CTC GTA TTA TTG

10563 LEU VAL TYR ARG THR HIS LEU ARG ILE ASN TYR VAL

      CTC GTT TAC CGT ACC CAT TTA AGA ATA AAT TAC GTG TAAG ATG TCT AAA TCA AGC AAT

10621 CTG ATC TTT CAT ACA CAT AAA GAT ATT GAA TGA ATT GGA TTA GAT GGA AAA CGG GAT GTG

10681 GGG AAA CTC GCC CGT AGG TGT GAA GTG AGG GGA AAA CCG GTG ATA AAG TAA AAA GCT TAC

10741 CTA ACA CTA TAG TAA CAA AGA AAG CCC AAT TAT CAA TTT TAG TGC TGA GGA ATT GGT CTC

10801 TTT AAT AAA TTT CCT TAA CGT TGT AAA TCC GCA TTT TCC TGA CGG TAC CCC
```

Ib (-) Strand
(corresponds to the sequence of the strand complementary to the (+) strand from 1 to 3189.

```
    1 CAA AAT ATC ACC TCA TTT TTG AGA CAA GTC TTA TGA GAC GCT CTT AAC TAT GAT TTT ATC

   61 AGT CTA CTA CAT TTG TAT CAA TAG AGT ACA CTC TAT TGA TAT ATA ATT GAA CTA ATA AAT

  121             Transposase         MET LYS ILE ALA ARG GLY ARG GLU  LEU LEU THR

      TGA AAA TAC AGA AAT GGA ATGATACTG AA ATG AAA ATT GCG AGA GGT AGA GAA TTG CTT ACA

  182 PRO GLU GLN ARG GLN ALA PHE MET GLN ILE PRO GLU ASP GLU TRP ILE LEU GLY THR TYR

      CCG GAA CAG AGA CAG GCT TTT ATG CAA ATC CCT GAA GAT GAA TGG ATA CTG GGG ACC TAC

  242 PHE THR PHE SER LYS ARG ASP LEU GLU ILE VAL ASN LYS ARG ARG ARG GLU GLU ASN ARG

      TTC ACT TTT TCC AAA CGG GAT TTA GAA ATA GTT AAT AAG CGA AGG AGG GAA GAA AAC CGT

  302 LEU GLY PHE ALA VAL GLN LEU ALA VAL LEU ARG TYR PRO GLY TRP PRO TYR THR HIS ILE

      TTA GGA TTT GCT GTT CAA TTA GCT GTT CTT CGG TAT CCC GGT TGG CCA TAC ACT CAT ATC

  362 LYS SER ILE PRO ASP SER VAL ILE GLN TYR ILE SER LYS GLN ILE GLY VAL SER PRO SER
```

-continued

I. Nucleotide sequence of the transposon and translation

```
     AAA AGC ATC CCA GAT TCG GTC ATA CAA TAT ATA TCG AAA CAG ATT GGT GTT AGT CCA TCC

 422 SER LEU ASP HIS TYR PRO GLN ARG GLU ASN THR LEU TRP ASP HIS LEU LYS GLU ILE ARG

     TCG CTT GAT CAT TAT CCT CAA AGG GAA AAT ACA CTT TGG GAT CAT TTG AAA GAA ATT CGA

 482 SER GLU TYR ASP PHE VAL THR PHE THR LEU SER GLU TYR ARG MET THR PHE LYS TYR LEU

     AGT GAA TAC GAC TTT GTA ACT TTT ACC CTG AGT GAA TAT CGA ATG ACA TTT AAG TAC CTT

 542 HIS GLN LEU ALA LEU GLU ASN GLY ASP ALA ILE HIS LEU LEU HIS GLU CYS ILE ASP PHE

     CAT CAA TTA GCT TTG GAA AAT GGT GAT GCC ATT CAT CTA CTG CAT GAA TGC ATA GAT TTT

 602 LEU ARG LYS ASN LYS ILE ILE LEU PRO ALA ILE THR THR LEU GLU ARG MET VAL TRP GLU

     CTA AGA AAA AAC AAA ATT ATA CTG CCT GCT ATC ACT ACA CTT GAA AGA ATG GTG TGG GAA

 662 ALA ARG ALA MET ALA GLU LYS LYS LEU PHE ASN THR VAL SER LYS SER LEU THR ASN GLU

     GCA AGG GCA ATG GCT GAA AAG AAG CTA TTT AAT ACG GTT AGT AAA TCT CTA ACA AAT GAG

 722 GLN LYS GLU LYS LEU GLU GLY ILE ILE THR SER GLN HIS PRO SER GLU SER ASN LYS THR

     CAA AAA GAA AAG CTT GAA GGG ATT ATT ACC TCG CAG CAT CCA TCC GAA TCC AAT AAA ACG

 782 ILE LEU GLY TRP LEU LYS GLU PRO PRO GLY HIS PRO SER PRO GLU THR PHE LEU LYS ILE

     ATA TTG GGT TGG TTA AAA GAG CCA CCG GGT CAT CCT TCA CCC GAA ACT TTT CTA AAA ATA

 842 ILE GLU ARG LEU GLU TYR ILE ARG GLY MET ASP LEU GLU THR VAL GLN ILE SER HIS LEU

     ATA GAA CGA CTC GAA TAC ATA CGA GGA ATG GAT TTA GAA ACA GTG CAA ATT AGT CAT TTG

 902 HIS ARG ASN ARG LEU LEU GLN LEU SER ARG LEU GLY SER ARG TYR GLU PRO TYR ALA PHE

     CAC CGT AAC CGC CTG TTG CAG CTG TCT CGC TTA GGC TCA AGA TAC GAG CCG TAT GCA TTC

 962 ARG ASP PHE GLN GLU ASN LYS ARG TYR SER ILE LEU THR ILE TYR LEU LEU GLN LEU THR

     CGT GAC TTT CAA GAA AAT AAA CGT TAT TCG ATA TTA ACC ATC TAT TTA TTA CAA CTT ACT

1022 GLN GLU LEU THR ASP LYS ALA PHE GLU ILE HIS ASP ARG GLN ILE LEU SER LEU LEU SER

     CAG GAG CTA ACG GAT AAA GCG TTT GAA ATT CAT GAT AGG CAA ATA CTT AGT TTG TTA TCA

1082 LYS GLY ARG LYS ALA GLN GLU GLU ILE GLN LYS GLN ASN GLY LYS LYS LEU ASN GLU LYS

     AAA GGT CGT AAG GCT CAA GAG GAA ATC CAG AAA CAA AAC GGT AAA AAG CTA AAT GAG AAA

1142 VAL ILE HIS PHE THR ASN ILE GLY GLN ALA LEU ILE LYS ALA ARG GLU GLU LYS LEU ASP

     GTT ATA CAC TTT ACG AAC ATC GGA CAA GCA TTA ATT AAA GCA AGA GAG GAA AAA TTA GAC

1202 VAL PHE LYS VAL LEU GLU SER VAL ILE GLU TRP ASN THR PHE VAL SER SER VAL GLU GLU

     GTT TTT AAG GTT TTA GAA TCG GTT ATT GAA TGG AAT ACC TTT GTC TCT TCA GTA GAA GAG

1262 ALA GLN GLU LEU ALA ARG PRO ALA ASP TYR ASP TYR LEU ASP LEU LEU GLN LYS ARG PHE

     GCT CAG GAA CTT GCA CGT CCT GCC GAC TAT GAT TAT TTA GAC TTA CTG CAA AAA CGG TTT

1322 TYR SER LEU ARG LYS TYR THR PRO THR LEU LEU ARG VAL LEU GLU PHE HIS SER THR LYS

     TAT TCA CTA AGA AAA TAT ACG CCA ACG CTA TTA AGA GTA TTG GAA TTT CAT TCT ACA AAG

1382 ALA ASN GLU PRO LEU LEU GLN ALA VAL GLU ILE ILE ARG GLY MET ASN GLU SER GLY LYS

     GCA AAT GAG CCA CTT TTA CAA GCT GTT GAG ATT ATC CGA GGA ATG AAC GAA TCT GGA AAG

1442 ARG LYS VAL PRO ASP ASP SER PRO VAL ASP PHE ILE SER LYS ARG TRP LYS ARG HIS LEU

     CGA AAA GTG CCT GAT GAC TCA CCT GTG GAT TTT ATT TCA AAA CGA TGG AAA AGA CAT TTA

1502 TYR GLU ASP ASP GLY THR THR ILE ASN ARG HIS TYR TYR GLU MET ALA VAL LEU THR GLU

     TAC GAG GAT GAT GGT ACA ACA ATT AAT CGT CAT TAC TAT GAA ATG GCT GTT TTA ACA GAA
```

-continued

I. Nucleotide sequence of the transposon and translation

```
1562 LEU ARG GLU HIS VAL ARG ALA GLY ASP VAL SER ILE VAL GLY SER ARG GLN TYR ARG ASP
     CTT CGG GAG CAT GTT CGG GCA GGA GAT GTT TCC ATT GTT GGC AGC AGA CAA TAT AGG GAT
1622 PHE GLU GLU TYR LEU PHE SER GLU ASP THR TRP ASN GLN SER LYS GLY ASN THR ARG LEU
     TTT GAG GAA TAT TTG TTT TCG GAA GAT ACA TGG AAT CAA TCG AAG GGG AAT ACG AGA TTA
1682 SER VAL SER LEU SER PHE GLU ASP TYR ILE THR GLU ARG THR SER SER PHE ASN GLU ARG
     TCA GTT AGT TTA TCA TTC GAA GAT TAT ATA ACG GAG AGA ACC AGC AGC TTT AAT GAA AGG
1742 LEU LYS TRP LEU ALA ALA ASN SER ASN LYS LEU ASP GLY VAL SER LEU GLU LYS GLY LYS
     TTA AAG TGG TTA GCT GCC AAT TCC AAT AAG TTA GAT GGG GTT TCT CTT GAA AAA GGA AAG
1802 LEU SER LEU ALA ARG LEU GLU LYS ASP VAL PRO GLU GLU ALA LYS LYS PHE SER ALA SER
     CTA TCA CTT GCA CGC TTA GAA AAA GAT GTT CCA GAA GAA GCA AAA AAA TTT AGT GCA AGC
1862 LEU TYR GLN MET LEU PRO ARG ILE LYS LEU THR ASP LEU LEU MET ASP VAL ALA HIS ILE
     CTT TAT CAG ATG CTA CCA AGA ATA AAA TTA ACT GAT TTA CTC ATG GAT GTG GCC CAT ATA
1922 THR GLY PHE HIS GLU GLN PHE THR HIS ALA SER ASN ASN ARG LYS PRO ASP LYS GLU GLU
     ACA GGA TTT CAT GAG CAA TTC ACT CAT GCT TCC AAT AAT CGA AAA CCA GAT AAG GAA GAA
1982 THR ILE ILE ILE MET ALA ALA LEU LEU GLY MET GLY MET ASN ILE GLY LEU SER LYS MET
     ACA ATC ATT ATC ATG GCT GCC CTT TTA GGA ATG GGA ATG AAT ATT GGC TTG AGC AAG ATG
2042 ALA GLU ALA THR PRO GLY LEU THR TYR LYS GLN LEU ALA ASN VAL SER GLN TRP ARG MET
     GCC GAA GCC ACA CCC GGA CTT ACA TAT AAG CAA CTA GCC AAT GTA TCT CAA TGG CGC ATG
2102 TYR GLU ASP ALA MET ASN LYS ALA GLN ALA ILE LEU VAL ASN PHE HIS HIS LYS LEU GLN
     TAT GAA GAT GCC ATG AAT AAA GCC CAA GCC ATA TTA GTA AAC TTT CAT CAT AAA TTA CAA
2162 LEU PRO PHE TYR TRP GLY ASP GLY THR THR SER SER SER ASP GLY MET ARG MET GLN LEU
     TTG CCT TTC TAT TGG GGC GAC GGT ACA ACA TCT TCG TCA GAT GGT ATG AGA ATG CAG CTA
2222 GLY VAL SER SER LEU HIS ALA ASP ALA ASN PRO HIS TYR GLY THR GLY LYS GLY ALA THR
     GGT GTT TCA TCA CTA CAT GCA GAT GCA AAT CCA CAT TAT GGA ACT GGA AAA GGA GCC ACC
2282 ILE TYR ARG PHE THR SER ASP GLN PHE SER SER TYR TYR THR LYS ILE ILE HIS THR ASN
     ATC TAC CGA TTT ACA AGT GAT CAA TTC TCT TCT TAC TAC ACA AAG ATT ATT CAT ACT AAT
2342 SER ARG ASP ALA ILE HIS VAL LEU ASP GLY LEU LEU HIS HIS GLU THR ASP LEU ASN ILE
     TCA AGA GAT GCG ATT CAT GTT TTG GAT GGT TTG TTA CAT CAT GAG ACG GAT CTA AAC ATA
2402 GLU GLU HIS TYR THR ASP THR ALA GLY TYR THR ASP GLN ILE PHE GLY LEU THR HIS LEU
     GAG GAA CAT TAT ACA GAC ACT GCC GGT TAC ACT GAC CAA ATA TTC GGA CTG ACT CAT TTA
2462 LEU GLY PHE LYS PHE ALA PRO ARG ILE ARG ASP LEU SER ASP SER LYS LEU PHE THR ILE
     TTA GGA TTT AAA TTT GCC CCA AGA ATA AGG GAT TTA TCG GAC TCA AAA TTA TTT ACG ATA
2522 ASP LYS ALA SER GLU TYR PRO LYS LEU GLU ALA ILE LEU ARG GLY GLN ILE ASN THR LYS
     GAT AAA GCA AGT GAG TAT CCA AAA CTA GAA GCC ATT TTA CGT GGA CAA ATA AAT ACA AAG
2582 VAL ILE LYS GLU ASN TYR GLU ASP VAL LEU ARG LEU ALA HIS SER ILE ARG GLU GLY THR
     GTC ATT AAA GAA AAT TAT GAG GAT GTT TTG CGA TTA GCT CAT TCT ATA AGG GAG GGA ACA
2642 AGT TTC AGC ATC CCT TAT TAT GGG GAA GCT AGG TTC CTA TTC AAG ACA AAA CAG CTT AGC
     VAL SER ALA SER LEU ILE MET GLY LYS LEU GLY SER TYR SER ARG GLN ASN SER LEU ALA
```

-continued

I. Nucleotide sequence of the transposon and translation

GTT TCA GCA TCC CTT ATT ATG GGG AAG CTA GGT TCC TAT TCA AGA CAA AAC AGC TTA GCT

2702 THR ALA LEU ARG GLU MET GLY ARG ILE GLU LYS THR ILE PHE ILE LEU ASN TYR ILE SER

ACA GCC TTA CGT GAG ATG GGC CGA ATA GAA AAA ACG ATC TTT ATT TTG AAT TAT ATA TCG

2762 ASP GLU SER LEU ARG ARG LYS ILE GLN ARG GLY LEU ASN LYS GLY GLU ALA MET ASN GLY

GAT GAA TCA TTA AGA AGA AAA ATA CAA AGA GGA TTG AAT AAA GGA GAA GCC ATG AAT GGA

2822 LEU ALA ARG ALA ILE PHE PHE GLY LYS GLN GLY GLU LEU ARG GLU ARG THR ILE GLN HIS

TTG GCA AGA GCT ATT TTC TTC GGA AAA CAA GGT GAG CTT AGA GAA CGC ACC ATA CAG CAT

2882 GLN LEU GLN ARG ALA SER ALA LEU ASN ILE ILE ILE ASN ALA ILE SER ILE TRP ASN THR

CAA TTG CAA AGA GCC AGT GCT TTA AAC ATA ATT ATC AAT GCT ATA AGT ATT TGG AAT ACT

2942 TCT CCA CCT AAC AAC AGC AGT TGA ATA TAA AAA ACG GAC AGG TAG CTT TAA TGA AGA TTT

LEU HIS LEU THR THR ALA VAL GLU TYR LYS LYS ARG THR GLY SER PHE ASN GLU ASP LEU

CTC CAC CTA ACA ACA GCA GTT GAA TAT AAA AAA CGG ACA GGT AGC TTT AAT GAA GAT TTG

3002 LEU HIS HIS MET SER PRO LEU GLY TRP GLU HIS ILE ASN LEU LEU GLY GLU TYR HIS PHE

TTA CAC CAT ATG TCG CCC TTA GGT TGG GAA CAT ATT AAT TTA CTA GGA GAA TAC CAT TTT

3062 ASN SER GLU LYS VAL VAL SER LEU ASN SER LEU ARG PRO LEU LYS LEU SER

AAC TCA GAG AAA GTA GTC TCA TTA AAT TCT TTA AGA CCA CTA AAA CTT TCT TAA CGT TG

3121 TTA AAA ACG AGG GAT TCG TCA GGA AAA TAG GCT TAG CGT TGT AAA TCC GCA TTT TCC TGA

3181 CGC TAC CCC

LIST OF SEQUENCES : ii SacI 42

GAGCTCTTCCTTCAACGCACTTCTGTACCAAGAGTTGTTGTC

CATTTGATCACTAACAATAGCTTCCCCTGCTTTCTTCAAGCCCTTTGTCATAAAATCGTTAGATTTTCA 111

TCATAAAAATACGAGAAAGACAACAGGAAGACCGCAAATTTTCTTTTCTTTTCCTAGGTACACTGAATG 180

RBS M K K I A V L F G G 244

TAACCTTAAAAGAAAAAAGGAAAGGAAGAAAATGATGAAAAAAATTGCCGTTTTATTTGGAGGG

N S P E Y S V S L T S A A S V I Q A I D 304

AATTCTCCAGAATACTCAGTGTCACTAACCTCAGCAGCAAGTGTGATCCAAGCTATTGAC

P L K Y E V N T I G I A P T M D W Y W Y 364

CCGCTGAAATATGAAGTAATGACCATTGGCATCGCACCAACAATGGATTGGTATTGGTAT

Q G M L A N V R N D T W L E D H K N C H 424

CAAGGAAACCTCGCGAATGTTCGCAATGATACTTGGCTAGAAGATCACAAAAACTGTCAC

Q L T F S S Q G F I L G E K R I V P D V 484

CAGCTGACTTTTTCTAGCCAAGGATTTATATTAGGAGAAAAACGAATCGTCCCTGATGTC

L F P V L H G K Y G E D G C I Q G L L E 544

CTCTTTCCAGTCTTGCATGGGAAGTATGGCGAGGATGGCTGTATCCAAGGACTGCTTGAA

L M N L P Y V G C H V A A S A L C M N K 604

CTAATGAACCTGCCTTATGTTGGTTGCCATGTCGCTGCCTCCGCATTATGTATGAACAAA

W L L H Q L A D T M G I A S A P T L L L 664

TGGCTCTTGCATCAACTTGCTGATACCATGGGAATCGCTAGTGCTCCCACTTTGCTTTTA

S R Y E N D P A T I D R F I Q D H G F P 724

-continued

I. Nucleotide sequence of the transposon and translation

```
TCCCGCTATGAAAACGATCCTGCCACAATCGATCGTTTTATTCAAGACCATGGATTCCCG

 I  F  I  K  P  N  E  A  G  S  S  K  G  I  T  K  V  T  D  K             784

ATCTTTATCAAGCCGAATGAAGCCGGTTCTTCAAAAGGGATCACAAAAGTAACTGACAAA

 T  A  L  Q  S  A  L  T  T  A  F  A  Y  G  S  T  V  L  I  Q             844

ACAGCGCTCCAATCTGCATTAACGACTGCTTTTGCTTACGGTTCTACTGTGTTGATCCAA

 K  A  I  A  G  I  E  I  G  C  G  I  L  G  N  E  Q  L  T  I             904

AAGGCGATAGCGGGTATTGAAATTGGCTGCGGCATCTTAGGAAATGAGCAATTGACGATT

 G  A  C  D  A  I  S  L  V  D  G  F  F  D  F  E  E  K  Y  Q             964

GGTGCTTGTGATGCGATTTCTCTTGTCGACGGTTTTTTTGATTTTGAAGAGAAATACCAA

 L  I  S  A  T  I  T  V  P  A  P  L  P  L  A  L  E  S  Q  I            1024

TTAATCAGCGCCACGATCACTGTCCCAGCACCATTGCCTCTCGCGCTTGAATCACAGATC

 K  E  Q  A  Q  L  L  Y  R  N  L  G  L  T  G  L  A  R  I  D            1084

AAGGAGCAGGCACAGCTGCTTTATCGAAACTTGGGATTGACGGGTCTGGCTCGAATCGAT

 F  F  V  T  N  Q  G  A  I  Y  L  N  E  I  N  T  M  P  G  F            1144

TTTTTCGTCACCAATCAAGGAGCGATTTATTTAAACGAAATCAACACCATGCCGGGATTT

 T  G  H  S  R  Y  P  A  M  M  A  E  V  G  L  S  Y  E  I  L            1204

ACTGGGCACTCCCGCTACCCAGCTATGATGGCGGAAGTCGGGTTATCCTACGAAATATTA

 V  E  Q  L  E  A  L  A  E  E  D  K  R  *                                1267

GTAGAGCAATTGATTGCACTGGCAGAGGAGGACAAACGATGAACACATTACAATTGATCAATA

AAAACCATCCATTGAAAAAAAATCAAGAGCCCCCGCACTTAGTGCTAGCTCCTTTTAGCGATCACGATG    1336

TTTACCTGCAG                                                               1347
       PstI
```

What is claimed is:

1. A composition comprising:

(a) an isolated protein having the amino acid sequence of SEQ ID NO:2 or a fragment of SEQ ID NO:2, wherein said protein or fragment when combined with (b) and (c) confers resistance to glycopeptides in Gram-positive bacteria;

(b) an isolated protein having the amino acid sequence of SEQ ID NO:6 or a fragment of SEQ ID NO:6, wherein said protein or fragment when combined with (a) and (c) confers resistance to glycopeptides in Gram-positive bacteria; and (c) an isolated protein or protein fragment selected from the group consisting of a protein having the amino acid sequence of SEQ ID NO:4, a fragment of SEQ ID NO:4, a protein having the amino acid sequence of SEQ ID NO:25, and a fragment of SEQ ID NO:25, wherein said protein or protein fragment when combined with (a) and (b) confers resistance to glycopeptides in Gram-positive bacteria;

wherein the composition confers resistance to glycopeptides in Gram-positive bacteria.

2. The composition of claim 1, which comprises the isolated protein having the amino acid sequence of SEQ ID NO:2, the isolated protein having the amino acid sequence of SEQ ID NO:6, and the isolated protein having the amino acid sequence of SEQ ID NO:4.

3. The composition of claim 1, which comprises the isolated protein having the amino acid sequence of SEQ ID NO:2, the isolated protein having the amino acid sequence of SEQ ID NO:6, and the isolated protein having the amino acid sequence of SEQ ID NO:25.

4. A composition comprising:

(a) an isolated protein encoded by a nucleotide sequence that hybridizes to SEQ ID NO: 17, or a protein encoded by a nucleotide sequence that hybridizes to SEQ ID NO:3, wherein said protein when combined with (b) and (c) confers resistance to glycopeptides in Gram-positive bacteria;

(b) an isolated protein encoded by a nucleotide sequence that hybridizes to SEQ ID NO:1, wherein said protein when combined with (a) and (c) confers resistance to glycopeptides in Gram-positive bacteria; and (c) an isolated protein encoded by a nucleotide sequence that hybridizes to SEQ ID NO:5, wherein said protein when combined with (a) and (b) confers resistance to glycopeptides in Gram-positive bacteria;

wherein the hybridization conditions are under high stringency conditions, wherein the high stringency conditions comprise hybridization overnight at 65° C. in a solution containing 0.1% SDS, 0.7% skim milk powder, 6×SSC and washing at 65° C. in 2×SSC, and 0.1% SDS.

5. The composition of claim 4, which comprises the isolated protein encoded by the nucleotide sequence that hybridizes to SEQ ID NO:17, the isolated protein encoded by the nucleotide sequence that hybridizes to SEQ ID NO:1; and the isolated protein encoded by the nucleotide sequence that hybridizes to SEQ ID NO:5.

6. The composition of claim 4, which comprises the isolated protein encoded by the nucleotide sequence that hybridizes to SEQ ID NO:3, the isolated protein encoded by the nucleotide sequence that hybridizes to SEQ ID NO:1; and the isolated protein encoded by the nucleotide sequence that hybridizes to SEQ ID NO:5.

* * * * *